(12) United States Patent
Harris et al.

(10) Patent No.: US 10,569,071 B2
(45) Date of Patent: Feb. 25, 2020

(54) MEDICANT ELUTING ADJUNCTS AND METHODS OF USING MEDICANT ELUTING ADJUNCTS

(71) Applicant: Ethicon Endo-Surgery, LLC, Guaynabo, PR (US)

(72) Inventors: Jason L. Harris, Lebanon, OH (US); Frederick E. Shelton, IV, Hillsboro, OH (US); Michael J. Vendely, Lebanon, OH (US); Tamara S. Widenhouse, Clarksville, OH (US)

(73) Assignee: Ethicon LLC, Guaynabo, PR (US)

( * ) Notice: Subject to any disclaimer, the term of this patent is extended or adjusted under 35 U.S.C. 154(b) by 41 days.

(21) Appl. No.: 14/840,613

(22) Filed: Aug. 31, 2015

(65) Prior Publication Data
US 2017/0055986 A1 Mar. 2, 2017

(51) Int. Cl.
*A61M 37/00* (2006.01)
*A61B 17/115* (2006.01)

(52) U.S. Cl.
CPC ......... *A61M 37/00* (2013.01); *A61B 17/1155* (2013.01); *A61M 2205/04* (2013.01)

(58) Field of Classification Search
CPC .............. A61M 37/00; A61M 2205/04; A61B 17/07207; A61B 17/07292; A61B 17/1155; A61B 2017/00893; A61B 2017/0046; A61B 2017/07271; A61B 17/068
USPC ................................ 227/175.1; 606/75, 219
See application file for complete search history.

(56) References Cited

U.S. PATENT DOCUMENTS

| | | | |
|---|---|---|---|
| 3,797,494 | A | 3/1974 | Zaffaroni |
| 3,993,072 | A | 11/1976 | Zaffaroni |
| 4,024,871 | A | 5/1977 | Stephenson |
| 4,512,038 | A | 4/1985 | Alexander et al. |

(Continued)

FOREIGN PATENT DOCUMENTS

| | | |
|---|---|---|
| EP | 0 640 315 A1 | 3/1995 |
| EP | 2008595 A2 | 12/2008 |

(Continued)

OTHER PUBLICATIONS

Brown et al. Fibroblast Migration in Fibrin Gel Matrices. American Journal of Pathology. 142:273-274, 1993.*

(Continued)

*Primary Examiner* — Kathleen S Holwerda
*Assistant Examiner* — Brooke Labranche
(74) *Attorney, Agent, or Firm* — Mintz Levin Cohn Ferris Glovsky and Popeo, P.C.

(57) ABSTRACT

Various exemplary devices and methods are provided for performing surgical procedures. In general, one or more adjuncts can be used in conjunction with surgical instruments. The adjunct(s) can have medicant(s) thereon and/or therein. The medicant(s) can vary depending on the desired effect of the medicant(s) on surrounding tissue. As a non-limiting example, medicant(s) can be provided to influence hemostasis, inflammation, macrophages, and/or fibroblasts. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples.

21 Claims, 76 Drawing Sheets

(56) References Cited

U.S. PATENT DOCUMENTS

| | | |
|---|---|---|
| 4,548,202 A | 10/1985 | Duncan |
| 5,071,417 A | 12/1991 | Sinofsky |
| 5,116,357 A | 5/1992 | Eberbach |
| 5,123,912 A | 6/1992 | Kaplan et al. |
| 5,282,829 A | 2/1994 | Hermes |
| 5,395,033 A | 3/1995 | Byrne et al. |
| 5,397,324 A | 3/1995 | Carroll et al. |
| 5,441,193 A | 8/1995 | Gravener |
| 5,446,108 A | 8/1995 | Jiang |
| 5,533,521 A | 7/1996 | Granger |
| 5,545,208 A | 8/1996 | Wolff et al. |
| 5,607,686 A | 3/1997 | Totakura et al. |
| 5,686,090 A | 11/1997 | Schilder et al. |
| 5,690,675 A | 11/1997 | Sawyer et al. |
| 5,752,965 A | 5/1998 | Francis et al. |
| 5,776,130 A | 7/1998 | Buysse et al. |
| 5,814,057 A | 9/1998 | Oi et al. |
| 5,836,970 A | 11/1998 | Pandit |
| 5,980,518 A | 11/1999 | Carr et al. |
| 6,162,537 A | 12/2000 | Martin et al. |
| 6,241,139 B1 | 6/2001 | Milliman et al. |
| 6,248,117 B1 | 6/2001 | Blatter |
| 6,325,810 B1 | 12/2001 | Hamilton et al. |
| 6,551,353 B1 | 4/2003 | Baker et al. |
| 6,620,166 B1 | 9/2003 | Wenstrom, Jr. et al. |
| 6,656,193 B2 | 12/2003 | Grant et al. |
| 6,702,850 B1 | 3/2004 | Byun et al. |
| 6,716,233 B1 | 4/2004 | Whitman |
| 6,821,273 B2 | 11/2004 | Mollenauer |
| 7,143,925 B2 | 12/2006 | Shelton, IV et al. |
| 7,160,299 B2 | 1/2007 | Baily |
| 7,238,195 B2 | 7/2007 | Viola |
| 7,316,693 B2 | 1/2008 | Viola |
| 7,401,721 B2 | 7/2008 | Holsten et al. |
| 7,464,847 B2 | 12/2008 | Viola et al. |
| 7,547,312 B2 | 6/2009 | Bauman et al. |
| 7,550,152 B2 | 6/2009 | Pandit et al. |
| 7,559,453 B2 | 7/2009 | Heinrich et al. |
| 7,601,118 B2 | 10/2009 | Smith et al. |
| 7,607,557 B2 | 10/2009 | Shelton, IV et al. |
| 7,655,288 B2 | 2/2010 | Bauman et al. |
| 7,708,180 B2 | 5/2010 | Murray et al. |
| 7,727,954 B2 | 6/2010 | McKay |
| 7,776,060 B2 | 8/2010 | Mooradian et al. |
| 7,794,475 B2 | 9/2010 | Hess et al. |
| 7,845,533 B2 | 12/2010 | Marczyk et al. |
| 7,950,561 B2 | 5/2011 | Aranyi |
| 8,062,330 B2 | 11/2011 | Prommersberger et al. |
| 8,097,017 B2 | 1/2012 | Viola |
| 8,118,206 B2 | 2/2012 | Zand et al. |
| 8,123,766 B2 | 2/2012 | Bauman et al. |
| 8,215,531 B2 | 7/2012 | Shelton, IV et al. |
| 8,273,369 B2 | 9/2012 | Moloye-Olabisi et al. |
| 8,317,070 B2 | 11/2012 | Hueil et al. |
| 8,319,211 B2 | 11/2012 | Sakuma et al. |
| 8,329,211 B2 | 12/2012 | Moloye-Olabisi et al. |
| 8,365,976 B2 | 2/2013 | Hess et al. |
| 8,383,147 B2 | 2/2013 | Shetty et al. |
| 8,383,156 B2 | 2/2013 | Zhao |
| 8,393,514 B2 | 3/2013 | Shelton, IV et al. |
| 8,464,925 B2 | 6/2013 | Hull et al. |
| 8,486,155 B2 | 7/2013 | McAlister et al. |
| 8,652,506 B2 | 2/2014 | Sikes et al. |
| 8,663,277 B2 | 3/2014 | Collier et al. |
| 8,672,206 B2 | 3/2014 | Aranyi et al. |
| 8,678,263 B2 | 3/2014 | Viola |
| 8,679,093 B2 | 3/2014 | Farra |
| 8,740,872 B2 | 6/2014 | Dormer et al. |
| 8,777,004 B2 | 7/2014 | Shelton, IV et al. |
| 8,814,025 B2 | 8/2014 | Miller et al. |
| 8,893,946 B2 | 11/2014 | Boudreaux et al. |
| 9,084,602 B2 | 7/2015 | Gleiman |
| 9,198,662 B2 | 12/2015 | Barton et al. |
| 9,204,880 B2 | 12/2015 | Baxter, III et al. |
| 9,211,120 B2 | 12/2015 | Scheib et al. |
| 9,220,500 B2 | 12/2015 | Swayze et al. |
| 9,277,919 B2 | 3/2016 | Timmer et al. |
| 9,301,752 B2 | 4/2016 | Mandakolathur Vasudevan et al. |
| 9,301,753 B2 | 4/2016 | Aldridge et al. |
| 9,320,523 B2 | 4/2016 | Shelton, IV et al. |
| 9,332,974 B2 | 5/2016 | Henderson et al. |
| 9,351,730 B2 | 5/2016 | Schmid et al. |
| 9,364,199 B2 | 6/2016 | Ostapoff et al. |
| 9,414,838 B2 | 8/2016 | Shelton, IV et al. |
| 9,572,574 B2 | 2/2017 | Shelton, IV et al. |
| 9,700,311 B2 | 7/2017 | Shelton, IV et al. |
| 9,801,630 B2 | 10/2017 | Harris et al. |
| 9,808,247 B2 | 11/2017 | Shelton, IV et al. |
| 9,839,420 B2 | 12/2017 | Shelton, IV et al. |
| 9,848,871 B2 | 12/2017 | Harris et al. |
| 9,937,283 B2 | 4/2018 | Shelton, IV et al. |
| 10,076,324 B2 | 9/2018 | Harris et al. |
| 10,085,745 B2 | 10/2018 | Dalessandro et al. |
| 10,086,116 B2 | 10/2018 | Vendely et al. |
| 10,111,661 B2 | 10/2018 | Widenhouse et al. |
| 2003/0236513 A1 | 12/2003 | Schwarz et al. |
| 2004/0043334 A1 | 3/2004 | Kobayashi et al. |
| 2004/0254608 A1 | 12/2004 | Huitema et al. |
| 2005/0119723 A1 | 6/2005 | Peacock |
| 2005/0119725 A1 | 6/2005 | Wang et al. |
| 2005/0131390 A1 | 6/2005 | Heinrich et al. |
| 2005/0165342 A1 | 7/2005 | Odland |
| 2005/0208100 A1 | 9/2005 | Weber et al. |
| 2005/0230453 A1 | 10/2005 | Viola |
| 2005/0267325 A1 | 12/2005 | Bouchier et al. |
| 2006/0025816 A1 | 2/2006 | Shelton |
| 2006/0085032 A1 | 4/2006 | Viola |
| 2006/0094318 A1 | 5/2006 | Matsuda et al. |
| 2006/0108393 A1 | 5/2006 | Heinrich et al. |
| 2006/0111738 A1 | 5/2006 | Wenchell |
| 2006/0173470 A1 | 8/2006 | Oray et al. |
| 2006/0212050 A1 | 9/2006 | D'Agostino et al. |
| 2006/0235469 A1 | 10/2006 | Viola |
| 2007/0066981 A1 | 3/2007 | Meagher |
| 2007/0102453 A1 | 5/2007 | Morgan et al. |
| 2007/0112414 A1 | 5/2007 | Parker et al. |
| 2007/0123781 A1 | 5/2007 | Callahan et al. |
| 2007/0134292 A1 | 6/2007 | Suokas et al. |
| 2007/0173787 A1 | 7/2007 | Huang et al. |
| 2007/0179528 A1 | 8/2007 | Soltz et al. |
| 2007/0275035 A1 | 11/2007 | Herman et al. |
| 2008/0110961 A1 | 5/2008 | Voegele et al. |
| 2008/0114381 A1 | 5/2008 | Voegele et al. |
| 2008/0128469 A1 | 6/2008 | Dalessandro et al. |
| 2008/0140115 A1 | 6/2008 | Stopek |
| 2008/0287878 A1 | 11/2008 | Tanaka |
| 2008/0290134 A1 | 11/2008 | Bettuchi et al. |
| 2009/0001122 A1* | 1/2009 | Prommersberger ............ A61B 17/07207 227/176.1 |
| 2009/0024144 A1 | 1/2009 | Zeiner et al. |
| 2009/0062799 A1 | 3/2009 | Holsten et al. |
| 2009/0104640 A1 | 4/2009 | Barron et al. |
| 2009/0120994 A1 | 5/2009 | Murray et al. |
| 2009/0143855 A1 | 6/2009 | Weber et al. |
| 2009/0206142 A1 | 8/2009 | Huitema et al. |
| 2009/0216104 A1 | 8/2009 | DeSimone et al. |
| 2010/0036379 A1 | 2/2010 | Prakash et al. |
| 2010/0062606 A1 | 3/2010 | Morikawa et al. |
| 2010/0065606 A1 | 3/2010 | Stopek |
| 2010/0076489 A1 | 3/2010 | Stopek et al. |
| 2010/0087840 A1 | 4/2010 | Ebersole et al. |
| 2010/0131050 A1 | 5/2010 | Zhao |
| 2010/0137990 A1 | 6/2010 | Apatsidis et al. |
| 2010/0147922 A1 | 6/2010 | Olson |
| 2010/0179545 A1 | 7/2010 | Twomey et al. |
| 2010/0239635 A1 | 9/2010 | McClain et al. |
| 2010/0312146 A1 | 12/2010 | Holsten |
| 2010/0318108 A1 | 12/2010 | Datta et al. |
| 2010/0331880 A1 | 12/2010 | Stopek |
| 2011/0066168 A1 | 3/2011 | Magnusson et al. |
| 2011/0087279 A1 | 4/2011 | Shah et al. |
| 2011/0112573 A1 | 5/2011 | Bloom |
| 2011/0168759 A1 | 7/2011 | Prommersberger |

(56) References Cited

U.S. PATENT DOCUMENTS

| | | |
|---|---|---|
| 2011/0177150 A1 | 7/2011 | Pathak et al. |
| 2011/0282446 A1 | 11/2011 | Schulte et al. |
| 2012/0080490 A1* | 4/2012 | Shelton, IV ..... A61B 17/00491 227/176.1 |
| 2012/0097194 A1 | 4/2012 | McDaniel et al. |
| 2012/0125792 A1 | 5/2012 | Cassivi |
| 2012/0187179 A1 | 7/2012 | Gleiman |
| 2012/0241491 A1 | 9/2012 | Aldridge et al. |
| 2012/0241496 A1 | 9/2012 | Mandakolathur Vasudevan et al. |
| 2012/0241497 A1* | 9/2012 | Mandakolathur Vasudevan ......... A61B 17/00491 227/176.1 |
| 2012/0241499 A1 | 9/2012 | Baxter, III et al. |
| 2012/0241503 A1 | 9/2012 | Baxter, III et al. |
| 2012/0241505 A1 | 9/2012 | Alexander, III et al. |
| 2012/0253298 A1 | 10/2012 | Henderson et al. |
| 2012/0312860 A1 | 12/2012 | Ming et al. |
| 2012/0318842 A1 | 12/2012 | Anim et al. |
| 2012/0318844 A1 | 12/2012 | Shelton, IV et al. |
| 2013/0037596 A1 | 2/2013 | Bear et al. |
| 2013/0062394 A1 | 3/2013 | Smith et al. |
| 2013/0075447 A1* | 3/2013 | Weisenburgh, II ......................... A61B 17/00491 227/176.1 |
| 2013/0116341 A1 | 5/2013 | Askari et al. |
| 2013/0146643 A1 | 6/2013 | Schmid et al. |
| 2013/0149343 A1 | 6/2013 | Pesnell et al. |
| 2013/0221065 A1 | 8/2013 | Aronhalt et al. |
| 2013/0256365 A1 | 10/2013 | Shelton, IV et al. |
| 2013/0256367 A1 | 10/2013 | Scheib et al. |
| 2013/0256377 A1 | 10/2013 | Schmid et al. |
| 2013/0256380 A1 | 10/2013 | Schmid et al. |
| 2014/0005600 A1* | 1/2014 | Cho ........................ A61K 9/209 604/93.01 |
| 2014/0048580 A1 | 2/2014 | Merchant et al. |
| 2014/0217148 A1 | 8/2014 | Penna |
| 2014/0276387 A1 | 9/2014 | Ostapoff et al. |
| 2014/0358167 A1 | 12/2014 | Armstrong |
| 2014/0364941 A1 | 12/2014 | Edmiston et al. |
| 2015/0005809 A1 | 1/2015 | Ayres et al. |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0196296 A1 | 7/2015 | Swayze et al. |
| 2015/0272575 A1 | 10/2015 | Leimbach et al. |
| 2015/0313591 A1 | 11/2015 | Baxter, III et al. |
| 2015/0351753 A1 | 12/2015 | Shelton, IV et al. |
| 2015/0351754 A1* | 12/2015 | Harris ................ A61B 17/0686 227/176.1 |
| 2015/0351757 A1 | 12/2015 | Harris et al. |
| 2015/0351758 A1 | 12/2015 | Shelton, IV et al. |
| 2015/0351763 A1 | 12/2015 | Shelton, IV et al. |
| 2015/0359529 A1 | 12/2015 | Ganiban et al. |
| 2015/0366684 A1 | 12/2015 | Seo et al. |
| 2015/0374376 A1 | 12/2015 | Shelton, IV |
| 2016/0199063 A1 | 7/2016 | Mandakolathur Vasudevan et al. |
| 2016/0206864 A1 | 7/2016 | Matonick et al. |
| 2016/0249935 A1* | 9/2016 | Hewitt ............. A61B 17/12145 606/200 |
| 2017/0055986 A1 | 3/2017 | Harris et al. |
| 2017/0119387 A1 | 5/2017 | Dalessandro et al. |

FOREIGN PATENT DOCUMENTS

| | | |
|---|---|---|
| EP | 2540311 A1 | 1/2013 |
| EP | 2644113 A2 | 10/2013 |
| EP | 2644124 A1 | 10/2013 |
| EP | 2764824 A1 | 8/2014 |
| EP | 2870937 A1 | 5/2015 |
| EP | 2910198 A2 | 8/2015 |
| WO | WO-2006044490 A2 | 4/2006 |
| WO | WO-2007025293 A2 | 3/2007 |
| WO | WO-2008140989 A2 | 11/2008 |
| WO | WO-2010/109021 A2 | 9/2010 |

OTHER PUBLICATIONS

Search Report for European Patent Application No. EP 16186384.0 dated Feb. 3, 2017.
Search Report for European Patent Application No. EP 16186416.0 dated Feb. 3, 2017.
U.S. Appl. No. 14/840,255 entitled "Adjunct Material to Promote Tissue Growth" filed Aug. 31, 2015.
U.S. Appl. No. 14/840,527 entitled "Composite Adjunct Materials for Delivering Medicants" filed Aug. 31, 2015.
U.S. Appl. No. 14/840,659 entitled "Adjunct Material to Provide Heterogeneous Drug Elution" filed Aug. 31, 2015.
U.S. Appl. No. 14/840,386 entitled "Surgical Adjuncts Having Medicants Controllably Releasable Therefrom" filed Aug. 31, 2015.
U.S. Appl. No. 14/840,716 entitled "Adjunct Material to Provide Controlled Drug Release," filed Aug. 31, 2015.
U.S. Appl. No. 14/840,406 entitled "Matrix Metalloproteinase Inhibiting Adjuncts for Surgical Devices" filed Aug. 31, 2015.
U.S. Appl. No. 14/841,139 entitled "Adjunct Material to Provide Controlled Drug Elution" filed Aug. 31, 2015.
U.S. Appl. No. 14/840,431 entitled "Surgical Adjuncts With Medicants Affected by Activator Materials" filed Aug. 31, 2015.
U.S. Appl. No. 14/840,523 entitled "Adjuncts for Surgical Devices Including Agonists and Antagonists" filed Aug. 31, 2015.
U.S. Appl. No. 14/498,145 entitled "Method for Creating a Staple Line" filed Sep. 26, 2014.
U.S. Appl. No. 14/667,842 entitled "Method of Applying a Buttress to a Surgical Stapler" filed Mar. 25, 2015.
U.S. Appl. No. 14/300,954, entitled "Adjunct Materials and Methods of Using Same in Surgical Methods for Tissue Sealing," filed Jun. 10, 2014.
U.S. Appl. No. 14/318,996 entitled "Fastener Cartridges Including Extensions Having Different Configurations" filed Jun. 30, 2014.
U.S. Appl. No. 14/667,874 entitled "Malleable Bioabsorbable Polymer Adhesive for Releasably Attaching a Staple Buttress to a Surgical Stapler" filed Mar. 25, 2015.
U.S. Appl. No. 14/840,589 entitled "Adjunct Material to Provide Drug Elution from Vessels" filed Aug. 31, 2015.
U.S. Appl. No. 14/840,758 entitled "Surgical Adjuncts With Medicants Affected by Activators" filed Aug. 31, 2015.
U.S. Appl. No. 14/840,878 entitled "Surgical Adjuncts and Medicants for Promoting Lung Function" filed Aug. 31, 2015.
U.S. Appl. No. 14/840,927 entitled "Adjunct Material to Promote Tissue Growth in a Colon" filed Aug. 31, 2015.
U.S. Appl. No. 14/841,060 entitled, "Tubular Surgical Constructs Including Adjunct Material" filed Aug. 31, 2015.
U.S. Appl. No. 14/841,074 entitled "Adjunct Material for Delivery to Stomach Tissue" filed Aug. 31, 2015.
U.S. Appl. No. 14/841,147 entitled "Inducing Tissue Adhesions Using Surgical Adjuncts and Medicants" filed Aug. 31, 2015.
U.S. Appl. No. 14/841,180 entitled "Adjunct Material for Delivery to Live Tissue" filed Aug. 31, 2015.
U.S. Appl. No. 14/841,115 entitled "Adjunct Material for Delivery to Colon Tissue" filed Aug. 31, 2015.
Abbas, Anastomotic leak: should we continue to accept the risks? Dis Colon Rectum. Jun. 2010;53(6):859-60.
Achneck et al., A comprehensive review of topical hemostatic agents. Ann Surg 2010; 251:217-228.
Adas et al., Mesenchymal stem cells improve the healing of ischemic colonic anastomoses (experimental study). Langenbecks Arch Surg. Jan. 2011;396(1):115-26.
Agren et al., Action of matrix metalloproteinases at restricted sites in colon anastomosis repair: an immunohistochemical and biochemical study. Surgery. Jul. 2006;140(1):72-82.
Al Jabri et al., Management and prevention of pelvic adhesions. Sem Rep Med 2011; 29(2):130-137.

(56) References Cited

OTHER PUBLICATIONS

Anegg et al., Efficiency of fleece-bound sealing (TachoSil) of air leaks in lung surgery: a prospective randomised trial. Eur J Cardiothoracic Surg 2007; 31(2):198-202.
Armstrong et al., The effect of three hemostatic agents on early bone healing in an animal model. BMC Surgery 2010; 10:37.
Arnold et al., A comparison of burst pressure between buttressed versus non-buttressed staple-lines in an animal model. Obes Surg. Feb. 2005;15(2):164-71.
Assalia et al., Staple-line reinforcement with bovine pericardium in laparoscopic sleeve gastrectomy: experimental comparative study in pigs. Obes Surg. Feb. 2007;17(2):222-8.
Astafiev GV [All State Laboratory for Surgery Research]. Investigation of processes relating to tissue compression in suturing and stapling apparatus. Surgical Staplers (Chirurgicheskiey Shivayushiye Apparaty). 1967;7 [translated from the Russian].
Attard et al., The effects of systemic hypoxia on colon anastomotic healing: an animal model. Dis Colon Rectum. Jul. 2005;48(7):1460-70.
Aydin et al., FACS, Bariatric Times. 2010;7(3):8-13.
Baca et al., Icodextrin and Seprafilm® do not interfere with colonic anastomosis in rats. Eur Surg Res 2007; 39:318-323.
Baker et al. The science of stapling and leaks. Obes Surg. 2004;14:1290-1298.
Bartczak et al., Manipulation of in vitro angiogenesis using peptide-coated gold nanoparticles. ACS Nano. Jun. 25, 2013;7(6):5628-36.
Belda-Sanchis et al., Surgical sealant for preventing air leaks after pulmonary resections in patients with lung cancer. Cochrane Database Syst Rev 2005; 3:CD003051.
Bezwada, Controlled Release of Drugs from Novel Absorbable Oligomers and Polymers, White Paper, Bezwada Biomedical, 2008.
Bezwada, Functionalized Triclosan for Controlled Release Applications. White Paper, Bezwada Biomedical. 2008.
Bezwada, Nitric Oxide and Drug Releasing Hydrolysable Macromers, Oligomers and Polymers, Ch. 11 of Biomaterials, ACS Symposium Series; American Chemical Society: Washington, DC, 2010.
Bezwada, Nitric Oxide and Drug Releasing Hydrolysable Macromers, Oligomers and Polymers. White Paper, Bezwada Biomedical. 2009.
Bischoff et al., A rheological network model for the continuum anisotropic and viscoelastic behavior of soft tissue. Biomech Model Mechanobiol. Sep. 2004;3(1):56-65.
Bischoff, Reduced parameter formulation for incorporating fiber level viscoelasticity into tissue level biomechanical models. Ann Biomed Eng. Jul. 2006:34(7)1164-72.
Blouhos et al., The integrity of colonic anastomoses following the intraperitoneal administration of oxaliplatin. Int J Colorectal Dis 2010; 25(7): 835-841.
Brady et al., Use of autologous platelet gel in bariatric surgery. Journal of Extra-Corporeal Technology 2006; 38(2):161-164.
Broughton G 2nd, Janis JE, Attinger CE. The basic science of wound healing. Plast Reconstr Surg. Jun. 2006;117(7 Suppl):12S-34S.
Callery et al., Collagen matrix staple line reinforcement in gastric bypass. Surg Obes Rel Dis 2010. Article in press.
D'Andrilli et al., A prospective randomized study to assess the efficacy of a surgical sealant to treat air leaks in lung surgery. Eur J Cardiothoracic Surg 2009; 35:817-821.
DeCamp et al., Patient and surgical factors influencing air leak after lung vol. reduction surgery: lessons learned from the National Emphysema Treatment Trial. Ann Thorac Surg. Jul. 2006;82(1):197-206.
Deshaies et al., Antiangiogenic agents and late anastomotic complications. J Surg Onc 2010; 101(2):180-183.
Dubay et al., Acute wound healing: the biology of acute wound failure. Surg Clin North Am. Jun. 2003;83(3):463-81.
Dujovny et al., Minimum vascular occlusive force. J Neurosurg. Nov. 1979;51(5):662-8.

Efthimiou et al., Fibrin sealant associated with increased body temperature and leukocytosis after laparoscopic gastric bypass. Surg Obes Rel Dis 2010; 6:46-49.
Elariny et al., Tissue thickness of human stomach measured on excised gastric specimens of obese patients. Surg Technol Int. XIV (2005); 14:119-124.
Enestvedt et al., Clinical review: Healing in gastrointestinal anastomoses, part II. Microsurgery. 2006;26(3)137-43.
Ersoy et al., Effects of oxaliplatin and 5-Fluorouracil on the healing of colon anastomoses. Surg Today 2009; 39:38-43.
Fedakar-Senyucel et al., The effects of local and sustained release of fibroblast growth factor on wound healing in esophageal anastomoses. J. Ped Surg 2008; 43 (2):290-295.
Fingerhut et al., Use of sealants in pancreatic surgery: Critical appraisal of the literature. Dig Surg 2009; 26:7-14.
Frank et al., Clamping the small intestineduring surgery: predicted and measured sealing forces. Proc Inst Mech Eng H. 1995;209(2):111-5.
Fullum et al., Decreasing anastomotic and staple line leaks after laparoscopic Roux-en-Y gastric bypass. Surg Endosc 2009; 23(6)1403-1408.
Goto et al., Evaluation of the mechanical strength and patency of functional end-to-end anastomoses. Surg Endosc. Sep. 2007;21(9)1508-11.
Gregersen et al., Biomechanics of the gastrointestinal tract. Neurogastroenterol Motil. Dec. 1996;8(4):277-97.
Gu et al., Effects of hydration and fixed charge density on fluid transport in charged hydrated soft tissues. Ann Biomed Eng. Nov. 2003;31(10):1162-70.
Hardy KJ. Non-suture anastomosis: the historical development. Aust N Z J Surg. Aug. 1990;60(8):625-33.
Hendriks et al., Healing of experimental intestinal anastomoses. Parameters for repair. Dis Colon Rectum. Oct. 1990;33(10):891-901.
Huh et al., Anastomotic leakage after laparoscopic resection of rectal cancer: the impact of fibrin glue. Am J Surg 2010; 1991(4):435-441.
Jönsson et al., Breaking strength of small intestinal anastomoses. Am J Surg. Jun. 1983;145(6):800-3.
Kaemmer et al., Erythropoietin (EPO) influences colonic anastomotic healing in a rat model by modulating collagen metabolism. J Surg Res. Oct. 2010;163(2):e67-72.
Kanellos et al., Healing of colonic anastomoses after immediate postoperative intraperitoneal administration of oxaliplatin. Int J Colorectal Dis 2008; 23(12):1185-1191.
Kennelly et al., Electrical field stimulation promotes anastomotic healing in poorly perfused rat colon. Int J Colorectal Dis 2011; 26:339-344.
Kirfel et al., Impaired intestinal wound healing in Fhl2-deficient mice is due to disturbed collagen metabolism. Exp Cell Res. Dec. 10, 2008;314(20):3684-91.
Kjaergard HK. Suture support: is it advantageous? Am J Surg. Aug. 2001;182(2 Suppl): 15S-20S.
Klein et al., Physiology and pathophysiology of matrix metalloproteases. Amino Acids. Springer, Jul. 18, 2010.
Lang et al., Efficacy and safety of topical application of human fibrinogen/thrombin-coated collagen patch (TachoComb) for treatment of air leakage after standard lobectomy. Eur J Cardiothorac Surg 2004; 25:160-166.
Lee et al., Efficacy of posterior fixation suture augmented with talc or doxycycline. Graefe's Archive for Clinical and Experimental Ophthamology 2010; 248(9):1287-1292.
Lee et al., Using Surgicel to buttress the staple line in lung volume reduction surgery for chronic obstructive pulmonary disease. J Thorac Card Surg 2006; 131(2):495-496.
Letowska-Andrzejewicz et al., The use of morphometric and fractal parameters to assess the effects of 5-fluorouracil, interferon and dexamethasone treatment on colonic anastomosis healing: An experimental study in rats. Folia Histochemica et Cytobiologica 2011; 49(1):80-89.

(56) References Cited

OTHER PUBLICATIONS

Li et al., Combination of fibrin glue with growth hormone augments healing of incomplete intestinal anastomoses in a rat model of intra-abdominal sepsis: a dynamic study. J Invest Surg. Sep.-Oct. 2007;20(5):301-6.
Li et al., Effect of the combination of fibrin glue and growth hormone on incomplete intestinal anastomoses in a rat model of intra-abdominal sepsis. J Surg Res 2006; 131(1)1110117.
Malapert et al., Surgical sealant for the prevention of prolonged air leak after lung resection: Meta-analysis. Ann Thor Surg 2010; 90(6):1779-1785.
Martens et al., Postoperative changes in collagen synthesis in between small and large bowel. intestinal anastomoses of the rat: differences Gut 1991;32;1482-1487.
McGuire et al., An in vitro assessment of tissue compression damage during circular stapler approximation tests, measuring expulsion of intracellular fluid and force. Proc Inst Mech Eng [H]. 2001;215(6):589-597.
Menzies et al., Use of icodextrin 4% solution in the prevention of adhesion formation following general surgery: From the multicentre ARIEL Registry. Ann Royal Coll Surg 2006; 88(4):375-382.
Mongardini et al., [The use of Floseal in the prevention and treatment of intra- and post-operative hemorrhage in the surgical treatment of hemorrhoids and colporectocele. Preliminary results]. G Chir. Oct. 2003;24(10):377-81. Italian.
Munireddy et al., Intra-abdominal healing: gastrointestinal tract and adhesions. Surg Clin North Am. Dec. 2010;90(6):1227-36.
Nandakumar et al., Anastomoses of the lower gastrointestinal tract. Nat Rev Gastroenterol Hepatol. Dec. 2009;6(12):709-16.
Nandakumar et al., Surgical adhesive increases burst pressure and seals leaks in stapled gastrojejunostomy. Surg Obes Rel Dis 2010; 6:498-502.
Nguyen et al., The efficacy of fibrin sealant in prevention of anastomotic leak after laparoscopic gastric bypass. J Surg Res 2004; 122:218-224.
Nomori et al., Gelatin-resorcinol-formaldehyde-glutaraldehyde glue-spread stapler prevents air leakage from the lung. Ann Thorac Surg 1997; 63(2):352-355.
Nomori et al., The efficacy and side effects of gelatin-resorcinol formaldehyde-glutaraldehyde (GRFG) glue for preventing and sealing pulmonary air leakage. Surgery Today 2000; 30(3):244-248.
Oz et al., Preliminary experience with laser reinforcement of vascular anastomoses. Proceedings of SPIE—The International Society for Optimal Engineering 1991; 1422:147-150.
Ozel et al., Effect of early preoperative 5-fluorouracil on the integrity of colonic anastomoses in rats. World J Gastroenterology 2009; 15(33):4156-4162.
Pascual et al., Adipose-derived mesenchymal stem cells in biosutures do not improve healing of experimental colonic anastomoses. Br J Surg 2008; 95(9)1180-1184.
Pascual et al., Biosutures improve healing of experimental weak colonic anastomoses. Int J Colorectal Dis 2010; 25(12):1447-1451.
Pasternak et al., Doxycycline-coated sutures improve mechanical strength of intestinal anastomoses. Int J Colorectal Dis 2008; 23(3):271-276.
Pavlidis et al., The effect of bevacizumab on colon anastomotic healing in rats. Int J Colorectal Dis 2010; 25(12):1465-1473.
Rena et al., Air-leak management after upper lobectomy in patients with fused fissure and chronic obstructive pulmonary disease: A pilot trial comparing sealant and standard treatment. Int Cardiovasc Thor Surg 2009; 9(6):973-977.
Rijcken et al., Insulin-like growth factor 1-coated sutures improve anastomotic healing in an experimental model of colitis. Br J Surg 2010; 97(2): 258-265.
Robson et al., Wound healing: biologic features and approaches to maximize healing trajectories. Curr Probl Surg. Feb. 2001;38(2):72-140.
Rusca et al., Everting versus inverting gastrointestinal anastomoses: bacterial leakage and anastomotic disruption. Ann Surg. May 1969;169(5):727-35.
Sakallioglu et al., Sustained local application of low-dose epidermal growth factor on steroid-inhibited colonic wound healing. J Ped Surg 2004; 39(4):591-595.
Saribeyoglu et al., Does becaplermin (platelet-derived growth factor-BB) reverse detrimental effects of ischemia on colonic anastomosis? Dis col. Rect 2003; 46(4):516-520.
Schnriger et al., Prevention of postoperative peritoneal adhesions: A review of the literature. Am J Surg 2011; 201(1):111-121.
Seyda, "Stem Cells and Tissue Engineering" PowerPoint Presentation, Aug. 18, 2009.
Shogan et al. Collagen degradation and MMP9 activation by Enterococcus faecalis contribute to intestinal anastomotic leak. Sci Trans Med. May 6, 2015;7(286):286ra68.
Siemonsma et al., Doxycycline improves wound strength after intestinal anastomosis in the rat. Surgery. Mar. 2003;133(3):268-76.
Sileshi et al., Application of energy-based technologies and topical hemostatic agents in the management of surgical hemostasis. Vascular 2010; 18(4):197-204.
Spector et al., Comparison of hemostatic properties between collagen and synthetic buttress materials used in staple line reinforcement in a swine splenic hemorrhage model. Surg Endosc 2011; 25(4):1148-1152.
Spector et al., In vitro large diameter bowel anastomosis using a temperature controlled laser tissue soldering system and albumin stent. Lasers in Surgery and Medicine 2009; 41(7):504-508.
Stammberger et al., Buttressing the staple line in lung vol. reduction surgery: a randomized three-center study. Ann Thorac Surg. Dec. 2000;70(6):1820-5.
Subhas et al., Topical gentamicin does not provide any additional anastomotic strength when combined with fibrin glue. Am J Surg 2001; 201 (3):339-343.
Suresh et al., Seprafilm slurry does not increase complication rates after laparoscopic colectomy. Surg Endosc. Aug. 2011;25(8):2661-5.
Syk et al., Inhibition of matrix metalloproteinases enhances breaking strength of colonic anastomoses in an experimental model. Br J Surg. Feb. 2001;88(2):228-34.
Thompson et al., Clinical review: Healing in gastrointestinal anastomoses, part I. Microsurgery. 2006;26(3):131-6.
Uludag et al., Covering the colon anastomoses with amniotic membrane prevents the negative effects of early intraperitoneal 5-FU administration on anastomotic healing. Int J Colorectal Dis 2010; 25(2):223-232.
Uludag et al., Effects of amniotic membrane on the healing of normal and high-risk colonic anastomoses in rats. Int J Colorectal Dis 2009; 24:809-817.
Uludag et al., Effects of amniotic membrane on the healing of primary colonic anastomoses in the cecal ligation and puncture model of secondary peritonitis in rats. Int J Colorectal Dis 2009; 24(5):559-567.
Uludag et al., Effects of the amniotic membrane on healing of colonic anastomoses in experimental leftsided colonic obstruction. Langebeck's Arch Surg 2010; 395(5):535-543.
van der Stappen et al., Collagenolytic activity in experimental intestinal anastomoses. Differences between small and large bowel and evidence for the presence of collagenase. Int J Colorectal Dis. Jun. 1992;7(2):95-101.
Wang et al., Effect of the combination of fibrin glue and growth hormone on intestinal anastomoses in a pig model of traumatic shock associated with peritonitis. Work J Surg 2009; 33(3):567-576.
Witte et al., Repair of full-thickness bowel injury. Crit Care Med. Aug. 2003;31(8 Suppl):S538-46.
Yo et al., Buttressing of the staple line in gastrointestinal anastomoses: overview of new technology designed to reduce perioperative complications. Dig Surg. 2006;23(5-6):283-91.
Zeng et al., Efficacy and safety of Seprafilm for preventing postoperative abdominal adhesion: Systematic review and meta-analysis. World J Surg 2007; 31:2125-2131.
European Search Report for EP16186385.7 dated Jan. 25, 2017 (6 pages).
European Examination Report for EP 16186419.4 dated May 29, 2018 (5 pages).

(56) References Cited

OTHER PUBLICATIONS

Okuda et al., "Platelet-rich plasma contains high levels of platelet-derived growth factor and transforming growth factor-beta and modulates the proliferation of periodontally related cells in vitro," Journal of Periodontology, col. 74, No. 6, Jan. 1, 2003, pp. 849-857, XP003016926, ISSN: 0022-3492, DOI: 10.1902/JOP.2003.74.6.849.

Eming et al., "Wound Repair and regeneration: Mechanisms, signaling, and translation," Science Translational Medicine, vol. 6, No. 265, Dec. 3, 2014.

International Search Report for App. No. PCT/US2016/048159 dated Nov. 29, 2016.

International Search Report for App. No. PCT/US2016/048267 dated Nov. 24, 2016.

International Search Report for App. No. PCT/US2016/048368 dated Dec. 5, 2016.

International Search Report for App. No. PCT/US2016/048588 dated Nov. 28, 2016.

International Search Report for App. No. PCT/US2016/048594 dated Nov. 8, 2016.

International Search Report for App. No. PCT/US2016/048600 dated Nov. 25, 2016.

International Search Report for App. No. PCT/US2016/048606 dated Dec. 6, 2016.

International Search Report for App. No. PCT/US2016/048181 dated Dec. 8, 2016.

International Search Report for App. No. PCT/US2016/048578 dated Jan. 4, 2017.

International Search Report for App. No. PCT/US2016/048589 dated Nov. 28, 2016.

International Search Report for App. No. PCT/US2016/048583 dated Dec. 2, 2016.

European Examination Report for EP App. No. 16186387.3 dated Aug. 10, 2018.

\* cited by examiner

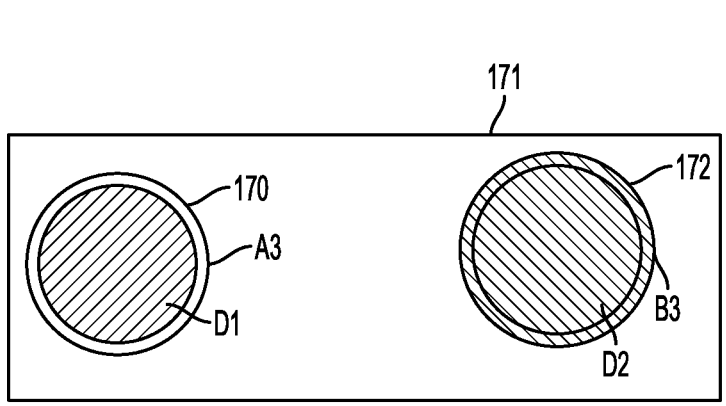
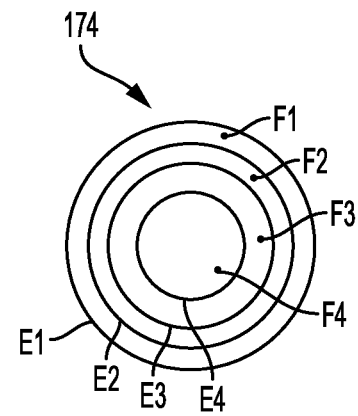
FIG. 30    FIG. 31
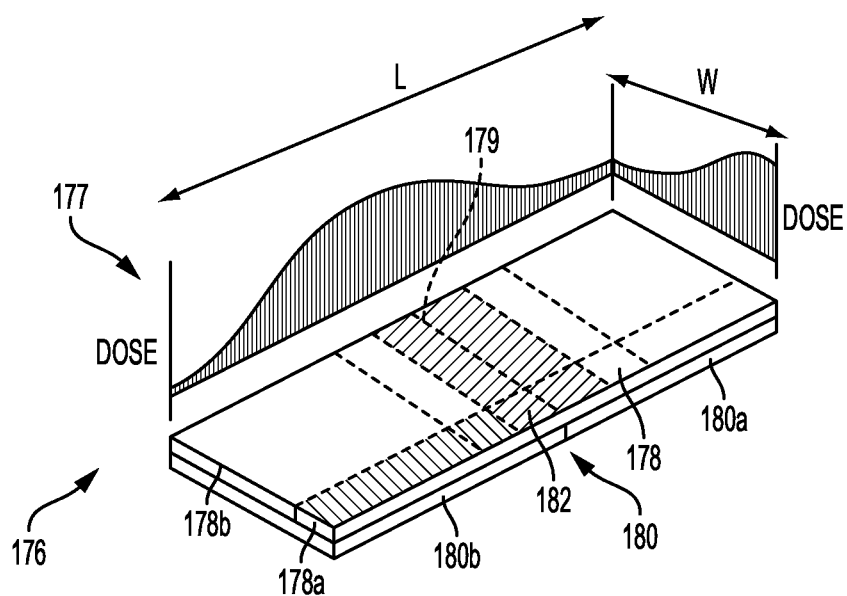
FIG. 32

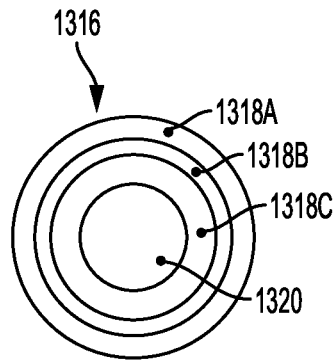
FIG. 138
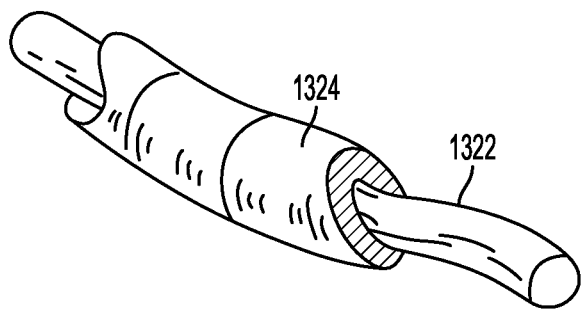 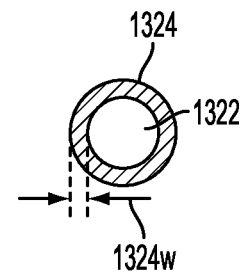
FIG. 139  FIG. 140
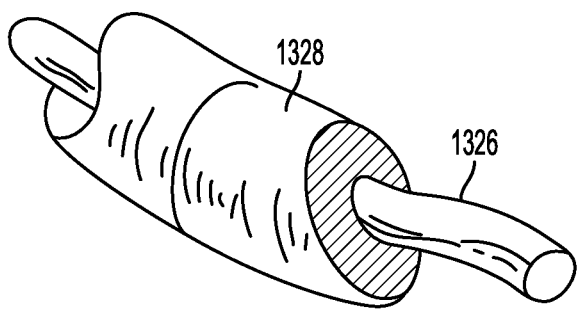 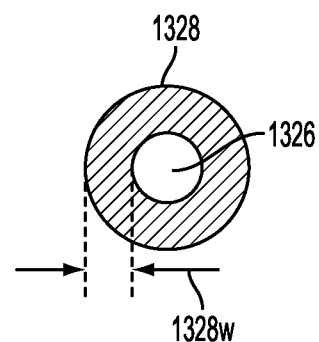
FIG. 141  FIG. 142

MEDICANT ELUTING ADJUNCTS AND METHODS OF USING MEDICANT ELUTING ADJUNCTS

FIELD OF THE INVENTION

The present disclosure relates generally to medicant eluting adjuncts and methods of using medicant eluting adjuncts.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

In some instances, biologic materials have been used in conjunction with tissue stapling. However, the use of biologic materials presents a number of additional problems. For example, it can be difficult to maintain a location of the biologic material with respect to jaws of the stapler prior to and during staple ejection. It can also be difficult to keep the biologic material at a desired location at the surgical site after stapling is completed. Further, it can be difficult to manufacture the biologic material to a desired shape and thickness. Common plastic and molding manufacturing techniques are not generally conducive to the manufacture of thin biologic layers for use in conjunction with surgical staplers. The fragile nature of many biologic materials also makes them difficult to use with surgical staplers because they lack structural support.

Accordingly, there remains a need for improved devices and methods for stapling tissue, blood vessels, ducts, shunts, or other objects or body parts such that leaking and inflammation is minimized while substantially maintaining the natural characteristics of the treatment region. There further remains a need for improved implantable materials that include biologics.

SUMMARY

In general, medicant eluting adjuncts and methods of using medicant eluting adjuncts are provided.

In one aspect, a surgical method is provided that in one implementation includes positioning an end effector of a surgical stapler adjacent tissue of a patient. The end effector has disposed therein a cartridge body including a plurality of staples, and the end effector has releasably disposed thereon a biocompatible adjunct material. The adjunct material has an effective amount of at least one medicant disposed within and releasable from the adjunct material. The method also includes actuating the stapler to deploy the staples from the cartridge body, thereby stapling the adjunct material to the tissue and releasing the adjunct material from the end effector. The at least one medicant is releasable from the adjunct material to the tissue according to at least one of a predetermined temporal pattern and a predetermined spatial pattern.

The method can vary in any number of ways. For example, the at least one medicant can be releasable from the adjunct material to the tissue according to at least the predetermined temporal pattern, and the predetermined temporal pattern can include a substantially immediate release of the at least one medicant upon the stapling of the adjunct material. For another example, the at least one medicant can be releasable from the adjunct material to the tissue according to at least the predetermined temporal pattern, and the predetermined temporal pattern can include the at least one medicant not being released from the adjunct material until a predetermined amount of time after the stapling of the adjunct material. For yet another example, the at least one medicant can be releasable from the adjunct material to the tissue according to at least the predetermined temporal pattern, and the predetermined temporal pattern can be defined by at least one of a degradation rate of a region within the adjunct material from which the at least one medicant is being released, a degradation rate of one or more coatings retaining the at least one medicant within the adjunct material, and an environmental condition at the tissue. For still another example, the at least one medicant can be releasable from the adjunct material to the tissue according to at least the predetermined spatial pattern, the adjunct material can include a plurality of distinct regions each releasably retaining therein the at least one medicant, and the at least one medicant can be releasable from each of the regions in a different spatial pattern. For another example, the method can include, prior to positioning the end effector adjacent the tissue of the patient, removably disposing the cartridge body into the end effector. For yet another example, the method can include removing the surgical stapler from the patient, the staples and the adjunct material remaining within the patient. For still another example, the adjunct material can include at least one of a film, a foam, an injection molded thermoplastic, a vacuum thermoformed material, and a fibrous structure. For yet another example, the at least one medicant can include at least one of an antimicrobial agent, an antifungal agent, an antiviral agent, an anti-inflammatory agent, a growth factor, an analgesic, an anesthetic, a tissue matrix degradation inhibitor, an anti-cancer agent, and a hemostatic agent.

In another implementation, a surgical method is provided that includes positioning an end effector of a surgical stapler adjacent an organ of a patient. The end effector has disposed therein a cartridge body including a plurality of staples, and the end effector has releasably disposed thereon a biocompatible adjunct material. The adjunct material has an effective amount of at least one medicant disposed within and releasable from the adjunct material. The method also includes actuating the stapler to deploy the staples from the cartridge body, thereby stapling the adjunct material to the organ and releasing the adjunct material from the end effector. The at least one medicant is releasable from the adjunct material to the organ to provide a predetermined treatment to the organ. The adjunct material causes regrowth of tissue of the organ in a predetermined manner.

The method can have any number of variations. For example, the predetermined treatment can include at least one of an antimicrobial effect, an antifungal effect, an antiviral effect, an anti-inflammatory effect, a growth factor effect, an analgesic effect, an anesthetic effect, tissue matrix degradation inhibition, an anti-cancer effect, and a hemostatic effect. For another example, the predetermined manner can include causing the tissue to regrow in a direction that mimics a natural direction of tissue fibers of the organ. For yet another example, the adjunct material can be stapled to an exterior surface of the organ. For another example, the adjunct material can be stapled to an interior surface of the organ. For still another example, the organ can include one of a stomach, an intestine, a liver, and a lung. For another example, the adjunct material can include at least one of a film, a foam, an injection molded thermoplastic, a vacuum thermoformed material, and a fibrous structure.

In general, adjunct material to promote tissue growth is provided.

In one aspect, a staple cartridge assembly for use with a surgical stapler is provided that in one implementation includes a cartridge body, a biocompatible adjunct material, and an effective amount of at least one medicant disposed within and releasable from the adjunct material. The cartridge body has a plurality of staple cavities. Each staple cavity has a surgical staple disposed therein. The biocompatible adjunct material is releasably retained on the cartridge body and is configured to be delivered to tissue by deployment of the staples in the cartridge body. The adjunct material is in the form of a fiber lattice. The fiber lattice has at least two distinct heterogeneous fiber lattice sections. Each of the fiber lattice sections of the adjunct material is arranged in a pattern configured to promote organized tissue remodeling in a desired manner Each of the at least one medicants are effective to provide a desired effect on tissue in-growth in a predetermined manner, and each of the at least one medicants are releasable from the adjunct material in a homogeneous manner.

The staple cartridge assembly can have any number of variations. For example, the adjunct material can be made of a plurality of fibers that are one of bioabsorbable and dissolvable. The at least one medicant can be eluted upon the absorption or dissolution of the fibers. For another example, the fiber lattice sections can differ from one another in at least one of fiber density in a first direction, fiber density in a second direction, fiber material, fiber construction, fiber diameter, fiber surface characteristics, fiber charge, and fiber elasticity. For yet another example, the at least two distinct heterogeneous fiber lattice sections can include three fiber lattice sections, and each of the three fiber lattice sections can differ from one another in at least one of fiber density in a first direction, fiber density in a second direction, fiber material, fiber construction, fiber diameter, fiber surface characteristics, fiber charge, and fiber elasticity. For another example, the at least one medicant can include at least one of an antimicrobial agent, an antifungal agent, an antiviral agent, an anti-inflammatory agent, a growth factor, an analgesic, an anti-cancer agent, an anti-adhesion agent, a tissue matrix degradation inhibitor, a nutrient, an oxygen expelling agent, an amino acids, a collageno synthetic agent, Glutamine, Insulin, Butyrate, and Dextran.

In another aspect, an end effector for a surgical instrument is provided that in one implementation includes a first jaw, a second jaw, a biocompatible adjunct material, and an effective amount of at least one medicant disposed within and releasable from the adjunct material. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is releasably retained on at least one of the tissue-facing surfaces of the first and second jaws and is configured to be delivered to tissue by deployment of the staples in the cartridge body. The adjunct material is in the form of a fiber lattice having at least two distinct heterogeneous fiber lattice sections. Each of the fiber lattice sections of the adjunct material is arranged in a pattern configured to promote organized tissue remodeling in a desired manner Each of the at least one medicants is effective to provide a desired effect on tissue in-growth in a predetermined manner, and each of the at least one medicants is releasable from the adjunct material in a homogeneous manner.

The end effector can vary in any number of ways. For example, the adjunct material can be made of a plurality of fibers that are one of bioabsorbable and dissolvable. The at least one medicant can be eluted upon the absorption or dissolution of the fibers. For another example, the fiber lattice sections can differ from one another in at least one of fiber density in a first direction, fiber density in a second direction, fiber material, fiber construction, fiber diameter, fiber surface characteristics, fiber charge, and fiber elasticity. For yet another example, the at least two distinct heterogeneous fiber lattice sections can include three fiber lattice sections, and each of the three fiber lattice sections can differ from one another in at least one of fiber density in a first direction, fiber density in a second direction, fiber material, fiber construction, fiber diameter, fiber surface characteristics, fiber charge, and fiber elasticity. For another example, the at least one medicant can include at least one of an antimicrobial agent, an antifungal agent, an antiviral agent, an anti-inflammatory agent, a growth factor, an analgesic, an anti-cancer agent, an anti-adhesion agent, a tissue matrix degradation inhibitor, a nutrient, an oxygen expelling agent, an amino acids, a collageno synthetic agent, Glutamine, Insulin, Butyrate, and Dextran.

In general, composite adjunct materials for delivering medicants are provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities, with each staple cavity having a surgical staple disposed therein. The biocompatible adjunct material is releasably retained on the cartridge body and is configured to be delivered to tissue by deployment of the staples in the cartridge body. The adjunct material is in the form of a composite having a conformable region and a distinct reinforcing region. The effective amount of at least one medicant is disposed within and releasable from at least one of the conformable region and the reinforcing region. Each of the at least one medicants is effective to provide a desired effect on tissue in-growth in a predetermined manner.

The staple cartridge assembly can have any number of variations. For example, the conformable region can be a layer within the adjunct material and the reinforcing region can be a separate layer within the adjunct material. The adjunct material can include a barrier layer between the conformable layer and the reinforcing layer. The conformable layer can be disposed between a first reinforcing layer and a second reinforcing layer. The conformable layer can be a fibrous layer that contains a hydrogel. The hydrogel can be applied as a coating to fibers in the fibrous layer.

In another example, the conformable region can be flowable and the reinforcing region can be non-flowable. The conformable region can be in a non-flowable state prior to use and deployment within a patient and can be in a flowable state upon deployment in the patient.

In one implementation, the reinforcing region can be formed as a substrate and the conformable region can be in the form of a plurality of channels formed in the substrate. Each channel can include a swellable hydrogel and a medicant.

In another example, the at least one medicant can be disposed within and releasable from the conformable region. Also, the at least one medicant can be disposed within and releasable from the reinforcing region and the medicant in the conformable region may not be the same as the medicant in the reinforcing region.

In another aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is releasably retained on at least one of the tissue-facing surfaces of the first and second jaws and is configured to be delivered to tissue by deployment of the staples in the cartridge body. The adjunct material is in the form of a composite having a conformable region and a distinct reinforcing region. The effective amount of at least one medicant is disposed within and releasable from the at least one of the conformable region and the reinforcing region. Each of the at least one medicant is effective to provide a desired effect on tissue in-growth in a predetermined manner.

The end effector can have any number of variations. For example, the conformable region can be a layer within the adjunct material and the reinforcing region can be a separate layer within the adjunct material. The adjunct material can include a barrier layer between the conformable layer and the reinforcing layer. The conformable layer can be disposed between a first reinforcing layer and a second reinforcing layer. The conformable layer can be a fibrous layer that contains a hydrogel. The hydrogel can be applied as a coating to fibers in the fibrous layer.

In another example, the conformable region can be flowable and the reinforcing region can be non-flowable. The conformable region can be in a non-flowable state prior to use and deployment within a patient and can be in a flowable state upon deployment in the patient.

In one implementation, the reinforcing region can be formed as a substrate and the conformable region can be in the form of a plurality of channels formed in the substrate. Each channel can include a swellable hydrogel and a medicant.

In another example, the at least one medicant can be disposed within and releasable from the conformable region. Also, the at least one medicant can be disposed within and releasable from the reinforcing region and the medicant in the conformable region may not be the same as the medicant in the reinforcing region.

The present disclosure relates generally to adjunct materials to provide medicants therefrom in heterogeneous temporal and spatial patterns.

In one aspect, a staple cartridge assembly for use with a surgical stapler is provided that includes a cartridge body having a plurality of staple cavities, each staple cavity having a surgical staple disposed therein, a biocompatible adjunct material releasably retained on the cartridge body, configured to be delivered to tissue by deployment of the staples in the cartridge body, and having a plurality of distinct regions, and an effective amount of at least one medicant disposed within and releasable from at least two of the regions. Each region from the plurality of distinct regions is at a different location on the adjunct material and each region has a different adjunct construction. Each of the at least one medicants is effective to provide a desired effect, and each of the at least one medicants is releasable from one of the regions in a non-homogeneous manner with respect to at least one of time of release and location of release.

The staple cartridge assembly can vary in a number of ways. For example, a first one of the regions can contain a first medicant, a second one of the regions can contain a second medicant, and a third one of the regions can contain a third medicant, each region being at a different location within the adjunct material. The first region can be configured to commence release of the first medicant substantially immediately upon delivery of the adjunct material to tissue, the second region can be configured to commence release of the second medicant after release of the first medicant, and the third region can be configured to commence release of the third medicant after release of the second medicant. In some aspects, the first region can be configured to complete delivery of the first medicant within about one day after delivery of the adjunct material to tissue, the second region can be configured to deliver of the second medicant within a period of about one day after delivery of the adjunct material to tissue to about three days after delivery of the adjunct material to tissue, and the third region can be configured to initiate delivery of the third medicant within about three days after delivery of the adjunct material to tissue. The first medicant can be a hemostatic agent. The second medicant can be an anti-inflammatory agent.

In some aspects, the cartridge body can have a slot formed along a longitudinal axis thereof that is configured to allow passage of a tissue cutting element therethrough. The first region is positioned within a central portion of the adjunct material on either side of the slot and is configured to be separated by passage of the cutting element through the slot such that release of the first medicant commences substantially simultaneously upon passage of the cutting element through the first region. The second region is in contact with a surface of the cartridge body, and the second medicant is effective to inhibit tissue growth adjacent the second region; and the third region is opposite the second region, and the third medicant is effective to promote tissue growth. The third medicant can be released after the first medicant.

In some aspects, the adjunct material can be formed of a fiber lattice, and each of the plurality of regions is formed of a different fiber lattice. The at least one medicant can be associated with the fiber lattice in a number of ways. For example, the at least one medicant can be adhered to fibers in the fiber lattices, and each of the plurality of regions can contain a different medicant. The medicant can be coated on the fibers. In some implementations, the at least one fiber lattice can have multiple drugs present in multiple degradable layers fibers within the at least one fiber lattice.

In other aspects, an end effector for a surgical instrument is provided that in some implementations includes a first jaw having a cartridge body removably attached thereto that has on a tissue-facing surface thereof a plurality of staple cavities configured to seat staples therein, a second jaw having an anvil with a plurality of staple forming cavities formed on a tissue-facing surface thereof, a biocompatible adjunct material releasably retained on at least one of the tissue-facing surfaces of the cartridge body and the anvil and having a plurality of distinct regions, and an effective amount of at least one medicant disposed within and releasable from at least two of the regions. At least one of the first and second jaws is movable relative to the other. The biocompatible adjunct material is configured to be delivered to tissue by deployment of the staples in the cartridge body. Each of the at least one medicants is effective to provide a desired effect, and each of the at least one medicants is releasable from one of the regions in a non-homogeneous manner with respect to at least one of time of release and location of release.

The biocompatible adjunct material of the effector can vary in a number of different ways. For example, a first one of the regions can contain a first medicant, a second one of the regions can contain a second medicant, and a third one of the regions can contain a third medicant, each region being at a different location within the adjunct material. The first region can be configured to commence release of the first medicant substantially immediately upon delivery of the adjunct material to tissue, the second region can be configured to commence release of the second medicant after release of the first medicant, and the third region can be configured to commence release of the third medicant after release of the second medicant. In some aspects, the first region can be configured to complete delivery of the first medicant within about one day after delivery of the adjunct material to tissue, the second region can be configured to deliver of the second medicant within a period of about one day after delivery of the adjunct material to tissue to about three days after delivery of the adjunct material to tissue, and the third region can be configured to initiate delivery of the third medicant within about three days after delivery of the adjunct material to tissue. The first medicant can be a hemostatic agent. The second medicant can be an anti-inflammatory agent.

In general, surgical adjuncts having medicants controllably releasable therefrom are provided.

In one aspect, a staple cartridge assembly for use with a surgical stapler is provided that includes a cartridge body, a biocompatible adjunct material, and an effective amount of at least one medicant. The cartridge body has a plurality of staple cavities. Each staple cavity has a surgical staple disposed therein. The biocompatible adjunct material is releasably retained on the cartridge body and is configured to be delivered to tissue by deployment of the staples in the cartridge body. The adjunct material has a plurality of distinct regions. Each region is formed of a biocompatible polymeric material and each region has a different construction. The effective amount of at least one medicant is disposed within and releasable from at least two of the regions. The polymeric material in at least one region is responsive to at least one environmental condition upon delivery of the adjunct material to tissue. The at least one environmental condition to which the adjunct material is subjected affects an elution profile of a medicant within the at least one region.

The staple cartridge assembly can have any number of variations. For example, the at least one environmental condition can include at least one chemical condition adjacent the adjunct material, a physical condition adjacent the adjunct material, and a mechanical condition to which the adjunct material is subjected. The chemical condition can include pH. The physical condition can include temperature. The mechanical condition can include strain and a rate of change in strain.

In another aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is releasably retained on the tissue-facing surface of at least one of the cartridge body and the anvil. The biocompatible adjunct material is configured to be delivered to tissue by deployment of the staples in the cartridge body. The adjunct material has a plurality of distinct regions. Each region is formed of a biocompatible polymeric material and each region has a different construction. The effective amount of at least one medicant is disposed within and releasable from at least two of the regions. The polymeric material in at least one region is responsive to at least one environmental condition upon delivery of the adjunct material to tissue. The at least one environmental condition to which the adjunct material is subjected affects an elution profile of a medicant within the at least one region.

The end effector can vary in any number of ways. For example, the at least one environmental condition can include at least one chemical condition adjacent the adjunct material, a physical condition adjacent the adjunct material, and a mechanical condition to which the adjunct material is subjected. The chemical condition can include pH. The physical condition can include temperature. The mechanical condition can include strain and a rate of change in strain.

In general, adjunct material to provide release of at least first and second medicants therefrom such that release of a first medicant affects release of a second medicant is provided.

In one aspect, a staple cartridge assembly for use with a surgical stapler is provided that in some implementations includes a cartridge body having a plurality of staple cavities, each staple cavity having a surgical staple disposed therein, a bioabsorbable adjunct material releasably retained on the cartridge body and configured to be delivered to tissue by deployment of the staples in the cartridge body, a first medicant component associated with a component of the staple cartridge assembly in a manner in which the first medicant is released as a bolus dose substantially immediately upon delivery of the adjunct material to tissue, and a second medicant component associated with a component of the staple cartridge assembly in a manner such that release of the second medicant component to tissue is regulated by the release of the first medicant component.

The staple cartridge assembly can vary in a number of different ways. For example, the second medicant component can be configured to be released to tissue at a time after the release of the first medicant component. The second medicant component can be disposed within the adjunct material.

The second medicant component can be configured to be released to tissue over a period of time commencing at a time following release of the first medicant component. The second medicant component can be a first active agent disposed within a bioabsorbable polymer that is configured to be released from the first medicant component upon release of the first medicant component, and the first active agent can be configured to be released to tissue upon degradation of the bioabsorbable polymer.

The first and second medicant components can contain the same active agent. In some aspects, the first medicant component can be a second active agent that is different than the first active agent.

The release of the first medicant component can be configured to be triggered by mechanical disruption of a carrier for the first medicant component. In some aspects, the first medicant component can be disposed within a coating formed on the staples, and the mechanical disruption can be deformation of the staples. In some aspects, the first medicant component can be disposed within a staple line of the cartridge body, and the mechanical disruption can be puncture of a film retaining the first medicant within the staple line.

In other aspects, an end effector for a surgical instrument is provided that in some implementations includes a first jaw having a cartridge body removably attached thereto, the cartridge body having on a tissue-facing surface thereof a plurality of staple cavities configured to seat staples therein, a second jaw having an anvil with a plurality of staple forming cavities formed on a tissue-facing surface thereof, a biocompatible adjunct material releasably retained on at least one of the tissue-facing surfaces of the cartridge body first and the anvil and configured to be delivered to tissue by deployment of the staples in the cartridge body, a first medicant component associated with a component of the staple cartridge assembly in a manner in which the first medicant is released as a bolus dose substantially immediately upon delivery of the adjunct material to tissue, and a second medicant component associated with a component of the staple cartridge assembly in a manner such that release of the second medicant component to tissue is regulated by the release of the first medicant component. At least one of the first and second jaws is movable relative to the other.

The end effector can vary in a number of different ways. For example, the second medicant component can be configured to be released to tissue at a time after the release of the first medicant component. The second medicant component can be disposed within the adjunct material. The second medicant component can be configured to be released to tissue over a period of time commencing at a time following release of the first medicant component. The second medicant component can be a first active agent disposed within a bioabsorbable polymer that is configured to be released from the first medicant component upon release of the first medicant component, and the first active agent can be configured to be released to tissue upon degradation of the bioabsorbable polymer.

The first and second medicant components can contain the same active agent. The first medicant component can be a second active agent that is different than the first active agent.

The release of the first medicant component can be configured to be triggered by mechanical disruption of a carrier for the first medicant component. In some aspects, the first medicant component can be disposed within a coating formed on the staples, and the mechanical disruption can be deformation of the staples. In some aspects, the first medicant component can be disposed within a staple line of the cartridge body, and the mechanical disruption can be puncture of a film retaining the first medicant within the staple line.

In general, MMP inhibiting adjuncts for surgical devices are provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities. Each staple cavity has a surgical staple disposed therein. The biocompatible adjunct material is releasably retained on the cartridge body and is configured to be delivered to tissue by deployment of the staples in the cartridge body to form a staple line. The effective amount of at least one medicant is disposed within the adjunct material and is releasable from the adjunct material along the staple line according to a predetermined release profile. The at least one medicant includes at least one of a tissue matrix degradation inhibitor and an agent configured to induce proliferation of fibroblasts.

The staple cartridge assembly can have any number of variations. For example, the tissue matrix degradation inhibitor can include a matrix metalloproteinase (MMP) inhibitor. For another example, the agent configured to induce proliferation of fibroblasts can include a fibroblast growth factor. For yet another example, the at least one medicant can be configured to begin releasing from the adjunct material no less than one day after the delivery of the adjunct material to the tissue. For still another example, the at least one medicant can be configured to begin releasing from the adjunct material in a range of one to seven days of the delivery of the adjunct material to the tissue.

For yet another example, the at least one medicant can be contained within a plurality of sealed vessels. Each of the vessels can be configured to release the at least one medicant therefrom starting after a predetermined amount of time has passed after the delivery of the adjunct material to the tissue. Each of the vessels can include a coating configured to begin disintegrating after passage of the predetermined amount of time after the delivery of the adjunct material to the tissue to begin release of the at least one medicant from the adjunct material.

For another example, the adjunct material can be configured to prevent the release of the at least one medicant therefrom until passage of a predetermined amount of time after the delivery of the adjunct material to the tissue. The adjunct material can be configured to prevent the release of the at least one medicant therefrom until passage of a predetermined amount of time after the delivery of the adjunct material to the tissue by at least one of including a coating thereon configured to begin disintegrating after passage of the predetermined amount of time after the delivery of the adjunct material to the tissue to begin release of the at least one medicant from the adjunct material, being formed of a polymer configured to begin disintegrating after passage of the predetermined amount of time after the delivery of the adjunct material to the tissue to begin release of the at least one medicant from the adjunct material, including a plurality of stacked layers each configured to begin disintegrating at different predetermined amounts of time after the delivery of the adjunct material, and being formed of a fiber lattice configured to begin disintegrating after passage of the predetermined amount of time after the delivery of the adjunct material to the tissue to begin release of the at least one medicant from the adjunct material.

In another aspect, a method of using the staple cartridge assembly is provided that in one implementation includes removably attaching the cartridge body to a surgical stapler, positioning the stapler at a target location adjacent tissue, and, with the stapler positioned at the target location, actuating the stapler to deploy the staples from the cartridge body. The method can vary in any number of ways.

In another aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is releasably retained on at least one of the tissue-facing surfaces of the cartridge body and the anvil, and is configured to be delivered to tissue by deployment of the staples in the cartridge body to form a staple line. The effective amount of at least one medicant is disposed within the adjunct material and is releasable from the adjunct material along the staple line according to a predetermined release profile. The at least one medicant includes at least one of a tissue matrix degradation inhibitor and an agent configured to induce proliferation of fibroblasts.

The end effector can have any number of variations. For example, the tissue matrix degradation inhibitor can include a matrix metalloproteinase (MMP) inhibitor. For another example, the agent configured to induce proliferation of fibroblasts can include a fibroblast growth factor. For yet another example, the at least one medicant can be configured to begin releasing from the adjunct material no less than one day after the delivery of the adjunct material to the tissue. For still another example, the at least one medicant can be configured to begin releasing from the adjunct material in a range of one to seven days of the delivery of the adjunct material to the tissue.

For yet another example, the at least one medicant can be contained within a plurality of sealed vessels. Each of the vessels can be configured to release the at least one medicant therefrom starting after a predetermined amount of time has passed after the delivery of the adjunct material to the tissue. Each of the vessels can include a coating configured to begin disintegrating after passage of the predetermined amount of time after the delivery of the adjunct material to the tissue to begin release of the at least one medicant from the adjunct material.

For another example, the adjunct material can be configured to prevent the release of the at least one medicant therefrom until passage of a predetermined amount of time after the delivery of the adjunct material to the tissue. The adjunct material can be configured to prevent the release of the at least one medicant therefrom until passage of a predetermined amount of time after the delivery of the adjunct material to the tissue by at least one of including a coating thereon configured to begin disintegrating after passage of the predetermined amount of time after the delivery of the adjunct material to the tissue to begin release of the at least one medicant from the adjunct material, being formed of a polymer configured to begin disintegrating after passage of the predetermined amount of time after the delivery of the adjunct material to the tissue to begin release of the at least one medicant from the adjunct material, including a plurality of stacked layers each configured to begin disintegrating at different predetermined amounts of time after the delivery of the adjunct material, and being formed of a fiber lattice configured to begin disintegrating after passage of the predetermined amount of time after the delivery of the adjunct material to the tissue to begin release of the at least one medicant from the adjunct material.

In another aspect, a method of using the end effector is provided that in one implementation includes positioning the stapler at a target location adjacent tissue, the stapler having the end effector at a distal end thereof, and, with the stapler positioned at the target location, actuating the stapler to deploy the staples from the cartridge body.

In general, adjunct material to provide controlled drug elution therefrom to promote tissue growth is provided.

In one aspect, a staple cartridge assembly for use with a surgical stapler is provided that in one implementation includes a cartridge body, a bioabsorbable adjunct material, and an effective amount of at least one medicant that is releasably disposed in the adjunct material. The cartridge body has a plurality of staple cavities, each staple cavity having a surgical staple disposed therein. The bioabsorbable adjunct material is releasably retained on the cartridge body and is configured to be delivered to tissue by deployment of the staples in the cartridge body. The adjunct material is formed from at least one bioabsorbable polymer. Each of the at least one medicant is effective to provide a desired effect on tissue in-growth in a predetermined manner Release of each of the at least one medicant from the adjunct material is controlled by a degradation rate of the at least one bioabsorbable polymer.

The staple cartridge assembly can have any number of variations. For example, the at least one bioabsorbable polymer can include first and second bioabsorbable polymers, the first bioabsorbable polymer having a faster degradation rate than the second bioabsorbable polymer, a first portion of the adjunct material being formed from the first bioabsorbable polymer and a second portion of the adjunct material being formed from the second bioabsorbable polymer. The at least one medicant disposed in the first portion of the adjunct material can be configured to be released prior to the at least one medicant disposed in the second portion of the adjunct material.

In some implementations of the described subject matter, the adjunct material can include a plurality of fibers formed from the at least one bioabsorbable polymer. The at least one bioabsorbable polymer can include first and second bioabsorbable polymers, the first bioabsorbable polymer having a faster degradation rate than the second bioabsorbable polymer, a first number of the plurality of fibers being formed from the first bioabsorbable polymer and a second number of the plurality of fibers being formed from the second bioabsorbable polymer. The at least one medicant disposed in the first number of the fibers can be configured to be released prior to the at least one medicant disposed in the second number of the fibers.

In some implementations of the described subject matter, the at least one bioabsorbable polymer can include a plurality of bioabsorbable polymers each having a different degradation rate, different ones of the fibers being formed from different ones of the bioabsorbable polymers. The plurality of fibers can include wound fibers that are configured to unwind in accordance with the degradation rate, the unwinding allowing release of the at least one medicant from the fibers.

The at least one bioabsorbable polymer can include a plurality of different bioabsorbable polymers, and the adjunct material can have distinct layers formed from each of the plurality of bioabsorbable polymers. The layers can be one of stacked layers and concentric layers.

The at least one medicant can be contained within the at least one bioabsorbable polymer, and the at least one bioabsorbable polymer can be configured to degrade over time at the degradation rate to release the at least one medicant from the adjunct material.

The adjunct material can have the at least one bioabsorbable polymer coated thereon and can have the at least one medicant disposed therein, the degradation of the at least one bioabsorbable polymer being configured to allow the at least one medicant to escape from the adjunct material.

In another aspect, an end effector for a surgical instrument that in some implementations includes a first jaw having a cartridge body removably attached thereto, a second jaw having an anvil with a plurality of staple forming cavities formed on a tissue-facing surface thereof, a bioabsorbable adjunct material releasably retained on at least one of the tissue-facing surfaces of the cartridge body and the anvil, and an effective amount of at least one medicant, the at least one medicant being releasably disposed in the adjunct material. The cartridge body has on a tissue-facing surface thereof a plurality of staple cavities configured to seat staples therein. At least one of the first and second jaws is movable relative to the other. The adjunct material is configured to be delivered to tissue by deployment of the staples in the cartridge body, and the adjunct material is formed from at least one bioabsorbable polymer. Each of the at least one medicants is effective to provide a desired effect on tissue in-growth in a predetermined manner Release of each of the at least one medicants from the adjunct material is controlled by a degradation rate of the at least one bioabsorbable polymer.

The end effector can vary in any number of ways. For example, the at least one bioabsorbable polymer can include first and second bioabsorbable polymers, the first bioabsorbable polymer having a faster degradation rate than the second bioabsorbable polymer, a first portion of the adjunct material being formed from the first bioabsorbable polymer and a second portion of the adjunct material being formed from the second bioabsorbable polymer. The at least one medicant disposed in the first portion of the adjunct material can be configured to be released prior to the at least one medicant disposed in the second portion of the adjunct material.

The adjunct material can include a plurality of fibers formed from the at least one bioabsorbable polymer. The at least one bioabsorbable polymer can include first and second bioabsorbable polymers, the first bioabsorbable polymer having a faster degradation rate than the second bioabsorbable polymer, a first number of the plurality of fibers being formed from the first bioabsorbable polymer and a second number of the plurality of fibers being formed from the second bioabsorbable polymer. The at least one medicant disposed in the first number of the fibers can be configured to be released prior to the at least one medicant disposed in the second number of the fibers.

The at least one bioabsorbable polymer can include a plurality of bioabsorbable polymers each having a different degradation rate, different ones of the fibers being formed from different ones of the bioabsorbable polymers. The plurality of fibers can include wound fibers, the fibers being configured to unwind in accordance with the degradation rate, the unwinding allowing release of the at least one medicant from the fibers. The at least one bioabsorbable polymer can include a plurality of different bioabsorbable polymers, the adjunct material having distinct layers formed from each of the plurality of bioabsorbable polymers. The layers can be one of stacked layers and concentric layers. The at least one medicant can be contained within the at least one bioabsorbable polymer, and the at least one bioabsorbable polymer can be configured to degrade over time at the degradation rate to release the at least one medicant from the adjunct material. The adjunct material can have the at least one bioabsorbable polymer coated thereon and has the at least one medicant disposed therein, the degradation of the at least one bioabsorbable polymer being configured to allow the at least one medicant to escape from the adjunct material.

In general, surgical adjuncts with medicants affected by activator materials are provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities. Each staple cavity has a surgical staple disposed therein. The biocompatible adjunct material is releasably coupled to the cartridge body. The adjunct material is configured to be delivered to tissue by deployment of the staples in the cartridge body. The effective amount of at least one medicant is disposed within and is releasable from the adjunct material. The at least one medicant is capable of being activated by an activator material not associated with any one of the adjunct material, the cartridge body, and the staples. Upon activation of the at least one medicant, an activated medicant yields at least one of a signal and an effect on the adjunct material.

The staple cartridge assembly can vary in any number of ways. For example, the adjunct material can be releasably retained on a tissue-contacting surface of the cartridge body. As another example, the adjunct material can be disposed on a surface of each of the staples. In another example, the signal can include a color change. In another example, the effect can include foaming. In still another example, the effect can include a change in conformation of the adjunct material. In another example, each of the at least one medicants can be effective to provide a desired effect on tissue in-growth in a predetermined manner, the activation of the at least one medicant ceasing the desired effect. In another example, the tissue can include a body lumen, and the at least one medicant can include a reactive polymer configured to react in the presence of the activator material to change a radiodensity of matter passing through the body lumen.

In another aspect, a method of using the staple cartridge assembly is provided that in one implementation includes deploying the staples from the cartridge body to deliver the adjunct material to an exterior surface of tissue of a patient where the tissue can include one of a colon of the patient and a lumen in a lung of the patient such that the adjunct material is delivered to an exterior surface of the colon or an exterior surface of the lumen in the lung.

The method can have any number of variations. For example, the method can include deploying the staples from the cartridge body to deliver the adjunct material to tissue of a patient and administering the activator material to the patient separately from the deployment of the staples.

In another aspect, an end effector for a surgical instrument is provided including a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is configured to be delivered to tissue by deployment of the staples in the cartridge body. The effective amount of at least one medicant is disposed within and releasable from the adjunct material. The at least one medicant is capable of being activated by an activator material not associated with any one of the adjunct material, the cartridge body, and the staples. Upon activation of the at least one medicant, an activated medicant yields at least one of a signal and an effect on the adjunct material.

The end effector can vary in any number of ways. For example, the adjunct material can be releasably retained on at least one of the tissue-facing surfaces of the cartridge body and the anvil. For another example, the adjunct material can be disposed on a surface of each of the staples. For still another example, the signal can include a color change. In another example, the effect can include foaming. In another example, the effect can include a change in conformation of the adjunct material. For still another example, each of the at least one medicants can be effective to provide a desired effect on tissue in-growth in a predetermined manner while the activation of the at least one medicant ceases the desired effect. In still another example, the tissue can include a body lumen. In a further example, the at least one medicant can include a reactive polymer configured to react in the presence of the activator material to change a radiodensity of matter passing through the body lumen.

In another aspect, a method of using the staple cartridge assembly is provided including deploying the staples from the cartridge body to deliver the adjunct material to an exterior surface of tissue of a patient where the tissue can include one of a colon of the patient and a lumen in a lung of the patient such that the adjunct material is delivered to an exterior surface of the colon or an exterior surface of the lumen in the lung.

The method can have any number of variations. For example, the method can include deploying the staples from the cartridge body to deliver the adjunct material to tissue of a patient, and administering the activator material to the patient separately from the deployment of the staples. In a further example, the method may include positioning a surgical stapler at a target location within a patient adjacent a body lumen where the stapler has the end effector at a distal end thereof and, with the stapler positioned at the target location, actuating the stapler to deploy the staples from the cartridge body and into the tissue, thereby delivering the adjunct material to the tissue.

In general, adjuncts for surgical devices including agonists and antagonists are provided.

In one aspect, a staple cartridge assembly for use with a surgical stapler is provided that in one implementation includes a cartridge body, a biocompatible adjunct material, a first medicant, and a second medicant. The cartridge body has a plurality of staple cavities. Each staple cavity has a surgical staple disposed therein. The biocompatible adjunct material is releasably retained on the cartridge body and is configured to be delivered to tissue by deployment of the staples in the cartridge body. The first medicant is disposed within and is releasable from the adjunct material according to a predetermined release profile. The first medicant includes an agonist configured to encourage a physiological response. The second medicant is disposed within and is releasable from the adjunct material according to a predetermined release profile. The second medicant includes an antagonist configured to discourage the physiological response encouraged by the agonist.

The staple cartridge assembly can have any number of variations. For example, according to the predetermined release profile of the first medicant the agonist can be released from the adjunct material before the antagonist is released from the adjunct material according to the predetermined release profile of the second medicant. For another example, according to the predetermined release profile of the first medicant the agonist can be substantially fully released from the adjunct material before the antagonist begins release from the adjunct material according to the predetermined release profile of the second medicant. For yet another example, the physiological response can includes inflammation such that the agonist is configured to encourage tissue inflammation and the antagonist is configured to discourage tissue inflammation. For still another example, the adjunct material can include a plurality of fibers, the first medicant can be coated on a first subset of the fibers, and the second medicant can be coated on a second subset of the fibers.

For another example, a first plurality of coated capsules can be disposed within the adjunct material, and a second plurality of coated capsules can be disposed within the adjunct material. Each of the first plurality of coated capsules can have a coating surrounding the first medicant. Each of the second plurality of coated capsules can have a coating surrounding the second medicant. The coating of each of the first plurality of coated capsules can be configured to be bioabsorbed or dissolved prior to bioabsorption or dissolution of the coating of each of the second plurality of coated capsules such that the first medicant is configured to be released from the adjunct material prior to the second medicant being released from the adjunct material.

For still another example, a plurality of capsules can be disposed within the adjunct material. Each of the capsules can include a plurality of bioabsorbable or dissolvable layers. The first medicant can be included in a layer outer of a layer that includes the second medicant. The layer including the first medicant can be disposed directly adjacent to the layer including the second medicant, or a layer including a third medicant can be disposed between the layer including the first medicant and the layer including the second medicant.

In another aspect, an end effector for a surgical instrument is provided that in one implementation includes a first jaw having a cartridge body removably attached thereto, a second jaw having an anvil with a plurality of staple forming cavities formed on a tissue-facing surface thereof, a biocompatible adjunct material, a first medicant, and a second medicant. The cartridge body has on a tissue-facing surface thereof a plurality of staple cavities configured to seat staples therein. At least one of the first and second jaws is movable relative to the other. The biocompatible adjunct material is releasably retained on at least one of the tissue-facing surfaces of the cartridge body and the anvil. The biocompatible adjunct material is configured to be delivered to tissue by deployment of the staples in the cartridge body.

The first medicant is disposed within and is releasable from the adjunct material according to a predetermined release profile. The first medicant includes an agonist configured to encourage a physiological response. The second medicant is disposed within and is releasable from the adjunct material according to a predetermined release profile. The second medicant includes an antagonist configured to discourage the physiological response encouraged by the agonist.

The end effector can vary in any number of ways. For example, according to the predetermined release profile of the first medicant the agonist can be released from the adjunct material before the antagonist is released from the adjunct material according to the predetermined release profile of the second medicant. For another example, according to the predetermined release profile of the first medicant the agonist can be substantially fully released from the adjunct material before the antagonist begins release from the adjunct material according to the predetermined release profile of the second medicant. For yet another example, the physiological response can include inflammation such that the agonist is configured to encourage tissue inflammation and the antagonist is configured to discourage tissue inflammation. For still another example, the adjunct material can include a plurality of fibers, the first medicant can be coated on a first subset of the fibers, and the second medicant can be coated on a second subset of the fibers.

For another example, a first plurality of coated capsules can be disposed within the adjunct material, and a second plurality of coated capsules can be disposed within the adjunct material. Each of the first plurality of coated capsules can have a coating surrounding the first medicant. Each of the second plurality of coated capsules can have a coating surrounding the second medicant. The coating of each of the first plurality of coated capsules can be configured to be bioabsorbed or dissolved prior to bioabsorption or dissolution of the coating of each of the second plurality of coated capsules such that the first medicant is configured to be released from the adjunct material prior to the second medicant being released from the adjunct material.

For yet another example, a plurality of capsules can be disposed within the adjunct material and can each include a plurality of bioabsorbable or dissolvable layers. The first medicant can be included in a layer outer of a layer that includes the second medicant. The layer including the first medicant can be disposed directly adjacent to the layer including the second medicant, or a layer including a third medicant can be disposed between the layer including the first medicant and the layer including the second medicant.

In general, surgical adjuncts with medicants affected by activators are provided.

In one aspect, a staple cartridge assembly for use with a surgical stapler is provided including a cartridge body, a biocompatible, bioabsorbable adjunct material, and an effective amount of at least one medicant. The cartridge body has a plurality of staple cavities. Each staple cavity has a surgical staple disposed therein. The biocompatible, bioabsorbable adjunct material is releasably coupled to the cartridge body and configured to be delivered to tissue within a body of a patient by deployment of the staples in the cartridge body. The effective amount of at least one medicant is disposed within and releasable from the adjunct material. The at least one medicant includes an actuatable material configured to be activated within the body of the patient by an activator located outside the body of the patient. The activation of the at least one medicant allows monitoring of the adjunct material after its delivery to the tissue.

The staple cartridge assembly can vary in any number of ways. For example, the actuatable material can include at least one of magnetic particles, a radio-opaque agent, a radioactive agent, a non-resorbable agent, and a non-digestible agent. In another example, the activator can include one of a magnet, an x-ray imaging system, a computed tomography (CT) imaging system, and a magnetic resonance imaging (MRI) imaging system. For yet another example, the actuatable material can be configured to be activated by a magnetic field induced by the activator.

In another aspect, a method of using the staple cartridge assembly is provided that in one implementation includes deploying the staples from the cartridge body to deliver the adjunct material to tissue and, using the activator, activating the adjunct material delivered to the tissue.

The method can have any number of variations. For example, the method can include monitoring the adjunct material to determine at least one of an amount of the at least one medicant released from the activated adjunct material and an amount of the at least one medicant disposed within the activated adjunct material. For another example, the activation can cause one of an increase in release of the at least one medicant from the adjunct material and a degradation of the adjunct material. For yet another example, the activator can include a magnet, and the method can include manipulating the magnet to move the at least one medicant within the body of the patient. For still another example, the activator can include one of an x-ray imaging system, a CT imaging system, and an MRI imaging system. For another example, the activating can occur post-operatively.

In another aspect, an end effector for a surgical instrument is provided that in one implementation includes a first jaw, a second jaw, a biocompatible, bioabsorbable adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible, bioabsorbable adjunct material is releasably retained on the tissue-facing surface of at least one of the cartridge body and the anvil and is configured to be delivered to tissue within a body of a patient by deployment of the staples in the cartridge body. An effective amount of at least one medicant is disposed within and releasable from the adjunct material. The at least one medicant includes an actuatable material configured to be activated within the body of the patient by an activator located outside the body of the patient. The activation of the at least one medicant allows monitoring of the adjunct material after its delivery to the tissue.

The end effector can vary in any number of ways. For example, the actuatable material can include at least one of magnetic particles, a radio-opaque agent, a radioactive agent, a non-resorbable agent, and a non-digestible agent. For another example, the activator can include one of a magnet, an x-ray imaging system, a CT imaging system, and an MRI imaging system. In yet another example, the actuatable material can be configured to be activated by a magnetic field induced by the activator.

In another aspect, a method of using the end effector is provided that includes deploying the staples from the cartridge body to deliver the adjunct material to tissue and, using the activator, activating the adjunct material delivered to the tissue.

The method can have any number of variations. For example, the method can include monitoring the adjunct material to determine at least one of an amount of the at least one medicant released from the activated adjunct material and an amount of the at least one medicant disposed within the activated adjunct material. In another example, the activation can cause one of an increase in release of the at least one medicant from the adjunct material and a degradation of the adjunct material. In a further example, the activator can include a magnet, and the method can further include manipulating the magnet to move the at least one medicant within the body of the patient. In another example, the activator can include one of an x-ray imaging system, a CT imaging system, and an MRI imaging system. In another example, the activating can occur post-operatively.

In general, adjunct material to provide drug elution from vessels disposed within reservoirs formed in the adjunct material are provided.

In one aspect, a staple cartridge assembly for use with a surgical stapler is provided that in some implementations includes a cartridge body having a plurality of staple cavities, each staple cavity having a surgical staple disposed therein, a biocompatible adjunct material releasably retained on the cartridge body and configured to be delivered to tissue by deployment of the staples in the cartridge body, and an effective amount of at least one medicant. The adjunct material includes a plurality of distinct reservoirs formed therein, and the adjunct material includes at least one biocompatible polymer. The at least one medicant is disposed within a plurality of vessels disposed within at least one of the reservoirs, and the at least one medicant is effective to provide a desired effect on tissue in-growth in a predetermined manner, wherein disruption of the at least one polymer is configured to allow release of the vessels from the at least one of the reservoirs.

The staple cartridge assembly can vary in a number of ways. For example, the disruption of the at least one polymer can be effective to expose the vessels to an environment external to the adjunct material into which the vessels are capable of migrating following the disruption of the at least one polymer. Each of the vessels can be configured to degrade over time in response to the exposure thereof to the external environment. Degradation of the vessels can cause the at least one medicant disposed therein to be released from the vessels.

In some aspects, the at least one medicant includes a plurality of different medicants each disposed with a different one of the vessels. The vessels can have a different rate of degradation such that the medicants are configured to be released from their respective vessels at different rates following the disruption of the at least one polymer.

In some aspects, the at least one polymer is one of bioabsorbable and dissolvable, and the disruption of the at least one polymer includes the bioabsorption or dissolution of the at least one polymer. The at least one polymer can include a plurality of different polymers each being configured to bioabsorb or dissolve at a different rate such that the vessels are configured to be released from the reservoirs at different times corresponding to the different rates.

The at least one polymer can be configured to be mechanically broken, and the disruption of the at least one polymer can include the mechanical breaking.

In other aspects, an end effector for a surgical instrument is provided that in some implementations includes a first jaw having a cartridge body removably attached thereto, the cartridge body having on a tissue-facing surface thereof a plurality of staple cavities configured to seat staples therein, a second jaw having an anvil with a plurality of staple forming cavities formed on a tissue-facing surface thereof, a biocompatible adjunct material releasably retained on at least one of the tissue-facing surfaces of the first and second jaws and configured to be delivered to tissue by deployment of the staples in the cartridge body, and an effective amount of at least one medicant. At least one of the first and second jaws is movable relative to the other. The adjunct material including a plurality of distinct reservoirs formed therein, and the adjunct material including at least one biocompatible polymer. The at least one medicant is disposed within a plurality of vessels disposed within at least one of the reservoirs, and the at least one medicant is effective to provide a desired effect on tissue in-growth in a predetermined manner Disruption of the at least one polymer is configured to allow release of the vessels from the at least one of the reservoirs.

The end effector can vary in a number of ways. For example, the disruption of the at least one polymer can be effective to expose the vessels to an environment external to the adjunct material into which the vessels are capable of migrating following the disruption of the at least one polymer. Each of the vessels can be configured to degrade over time in response to the exposure thereof to the external environment. Degradation of the vessel can cause the at least one medicant disposed therein to be released from the vessel.

The at least one medicant can include a plurality of different medicants each disposed with a different one of the vessels. The vessels can have a different rate of degradation such that the medicants can be configured to be released from their respective vessels at different rates following the disruption of the at least one polymer. The at least one polymer can be one of bioabsorbable and dissolvable, and the disruption of the at least one polymer can include the bioabsorption or dissolution of the at least one polymer. The at least one polymer can include a plurality of different polymers each being configured to bioabsorb or dissolve at a different rate such that the vessels can be configured to be released from the reservoirs at different times corresponding to the different rates.

In some aspects, the at least one polymer is configured to be mechanically broken, and the disruption of the at least one polymer includes the mechanical breaking.

In general, adjunct materials for delivery to stomach tissue are provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities, with each staple cavity having a surgical staple disposed therein. The biocompatible adjunct material is in the form of at least one of a film and a foam that is releasably retained on the cartridge body and configured to be delivered to stomach tissue of a patient by deployment of the staples in the cartridge body. The adjunct material has a structure effective to cause a desired reaction in the stomach tissue. The medicant is disposed within the adjunct material and is effective to encourage the desired reaction in the stomach tissue.

The staple cartridge assembly can have any number of variations. For example, the adjunct material can be configured to be stapled to an external surface of the stomach tissue. In some aspects, the adjunct material can be a film having an abrasive surface. The adjunct material can be non-bioabsorbable.

The medicant can be effective to encourage a variety of desired reactions in the stomach tissue. For example, the desired reaction can include movement of the adjunct material from the external surface of the stomach tissue into the patient's stomach cavity. In one aspect, the desired reaction can include faster healing of the stapled stomach tissue.

In one aspect, a method of using the staple cartridge assembly described above is provided. The method includes in one implementation removably attaching the cartridge body to a surgical stapler; positioning the stapler at a target location adjacent stomach tissue of a patient; and with the stapler positioned at the target location, actuating the stapler to deploy the staples from the cartridge body.

The method can vary in a number of ways. For example, delivering the adjunct material can include stapling the adjunct material to an external surface of the stomach tissue and the stapled adjunct material can be configured to erode into the stomach tissue over time. In another example, the erosion can include the adjunct material moving from the external surface of the stomach tissue into the patient's stomach cavity. In a further example, the adjunct material can be loose in the patient's stomach cavity with a portion of the stomach tissue attached thereto. In some aspects, after the deployment of the staples, the method can include applying pressure to the stomach tissue to further encourage the desired reaction in the stomach tissue.

In one aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is in the form of at least one of a film and a foam that is releasably retained on at least one of the tissue-facing surfaces of the first and second jaws and is configured to be delivered to tissue by deployment of the staples in the cartridge body. The adjunct material has a structure effective to cause a desired reaction in the stomach tissue. The medicant is disposed within the adjunct material and is effective to encourage the desired reaction in the stomach tissue.

The end effector can vary in a number of ways. For example, the adjunct material can be configured to be stapled to an external surface of the stomach tissue. The desired reaction can include movement of the adjunct material from the external surface of the stomach tissue into the patient's stomach cavity. In another example, the desired reaction can include faster healing of the stapled stomach tissue. Further, the adjunct material can be a film having an abrasive surface. In some aspects, the adjunct material can be non-bioabsorbable.

In one aspect, a method of using the end effector described above includes in one implementation positioning a surgical stapler at a target location within a patient adjacent stomach tissue, the stapler having the end effector at a distal end thereof; and with the stapler positioned at the target location, actuating the stapler to deploy the staples from the cartridge body, thereby delivering the adjunct material to the stomach tissue.

The method of using the end effector can vary in a number of ways. For example, delivering the adjunct material can include stapling the adjunct material to an external surface of the stomach tissue. In some aspects, the stapled adjunct material can be configured to erode into the stomach tissue over time. The erosion of the adjunct material can include the adjunct material moving from the external surface of the stomach tissue into the patient's stomach cavity. In one aspect, the adjunct material can be loose in the patient's stomach cavity with a portion of the stomach tissue attached thereto. In one example, the method can include, after the deployment of the staples, applying pressure to the stomach tissue to further encourage the desired reaction in the stomach tissue.

In general, surgical adjuncts and medicants for promoting lung function are provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities. Each staple cavity has a surgical staple disposed therein. The biocompatible adjunct material is releasably retained on the cartridge body and is configured to be delivered to lung tissue by deployment of the staples in the cartridge body to form at least one line of deployed staples. The effective amount of at least one medicant is disposed within and releasable from the adjunct material. The at least one medicant is effective to increase oxygen concentration of blood adjacent to the at least one line of deployed staples.

The staple cartridge assembly can vary in any number of ways. For example, the at least one medicant can be effective to increase oxygen concentration of blood by being effective to promote elastic deposition. In another example, the at least one medicant can be effective to increase oxygen concentration of blood by being effective to promote elastin release. Furthermore in another example, the at least one medicant can be effective to increase oxygen concentration of blood by being effective to promote separation of alveoli by promoting presence of surfactant at the alveoli. In another example, the at least one medicant can include at least one an antimicrobial agent, an immunosuppresant, a bronchodilator, and a corticosteroid.

In another aspect, a method of using the staple cartridge assembly is provided that in one implementation includes removably attaching the cartridge body to a surgical stapler, positioning the stapler at a target location adjacent lung tissue, and with the stapler positioned at the target location, actuating the stapler to deploy the staples from the cartridge body and into the lung tissue, thereby delivering the adjunct material to the lung tissue.

The method can vary in any number of ways. For example, the adjunct material can be delivered to an exterior surface of the lung tissue and stapled thereon. In still another example, the at least one medicant can be effective to increase oxygen concentration of blood by being effective to promote elastic deposition, to promote elastin release, and/or to promote separation of alveoli by promoting presence of surfactant at the alveoli.

In another aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is releasably retained on at least one of the tissue-facing surfaces of the first and second jaws and configured to be delivered to tissue by deployment of the staples in the cartridge body to form at least one line of deployed staples. The effective amount of at least one medicant is disposed within and releasable from the adjunct material. The at least one medicant is effective to increase oxygen concentration of blood adjacent the least one line of deployed staples.

The end effector can vary in any number of ways. For example, the at least one medicant can be effective to increase oxygen concentration of blood by being effective to promote elastic deposition. In another example, the at least one medicant can be effective to increase oxygen concentration of blood by being effective to promote elastin release. In still another example, the at least one medicant can be also effective to increase oxygen concentration of blood by being effective to promote separation of alveoli by promoting presence of surfactant at the alveoli. In another example, the at least one medicant can include at least one an antimicrobial agent, an immunosuppresant, a bronchodilator, and a corticosteroid.

In another aspect, a method of using the end effector is provided that in one implementation includes positioning a surgical stapler at a target location within a patient adjacent lung tissue. The stapler can have the end effector at a distal end thereof. The method also includes, with the stapler positioned at the target location, actuating the stapler to deploy the staples from the cartridge body and into the tissue, thereby delivering the adjunct material to the lung tissue.

The method can have any number of variations. For example, the adjunct material can be delivered to an exterior surface of the lung tissue and stapled thereon. In yet another example, the at least one medicant can be effective to increase oxygen concentration of blood by being effective to promote elastic deposition, promote elastin release, and/or to promote separation of alveoli by promoting presence of surfactant at the alveoli.

In general, adjunct materials for delivery to colon tissue are provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities, each staple cavity having a surgical staple disposed therein. The biocompatible adjunct material, formed of a fiber matrix, is releasably retained on the cartridge body and configured to be delivered to colon tissue by deployment of the staples in the cartridge body to form at least one line of deployed staples. The medicant is disposed within and releasable from the adjunct material, and effective to encourage a desired effect on blood vessels along the at least one line of deployed staples.

The adjunct material can have any number of variations. For example, the medicant can be effective to encourage a variety of desired effect on blood vessels. For example, the desire effect can include angiogenesis. In another example, the desired effect can include vasodilation.

The adjunct material can be configured in various ways. In some aspects, the adjunct material includes first and second portions each having different configurations. For example, the second portion can be configured to detach from the first portion following deployment of the staples. The first portion can include a first plurality of longitudinal fibers and the second portion can include a second plurality of longitudinal fibers extending transversely to the first plurality of longitudinal fibers. The adjunct material can be releasably retained on the cartridge body such that the staples, when deployed from the cartridge body, extend substantially parallel to the first plurality of longitudinal fibers.

In another example, the second portion can be configured to detach from the first portion following deployment of the staples. The first portion can include at least one of a buttress and a film. The second portion can include a plurality of fibers releasably attached to one another.

The adjunct material can be made from a variety of materials. In one example, the first portion of the adjunct material can be formed of a material having a higher molecular weight than a material that forms the second portion of the adjunct material.

In one implementation, the adjunct material can have a plurality of reservoirs formed therein. Each of the reservoirs can be sealed with at least one coating on the adjunct material. Each of the reservoirs can have at least some of the at least one medicant disposed therein. The at least one coating can be configured to disintegrate to allow release of the at least one medicant from the reservoirs.

In another aspect, a method of using the staple cartridge assembly described above is provided. The method includes in one implementation removably attaching the cartridge body to a surgical stapler; positioning the stapler at a target location adjacent colon tissue; and with the stapler positioned at the target location, actuating the stapler to deploy the staples from the cartridge body.

The method can vary in a number of ways. For example, the adjunct material can include a first plurality of longitudinal fibers and a second plurality of longitudinal fibers. The second plurality of longitudinal fibers can extend transversely to the first plurality of longitudinal fibers. The deployed staples can extend substantially parallel to the first plurality of longitudinal fibers. The second plurality of longitudinal fibers can be configured to detach from the first plurality of longitudinal fibers following the deployment of the staples, thereby allowing the second plurality of longitudinal fibers to migrate relative to the colon tissue while the first plurality of longitudinal fibers remain stapled to the colon tissue.

In one aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material, formed of a fiber matrix, is releasably retained on at least one of the tissue-facing surfaces of the first and second jaws and is configured to be delivered to tissue by deployment of the staples in the cartridge body to form at least one line of deployed staples. The at least one medicant is disposed within and releasable from the adjunct material, and is effective to encourage a desired effect on blood vessels along the at least one line of deployed staples.

The end effector can have any number of variations. For example, the desired effect can include angiogenesis. In another example, the desired effect can include vasodilation.

The end effector can be configured in various ways. In some aspects, the adjunct material includes first and second portions each having different configurations. For example, the second portion can be configured to detach from the first portion following deployment of the staples. The first portion can include a first plurality of longitudinal fibers and the second portion can include a second plurality of longitudinal fibers extending transversely to the first plurality of longitudinal fibers. The adjunct material can be releasably retained on the cartridge body such that the staples, when deployed from the cartridge body, extend substantially parallel to the first plurality of longitudinal fibers.

In another example, the second portion can be configured to detach from the first portion following deployment of the staples. The first portion can include at least one of a buttress and a film. The second portion can include a plurality of fibers releasably attached to one another.

The adjunct material can be made from a variety of materials. In one example, the first portion of the adjunct material can be formed of a material having a higher molecular weight than a material that forms the second portion of the adjunct material.

In one implementation, the adjunct material can have a plurality of reservoirs formed therein. Each of the reservoirs can be sealed with at least one coating on the adjunct material. Each of the reservoirs can have at least some of the at least one medicant disposed therein. The at least one coating can be configured to disintegrate to allow release of the at least one medicant from the reservoirs.

In another aspect, a method of using the end effector described above is provided. The method includes in one implementation positioning the stapler at a target location adjacent colon tissue, the stapler having the end effector at a distal end thereof; and with the stapler positioned at the target location, actuating the stapler to deploy the staples from the cartridge body.

The method can vary in a number of ways. For example, the adjunct material can include a first plurality of longitudinal fibers and a second plurality of longitudinal fibers. The second plurality of longitudinal fibers can extend transversely to the first plurality of longitudinal fibers. The deployed staples can extend substantially parallel to the first plurality of longitudinal fibers. The second plurality of longitudinal fibers can be configured to detach from the first plurality of longitudinal fibers following the deployment of the staples, thereby allowing the second plurality of longitudinal fibers to migrate relative to the colon tissue while the first plurality of longitudinal fibers remain stapled to the colon tissue.

In general, adjunct material to promote tissue growth in a colon is provided.

In one aspect, a staple cartridge assembly for use with a surgical stapler is provided that in one embodiment includes a cartridge body, a biocompatible adjunct material, and an effective amount of at least one medicant disposed within and releasable from the adjunct material. The cartridge body has at least one annular row of staple cavities. Each staple cavity has a surgical staple disposed therein. The biocompatible adjunct material is releasably retained on the cartridge body and is configured to be delivered to colon tissue in connection with deploying the staples from the cartridge body to form at least one line of deployed staples. The adjunct material is delivered along the at least one line of deployed staples. The adjunct material is in the form of a fiber lattice. The fiber lattice has at least two distinct heterogeneous fiber lattice sections. Each of the fiber lattice sections of the adjunct material is arranged in a pattern configured to promote organized colon tissue remodeling in a desired manner Each of the at least one medicants is effective to provide a desired effect on colon tissue in-growth in a predetermined manner, and each of the at least one medicants is releasable from the adjunct material in a homogeneous manner.

The staple cartridge assembly can vary in any number of ways. For example, the adjunct material can be made of a plurality of fibers that are one of bioabsorbable and dissolvable. The at least one medicant can be eluted upon the absorption or dissolution of the fibers. For another example, the pattern configured to promote organized colon tissue remodeling in a desired manner can be configured to promote colon tissue growth in a natural direction of fibers of the colon tissue, thereby facilitating radial expansion of the colon in an area of the colon adjacent to the at least one line of deployed staples. For yet another example, the at least two distinct heterogeneous fiber lattice sections can include a first fiber lattice section having fibers extending along a longitudinal axis of the adjunct material and a second fiber lattice section having fibers extending annularly around the longitudinal axis of the adjunct material. The longitudinal axis of the adjunct material can be substantially parallel to a longitudinal axis of the colon having the staples deployed therein and the adjunct material delivered thereto. For still another example, the at least one medicant can includes an angiogenic medicant configured to provide a desired effect of blood vessel growth.

In another aspect, a method of using the staple cartridge assembly is provided that in one embodiment includes removably attaching the cartridge body to a circular surgical stapler, positioning the stapler at a target location adjacent colon tissue, and with the stapler positioned at the target location, actuating the stapler to deploy the staples from the cartridge body and into the colon tissue, thereby delivering the adjunct material along a staple line defined by the deployed staples. The at least two distinct heterogeneous fiber lattice sections include a first fiber lattice section having fibers extending along a longitudinal axis of the adjunct material and a second fiber lattice section having fibers extending annularly around the longitudinal axis of the adjunct material. The longitudinal axis of the deployed adjunct material is substantially parallel to a longitudinal axis of the colon tissue having the staples deployed therein and the adjunct material delivered thereto. The method can have any number of variations.

In another aspect, an end effector for a circular surgical stapler is provided that in one embodiment includes a cartridge assembly, an anvil assembly, a biocompatible adjunct material, and an effective amount of at least one medicant disposed within and releasable from the adjunct material. The cartridge assembly has a cartridge body removably attached thereto. The cartridge body has on a tissue-facing surface thereof a plurality of annularly-arranged staple cavities configured to seat staples therein. The anvil assembly has an anvil with a plurality of annularly-arranged staple forming cavities formed on a tissue-facing surface thereof. At least one of the cartridge assembly and the anvil assembly is movable relative to the other. The biocompatible adjunct material is releasably retained on at least one of the tissue-facing surfaces of the cartridge assembly and the anvil assembly and is configured to be delivered to colon tissue by deployment of the staples in the cartridge body. The adjunct material is in the form of a fiber lattice having at least two distinct heterogeneous fiber lattice sections. Each of the fiber lattice sections of the adjunct material is arranged in a pattern configured to promote organized colon tissue remodeling in a desired manner Each of the at least one medicants is effective to provide a desired effect on colon tissue in-growth in a predetermined manner, and each of the at least one medicants is releasable from the adjunct material in a homogeneous manner.

The end effector can vary in any number of ways. For example, the adjunct material can be made of a plurality of fibers that are one of bioabsorbable and dissolvable. The at least one medicant can be eluted upon the absorption or dissolution of the fibers. For another example, the pattern configured to promote organized colon tissue remodeling in a desired manner can be configured to promote colon tissue growth in a natural direction of fibers of the colon tissue, thereby facilitating radial expansion of the colon in an area of the colon adjacent to the at least one line of deployed staples. For yet another example, the at least two distinct heterogeneous fiber lattice sections can include a first fiber lattice section having fibers extending along a longitudinal axis of the adjunct material and a second fiber lattice section having fibers extending annularly around the longitudinal axis of the adjunct material. The longitudinal axis of the adjunct material can be substantially parallel to a longitudinal axis of the colon having the staples deployed therein and the adjunct material delivered thereto. For still another example, the at least one medicant can include an angiogenic medicant configured to provide a desired effect of blood vessel growth.

In another aspect, a method of using the end effector is provided that in one embodiment includes removably attaching the cartridge body to a circular surgical stapler, positioning the stapler at a target location adjacent colon tissue, and with the stapler positioned at the target location, actuating the stapler to deploy the staples from the cartridge body and into the colon tissue, thereby delivering the adjunct material along a staple line defined by the deployed staples. The at least two distinct heterogeneous fiber lattice sections includes a first fiber lattice section having fibers extending along a longitudinal axis of the adjunct material and a second fiber lattice section having fibers extending annularly around the longitudinal axis of the adjunct material. The longitudinal axis of the deployed adjunct material is substantially parallel to a longitudinal axis of the colon tissue having the staples deployed therein and the adjunct material delivered thereto. The method can have any number of variations.

In general, adjunct materials for delivery to liver tissue are provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities, each staple cavity having a surgical staple disposed therein. The biocompatible adjunct material is releasably retained on the cartridge body in an unexpanded configuration and configured to be delivered to liver tissue by deployment of the staples in the cartridge body. The adjunct material is configured to transition from the unexpanded configuration to an expanded configuration after delivery thereof to the liver tissue. The medicant is disposed within and releasable from the adjunct material.

The staple cartridge assembly can have any number of variations. For example, the medicant can include at least one of a hemostatic agent and a tissue healing agent. In another example, the adjunct material can include a swellable absorbable material configured to facilitate transitioning of the adjunct material from the unexpanded configuration to the expanded configuration. The adjunct material can include a plurality of pores. The swellable absorbable material can be configured to pass through the pores when the adjunct material transitions from the unexpanded configuration to the expanded configuration. The at least one medicant can also be configured to be released through the pores from the adjunct material in the expanded configuration. In a further example, the adjunct material can include a plurality of reinforcement fibers that define zones therebetween in which the swellable absorbable material is disposed. The plurality of fibers can be compressed in the unexpanded configuration and can be lengthened in the expanded configuration.

The adjunct material can have any number of other variations. For example, the adjunct material can be folded or rolled in the unexpanded configuration and can be correspondingly unfolded or unrolled in the expanded configuration. In another example, the adjunct material can include a plurality of pores through which the at least one medicant is configured to be released from the adjunct material in the expanded configuration.

In one aspect, a method of using the staple cartridge assembly described above is provided. The method includes in one implementation removably attaching the cartridge body to a surgical stapler; positioning the stapler at a target location adjacent liver tissue; and, with the stapler positioned at the target location, actuating the stapler to deploy the staples from the cartridge body. The adjunct material in the expanded configuration applies pressure to the liver tissue to facilitate sealing of one or more fractures in the liver tissue.

The method can vary in a number of ways. For example, the deployed staples can define a staple line, and the adjunct material can move away from the staple line when transitioning from the unexpanded configuration to the expanded configuration. In another example, the deployed staples can secure the adjunct material to an external surface of the liver tissue to cover a first surface area thereof, and the adjunct material transitioning to the expanded configuration can include the adjunct material expanding to cover a second surface area of the external surface of the liver tissue that is greater than the first surface area.

In one aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is releasably retained on at least one of the tissue-facing surfaces of the first and second jaws in an unexpanded configuration. The adjunct material is configured to be delivered to liver tissue by deployment of the staples in the cartridge body. The adjunct material is also configured to transition from the unexpanded configuration to an expanded configuration after delivery thereof to the liver tissue. The at least one medicant is disposed within and is releasable from the adjunct material.

The end effector can have any number of variations. For example, the at least one medicant can include at least one of a hemostatic agent and a tissue healing agent. The adjunct material can include a swellable absorbable material configured to facilitate transitioning of the adjunct material from the unexpanded configuration to the expanded configuration.

The adjunct material can include a plurality of pores. The swellable absorbable material can be configured to pass through the pores when the adjunct material transitions from the unexpanded configuration to the expanded configuration. The at least one medicant can also be configured to be released through the pores from the adjunct material in the expanded configuration.

In a further example, the adjunct material can include a plurality of reinforcement fibers that define zones therebetween in which the swellable absorbable material is disposed. The plurality of fibers can be compressed in the unexpanded configuration and can be lengthened in the expanded configuration.

The adjunct material can have any number of other configurations. For example, the adjunct material can be folded or rolled in the unexpanded configuration and can be correspondingly unfolded or unrolled in the expanded configuration. In another example, the adjunct material can include a plurality of pores through which the at least one medicant is configured to be released from the adjunct material in the expanded configuration.

In another aspect, a method of using the end effector described above is provided. The method includes in one implementation positioning a stapler at a target location adjacent liver tissue, the stapler having the end effector at a distal end thereof; and with the stapler positioned at the target location, actuating the stapler to deploy the staples from the cartridge body. The adjunct material in the expanded configuration applies pressure to the liver tissue to facilitate sealing of one or more fractures in the liver tissue.

The method can have any number of variations. For example, the deployed staples can define a staple line. The adjunct material can move away from the staple line when transitioning from the unexpanded to the expanded configuration. In another example, the deployed staples can secure the adjunct material to an external surface of the liver tissue to cover a first surface area thereof. The adjunct material transitioning to the expanded configuration can include the adjunct material expanding to cover a second surface area of the external surface of the liver tissue that is greater than the first surface area.

In general, tubular surgical constructs including adjunct material are provided.

In one aspect, a surgical device is provided that in one implementation includes a tubular construct having an inner lumen extending therethrough, a biocompatible adjunct material disposed on the tubular construct, and an effective amount of at least one medicant disposed within and releasable from the adjunct material. The tubular construct is configured to be delivered to a tissue lumen and be positioned therein so as to provide structural support to the tissue lumen. The tubular construct is radially collapsible. The adjunct material is configured to be delivered to the tissue lumen with the tubular construct. Each of the at least one medicants is effective to provide a desired effect on tissue in a predetermined manner.

The surgical device can vary in any number of ways. For example, the adjunct material can be in the form of a fiber lattice. The fiber lattice can have at least two distinct heterogeneous fiber lattice sections. Each of the fiber lattice sections of the adjunct material can be arranged in a pattern configured to promote organized tissue remodeling in a desired manner. The at least two distinct heterogeneous fiber lattice sections can include a first fiber lattice section having fibers extending along a longitudinal axis of the tubular construct and a second fiber lattice section having fibers extending annularly around the longitudinal axis of the tubular construct.

For another example, the adjunct material can be in the form of a fiber lattice and/or a film. For yet another example, the tubular construct can include a scaffold having a plurality of pores configured to facilitate tissue ingrowth. For still another example, the tubular construct can include a funnel shape with a smaller diameter at a first end of the shape than at a second, opposite end of the shape. For another example, the tubular construct can include at least two rings extending circumferentially therearound, the tubular construct can include at least one support structure extending between the at least two rings, and the adjunct material can be disposed as a covering over the at least two rings and the at least one support structure. For still another example, the tubular construct can include first and second independent tubular members.

In another aspect, a method of using the surgical device is provided that in one implementation includes positioning a circular surgical stapler at a target location within a patient within a lumen of a tissue of the patient. The stapler has releasably coupled to a distal end thereof the tubular construct having the adjunct material disposed thereon. The method also includes, with the stapler positioned at the target location, actuating the stapler to deploy staples from the stapler and into the tissue. The deployed staples secure the tubular construct within the lumen of the tissue. The method also includes removing the stapler from the patient, the tubular construct remaining within the lumen.

The method can have any number of variations. For example, the tissue can include one of an intestine and an esophagus. For another example, the adjunct material can be in the form of a fiber lattice having at least two distinct heterogeneous fiber lattice sections. The at least two distinct heterogeneous fiber lattice sections can include a first fiber lattice section having fibers extending along a longitudinal axis of the tubular construct and a second fiber lattice section having fibers extending annularly around the longitudinal axis of the tubular construct. The longitudinal axis of the tubular construct can be substantially parallel to a longitudinal axis of the lumen having the tubular construct secured therein.

For still another example, the tubular construct can include first and second independent tubular members. Prior to the actuation of the stapler, the first tubular member can be releasably retained on an anvil of the stapler and the second tubular member can be releasably retained on a cartridge assembly at the distal end of the stapler. The actuation can release the first tubular member from the anvil and can release the second tubular member from the cartridge assembly. The first tubular member can be releasably retained on the anvil such that an inner passageway of the first tubular member is aligned with the lumen of the tissue following the securing of the tubular construct within the lumen, and the second tubular member can be releasably retained on the cartridge assembly such that an inner passageway of the second tubular member is aligned with the lumen of the tissue following the securing of the tubular construct within the lumen.

In another aspect, an end effector for a circular surgical stapler is provided that in one implementation includes a cartridge assembly, an anvil, a tubular construct releasably retained on each of the cartridge assembly and the anvil, a biocompatible adjunct material disposed on the tubular construct, and an effective amount of at least one medicant disposed within and releasable from the adjunct material. The cartridge assembly has a cartridge body removably attached thereto. The cartridge body has on a tissue-facing surface thereof a plurality of annularly-arranged staple cavities configured to seat staples therein. The anvil has a plurality of annularly-arranged staple forming cavities formed on a tissue-facing surface thereof. At least one of the cartridge assembly and the anvil is movable relative to the other. The tubular construct has an inner lumen extending therethrough. The tubular construct is configured to be delivered to a tissue lumen by deployment of the staples in the cartridge body. The tubular construct is radially collapsible. The adjunct material is configured to be delivered to the tissue lumen with the tubular construct. Each of the at least one medicants is effective to provide a desired effect on tissue in a predetermined manner.

The end effector can vary in any number of ways. For example, the adjunct material can be in the form of a fiber lattice. The fiber lattice can have at least two distinct heterogeneous fiber lattice sections. Each of the fiber lattice sections of the adjunct material can be arranged in a pattern configured to promote organized tissue remodeling in a desired manner. The at least two distinct heterogeneous fiber lattice sections can include a first fiber lattice section having fibers extending along a longitudinal axis of the tubular construct and a second fiber lattice section can have fibers extending annularly around the longitudinal axis of the tubular construct.

For another example, the adjunct material can be in the form of a fiber lattice and/or a film. For yet another example, the tubular construct can include a scaffold having a plurality of pores configured to facilitate tissue ingrowth. For still another example, the tubular construct can include a funnel shape with a smaller diameter at a first end of the shape than at a second, opposite end of the shape. For another example, the tubular construct can include at least two rings extending circumferentially therearound, the tubular construct can include at least one support structure extending between the at least two rings, and the adjunct material can be disposed as a covering over the at least two rings and the at least one support structure. For still another example, the tubular construct can include first and second independent tubular members. The first tubular member can be releasably retained on the anvil, and the second tubular member can be releasably retained on the cartridge assembly. Each of the first and second tubular members can have a continuous tubular wall.

In another aspect, a method of using the end effector is provided that in one implementation includes positioning a circular surgical stapler at a target location within a patient within a lumen of a tissue of the patient. The stapler has the end effector at a distal end thereof. The method also includes, with the stapler positioned at the target location, actuating the stapler to deploy the staples from the cartridge body and into the tissue. The deployed staples secure the tubular construct within the lumen of the tissue. The method also includes removing the stapler from the patient, the tubular construct remaining within the lumen.

The method can have any number of variations. For example, the tissue can include one of an intestine and an esophagus. For another example, the adjunct material can be in the form of a fiber lattice having at least two distinct heterogeneous fiber lattice sections. The at least two distinct heterogeneous fiber lattice sections can include a first fiber lattice section having fibers extending along a longitudinal axis of the tubular construct and a second fiber lattice section having fibers extending annularly around the longitudinal axis of the tubular construct. The longitudinal axis of the tubular construct can be substantially parallel to a longitudinal axis of the lumen having the tubular construct secured therein.

For still another example, the tubular construct can include first and second independent tubular members. Prior to the actuation of the stapler, the first tubular member can be releasably retained on the anvil and the second tubular member can be releasably retained on the cartridge assembly. The actuation can release the first tubular member from the anvil and can release the second tubular member from the cartridge assembly. The first tubular member can be releasably retained on the anvil such that an inner passageway of the first tubular member is aligned with the lumen of the tissue following the securing of the tubular construct within the lumen, and the second tubular member can be releasably retained on the cartridge assembly such that an inner passageway of the second tubular member is aligned with the lumen of the tissue following the securing of the tubular construct within the lumen.

In general, inducing tissue adhesions using surgical adjuncts and medicants is provided.

In one aspect, a staple cartridge assembly for use with a surgical stapler is provided that in one implementation includes a cartridge body, a biocompatible adjunct material, and an effective amount of at least one medicant. The cartridge body has a plurality of staple cavities. Each staple cavity has a surgical staple disposed therein. The biocompatible adjunct material is releasably retained on the cartridge body and is configured to be delivered to lung tissue by deployment of the staples in the cartridge body to form at least one line of deployed staples. The effective amount of at least one medicant is disposed within and releasable from the adjunct material. The at least one medicant is effective to induce tissue adhesions adjacent to the at least one line of deployed staples.

The staple cartridge assembly can vary in any number of ways. For example, the adjunct material can be configured to release the at least one medicant therefrom in a gradual time release manner. In another example, the adjunct material can be configured to release the at least one medicant therefrom as a single released dose. For another example, the adjunct material can include a carrier configured to undergo a phase change from a solid state to a liquid state, and the at least one medicant can be configured to be released from the adjunct material with the carrier in the liquid state but not in the solid state. For yet another example, the at least one medicant can include a growth factor. For still another example, the at least one medicant can include at least one of interleukin (IL) beta, Tissue Growth Factor Beta (TGF-B), and platelet rich plasma.

In another aspect, a method of using the staple cartridge assembly is provided that in one implementation includes removably attaching the cartridge body to a surgical stapler, positioning the stapler at a target location adjacent lung tissue, and with the stapler positioned at the target location, actuating the stapler to deploy the staples from the cartridge body and into the lung tissue, thereby delivering the adjunct material to the lung tissue.

The method can vary in any number of ways. For example, the at least one medicant can be effective to induce tissue adhesions between pleural surfaces of the lung tissue having the adjunct material delivered thereto.

In another aspect, an end effector for a surgical instrument is provided that in one implementation includes a first jaw, a second jaw, a biocompatible adjunct material, and an effective amount of at least one medicant. The first jaw has a cartridge body removably attached thereto. The cartridge body has on a tissue-facing surface thereof a plurality of staple cavities configured to seat staples therein. The second jaw has an anvil with a plurality of staple forming cavities formed on a tissue-facing surface thereof. At least one of the first and second jaws is movable relative to the other. The biocompatible adjunct material is releasably retained on at least one of the tissue-facing surfaces of the first and second jaws and is configured to be delivered to tissue by deployment of the staples in the cartridge body to form at least one line of deployed staples. The effective amount of at least one medicant is disposed within and releasable from the adjunct material. The at least one medicant is effective to induce tissue adhesions adjacent the least one line of deployed staples.

The end effector can vary in any number of ways. For example, the adjunct material can be configured to release the at least one medicant therefrom in a gradual time release manner. In another example, the adjunct material can be configured to release the at least one medicant therefrom as a single released dose. In another example, the adjunct material can include a carrier configured to undergo a phase change from a solid state to a liquid state, and the at least one medicant can be configured to be released from the adjunct material with the carrier in the liquid state but not in the solid state. For yet another example, the at least one medicant can include a growth factor. For still another example, the at least one medicant can include at least one of IL beta, TGF-B, and platelet rich plasma.

In another aspect, a method of using the end effector is provided that in one implementation includes positioning a surgical stapler at a target location within a patient adjacent lung tissue. The stapler has the end effector at a distal end thereof. The method also includes, with the stapler positioned at the target location, actuating the stapler to deploy the staples from the cartridge body and into the tissue, thereby delivering the adjunct material to the lung tissue.

The method can have any number of variations. For example, the at least one medicant can be effective to induce tissue adhesions between pleural surfaces of the lung tissue having the adjunct material delivered thereto.

BRIEF DESCRIPTION OF THE DRAWINGS

This invention will be more fully understood from the following detailed description taken in conjunction with the accompanying drawings, in which:

FIG. 30 is a graphical representation of an adjunct material having vessels configured to release at least one medicant encapsulated therein in a non-homogeneous manner;

FIG. 31 is a graphical representation of a vessel configured to release multiple medicants encapsulated at different layers thereof in a non-homogeneous manner;

FIG. 32 is a graphical representation of an adjunct material having different portions configured to release at least one medicant in a non-homogeneous manner;

FIG. 119 is a perspective view of an adjunct including multiple different fibers;

FIG. 120 is a perspective view of an adjunct formed from multiple concentric layers of fibers;

FIG. 121 is a perspective view of a fiber;

FIG. 122 is a perspective view of a portion of an implementation of an adjunct formed from a plurality of fibers;

FIG. 123 is a perspective view of a portion of another implementation of an adjunct formed from a plurality of fibers woven together;

FIG. 124 is a representation of an adjunct including multiple fibers associated with vessels having at least one medicant disposed therein;

FIG. 125 is representation of the adjunct of FIG. 124 showing the at least one medicant released therefrom;

FIG. 126 is a perspective, partial cutaway view of an implementation of an adjunct that includes a plurality of heterogeneous layers or portions;

FIG. 127 is a graph showing an implementation of an elution profile of the adjunct of FIG. 126;

FIG. 128 is a graph showing another implementation of an elution profile of the adjunct of FIG. 126;

FIG. 129 is a graph showing another implementation of an elution profile of the adjunct of FIG. 126;

FIG. 130 is a cross-sectional side view of an implementation of an adjunct applied to tissue with staples, the adjunct being configured to be affected by an activator material;

Figure 1:
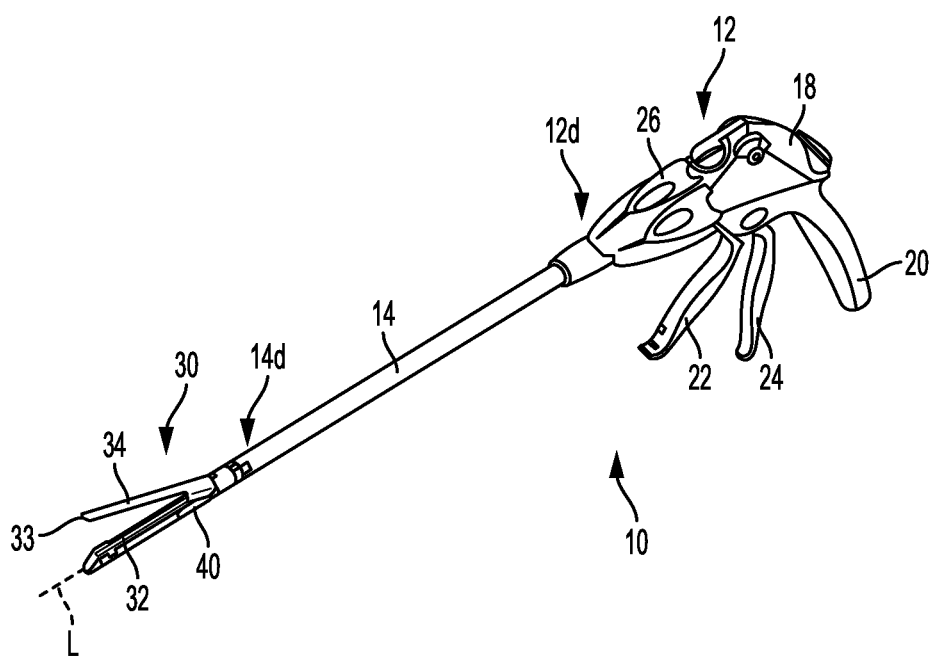
FIG. 1 is a perspective view of one embodiment of a surgical stapler.
Figure 130:
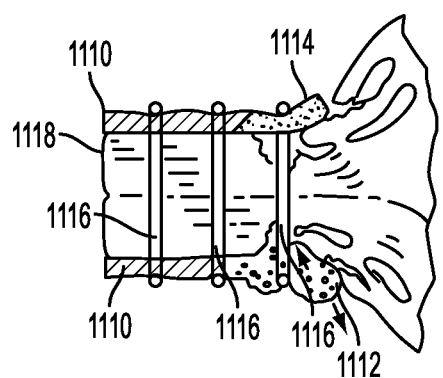
Figure 131:
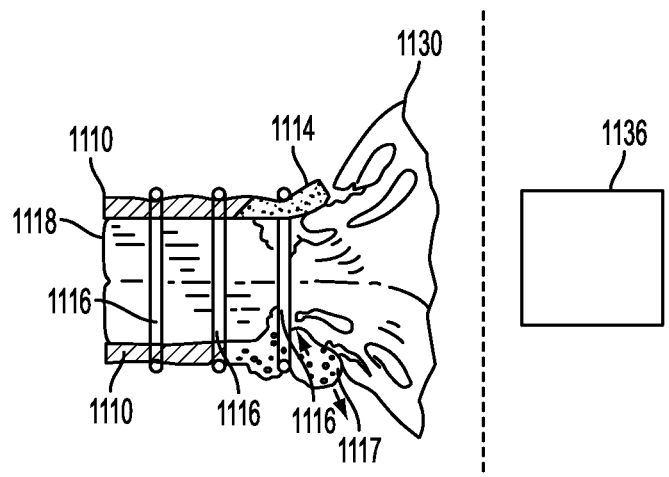
Figure 132:
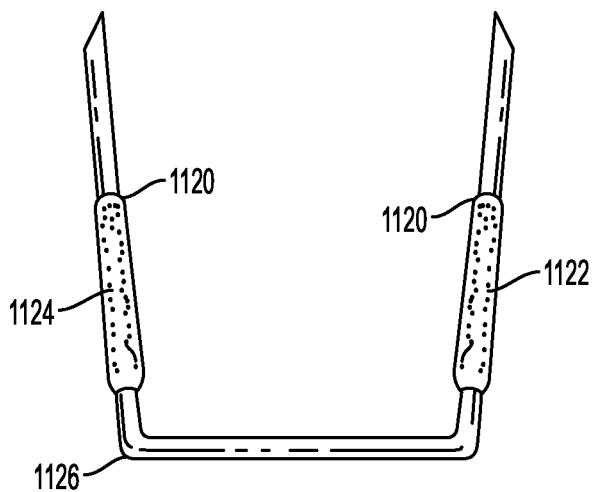
Figure 133:
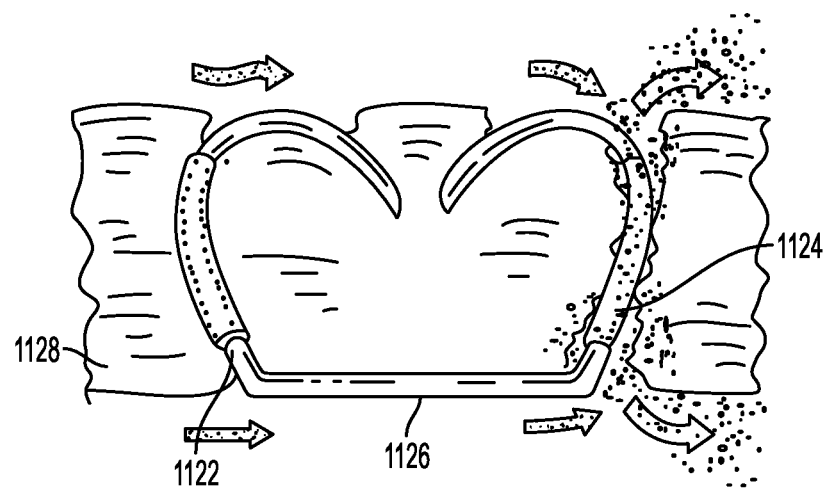
Figure 134:
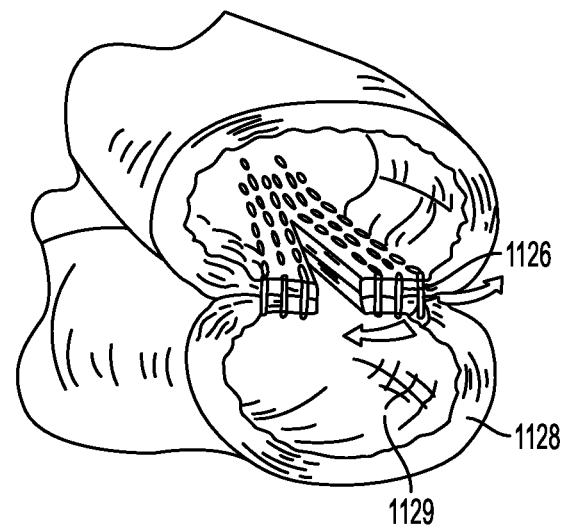
Figure 135:
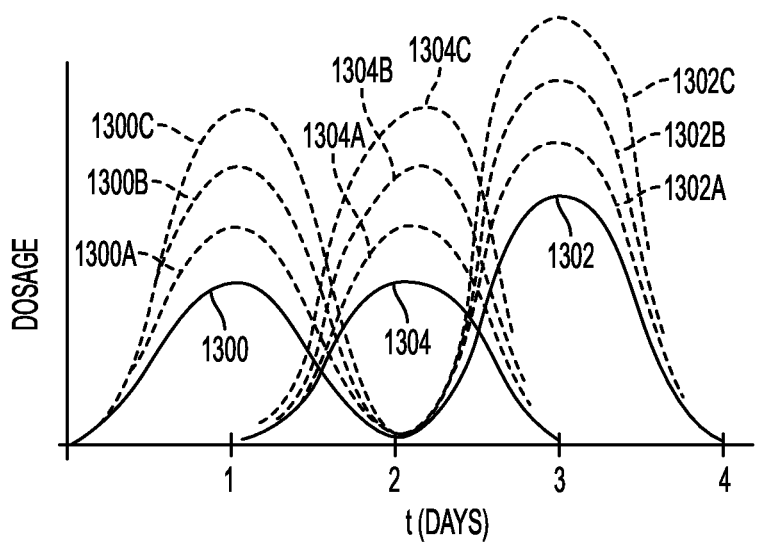
Figure 136:
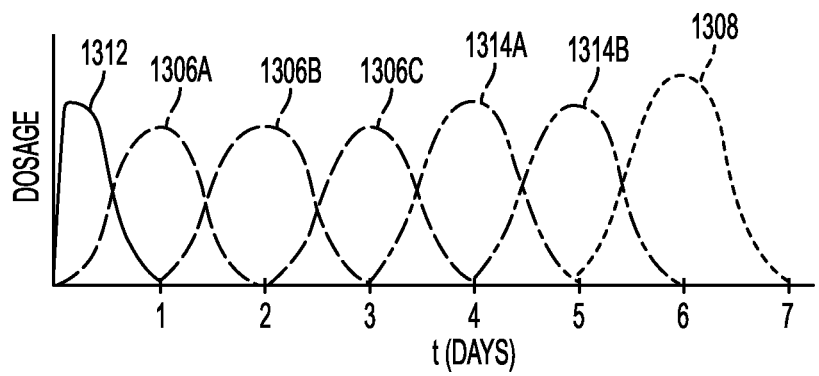
Figure 137:
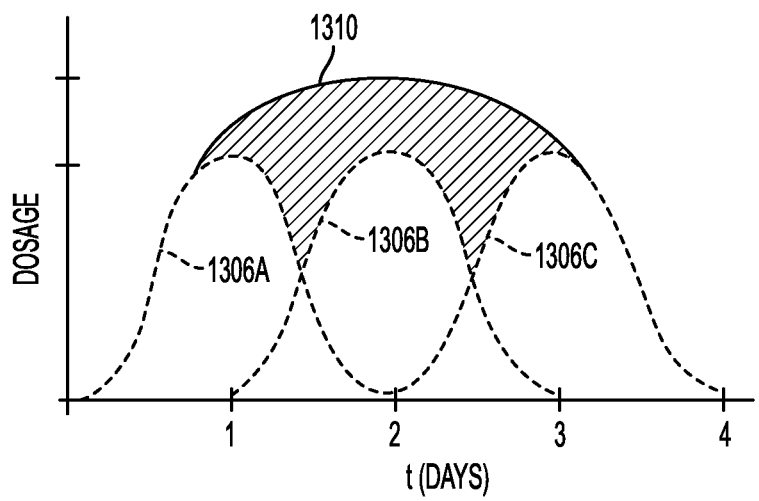
Figure 143:
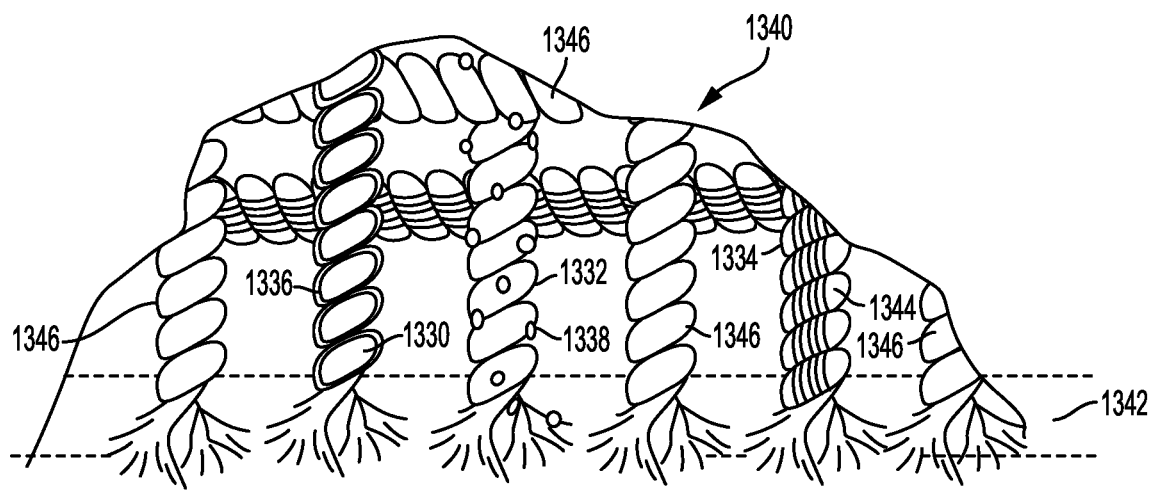
Figure 144:
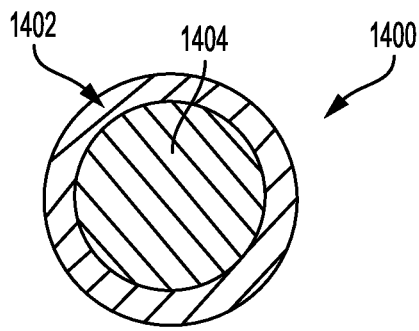
Figures 145, 146:
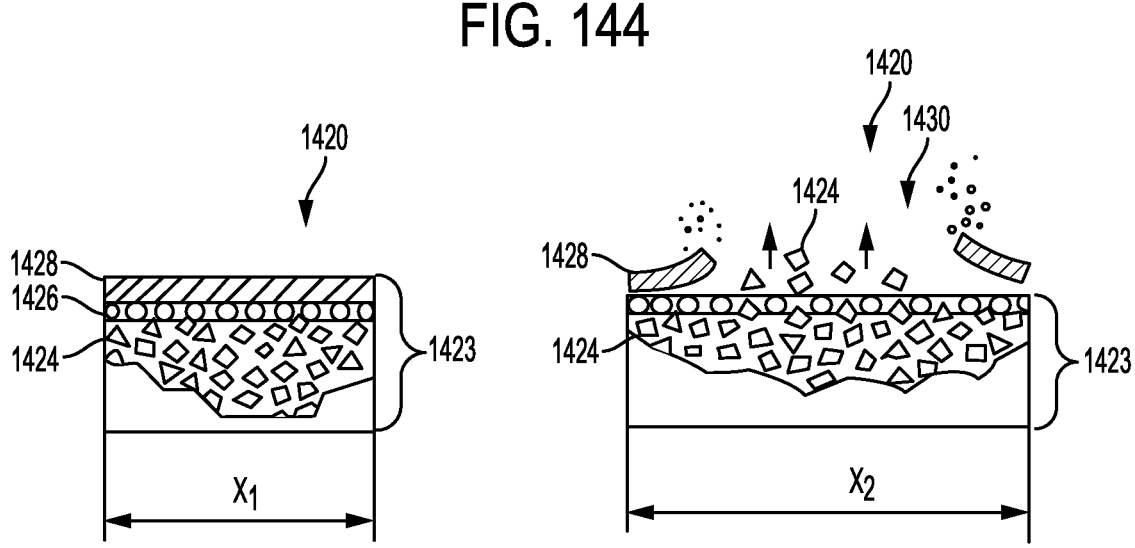
Figure 147:
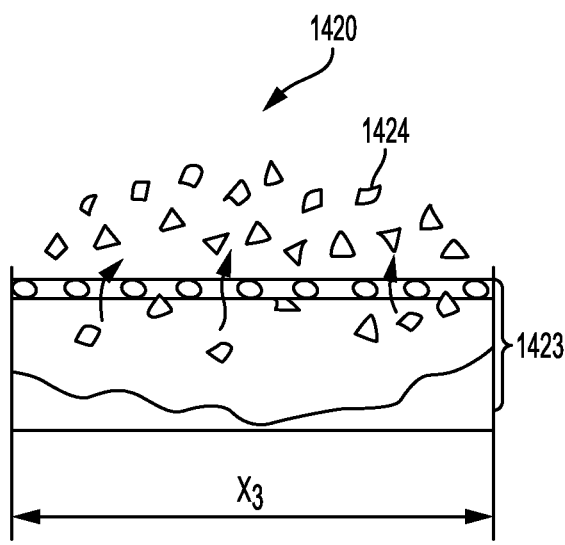
Figure 148:
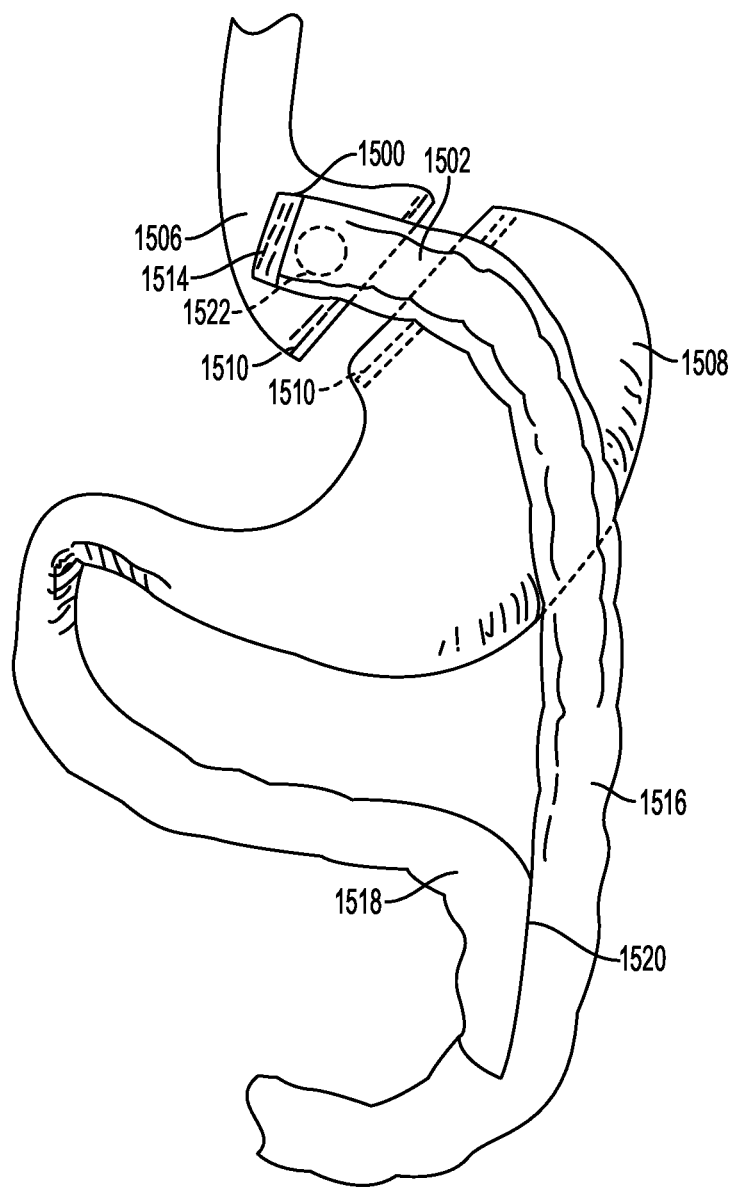
Figure 149:
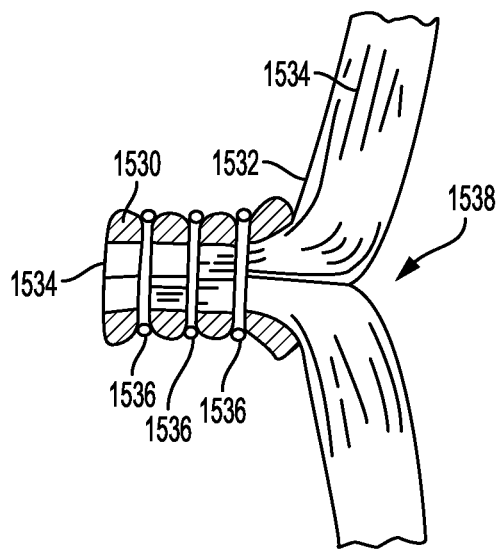
Figure 150:
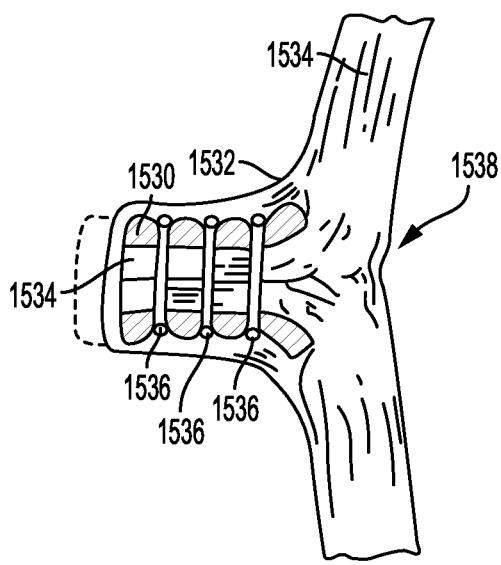
Figure 151:
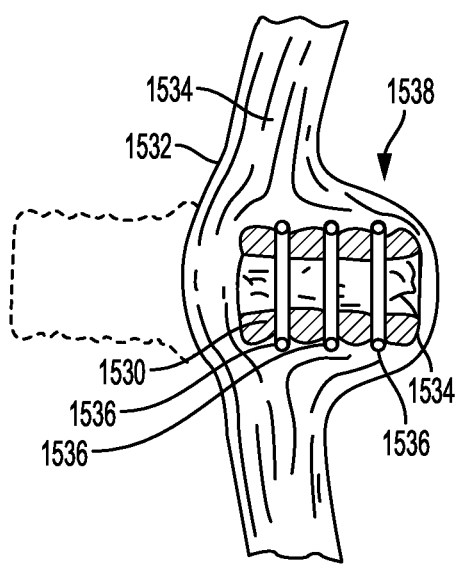
Figure 152:
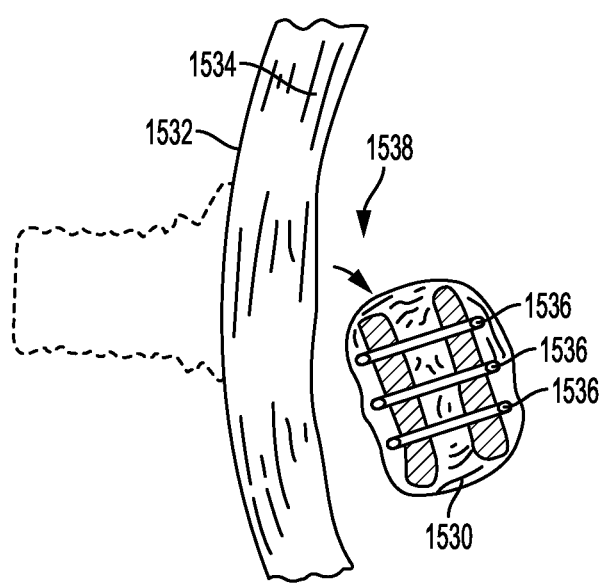
Figure 153:
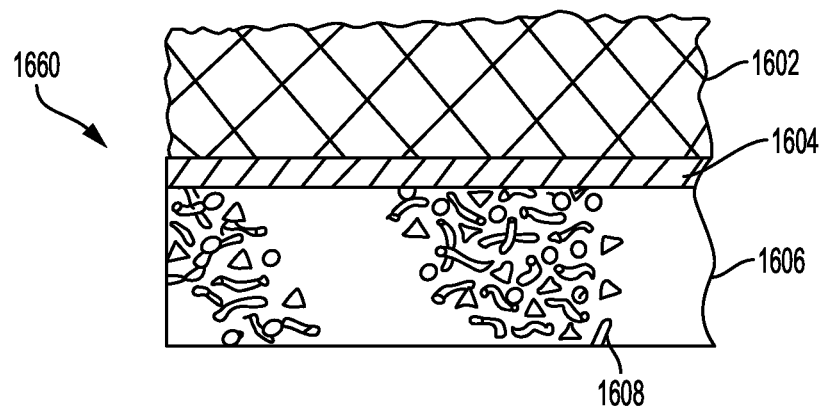
Figure 154:
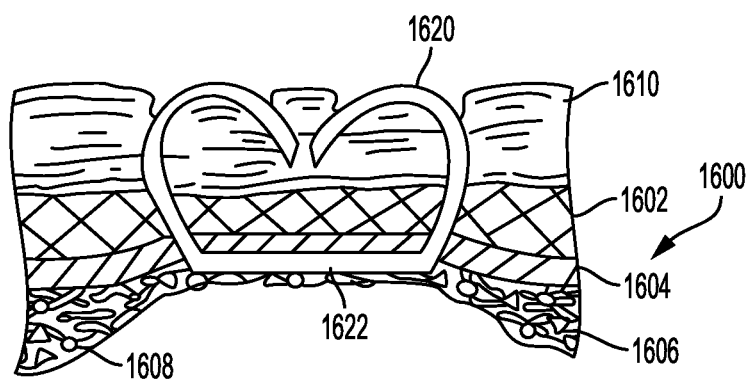
Figure 155:
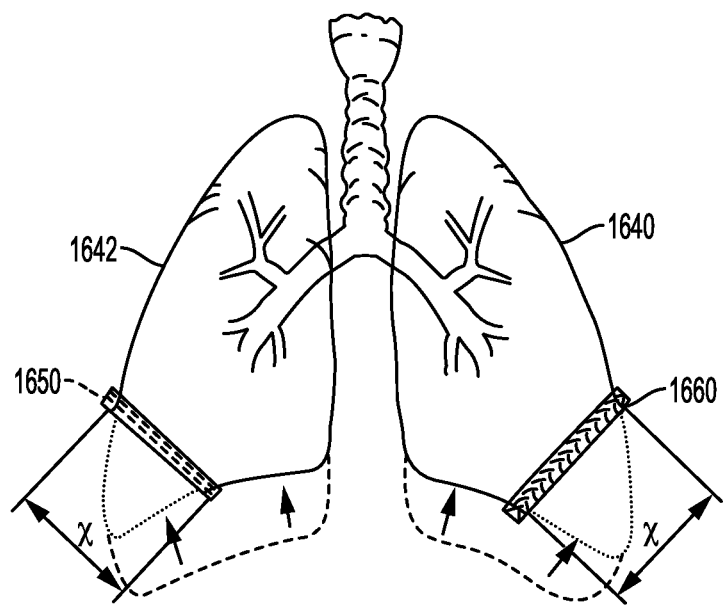
Figure 156:
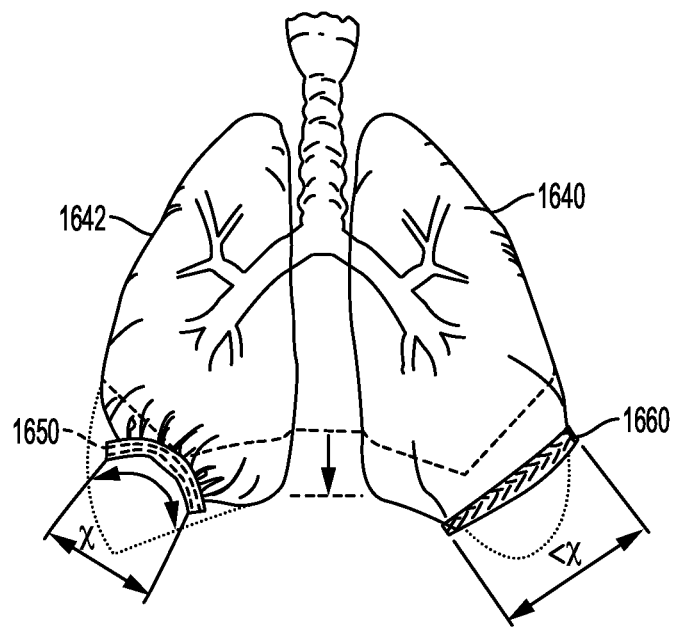
Figure 157:
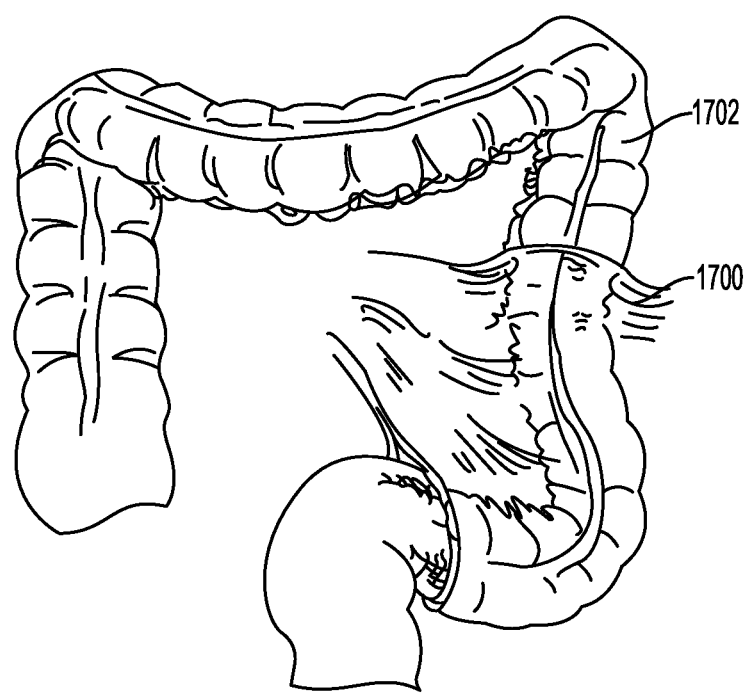
Figure 158:
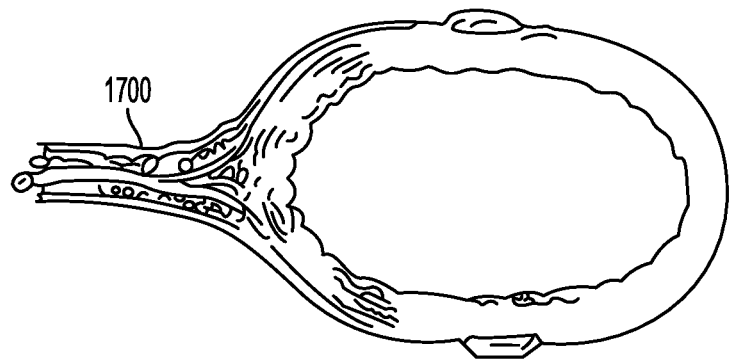
Figure 159:
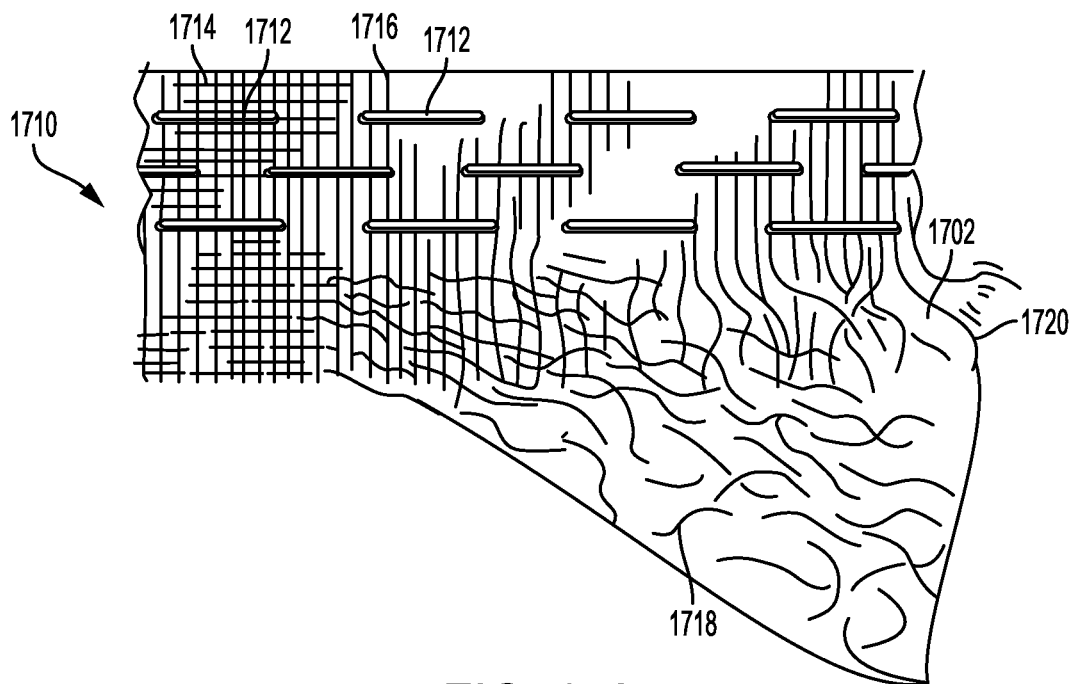
Figure 160:
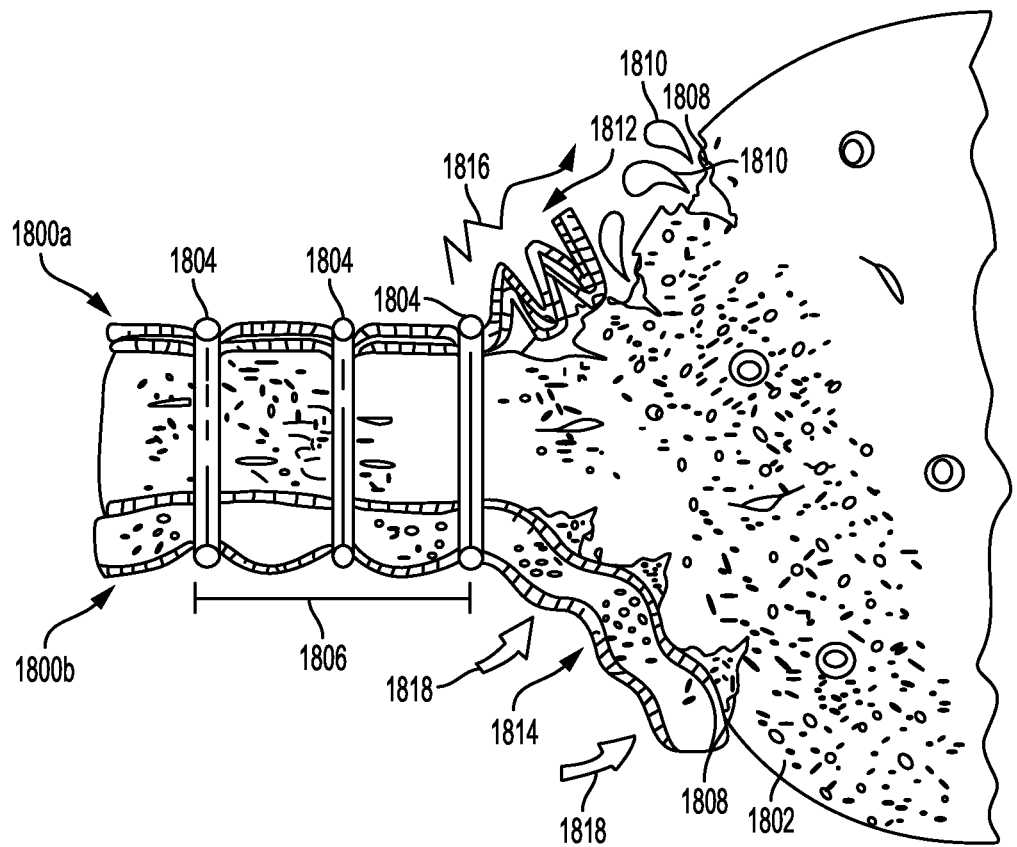
Figure 161:
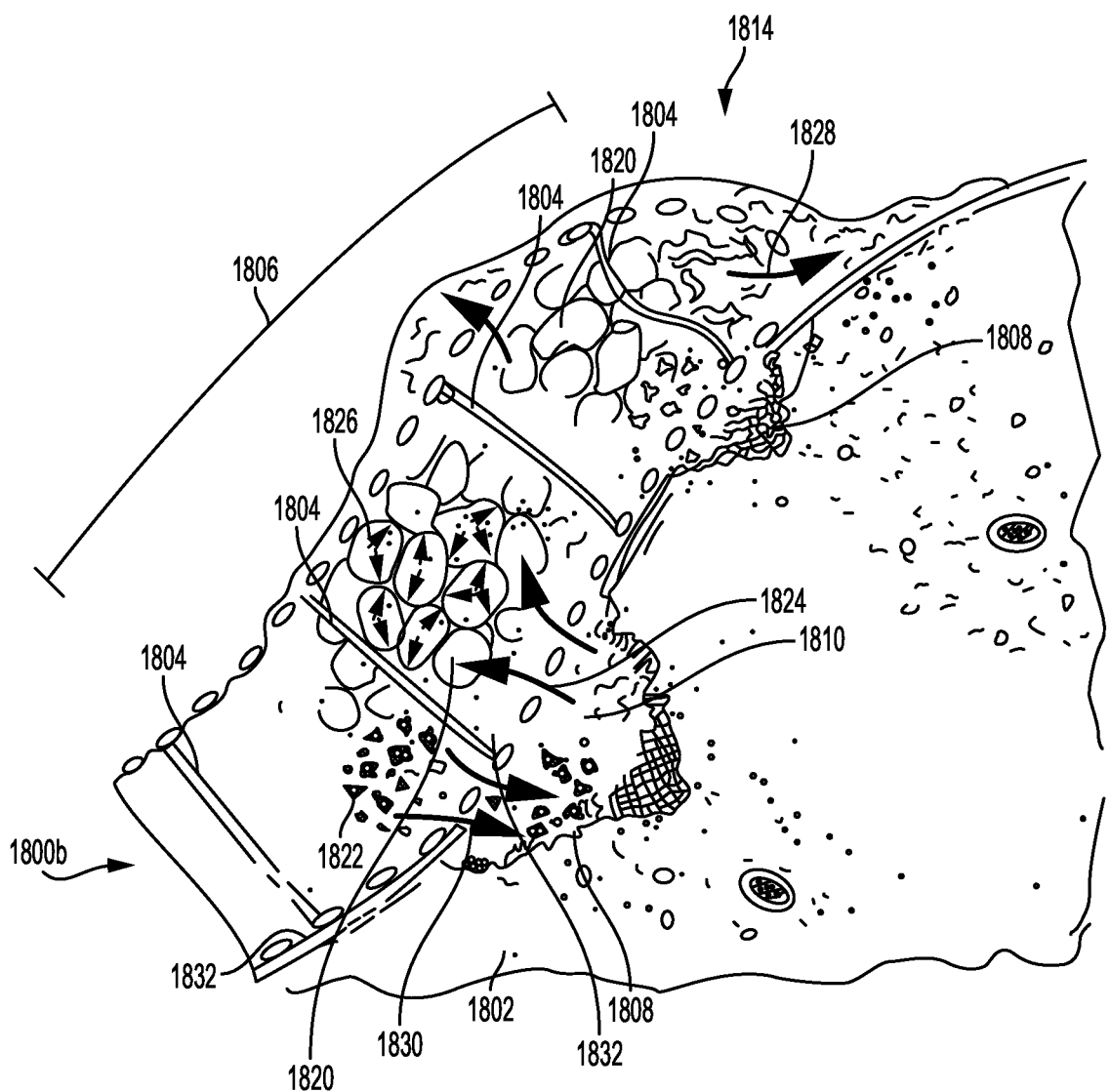
Figure 162:
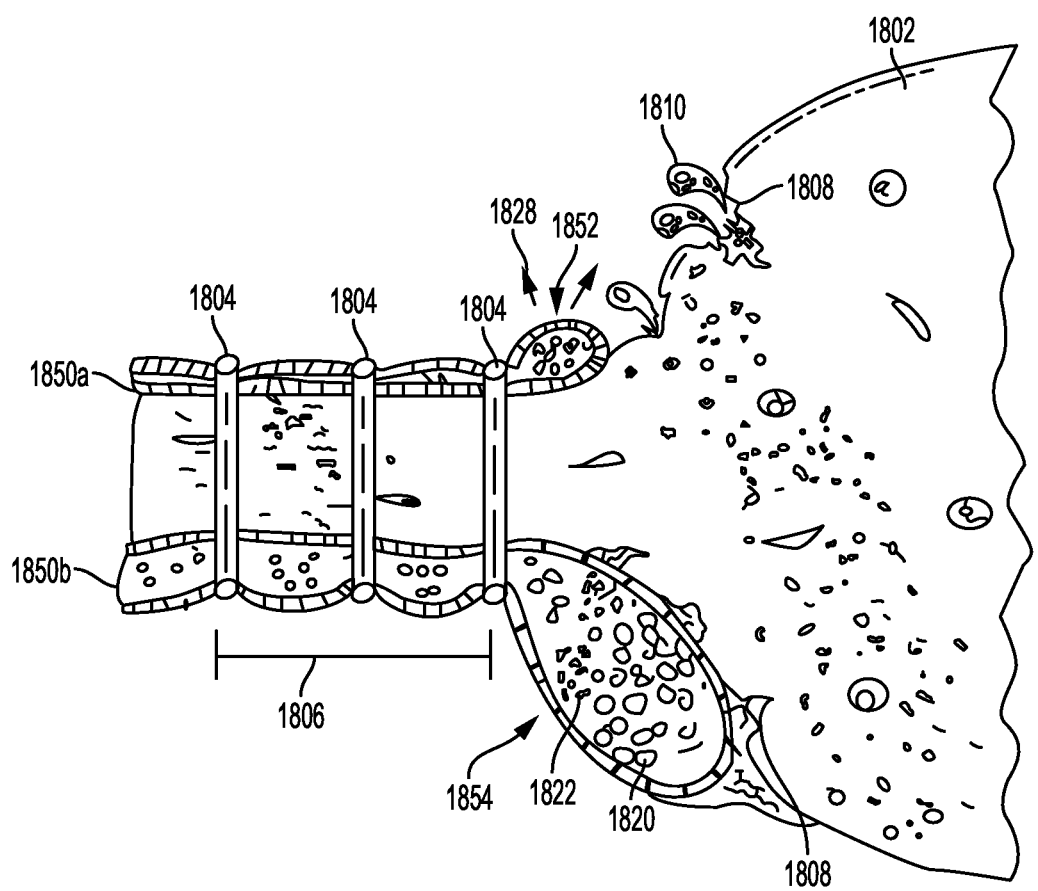
Figure 163:
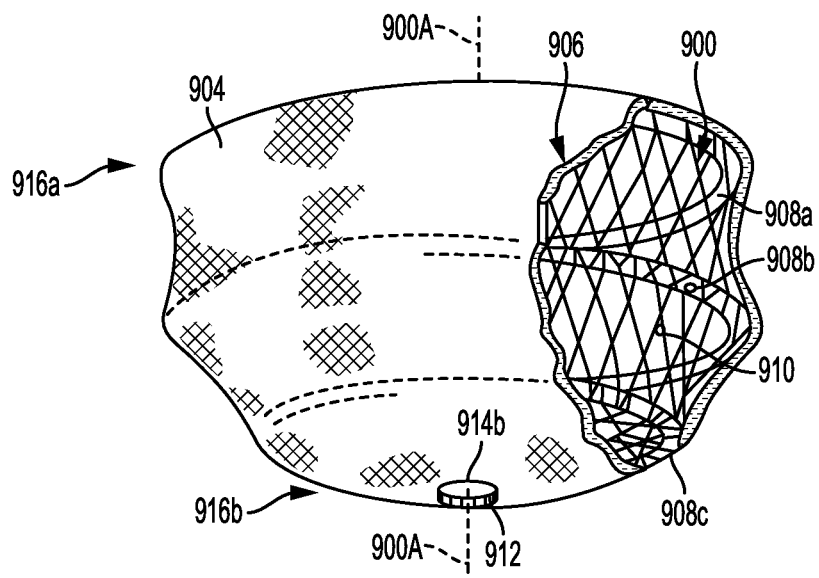
Figure 164:
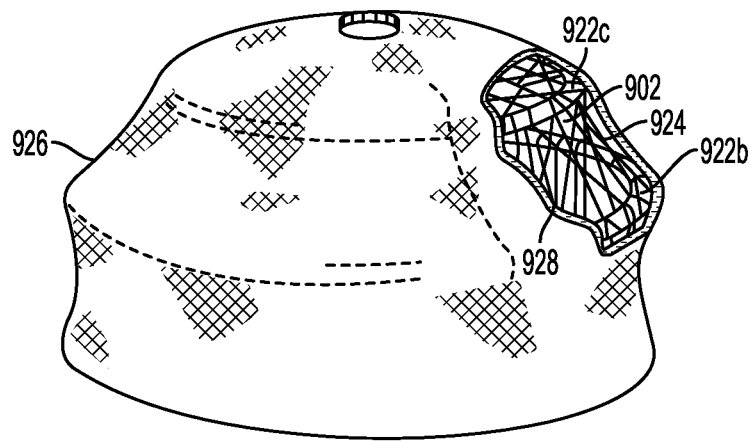
Figure 165:
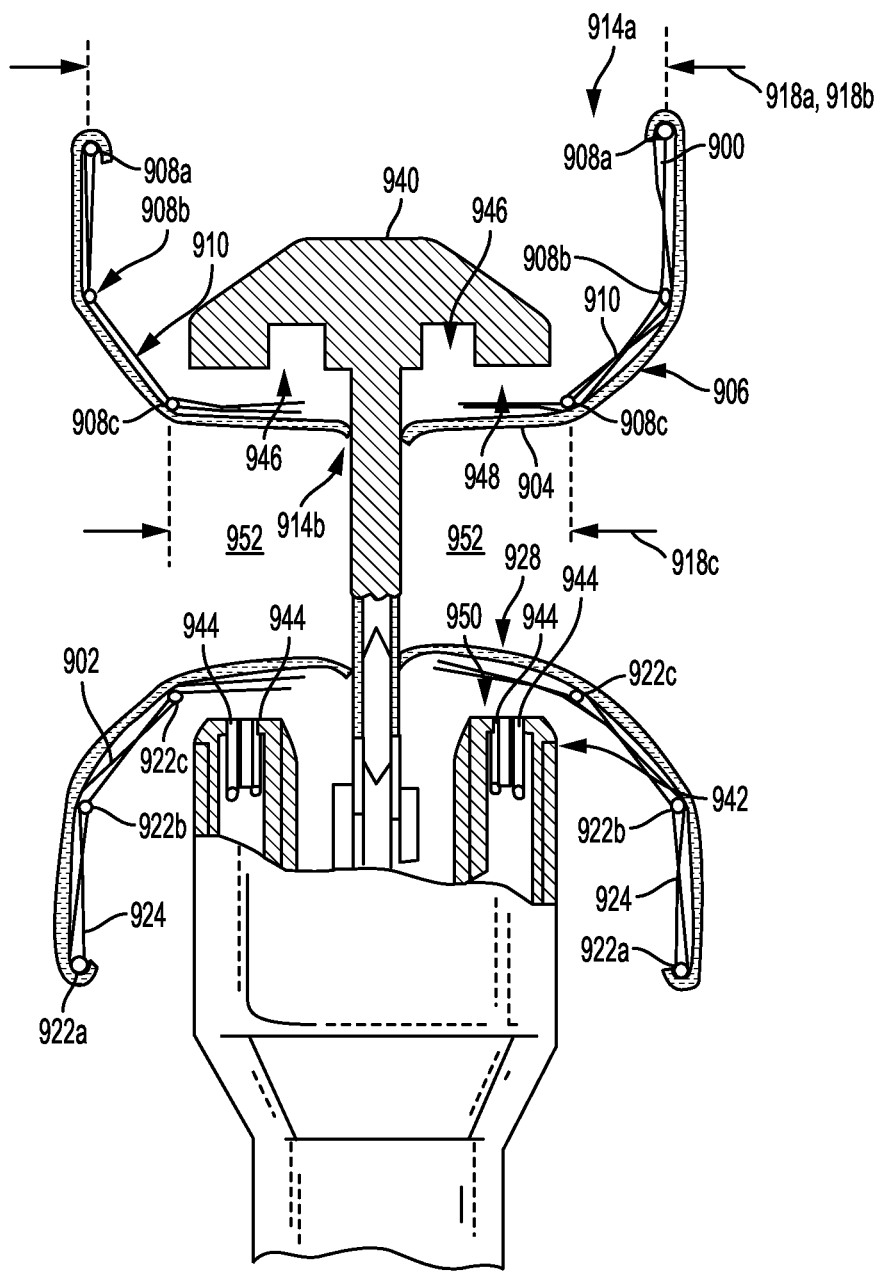
Figure 166:
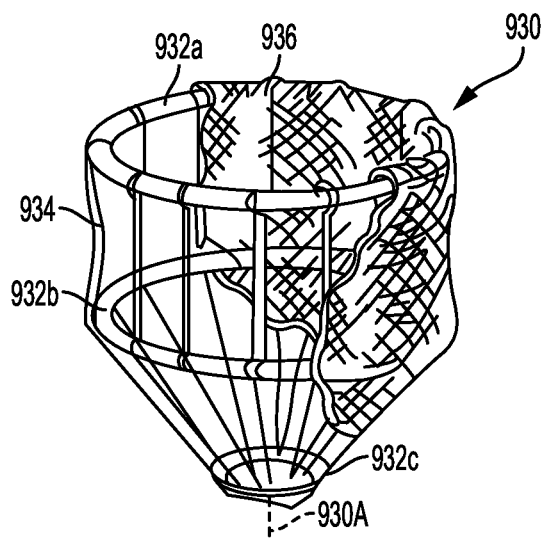
Figure 167:
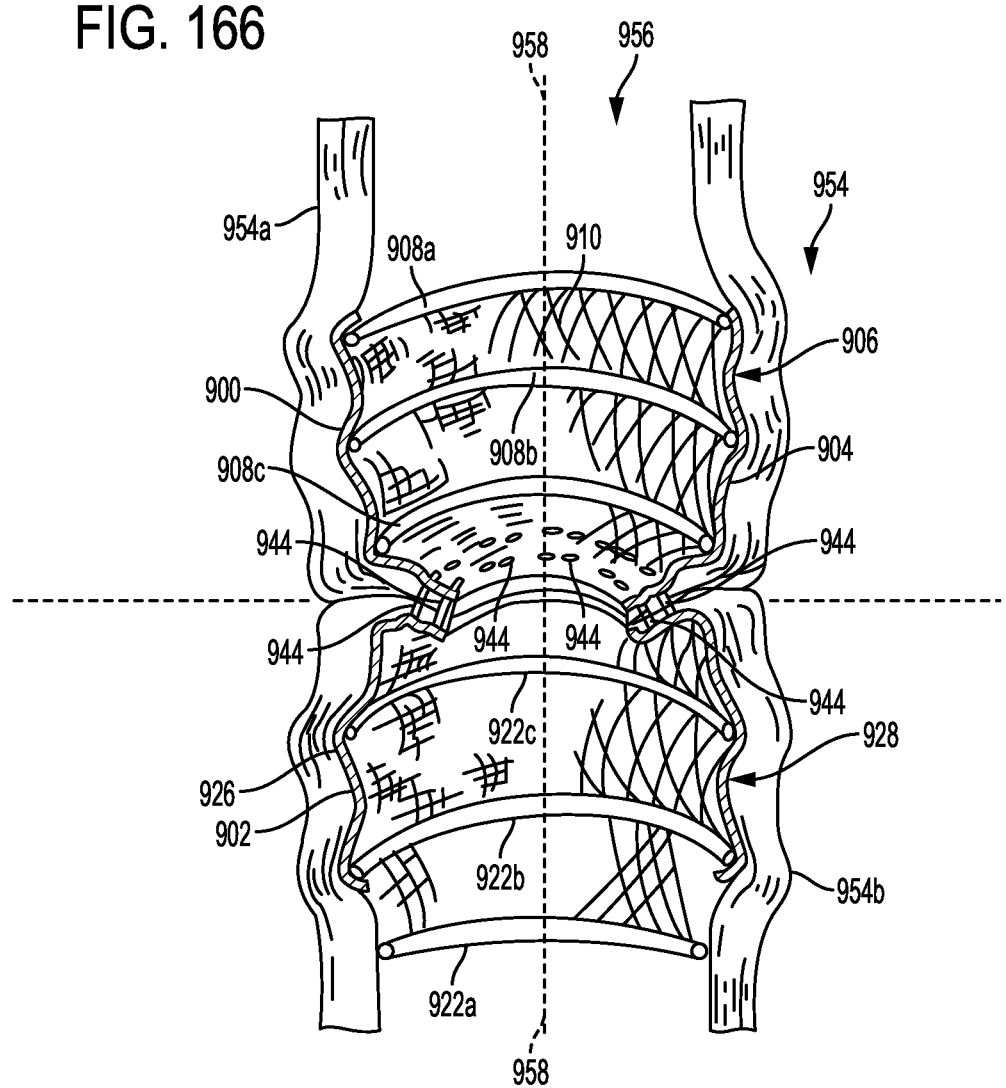
Figure 168:
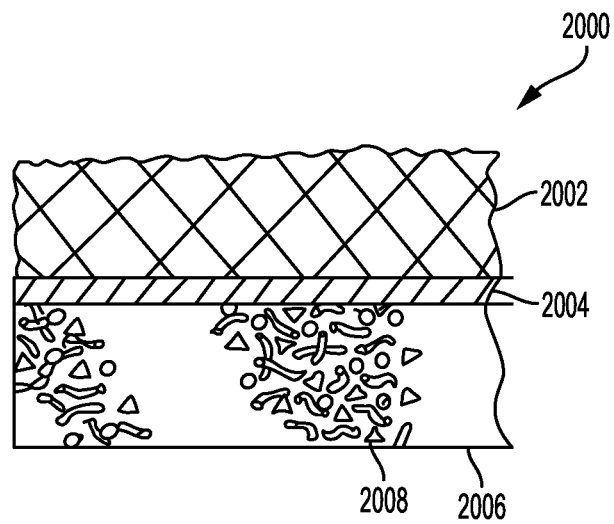
Figure 169:
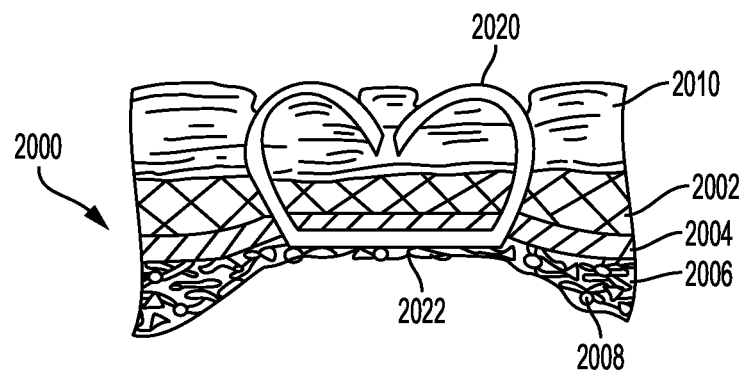
Figure 170:
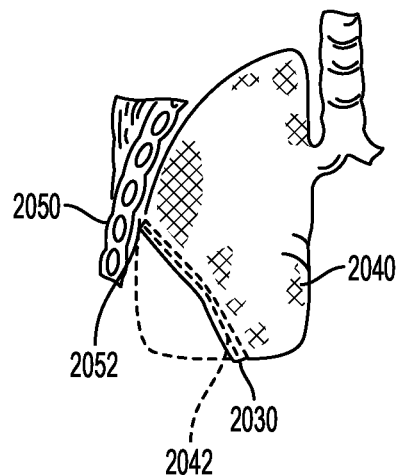
Figure 171:
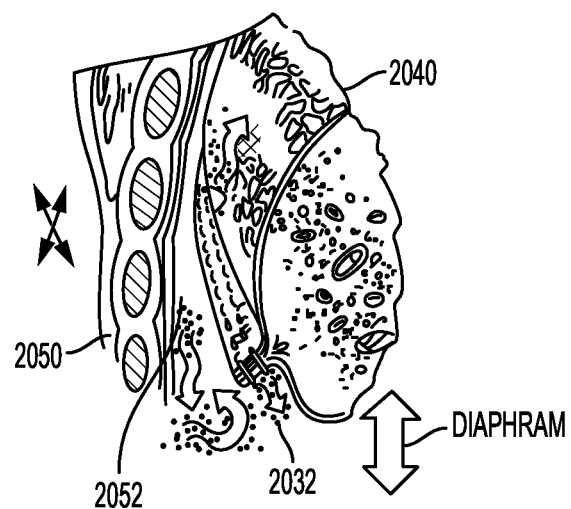

FIG. 131 is a cross-sectional side view of the adjunct of FIG. 130 and an imaging system;

FIG. 132 is a perspective view of an implementation of a staple having an adjunct disposed thereon, the adjunct being configured to be affected by an activator material;

FIG. 133 is a partial cross-sectional side view of the staple of FIG. 132 applied to tissue;

FIG. 134 is a perspective, zoomed-out view of the tissue of FIG. 133 having the staple and a plurality of additional staples applied thereto;

FIG. 135 is a graph showing implementations of cumulative doses of medicants in which the medicants include at least one agonist and at least one antagonist;

FIG. 136 is a graph showing an implementation of doses of medicants in which the medicants include at least one agonist and at least one antagonist;

FIG. 137 is a graph showing a portion of the graph of FIG. 136 and indicating a cumulative dose;

FIG. 138 is a graphical representation of an implementation of a layered vessel including a medicant that includes an agonist and another medicant that includes an antagonist;

FIG. 139 is a perspective view of an implementation of a fiber having a coating therearound configured to facilitate release of an agonist and/or an antagonist;

FIG. 140 is a cross-sectional view of the fiber and coating of FIG. 139;

FIG. 141 is a perspective view of another implementation of a fiber having a coating therearound configured to facilitate release of an agonist and/or an antagonist;

FIG. 142 is a cross-sectional view of the fiber and coating of FIG. 141;

FIG. 143 is a perspective view of a portion of an implementation of an implantable adjunct formed from a plurality of fibers woven together to form a sheet-like fiber woven mesh configured to facilitate release of an agonist and an antagonist;

FIG. 144 is a representation of a vessel having at least one medicant encapsulated therein;

FIG. 145 is a representation of an adjunct configured to releasably retain at least one medicant;

FIG. 146 is a representation of the adjunct of FIG. 145, showing the at least one medicant partially released from the adjunct;

FIG. 147 is another representation of the adjunct of FIG. 145, showing the at least one medicant substantially entirely released from the adjunct;

FIG. 148 is a schematic view of an example of an adjunct material applied to the external surface of a stomach wall in a gastric bypass procedure;

FIG. 149 is a cross-sectional side view of an exemplary adjunct material stapled to an external surface of stomach tissue;

FIG. 150 represents the adjunct material of FIG. 149 after a period of time;

FIG. 151 represents the adjunct material of FIG. 150 after another period of time where the adjunct material has eroded into the stomach tissue;

FIG. 152 represents the adjunct material of FIG. 151 after the adjunct material has eroded through the stomach tissue and into the stomach cavity FIG. 153 is a partial, cross-sectional side view of an example of a multi-layer adjunct containing at least one medicant therein configured to promote lung function;

FIG. 154 is a partial, cross-sectional side view of the adjunct of FIG. 153 secured to lung tissue with a staple;

FIG. 155 is a schematic view of a lung in a deflated state with two staple lines having adjuncts thereat;

FIG. 156 is a schematic view of the lung of FIG. 155 in an inflated state;

FIG. 157 is a schematic representation of a portion of mesentery attached to a portion of colon tissue;

FIG. 158 is a representation of the mesentery shown in FIG. 157;

FIG. 159 is a plan view of an example of an adjunct material having a first portion including a first plurality of longitudinal fibers and a second portion including a second plurality of longitudinal fibers FIG. 160 is a cross-sectional side view of an exemplary adjunct material along a staple line that is applied to liver tissue where the top portion shows the adjunct material in a folded position and the bottom portion shows the adjunct material in an unfolded position;

FIG. 161 is a detailed view of a portion of the adjunct material of FIG. 1 in the expanded and unfolded position;

FIG. 162 is a cross-sectional side view of an exemplary adjunct material along a staple line that is applied to liver tissue where the top portion shows the adjunct material partially expanded and the bottom portion shows the adjunct material fully expanded FIG. 163 is a partial cutaway perspective view of an implementation of a tubular surgical construct including adjunct material;

FIG. 164 is a partial cutaway perspective view of another implementation of a tubular surgical construct including adjunct material;

FIG. 165 is a side cross-sectional view of a distal portion of an implementation of a circular surgical stapler having the tubular surgical constructs of FIG. 163 and FIG. 164 releasably coupled thereto;

FIG. 166 is a partial cutaway perspective view of yet another implementation of a tubular surgical construct including adjunct material;

FIG. 167 is a side cross-sectional view of an implementation of a tissue lumen having the tubular surgical constructs of FIG. 163 and FIG. 164 stapled thereto;

FIG. 168 is a partial, cross-sectional side view of an example of a multi-layer adjunct containing at least one medicant therein configured to induce tissue adhesions;

FIG. 169 is a partial, cross-sectional side view of the adjunct of FIG. 168 secured to lung tissue with a staple;

FIG. 170 is a schematic view of a resected lung with a staple line containing an adjunct; and FIG. 171 is an enlarged schematic view of the lung and adjunct of FIG. 170.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments.

Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

The adjunct(s) can also have medicant(s) thereon and/or therein. The medicant(s) can vary depending on the desired effect of the medicant(s) on the surrounding tissue. As a non-limiting example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As non-limiting examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIG. 1 and FIG. 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
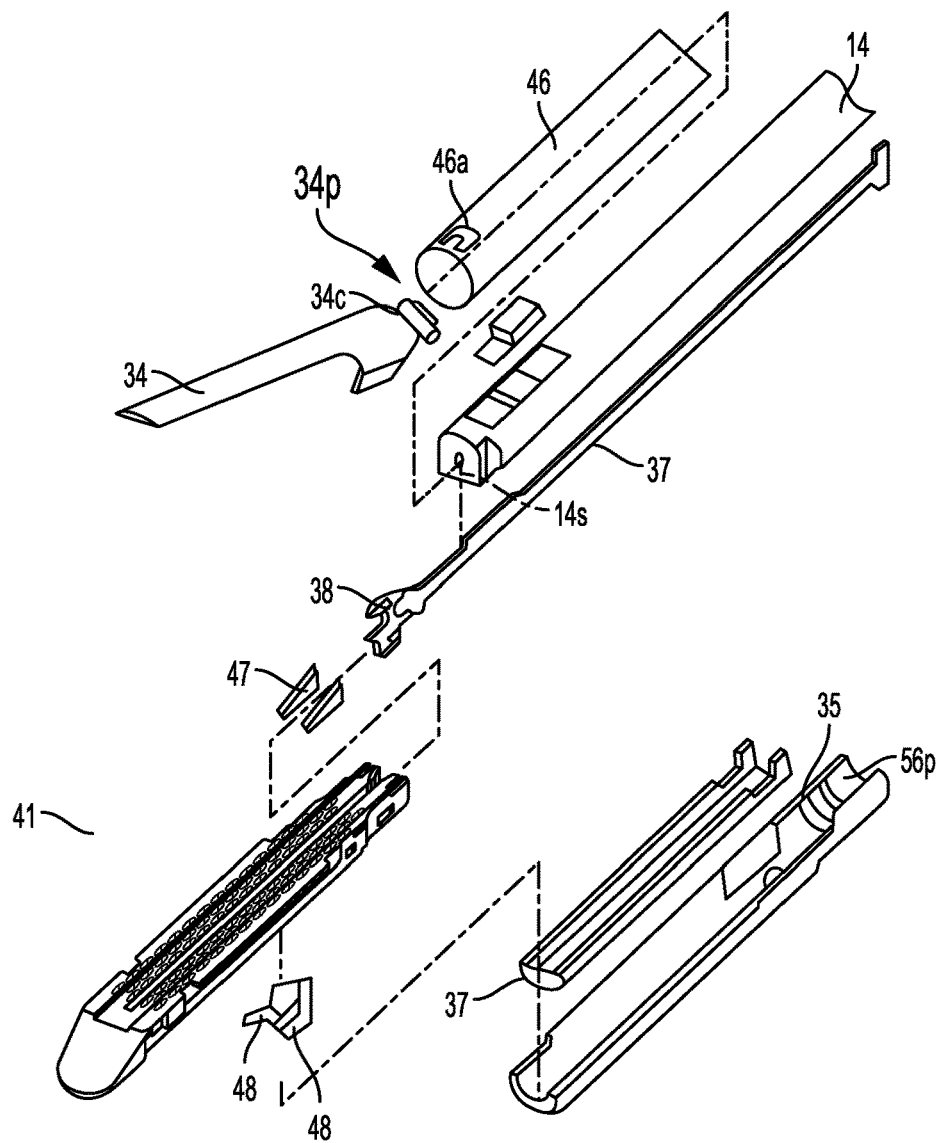
FIG. 2 is an exploded view of a distal portion of the surgical stapler of FIG. 1.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement with the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
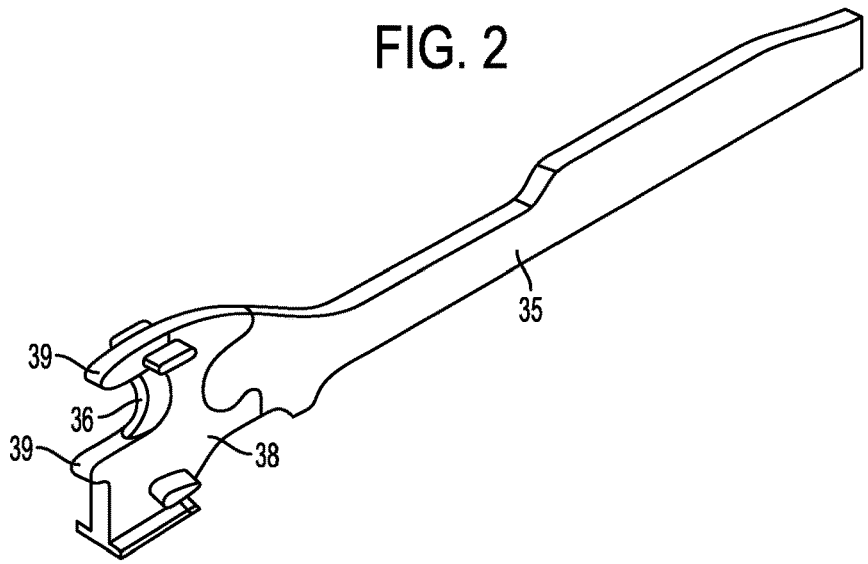
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
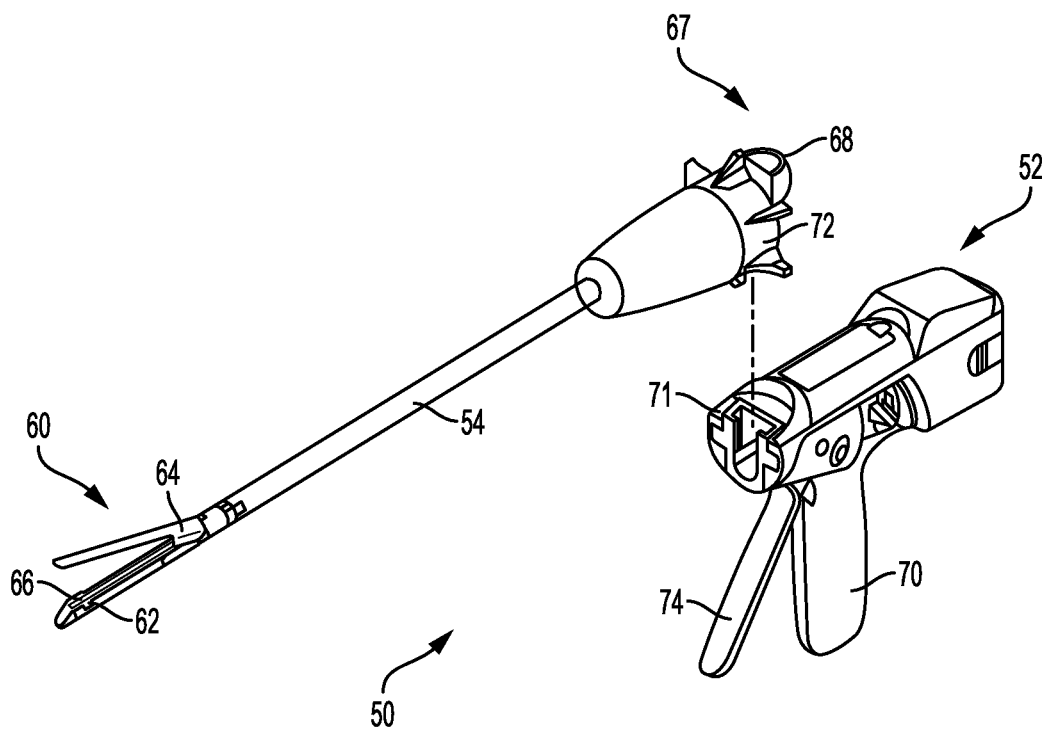
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
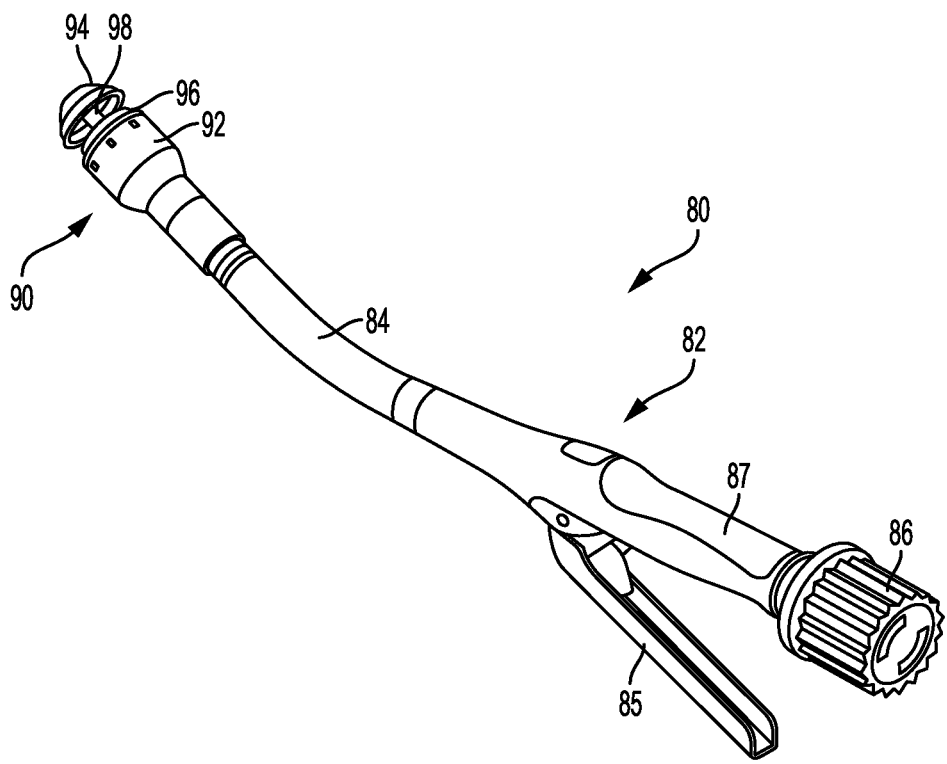
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIG. 1 and FIG. 4, but with some features accommodating its functionality as a circular stapler. Similar to the surgical instruments 10, 50, the stapler 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator, shown as a trigger in this illustrated embodiment, 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft 84 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

Materials

The adjuncts in accordance with the described techniques can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include poly (lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly (glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima).

An adjunct can also include active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+, Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, Neo-Recormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Non-limiting examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), vinca alkaloids gents that inhibit mitosis and microtubule formation (e.g., Vinblastine, Vincristine, Vindesine, Vinorelbine), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

Drug Release

An adjunct in accordance with the described techniques can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Figure 6:
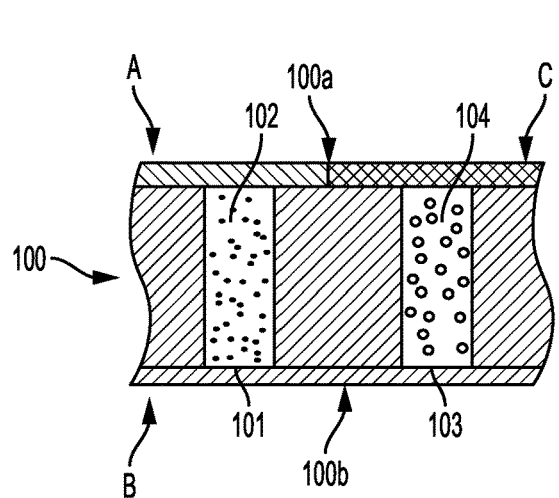
FIG. 6 is a graphical representation of an embodiment of an adjunct material with different types of medicants encapsulated using different release mechanisms before medicant release.
Figure 7:
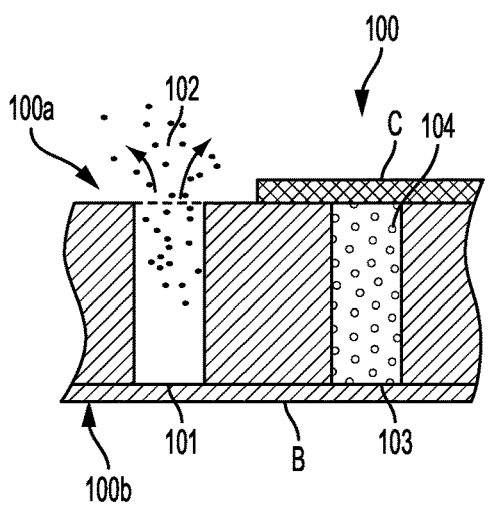
FIG. 7 is a graphical representation of the adjunct material of FIG. 6, showing release of a first medicant.
Figure 8:
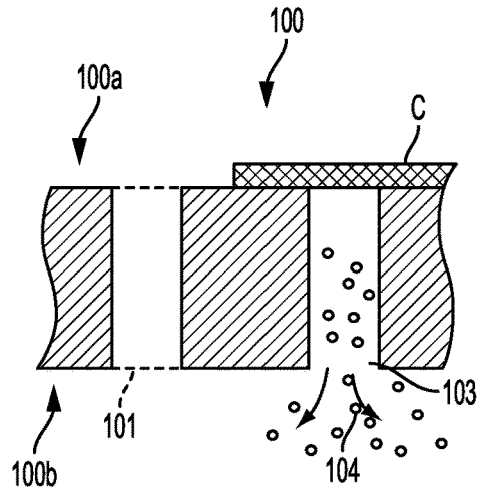
FIG. 8 is a graphical representation of the adjunct material of FIG. 6, showing release of a second medicant.

FIG. 6 through FIG. 8 illustrate a biocompatible adjunct 100 having multiple pores carrying different medicants that are encapsulated within the pores disposed at different locations and using different absorbable coatings. The coatings can absorb, dissolve or otherwise disintegrate at different times after delivery of the adjunct 100 to a treatment site and staple deployment so as to allow the medicants to also release at different times and in different directions. Thus, the medicants can be released from the adjunct 100 in a non-homogeneous manner. For example, one of the medicants can be released immediately after delivery and/or staple deployment whereas one or more of other medicants can be released at a later time, such as over a predetermined release profile. The release of these subsequently released medicants can be controlled by or depend upon the release of the first medicant. The opposite sides of the adjunct 100 can be covered by coatings (or be formed of materials) having different absorption rates such that certain medicant(s) are released on one side of the adjunct while other medicant(s) are released on another side of the adjunct. This provides a more controlled and targeted way of delivering therapies to tissue.

In this example, the adjunct 100 is in the form of a layer having multiple porous regions, two of which are shown by way of example as pores 101, 103. As shown in FIG. 6, the porous regions 101, 103 carry respective first and second medicants 102, 104 which can be different medicants. It should be appreciated that the adjunct 100 has multiple porous regions which can carry the medicants 102, 104 in an alternating manner or in any other patterns.

As shown in FIG. 6, a first side 100a of the adjunct 100 has coatings A, C such that the coating A seals the porous region 101 with the first medicant 102 and the coating C seals the porous region 103 with the second medicant 104. A second, opposite side 100b of the adjunct 100 is covered by a coating B. In the illustrated example, the coatings A, B, C that create a barrier that affects release of a medicant can be selected such that the coating A absorbs first after the staple deployment, the coating B absorbs after the coating A has been at least partially absorbed, and the coating C is not absorbable.

As shown in FIG. 7, after the delivery and/or staple deployment, the coating A is first absorbed so as to allow the first medicant 102 to be released from the porous region 101 at the first side 100a of the adjunct 100. For example, if the first side 100a is a tissue-contacting surface, the first medicant 102 can be a medicant that promotes healing at the treatment site. Subsequently, after a certain time period, the coating B can be absorbed so as to allow the second medicant 104 to be released from the porous region 103 at the second side 100b of the adjunct 100, as shown in FIG. 8. For example, if the second side 100b is a non-tissuecontacting surface, the second medicant 104 can be a medicant that prevents adhesion. As also shown in FIG. 8, the coating C seals the porous region 103 at the first side 100a and thus prevents the second medicant 104 from being released at the first side 100a of the adjunct 100. Although in this example the coating C is not absorbable, it can alternatively be absorbable after the coating B has been absorbed and the second medicant 104 can been released at the second side 100b. It should be appreciated that, to allow a porous region to be exposed and a medicant to release, a coating can be absorbed in its entirety or at least partially. A rate of absorption of a coating can control a rate of release of a medicant.

A person skilled in the art will appreciate that more than two different medicants can be releasably incorporated into different porous regions or other structures within an adjunct. The medicants can be retained within the adjunct using various coatings that can be selected so as to control rate and direction of release of the medicants.

Figure 9:
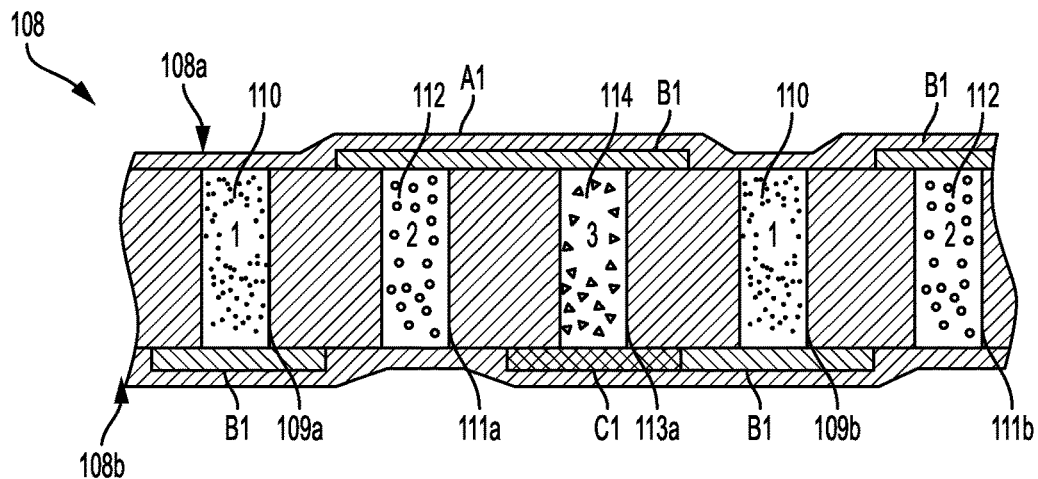
FIG. 9 is another graphical representation of an embodiment of an adjunct material with different types of medicants encapsulated using different release mechanisms before medicant release.
Figure 10:
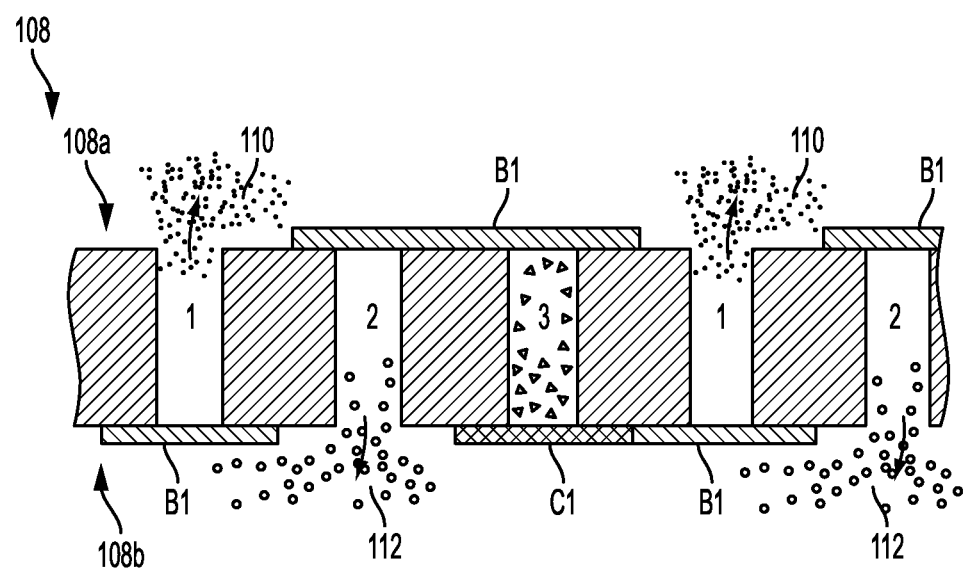
FIG. 10 is a graphical representation of the adjunct material of FIG. 9, showing release of the medicants as a result of absorption of a first coating.
Figure 11:
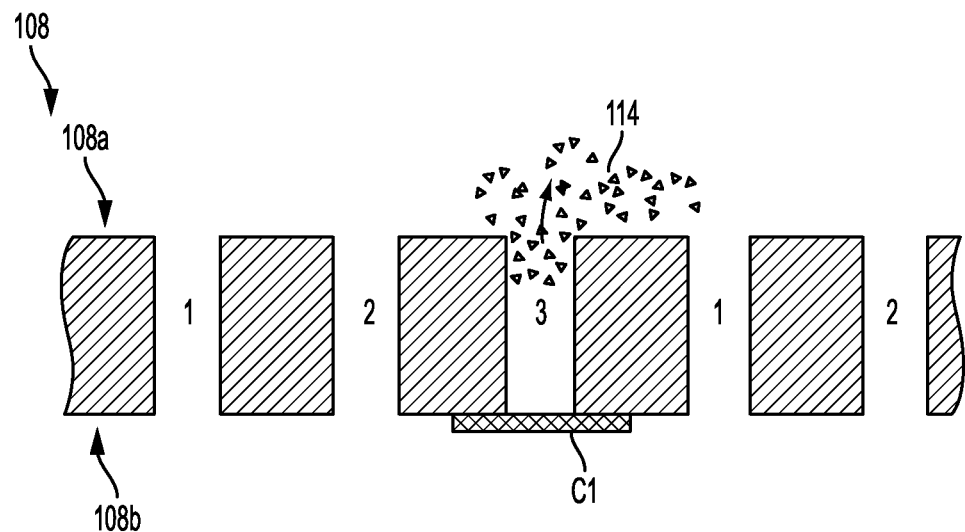
FIG. 11 is a graphical representation of the adjunct material of FIG. 9, showing release of the medicants as a result of absorption of a second coating.

An adjunct can include regions (e.g., pores or other reservoirs) releasably retaining a plurality of vessels, such as micro beads or other vessels, that have one or more medicants encapsulated therein. FIG. 9 through FIG. 11 illustrate an adjunct 108 including at least one medicant encapsulated in a plurality of vessels that are releasably retained by respective regions that regulate the dispersion of the vessels from the adjunct. The vessels can be micro capsules, micro beads, or any other types of vessels of a suitable size and shape. Each vessel can have an absorbable outer layer that can degrade and thus release a medicant retained within that vessel once the vessels are released from an adjunct. The adjunct can be used to deliver medicants in a non-homogeneous manner with respect to at least time of release and location of release.

As shown in FIG. 9, the adjunct 108 has multiple reservoirs or regions, five of which are shown as regions 109a, 111a, 113a, 109b, 111b that carry respective vessels 110, 112, 114, 110, 112. Thus, as shown schematically in FIG. 9, the regions 109a, 109b carry the same first type of vessels 110, the regions 111a, 111b carry the same second type of vessels 112, and the region 113a carries a third type of vessels 114.

As shown in FIG. 9, on a first side 108a of the adjunct 108, a layer of coating B1 seals the regions 111a, 113a and the region 111b. A layer of a coating A1 is disposed over the entire first side 108a and covers the layers of the coating B1. On a second, opposite side 108b of the adjunct 108, a layer of the coating B1 seals the region 109a and another layer of the coating B1 seals the region 109b. A layer of a coating C1 seals the region 113a on the second side 108b. Similar to the first side 108a, the entire second side 108b is covered by the coating A1.

In this example, the coatings A1, B1, C1 have different degradation or absorption rates such that the coating A1 begins to absorb first, upon a delivery of the adjunct to tissue, the coating B1 absorbs after the coating A1 is at least partially absorbed, and the coating C1 is not absorbable. The coating A1 can be selected such that it absorbs substantially immediately after the delivery of the adjunct to tissue or at some later time. The coating A1 can be absorbed before the coating B1 because the coating A1 is disposed on the surface of the adjunct and is therefore more accessible to water and/or other agents at a treatment side. Other properties of the coating A1 can contribute to its absorption rate additionally or alternatively.

Because of the different absorption characteristics of the coating used, the coating A1 absorbs so as to release the first medicant 110 from the regions 109a, 109b at the first side 108a and to release the second medicant 112 from the regions 111a, 111b at the second side 108b, as shown in FIG. 10. As also shown in FIG. 10, the layers of the coating B1 remain associated with the adjunct 108. As shown in FIG. 11, after the first medicant 110 is released at the first side 108a and the second medicant 112 is released at the second side 108b, the coating B1 absorbs so as to release the third medicant 114 from the region 113a at the first side 108a. In this way, different medicants can be delivered at appropriate times to desired locations in tissue being treated. It should be appreciated that an adjunct can have any suitable pattern of regions releasably retaining various medicants to create a desired healing process/profile.

In some aspects, alternatively or in addition to using various coatings, an adjunct can be in a form of a fiber lattice having regions with different absorption characteristics. For example, each of the regions can be in the form of fiber lattices having different absorption rates. A medicant associated with a fiber lattice can be released as the fiber lattice disintegrates. Because of the heterogeneous degradation of absorbable polymers forming the adjunct, the adjunct can be configured such that one or more medicants associated therewith can release in various spatial and temporal patterns. The medicant can be incorporated into pellets having a dissolvable coating (e.g., like a gobstopper) such that, as the coating is disintegrated, the medicant can be distributed as a bolus dose or as a time release dosage.

Figure 12:
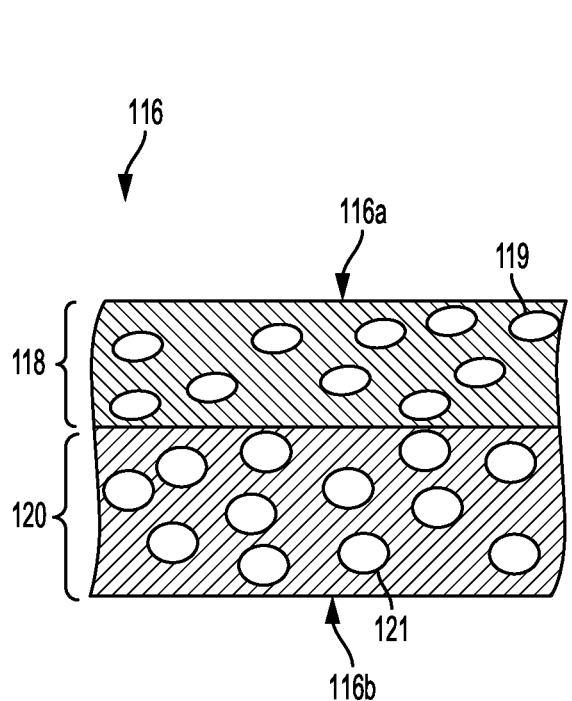
FIG. 12 is a graphical representation of an adjunct material including top and bottom layers of an absorbable polymer having different degradation rates.
Figure 13:
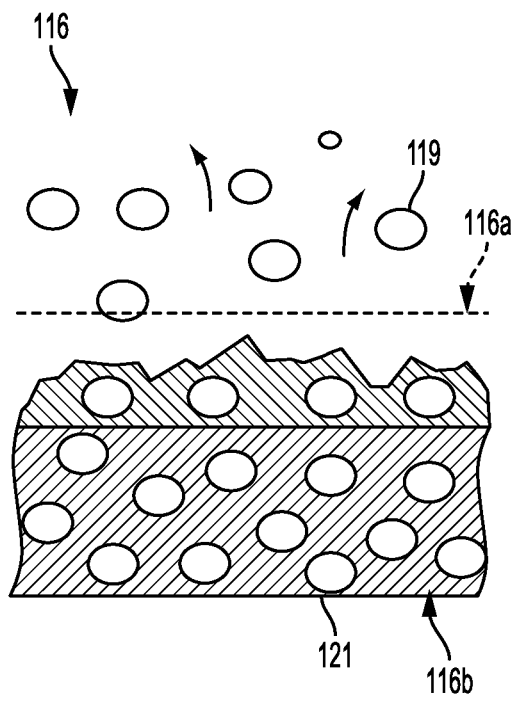
FIG. 13 is a graphical representation of the adjunct material of FIG. 12, showing a top layer partially degraded.
Figure 14:
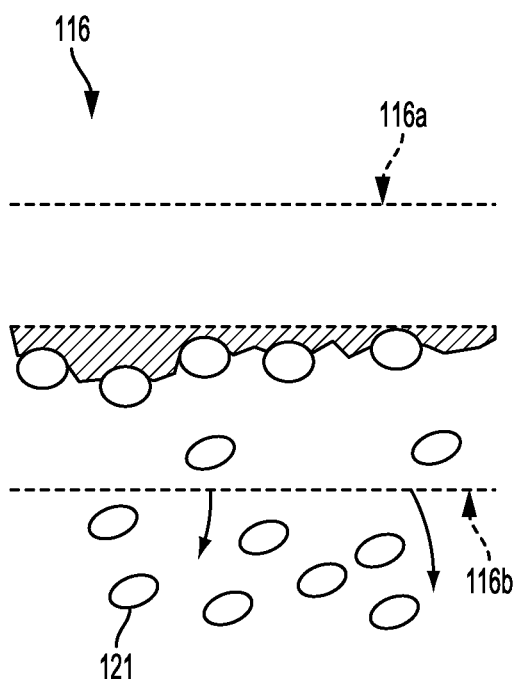
FIG. 14 is a graphical representation of the adjunct material of FIG. 12, showing a bottom layer partially degraded after the top layer has been degraded.

FIG. 12 through FIG. 14 illustrate an adjunct 116 having first (top) and second (bottom) layers 118, 120 formed from absorbable polymers having different degradation rates. For example, the first layer 118 can be a low molecular weight absorbable polymer that absorbs during a first time period after the adjunct 116 is delivered to tissue and the second layer 120 can be a high molecular weight absorbable polymer that absorbs during a second time period after the first time period is completed. The first and second layers 118, 120 can be formed from different polymers or from the same type of polymer that is treated so as to form layers or other structures having different degradation properties.

In the example of FIG. 12 through FIG. 14, the first layer 118 has a first medicant 119 present therein, and the second layer 120 has second medicant 121 present therein. It should be appreciated, however, that each of the first and second layers 118, 120 can include more than one type of different medicant. The medicants can be retained in association with the first and second layers 118, 120 in a number of suitable ways. The first medicant 119 can be released first due to absorption of the first layer 118, as shown in FIG. 13 where the first layer 118 is shown partially disintegrated such that the pellets containing the first medicant 119 are being released. As shown, the first layer 118 begins to absorb from its surface that is more accessible to water and other agents than portions of the first layer 118 removed farther from the surface. After the first layer 118 has been entirely or partially absorbed, the second layer 120 can commence to disintegrate from its surface so as to release pellets harboring the second medicant 121, as shown in FIG. 14 where the second layer 120 is shown partially disintegrated and the pellets containing the second medicant 121 are being released from the adjunct 116.

In some aspects, an adjunct releasably retaining one or more medicants can be configured such that one or more regions of the adjunct disintegrate due to effects of temperature, pH, light, or other environmental factors so as to release the medicant(s). Alternatively, the adjunct can break under the strain exerted upon one or more of its portions.

Figure 16:
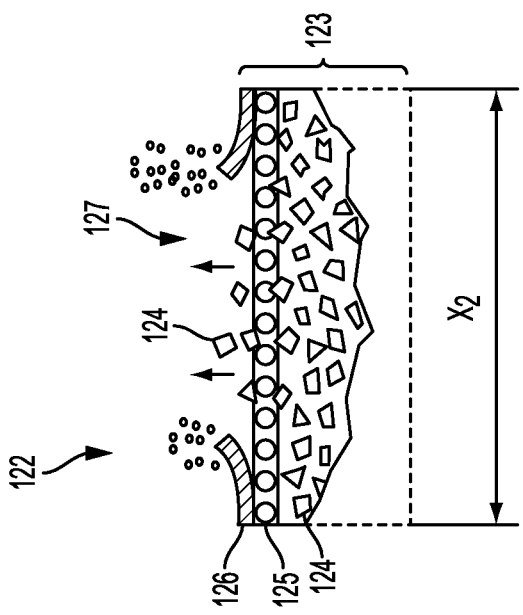
FIG. 16 is a graphical representation of the adjunct material of FIG. 15, showing the at least one medicant partially released from the adjunct material in response to at least one environmental condition.
Figure 17:
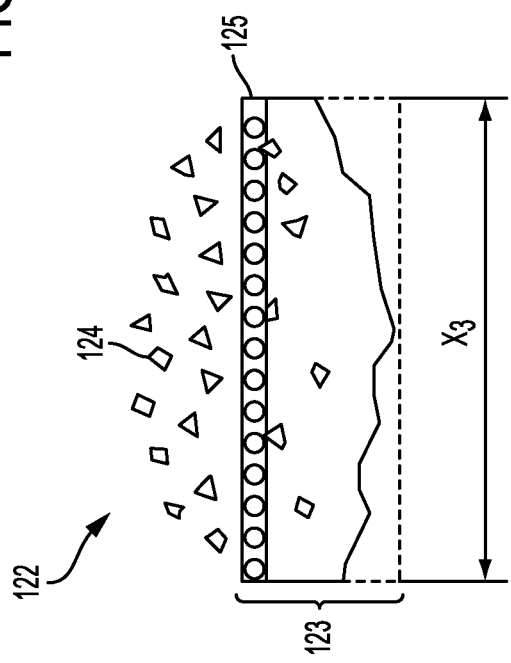
FIG. 17 is another graphical representation of the adjunct material of FIG. 15, showing the at least one medicant substantially entirely released from the adjunct material in response to at least one environmental condition.
Figure 15:
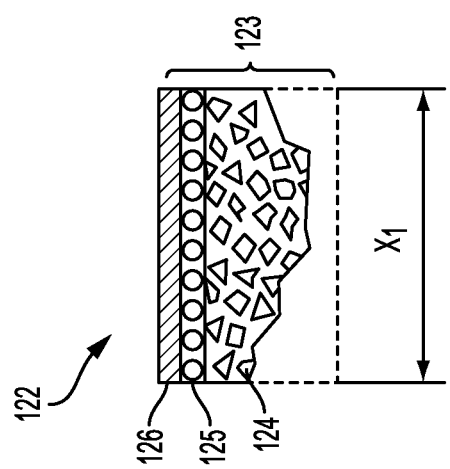
FIG. 15 is a graphical representation of an adjunct material configured to release at least one medicant in response to at least one environmental condition.

FIG. 15 through FIG. 17 illustrate an adjunct 122 having a body 123 retaining a medicant 124, a porous layer 125 disposed over the body 123, and an absorbable outer film layer 126 disposed over the porous layer 125. The medicant 124 can be in the form of pellets (e.g., solid micro-capsules or micro-beads or other vessels) releasably carrying one or more medicants.

In the example illustrated, in its original configuration, the adjunct 122 has a first width X1, as shown in FIG. 15. In such configuration, the outer film layer 126 restrains the porous layer 125 and pores in the porous layer 125 have a size that does not allow the medicant 124 to escape the adjunct 122. However, when the adjunct 122 is delivered to tissue and the outer film layer 126 thus becomes exposed to pH, temperature, various agents, and/or other environmental conditions at the treatment site, the absorbable outer film layer 126 can begin to disintegrate, as shown by a tear or opening 127 in the film layer 126 in FIG. 16. Additionally or alternatively, the outer film layer 126 can break upon strain due to deployment of staples or other mechanical strain on the adjunct 122.

Regardless of the specific factors that result in disintegration or breaking of the outer film layer 126, the adjunct 122 can swell or otherwise alter its conformation such that its width increases from the original width X1 to a larger width X2. As also shown in FIG. 15, the size of the pores of porous layer 125 increases, allowing the pores' content, the pellets carrying the medicant 124, to pass through the enlarged pores and to be thus released from the adjunct 122.

A period of time during which the adjunct body 123 expands and the pellets with the medicant 124 are released can vary based on an absorption rate of the outer film 126, properties of the adjunct body 123, characteristics of the environment to which the adjunct 122 is delivered, and other factors. After a certain time period, the outer film layer 126 can disintegrate and the adjunct 122 can expand further to have a width X3 such that the entirety or substantially the entirety of the medicant 124 becomes released from the body 123 to deliver appropriate therapy or achieve the desired effect, as shown in FIG. 17. The adjunct 122 can be formed from at least one absorbable polymer (e.g., gelatin, cellulose, etc.) that regulates dispersion of the vessels. Thus, the adjunct 122 can act as a space filler that creates a temporary seal at a treatment site and is then dissolved to be subsequently replaced with tissue.

Figure 18:
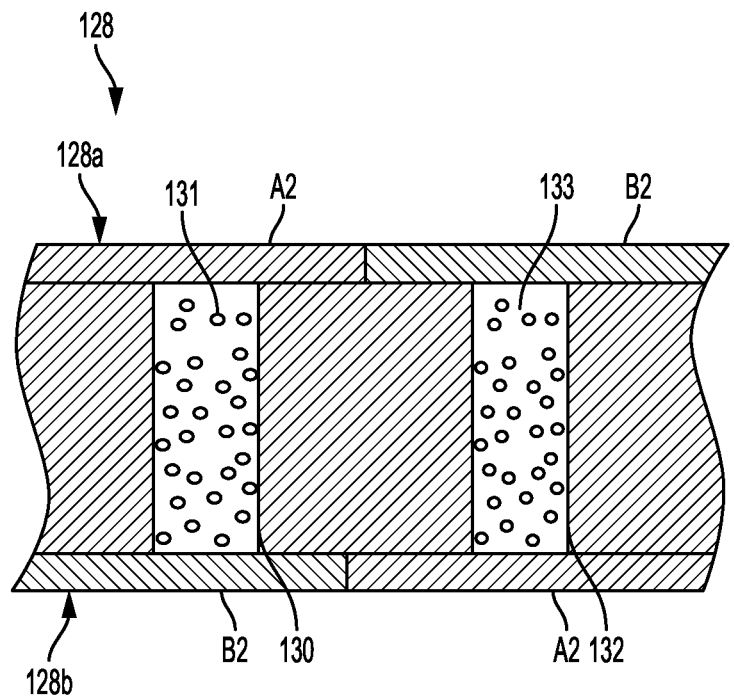
FIG. 18 is a graphical representation of an adjunct material configured to release at least one medicant by changing its conformation.
Figure 19:
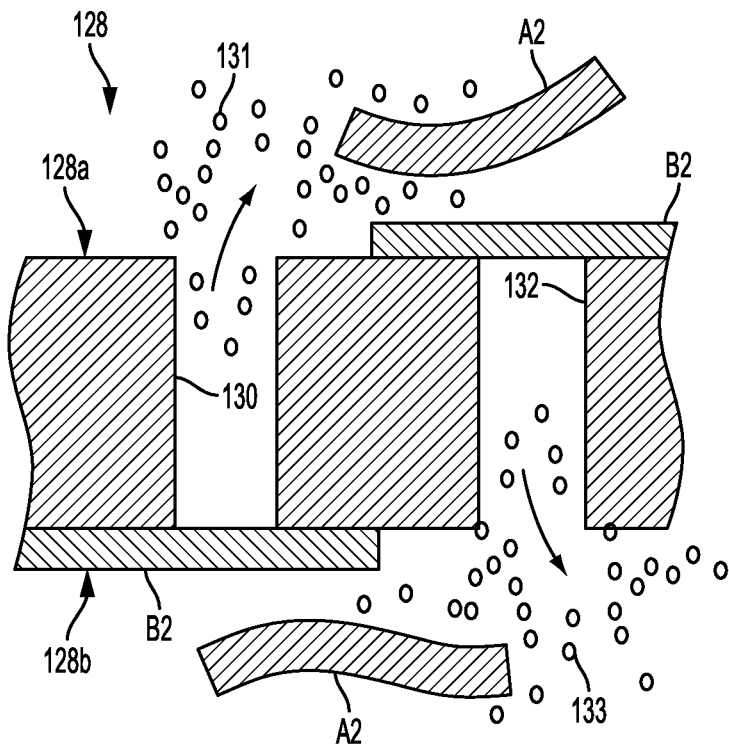
FIG. 19 is a graphical representation of the adjunct material of FIG. 18, showing the adjunct material with its conformation changes and the at least one medicant partially released.

FIG. 18 and FIG. 19 illustrate another example of an adjunct 128 releasably retaining different medicants and configured to release the medicants in a non-homogeneous manner. The adjunct 128 can be configured to release the medicants due the effects of temperature, pH, various agents, and/or other environmental factors upon the adjunct 128. The adjunct 128 can change a conformation of one or more of its portions in response to the environmental factors. As shown in FIG. 18, the adjunct 128 can have multiple regions or reservoirs two of which, first and second reservoirs 130, 132 carrying first and second medicants 131, 133, respectively, are shown. The reservoirs 130, 132 can be in the form of tubes, cavities, holes, or any other structures. The first reservoir 130 is sealed by a first coating A2 at a first side 128a of the adjunct 128 and by a second coating B2 at a second side 128b of the adjunct 128. The second reservoir 131 is sealed by the second coating B2 at the first side 128a and by the first coating A2 at the second side 128. In this example, the first and second coatings A2, B2 are selected such that the first coating A2 and its properties and/or configuration can be altered by the effects of temperature, pH, active agents, and/or other factors and thus open a reservoir that it seals. For example, the first coating A2 can swell, soften, or otherwise become altered.

Accordingly, as shown in FIG. 19, upon the delivery of the adjunct 128 to a treatment site, the first coating A2 can change its configuration such that it no longer seals the reservoir 130 at the first side 128a of the adjunct 128 and it no longer seals the reservoir 132 at the second side 128b of the adjunct 128. As a result, the first and second medicants 131, 133 are released at the first and second sides 128a, 128b of the adjunct, respectively, as also shown in FIG. 19. The second coating B2 remains in place at least until the entirety of the medicants are released into desired tissue locations, such preventing the release of the medicants.

In some aspects, the adjunct can be in the form of fibers or other structural components associated with one or more viscous fluid components (e.g., vessels) retaining the medicant. The viscous component can be in a dry form (e.g., in a freeze-dried powder form) and it can re-hydrate upon deployment of the adjunct. As the viscous component rehydrates, it can open and thus release a medicant. Additionally or alternatively, the vessel retaining the medicant can be disrupted by strain such as, for example, mechanical breaking imposed thereon by the staples or other means.

Figure 20:
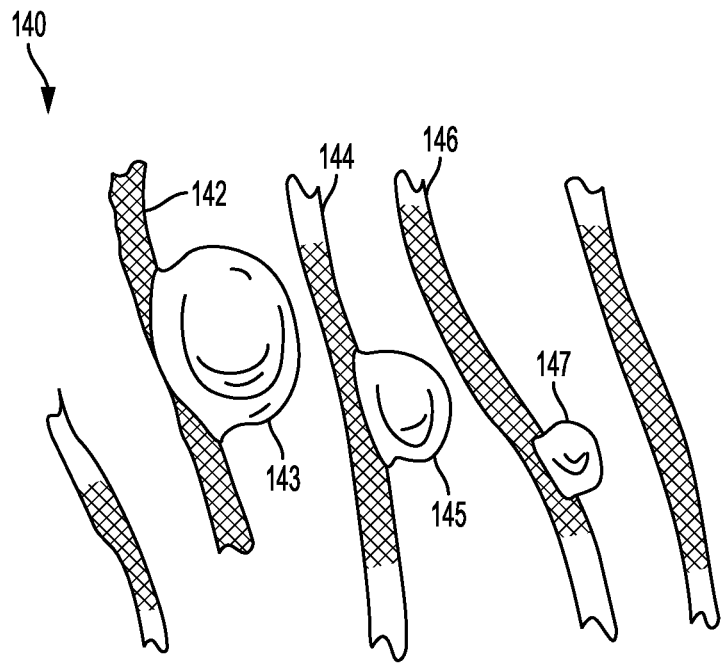
FIG. 20 is a graphical representation of an adjunct material including multiple fibers associated with vessels having at least one medicant disposed therein.
Figure 21:
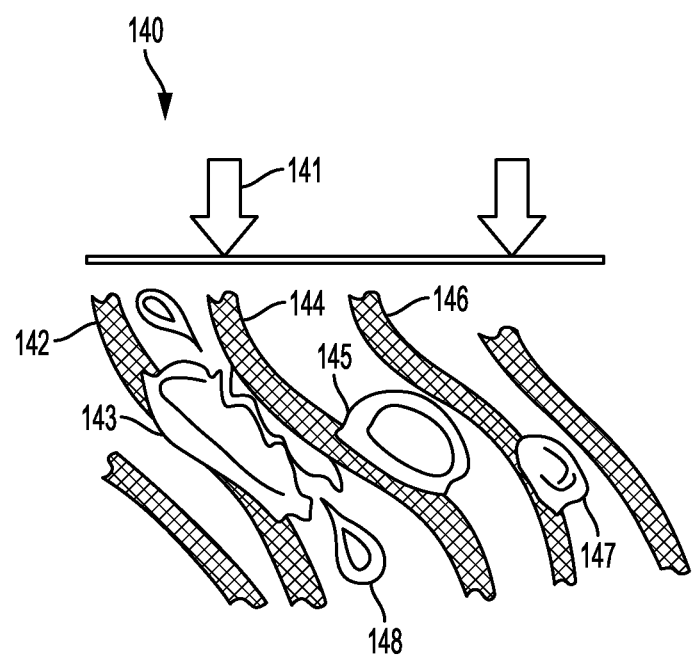
FIG. 21 is a graphical representation of the adjunct material of FIG. 20, showing the at least one medicant released from the adjunct material under the effect of strain.

FIG. 20 and FIG. 21 illustrate an adjunct 140 in the form of multiple fibers, three of which are denoted by way of example as fibers 142, 144, 146. As shown, each of the fibers 142, 144, 146 is associated with a respective one of vessels 143, 145, 147 retaining a medicant. The vessels 143, 145, 147 can retain the same or different medicants. In the illustrated example, the vessels 143, 145, 147 are in the form of irregularly shaped rounded beads having different sizes, however they can be shaped in any other manner and can have various sizes. The vessels can be applied to the fibers as a powder or they can be bonded, anchored to, or otherwise associated with the fiber strands. The vessels can remain associated with the fibers or they can be released from the fibers to thus deliver a desired treatment using the adjunct.

As shown in FIG. 21, when strain is applied to the adjunct 140, which is schematically shown by arrows 141, the fibers can deform and vessels can break and release the medicant incorporated therein. The magnitude of the strain can control rates of release of the medicants. For example, as shown in FIG. 21, the vessel 143 is broken and a medicant 148 is being released. In some aspects, the vessels can be broken at different times, depending on their size and/or other properties. In this example, the vessel 143 can be broken first to release the medicant 148 retained therein, as shown in FIG. 21, after which the smaller vessel 145 and then even smaller vessel 147 can break thus releasing respective medicants at different times (not shown). However, depending on the applied pressure and other factors, one or more vessels can break simultaneously. Furthermore, as mentioned above, the vessels 143, 145, 147 can absorb at different times so as to release the respective medicants at different times.

Figure 22:
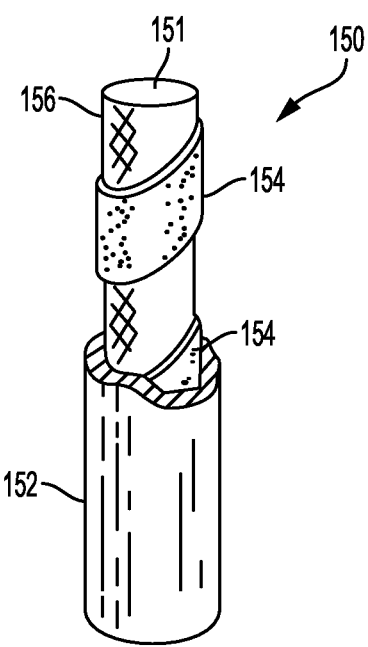
FIG. 22 is a graphical representation of an adjunct material configured to release at least one medicant in response to strain applied to the adjunct material.

In some aspects, an adjunct can have various surface textures of its fibers and it can release one or more medicants in various ways to influence or control re-growth of tissue. The adjunct can be delivered by staples carrying the adjunct thereon such that the medicants release when the staple is deformed upon staple deployment. For example, FIG. 22 illustrates an adjunct 150 having an outer layer or coating 152 encapsulating an inner layer 154 disposed over a staple 151 of a surgical device used to deliver the adjunct 150. However, in some aspects, rather than being disposed over a staple, the adjunct 150 can be disposed over a fiber lattice which can be folded into a tubular or other shape.

Figure 23:
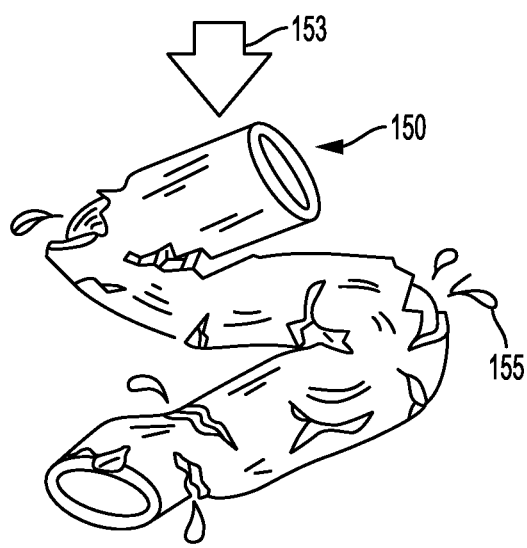
FIG. 23 is a graphical representation of the adjunct material of FIG. 22, showing the at least one medicant being released in response to strain applied to the adjunct material.

A first medicant can be retained between the outer coating 152 and the inner layer 154, and a second medicant can be incorporated into the inner layer 154. The inner layer 154 can be in the form of a flexible mesh wound over the fiber 156. When strain is applied to the adjunct 150 (e.g., when the staple 151 is deformed), as schematically shown by an arrow 153 in FIG. 23, the outer coating 152 can be caused to also deform and rupture. Upon the rupture of the outer coating 152, the first medicant retained between the outer coating 152 and the inner layer 154 can release (155) the first medicant as a bolus dose. The second medicant incorporated into the inner layer 154 can commence its release as a timed release after the first medicant is released or during the time when the first medicant is released. The release of the second medicant to tissue can be regulated by the release of the first medicant. The second medicant can alternatively be released at a bolus dose. It should be appreciated that the adjunct 150 can include one medicant disposed within the inner layer 154 that can release as a bolus dose.

Figure 24:
FIG. 24 is a graphical representation of a vessel having at least one medicant encapsulated therein.
Figure 25:
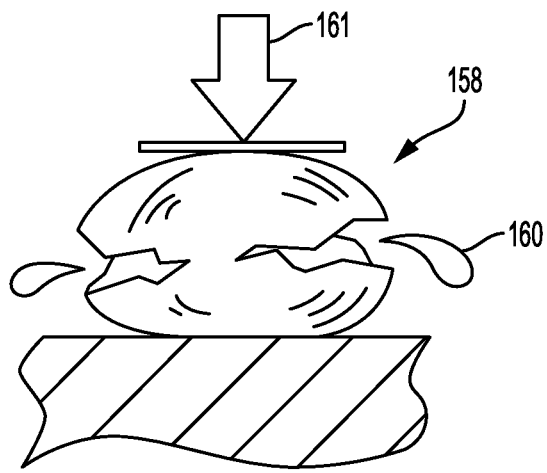
FIG. 25 is a graphical representation of the vessel of FIG. 24, showing the at least one medicant being released in response to strain applied to the vessel.

As mentioned above, an effective amount of at least one medicant disposed within or associated with an adjunct can be retained within distinct vessels carried by the adjunct. The vessels can be disposed within one or more regions of the adjunct or otherwise associated therewith. FIG. 24 and FIG. 25 illustrate an example of a vessel 158 in the form of a pellet or capsule having an outer coating 159 encapsulating therewithin at least one medicant 160. In this example, the vessel 158 has a spherical shape and resembles a gobstopper. However, it should be appreciated that the vessel can have any other shape. Furthermore, in some exemplary implementations, the outer coating 159 can encapsulate an inner region including at least one bioabsorbable polymer having at least one medicant incorporated therein. The vessels 158 can include multiple layers having different degradation rates and releasably retaining therein one or more medicants. Each of the layers can retain a different medicant, or two or more of the layers can carry the same medicant.

When a strain is applied to the vessel 158 as schematically shown by an arrow 161 in FIG. 25, the outer coating 159 can break or rupture such that its contents in the form of the at least one medicant 160 are released. Additionally or alternatively, the outer coating 159 can absorb, dissolve or otherwise disintegrate upon exposure of the vessel 158 to one or more environmental conditions such that the at least one medicant 160 is released from the vessel 158.

Figure 26:
FIG. 26 is a graphical representation of an adjunct material configured to release at least one medicant when the adjunct material changes its conformation.
Figure 27:
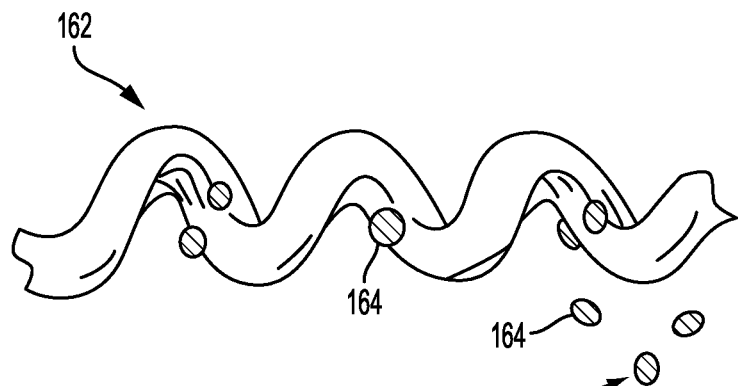
FIG. 27 is a graphical representation of the adjunct material of FIG. 26, showing the at least one medicant being released in response a change in the conformation of the adjunct material.

FIG. 26 and FIG. 27 illustrate an example of an adjunct 162 in the form of a fiber lattice having a certain conformation that is changeable, such as by the action of water and/or other agents that the adjunct is subjected to at the treatment site. As shown in FIG. 26, the adjunct 162 having a shape of a tightly wound spiral can retain therein one or more vessels carrying a medicant 164. The medicant 164 can be retained in association with the adjunct 162 by being held tightly by fibers of the adjunct. For example, the medicant can include a multilayered medicant/absorbable polymer structure where an outermost one of the layers includes an absorbable polymer that can be bound to the fibers of the adjunct, e.g., bonding of one absorbable polymer to another absorbable polymer, as will be appreciated by a person skilled in the art.

When the adjunct 162 is delivered at the treatment site, the wound fibers thereof can swell and increase in length, or elongate, such that the distances between the fibers increase and the adjunct 162 "unwinds" and releases the medicant 164 "trapped" within the adjunct 162, as shown in FIG. 27. The fibers of the adjunct 162 can unwind such that the entire adjunct 162 adopts a different conformation, like in the example of FIG. 26 and FIG. 27. However, in some aspects, the fibers of the adjunct can begin to unwind or fray from an end or other surface of the adjunct.

Figure 28:
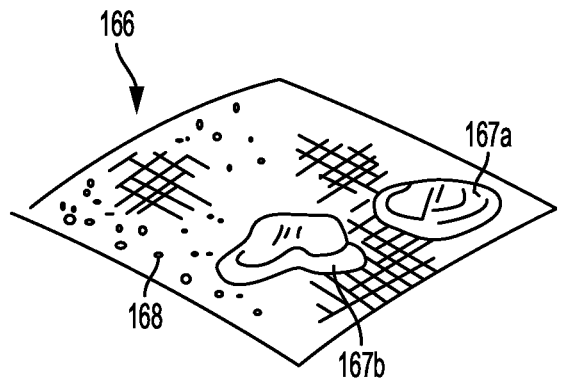
FIG. 28 is another graphical representation of an adjunct material configured to release at least one medicant when the adjunct material changes its conformation.
Figure 29:
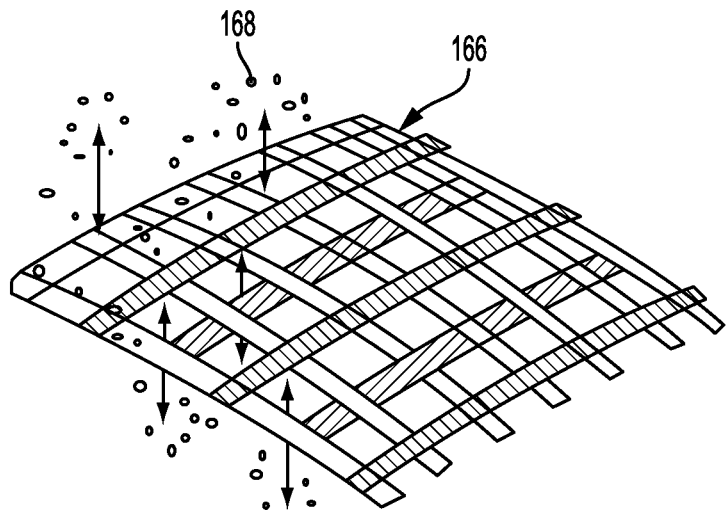
FIG. 29 is a graphical representation of the adjunct material of FIG. 28, showing the at least one medicant being released in response a change in the conformation of the adjunct material.

FIG. 28 and FIG. 29 illustrate another example of an adjunct 166 having a medicant 168 releasably retained therein. In this example, the adjunct 166 is in the form of a sheet-like fiber woven mesh. As shown in FIG. 28, the tight fibers of the adjunct 166 in its original configuration allow the medicant 168 to be retained therein. When the adjunct 166 is delivered at the treatment site, water and/or other agents, shown schematically as drops 167a, 167b in FIG. 28, can cause the fibers to swell and elongate such that the distances between the fibers increase, as shown in FIG. 29. In this way, the medicant 168 is released, as also shown in FIG. 29. A person skilled in the art will appreciate that the adjunct 166 can be formed from different types of fibers. The fibers can have different absorption rates, density, direction, patterns, size, and other properties that are selected so as to provide desired tissue re-growth. While some regions of the adjunct can be configured to release at least one medicant so as to encourage tissue re-growth, one or more regions of the adjunct can be configured to release at least one medicant so as to discourage tissue re-growth.

In aspects in which at least one medicant is disposed within a vessel formed from a bioabsorbable polymer coating encapsulating the medicant, the medicant can be configured to be released from the vessel at certain time based on various factors. The factors can include, for example, a degradation rate of the bioabsorbable polymer, a volume of the vessel, a surface area of the vessel, environmental conditions in a physiological environment surrounding the vessel and responsiveness of the bioabsorbable polymer to such conditions, a number of layers of the bioabsorbable polymer, a concentration of the medicant, and a type of association between the medicant and the bioabsorbable polymer.

FIG. 30 illustrates an example of first and second vessels 170, 172 that can be associated with a schematically shown adjunct 171. In this example, the first and second vessels 170, 172 are in the form of spherical beads. However, other types of vessels can be used additionally or alternatively such that the adjunct 171 can include one or more different types of vessels carrying different types of medicants. The first and second vessels 170, 172 have absorbable polymer outer coatings A3, B3 that have different degradation rates which therefore control release of first and second medicants D1, D2 encapsulated within the coatings A3, B3 in different manners. A degradation rate of the outer coating A3 can be higher than a degradation rate of the outer coating B3. Thus, the first medicant D1 is released from the first vessel 170 before the second medicant D2 is released from the second vessel 172. For example, the first medicant D1 can be an inflammatory agent that is released within 1-2 days after the adjunct 171 is delivered to a treatment site. The second medicant D2 can be an anti-inflammatory agent that is released within 3-5 days after the delivery of the adjunct 171. In this way, the release of the medicants D1, D2 from the first and second vessels 170, 172 can provide a desired effect on tissue in-growth.

A vessel having at least one medicant encapsulated therein can have multiple medicants associated therewith in a number of different ways. FIG. 31 illustrates an example of a vessel 174 in a form of a sphere having multiple concentric layers each carrying a respective at least one medicant. In this example, as shown in FIG. 31, the vessel 174 has, from the outside to the inside, four distinct layers E1, E2, E3, E4 having first, second, third, and fourth medicants F1, F2, F3, F4, respectively. Each of the layers E1, E2, E3, E4 can have different degradation rate, thickness, density, responsiveness to environmental conditions, and other properties that control release of the medicants disposed therein. For example, the outermost first layer E1 can be configured to degrade first such the medicant is released first, and the other layers E2, E3, E4 can be configured to degrade such that an outer layer degrades before an inner layer does.

As each layer degrades, a respective medicant incorporated therein is released. It should be appreciated that the layers can be selected such that at least one inner layer can start to degrade after only a portion of at least one outer layer has been degraded. The medicants F1, F2, F3, F4 disposed within the multi-layer vessel 174 can be different or at least some of the medicants can be the same. The medicants can be released as a bolus dose or in other manners. For example, the first medicant F1 disposed within the first layer E1 can be released as a bolus dose substantially immediately upon delivery of an adjunct retaining the vessel 174 to tissue. Release of the second medicant F2 disposed within the second layer E2 can be regulated by the release of the first medicant F1.

A spatial distribution of medicants in an adjunct can vary depending on a type of the medicants and a desired effect on tissue in-growth. Targeted delivery of the medicants can be accomplished in a number of ways. For example, an adjunct can be configured to release one or more medicants in a heterogeneous manner such that various medicants can be delivered to tissue at different times, to facilitate desired healing. Different portions of the adjunct can be formed from different materials or form the same material treated so as to have different absorption rates.

FIG. 32 illustrates an adjunct 176 in the form of a laminate including heterogeneous portions or layers having different degradation rates and incorporating different medicants. As shown, the adjunct 176 has a top layer or portion 178 and a bottom layer or portion 180 that have different degradation rates. Furthermore, each of the top and bottom portions 178, 180 can have various portions having degradation rates that vary in a distinct or continuous manner. The degradation rates can vary across the adjunct in a number of suitable ways that depend on a desired treatment effect to be provided by the adjunct.

In the example of FIG. 32, the top portion 178 of the adjunct 176 has two portions 178a, 178b having different degradation rates. The bottom portion 180 has two portions 180a, 180b having different degradation rates. Each of the portions can include a different medicant such that, as a portion degrades, a respective medicant is eluted or released. The degradation rates and distribution of the medicants within one or more of the portions 178a, 178b, 180a, 180b can further vary in a distinct or continuous manner such that the adjunct 176 can provide an elution profile shown in a graph 177 in FIG. 32. As shown, a central area 182 of the adjunct 176 centered around a mid-portion 179 thereof has an increased elution rate of one or more medicants that peaks at the mid-portion 179, whereas smaller amount of the medicant(s) is eluted from opposite sides of the adjunct 176 along its length L. The increased elution rate can be due to properties of the adjunct 176 at the central area 182 and the concentration of the medicants.

As further shown in FIG. 32, the adjunct 176 is configured to release medicants in different elution profiles along the length L thereof and along a width W thereof. For example, the medicants can be released along the width W as a bolus dose and along the length as a time-release dose. Release of one or more of the medicants can regulate release of at least one other of the medicants. However, the medicants can be released in any other manner, depending on a desired treatment to be delivered.

Figure 33:
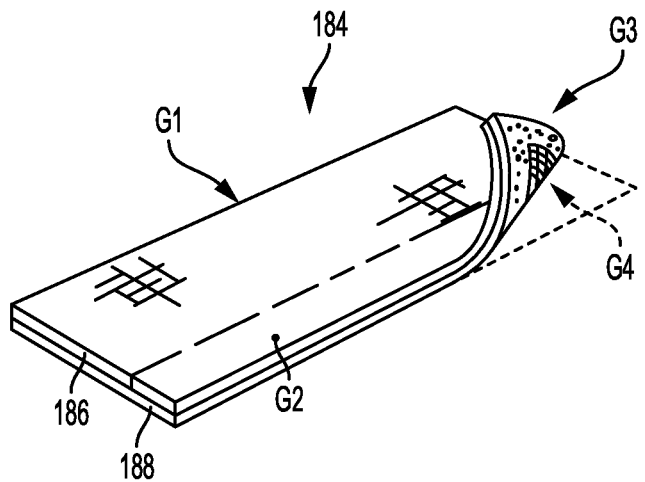
FIG. 33 is another graphical representation of an adjunct material having different portions configured to release at least one medicant in a non-homogeneous manner.
Figure 34:
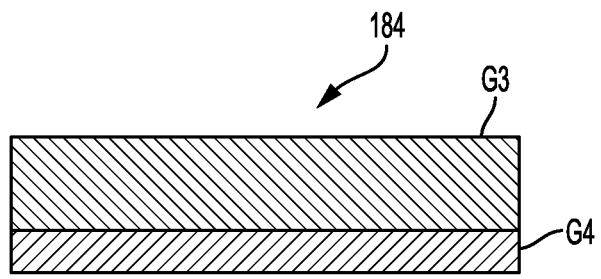
FIG. 34 is a graphical representation of a side view of the adjunct material of FIG. 33.

FIG. 33 illustrates another example of an adjunct 184 having top and bottom layers or portions 186, 188. Similar to the adjunct 176 in FIG. 32, each of the top and bottom portions 186, 188 of the adjunct 184 can have different medicants disposed therein. Thus, as shown in FIG. 33, the top portion 186 can have first and second medicants G1 and G2, at respective portions thereof. The bottom portion 188 can have third and fourth medicants G3 and G4 at respective portions thereof disposed such that the third medicant G3 is in a portion disposed over a portion carrying the fourth medicant G4, as also shown in FIG. 34.

Figure 35:
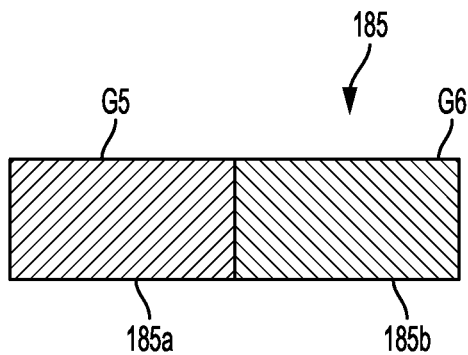
FIG. 35 is a graphical representation of a side view of an adjunct material having different portions configured to release at least one medicant in a non-homogeneous manner.
Figure 36:
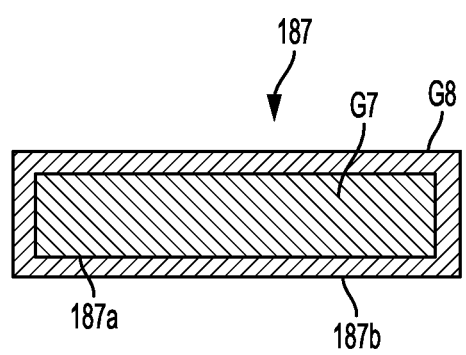
FIG. 36 is another graphical representation of a side view of an adjunct material having different portions configured to release at least one medicant in a non-homogeneous manner.

FIG. 35 illustrates an example of a portion of an adjunct 185 that can be similar to adjunct 176 (FIG. 32) or adjunct 184 (FIG. 33). As shown in FIG. 35, the adjunct 185 can have side-to-side portions 185a, 185b having different medicants G5, G6 disposed therein. FIG. 36 illustrates another example of a portion of an adjunct 187 having an inner portion 187a and an outer portion 187b having different medicants G7, G8 disposed therein.

In some aspects, elution rates of at least one medicant from an adjunct having one or more distinct portions formed from at least one bioabsorbable polymer can depend on a position of the portions within the adjunct, a degradation rate of the at least one bioabsorbable polymer, responsiveness of the at least one bioabsorbable polymer to environmental conditions, and an overall configuration of the adjunct.

Figure 37:
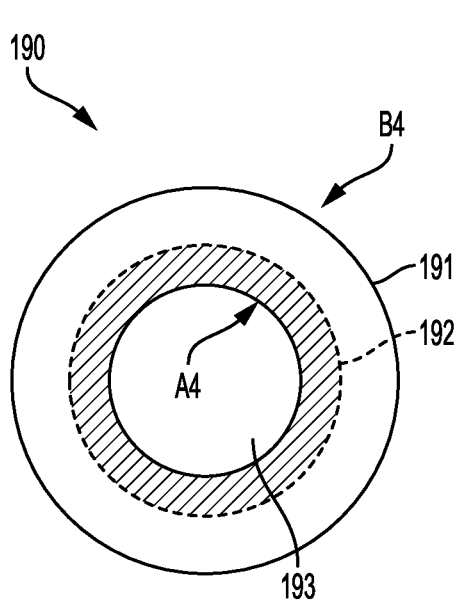
FIG. 37 is a graphical representation of an adjunct material having different concentric regions configured to release at least one medicant at different rates.

FIG. 37 illustrates an example of an adjunct 190 in a form of a cylinder that has outer and inner concentric layers 191, 192 which can be formed from different types of absorbable polymer and can have different thickness and other properties. The outer and inner layers 191, 192 can have different medicants B4, A4 disposed therein and that can be released from the respective layers 191, 192 at different times and at different rates. In this example, an innermost cavity 193 lined by the inner layer 192 can be empty. The medicant A4 can be configured to commence to release before the medicant B4 is released. It should be appreciated that, in some aspects, the outer and inner layers 191, 192 can be disposed over a fiber.

Figure 38:
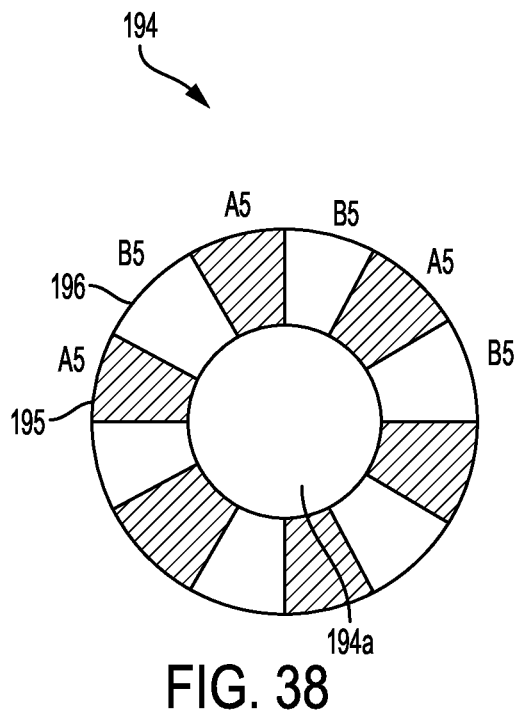
FIG. 38 is a graphical representation of an adjunct material having different radial regions configured to release at least one medicant at different rates.

FIG. 38 illustrates an example of a tubular adjunct 194 that has multiple radial portions formed from different types of absorbable polymer. As shown, the adjunct 194 has an inner cavity 194a having the radial portions disposed concentrically therearound. In the example illustrated, the portions can be formed from first and second types of polymer in an alternating manner, as shown by portions 195, 196 in FIG. 38 formed from the first and second polymers, respectively. The portion 195 formed from the first polymer has a medicant A5 disposed therein, the portion 197 formed from the second polymer has a medicant B5 disposed therein, and other portions formed from the first and second polymers have the medicants A5, B5 disposed therein in the same alternating manner, as shown in FIG. 38. Similar to the examples before, the medicants A5, B5 can be released from the respective layers at different times and at different rates. For example, the medicant A5 can be configured to commence to release before the medicant B5 is released.

Figure 39:
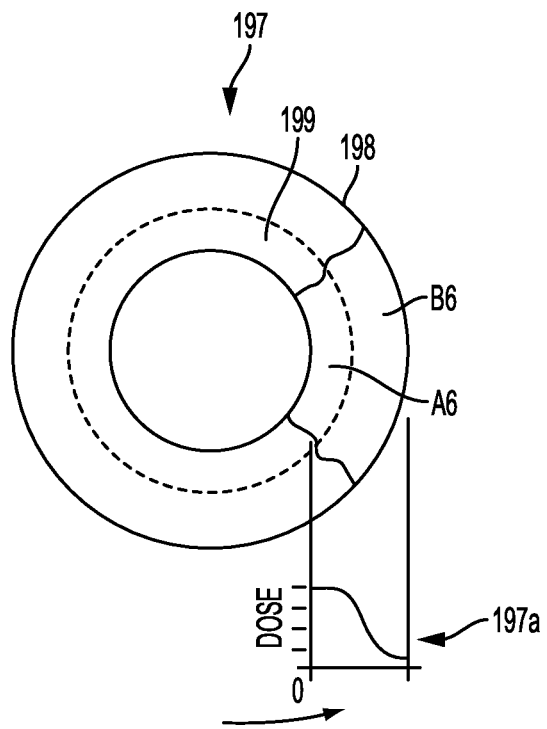
FIG. 39 is another graphical representation of an adjunct material having different concentric regions configured to release at least one medicant at different rates.

FIG. 39 illustrates an example of a tubular adjunct 197 similar to adjunct 190 (FIG. 37). As shown in FIG. 39, the adjunct 197 has outer and inner concentric layers 198, 199 which can be formed from different types of absorbable polymer and can have different thickness and other properties. The outer and inner layers 198, 199 can have different medicants B6, A6 disposed therein and that can be released from the respective layers 198, 199 at different times and at different rates. For example, as shown in a graph 197a in FIG. 39, the medicant A6 can release before the medicant B6 is released. Furthermore, the medicant A6 can release at a higher dosage than the medicant B6, as also shown in the graph 197a.

In at least some implementations, a staple cartridge can include a lubricant (e.g., sodium stearate or other lubricant) applied thereto that includes at least one medicant (e.g., LAE, Doxycycline, and/or other antimicrobial agent) releasable therefrom. The lubricant can be applied to the staple cartridge as a spray and can coat the cartridge and the staples releasably disposed therein. The lubricant including one or more medicants may allow the medicant(s) to be applied to the staples. In this way, the medicant(s) may be delivered to a targeted area (e.g., along a staple line defined by the staples) where the medicant(s) may be best able to facilitate wound healing, as discussed herein. The lubricant including one or more medicants can be used with an adjunct including one or more medicants, which may facilitate targeted wound healing.

Wound Healing

During performance of a surgical procedure, tissue of a patient can be wounded (e.g., cut, torn, punctured, etc.) in any of a variety of ways. The wounding may be an intended aspect of the surgical procedure, such as in an anastomosis procedure and/or when tissue is cut and fastened using a surgical device such as a surgical stapler. The wounded tissue typically heals over time in generally the same way for all patients.

Wound healing is traditionally considered to include four stages: hemostasis, inflammation, proliferation, and remodeling. The hemostasis stage generally involves blood clotting, e.g., stopping bleeding. In general, damaged blood vessels constrict to slow blood flow, platelets aggregate to help seal the wound site, the platelets activate fibrin to further facilitate wound sealing, and a blood clot forms at the wound site. The inflammation stage generally involves cleaning of the wound site. In general, the immune system provides a response to the threat of possible infection at the wound site via signaling to defensive immune cells such as neutrophils and macrophages. The proliferation stage generally involves rebuilding tissue with tissue growth and angiogenesis (blood vessel growth). In general, fibroblasts arrive at the wound site, the fibroblasts lay down collagen, the fibroblasts release growth factors that attract epithelial cells, and the epithelial cells attract endothelial cells. The remodeling stage, also referred to as a maturation stage, generally involves strengthening scar tissue at the wound site. In general, collagen fibers align and crosslink, and the scar matures to eventually fade away. Each of these four stages is discussed further below.

While each of wound healing's four stages involves a different aspect of the healing process, stages typically overlap with one another. Namely, each of the last three stages typically overlaps with its preceding stage, e.g., inflammation overlaps with hemostasis, proliferation overlaps with inflammation, and remodeling overlaps with proliferation. The speed at which the transition between stages occurs generally affects the speed of overall wound healing and thus generally affects patient recovery time, chances of complications arising, and/or patient comfort. Similarly, the length of each of the four individual stages generally affects the speed of overall wound healing and the patient's general recovery. In general, the slower the wound healing process, and in particular the longer it takes to begin the remodeling stage, the more likely that the wound will become infected, cause the patient discomfort, become a chronic wound, cause an ulcer, and/or develop pathological scarring.

The hemostasis stage generally begins within minutes of the initial injury, unless there are underlying clotting disorders, in which case hemostasis may be delayed. The hemostasis stage typically lasts for 30 to 60 minutes before the inflammation stage begins (e.g., before neutrophils arrive, as discussed below) and typically ends hours after the injury, e.g., 2 to 6 hours post-injury. Poor hemostatic control that results in a longer hemostasis stage can lead to increased bleeding and tissue damage. Additionally, a prolonged hemostasis stage can result in additional scar formation that delays the proliferation and remodeling stages.

In the hemostasis stage, injured blood vessels at the wound site are sealed. The blood vessels constrict in response to injury, e.g., in response to being cut, but this spasm ultimately relaxes. Blood platelets secrete vasoconstrictive substances to aid in this process. The platelets also form a stable clot sealing the damaged vessels. Under the influence of adenosine diphosphate (ADP) leaking from the damaged tissue at the wound site, the blood platelets aggregate and adhere to exposed collagen. The blood platelets secrete factors, which interact with and stimulate an intrinsic clotting cascade through the production of thrombin, which in turn initiates the formation of fibrin from fibrinogen. The clotting cascade occurs to achieve hemostasis, or stop blood loss by way of a fibrin clot. More particularly, the fibrin forms a mesh that strengthens the platelet aggregate into a stable hemostatic plug or clot, thereby reducing and/or preventing bleeding. The mesh serves as a scaffold for invading cells, such as neutrophils, macrophages, fibroblasts, and endothelial cells, during the inflammation and proliferation stages. Additionally, the platelets secrete various soluble factors, such as chemokines, cytokines, and platelet-derived growth factor (PDGF). This secretion generally initiates the inflammation stage of wound healing, as the soluble factors attract cells that phagocytize material (e.g., debris, microorganisms such as bacteria, and damaged tissue).

The clotting cascade occurs in the hemostasis stage just before the inflammatory stage begins. The inflammation stage typically begins within an hour of the injury and typically lasts for 2 to 6 days but can last even longer, e.g., up to 10 days. The longer the inflammation stage, the more likely that additional scarring will occur, thereby delaying the proliferation and remodeling stages. During the inflammation stage, the wounded tissue can show various signs of inflammation, such as erythema, heat, edema, pain, and functional disturbance. These signs can last for most or all of the inflammation stage. Accordingly, the longer the inflammation stage, the longer the tissue experiences these adverse effects of inflammation, which in turn can prolong patient discomfort and/or prolong the period of time in which the patient is particularly susceptible to infection. The adverse effects of inflammation can be severe enough in some patients to cause death. Inflammation must occur during proper wound healing, however, and its adverse effects tolerated in order for the final stages of wound healing to commence.

In the inflammation stage, the cells attracted by the soluble factors secreted in the hemostasis stage phagocytize material. Namely, immune cells including phagocytic cells, neutrophils, and macrophages destroy material in an effort to help prevent infection. The arrival of neutrophils generally signals the start of the inflammation stage. Neutrophils typically arrive at the wound site within an hour of wounding. The neutrophils are able to phagocytize debris and microorganisms and provide a first line of defense against infection. They are aided by local mast cells. Fibrin is broken down, and the degradation products attract macrophages. Macrophages typically appear 1 to 2 days post-injury. The macrophages are able to phagocytize bacteria and provide a second line of defense against infection. The macrophages secrete a variety of chemotactic factors and growth factors such as fibroblast growth factor (FGF), epidermal growth factor (EGF), transforming growth factor beta (TGF-β), and interleukin-1 (IL-1), which are traditionally recognized as directing the subsequent proliferation and remodeling stages. In other words, the macrophages release angiogenic substances to help begin the proliferation stage to stimulate capillary growth and granulation, thereby setting the stage for the remodeling stage. Lymphocytes (e.g., T lymphocytes) attracted to the wound site typically appear at the wound site after the macrophages appear.

The proliferation stage typically begins 2 to 5 days post-injury and typically lasts for 2 to 21 days. In the proliferation stage, the macrophages' secretion induces the proliferation of fibroblasts. The fibroblasts enter the wound site and form an extracellular matrix (ECM) by excreting collagen and fibronectin. The wound is thus "rebuilt" with new granulation tissue that includes the collagen and the ECM into which a new network of blood vessels develop, a process traditionally known as angiogenesis. The collagen increases the strength of the wound. Accordingly, the sooner collagen can be produced, e.g., the sooner that fibroblasts enter the wound area, the sooner the wound can gain strength and thereby be less likely to cause any number of problems such as infection and patient discomfort.

Concurrent with the ECM formation, epithelial cells (e.g., keratinocytes) migrate from the wound's edge to cover the wound and form a barrier between the wound and its environment. In other words, the epithelial cells resurface the wound, in a process traditionally known as epithelialization. The epithelial cells migrate over the granulation tissue but underneath the scab on the wound (if a scar was earlier formed). The epithelial cells must dissolve the clot, debris, and parts of the ECM in order to properly migrate over the wound. To facilitate their migration, the epithelial cells secrete a plasminogen activator, which activates plasminogen, turning it into plasmin to dissolve the clot, debris, and parts of the ECM. Additionally, since cells can only migrate over living tissue, the epithelial cells excrete collagenases and proteases such as matrix metalloproteinases (MMPs) to dissolve damaged parts of the ECM in their migrational path. In the final phase of epithelialization, contraction of the wound occurs as the fibroblasts differentiate into myofibroblasts to form the protective outer layer, or stratum corneum. Contraction can last for days or several weeks and continues even after the wound is completely reepithelialized. Contraction is the main cause of scarring associated with wound healing.

The remodeling stage generally begins when the levels of collagen production and degradation equalize. In other words, remodeling generally begins once a scar has formed and the tensile strength of the wound has begun to increase. The remodeling stage typically begins 7 to 21 days post-injury and typically lasts for at least 3 weeks and can last for months or years depending on factors such as wound size and re-injury.

In the remodeling stage, the wound matures to become stronger, e.g., to have increased tensile strength. In general, weaker type III collagen, which is common at the wound site in the proliferation stage, is replaced by stronger type I collagen. This replacement generally involves reorganizing, crosslinking, and aligning the temporary collagen fibers. As remodeling progresses, the scar disappears.

Figure 40:
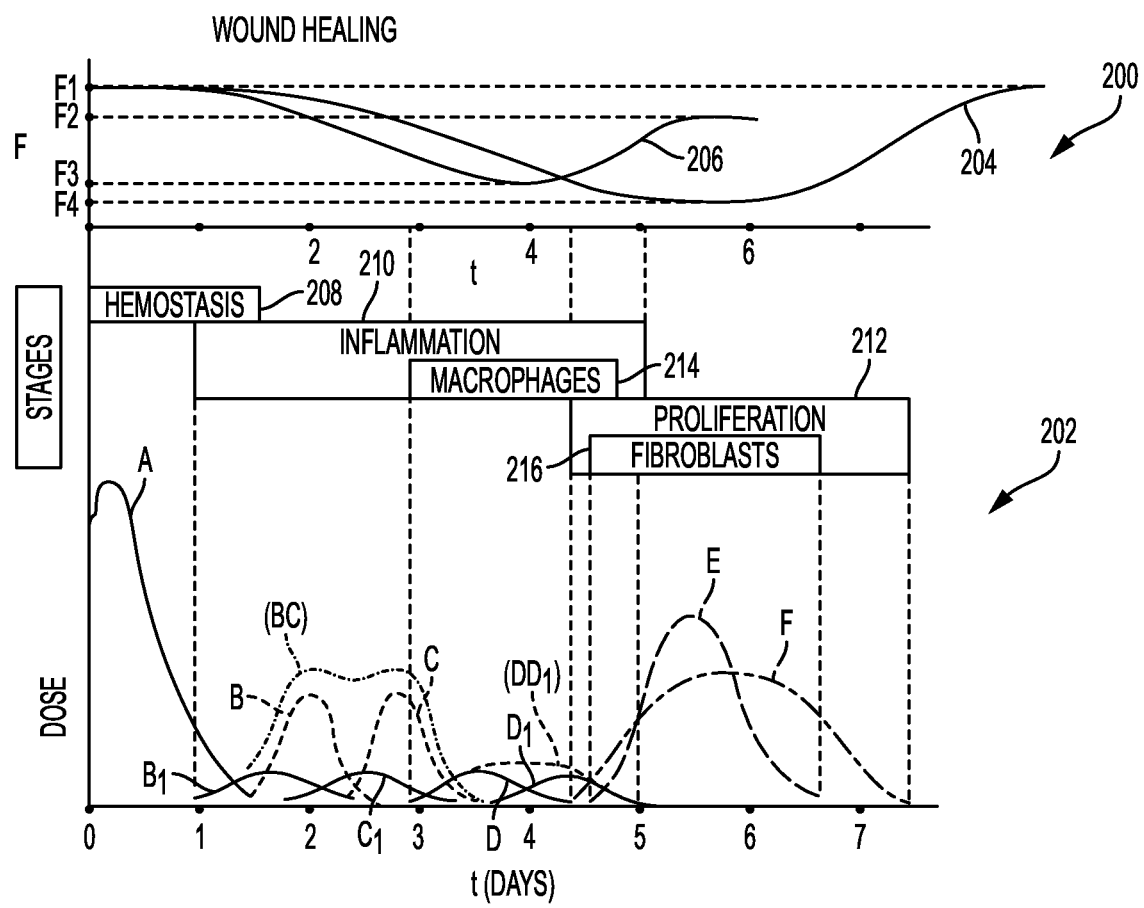
FIG. 40 is a graphical representation of an embodiment of wound healing over time with doses of medicants.

FIG. 40 illustrates a depiction of wound healing over time. An upper portion of FIG. 40 shows a first wound healing graph 200 of tissue strength (tensile force F) versus time (t). A lower portion of FIG. 40 shows a second wound healing graph 202 of medicant dose amount versus time (t). The first and second graphs 200, 202 are plotted with a shared horizontal axis to facilitate comparison of data shown in the first and second graphs 200, 202. Time zero (t=0) in the first and second graphs 200, 202 represents a time of injury, e.g., when a wound occurs. A first tissue strength F1 in the first graph 200 thus represents the tissue's strength at the wound at the time of injury.

The first graph 200 includes a first curve 204 of tissue strength over time during typical wound healing, and includes a second curve 206 of tissue strength over time during accelerated wound healing in accordance with at least some methods, systems, and devices provided herein. The second curve 206 of accelerated wound healing can be achieved using one or more doses of medicants provided in the second graph 202, as discussed further below. Stages of wound healing (a hemostasis stage 208, an inflammation stage 210, and a proliferation stage 212) are shown in FIG. 40 with reference to the second graph 202, and hence also to the second curve 206 of the first graph 200. The first curve 204 in the first graph 200 has a different timing of hemostasis, inflammation, and proliferation stages, as discussed below.

The time scale in FIG. 40 is an example only. As discussed above, the timing of wound healing can vary, e.g., the stages of wound healing can begin at different times for different wounds and/or for different patients. FIG. 40 demonstrates that for the same wound in the same patient, the wound's typical healing, as illustrated by the first curve 204, is improved when one or more medicants are dosed to the patient in accordance with the second graph 202, as illustrated by the second curve 206. In other words, regardless of the time scale of the horizontal axis of the first and second graphs 200, 202, the dosing of one or more medicants may provide for faster wound healing than typical wound healing and may provide a shorter period of minimum tissue tensile strength than typical wound healing.

As demonstrated by the first curve 204, typical wound healing involves the tissue having the first tissue strength F1 at time zero and decreasing in strength over time to a minimum tissue strength F4 that begins during day four (5>t>4) during an inflammation stage and persists until sometime during day six (7>t>6) before tissue strength begins to gradually improve back toward the first tissue strength F1. The first tissue strength F1 can be re-achieved during typical wound healing, as shown by the first curve 204, at some point during or after a proliferation stage. The tissue's strength begins to decrease from the first tissue strength F1 in response to inflammation, e.g., in response to entry into the inflammation stage, during day one (2>t>1) and continues decreasing toward and/or remains at its lowest level F4 until inflammation of the tissue begins to subside, e.g., until the proliferation stage begins, during day six. The tissue is thus decreasing in strength and is at its most vulnerable to succumb to any number of inflammation's adverse effects for a relatively long period of time that starts during day one and lasts into day six.

As demonstrated by the second curve 206, accelerated wound healing in accordance with at least some embodiments of the methods, systems, and devices provided herein involves the tissue having the first tissue strength F1 at time zero and decreasing in strength over time to a minimum tissue strength F3 that begins during day three (4>t>3) during the inflammation stage 210 and persists until sometime during day four (5>t>4) before tissue strength begins to gradually improve back toward the first tissue strength F1. The minimum tissue strength F3 in the accelerated wound healing is greater than the minimum tissue strength F4 in the typical wound healing. The tissue experiencing the accelerated wound healing thus never has strength as low as that during typical wound healing. In other words, the accelerated wound healing allows for less tissue weakening than typical wound healing. The tissue's strength begins to decrease from the first tissue strength F1 in response to inflammation, e.g., in response to entry into the inflammation stage 210, during day one (2>t>1) and continues decreasing toward and/or remains at its lowest level F3 until inflammation begins to improve, e.g., until the proliferation stage 212 begins, during day four. The tissue is thus decreasing in strength and is at its most vulnerable to succumb to any number of inflammation's adverse effects sooner and for a shorter period of time than typical wound healing, i.e., starting during day one and lasting into day four instead of starting during day one and lasting into day six. In other words, the accelerated wound healing can provide for a shorter inflammation stage than typical wound healing. The tissue's strength may not increase back to its pre-wound tissue strength F1 after the inflammation stage 210 in the accelerated healing but can increase to a level close thereto, as shown by the second curve 206 reaching a new maximum tissue strength F2 during the proliferation stage 212.

Figure 41:
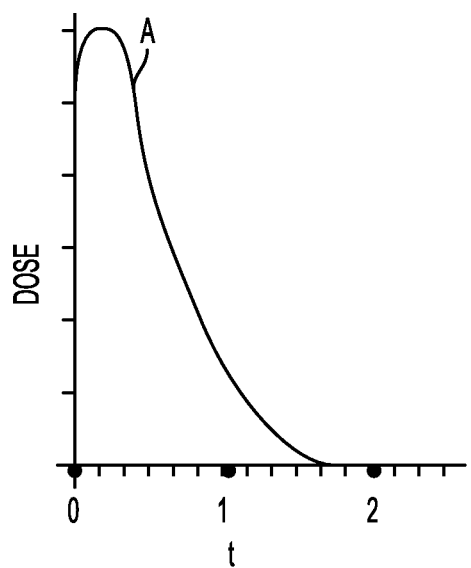
FIG. 41 is a graphical representation of a hemostatic stage in the wound healing of FIG. 40.
Figure 42:
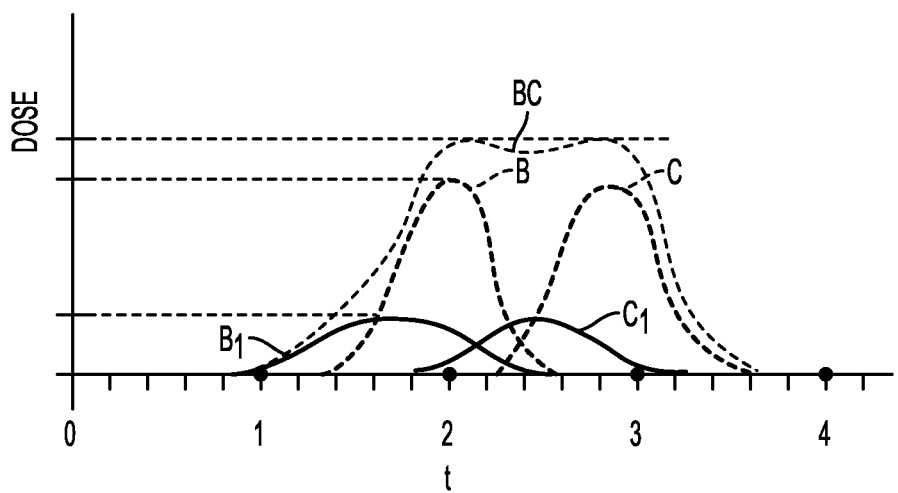
FIG. 42 is a graphical representation of a portion of an inflammation stage in the wound healing of FIG. 40.
Figure 43:
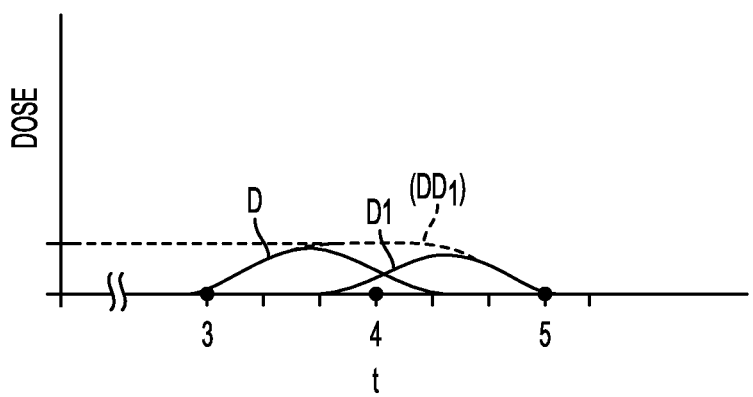
FIG. 43 is a graphical representation of another portion of the inflammation stage in the wound healing of FIG. 40.
Figure 44:
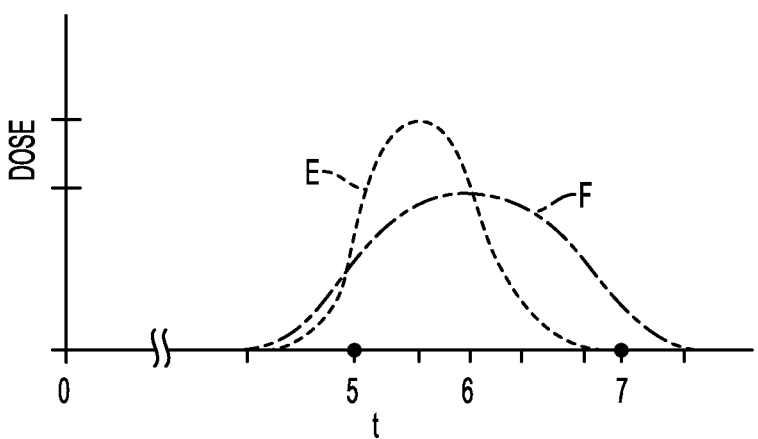
FIG. 44 is a graphical representation of a proliferation stage in the wound healing of FIG. 40.

The second graph 202 illustrates an example of doses of medicants that can be administered to the patient to achieve the accelerated wound healing indicated by the second curve 206. The doses of medicants can include a dose of medicant A configured to facilitate hemostasis in the hemostasis stage 208 as also shown in FIG. 41; doses of medicant B, medicant $B_1$, medicant C, and medicant $C_1$ configured to facilitate inflammation in the inflammation stage 210 as also shown in FIG. 42; doses of medicant D and medicant $D_1$ configured to inhibit MMPs during a macrophages phase 214 of the inflammation stage 210 (e.g., during a time when macrophages are present and active at the wound site in the inflammation stage 210) as also shown in FIG. 43; a dose of medicant E configured to prevent inflammation in the proliferation stage 212 during a fibroblasts phase 216 of the proliferation stage 212 (e.g., during a time when fibroblasts are present and active at the wound site in the proliferation stage 212) as also shown in FIG. 44; and a dose of medicant F configured to facilitate tissue growth in the proliferation stage 212 during a fibroblasts phase 216 of the proliferation stage 212 (e.g., during a time when fibroblasts are present and active at the wound site in the proliferation stage 212) as also shown in FIG. 44. Each of the medicants A, B, $B_1$, C, $C_1$, D, $D_1$, E, F is discussed further below.

In one example, at least one medicant can be administered to tissue during each of the hemostasis, inflammation, and proliferation stages 208, 210, 212 of the wound healing to overall improve the wound healing process with all of the medicants shown in the second graph 202 being administered, e.g., the medicant A in the hemostasis stage 208, the medicants B, $B_1$, C, $C_1$, D, $D_1$ in the inflammation stage 210, and the medicants E, F in the proliferation stage 212. In another example, at least one medicant can be administered to tissue during each of the hemostasis, inflammation, and proliferation stages 208, 210, 212 of the wound healing to overall improve the wound healing process without all of the medicants shown in the second graph 202 being administered, e.g., the medicant A in the hemostasis stage 208, at least one of the medicants B, $B_1$, C, $C_1$, D, $D_1$ in the inflammation stage 210 (and in a further example, at least two of the medicants B, $B_1$, C, $C_1$, D, $D_1$), and one or both of the medicants E, F in the proliferation stage 212. The subset of the medicants A, B, $B_1$, C, $C_1$, D, $D_1$, E, F administered can be determined on a case-by-case basis based on any one or more factors such as wound type, wound size, surgeon preference, available medicants at a time of surgery, patient medical history, etc. In yet another example, at least one medicant can be administered to tissue during only one or two of the hemostasis, inflammation, and proliferation stages 208, 210, 212 to improve select stages of the wound healing process (with an improvement in one stage being able to improve subsequent stage(s) of the wound healing process, as discussed above) without all of the medicants shown in the second graph 202 being administered. Further, the medicants can be administered in the selected one or two stages as shown in the second graph 202 (e.g., the medicant A in the hemostasis stage, the medicants B, $B_1$, C, $C_1$, D, $D_1$ in the inflammation stage 210, the medicants E, F in the proliferation stage 212) or can be selectively administered in the selected one or two stages (e.g., the medicant A in the hemostasis stage 208, at least one of the medicants B, $B_1$, C, $C_1$, D, $D_1$ in the inflammation stage 210 (and in a further example, at least two of the medicants B, $B_1$, C, $C_1$, D, $D_1$), one or both of the medicants E, F in the proliferation stage 212). The one or two of the stages 208, 210, 212 in which medicant doses are administered can be determined on a case-by-case basis based on any one or more factors such as wound type, wound size, surgeon preference, available medicants at a time of surgery, patient medical history, etc.

As discussed herein, an adjunct material including one or more medicants releasable therefrom can be delivered to tissue, e.g., using a surgical stapler. The adjunct material's one or more medicants can include each of the medicants A, B, $B_1$, C, $C_1$, D, $D_1$, E, F being administered, whether it be all of the medicants A, B, $B_1$, C, $C_1$, D, $D_1$, E, F or a subset thereof. The administered ones of the medicants A, B, $B_1$, C, $C_1$, D, $D_1$, E, F can thus be delivered to the patient concurrent with a time of the injury (t=0). As discussed herein, the adjunct material's medicants can be releasable therefrom in a variety of ways. The timing of the release can allow the medicants to be administered to tissue at the appropriate time in the wound healing process, as also discussed herein. The medicants A, B, $B_1$, C, $C_1$, D, $D_1$, E, F (or the selected subset thereof) can thus be simultaneously delivered to the patient but can be released to the patient's tissue at different times and over time to achieve the desired effects.

The medicant A configured to facilitate hemostasis can have a variety of configurations. In general, the medicant A can include a hemostatic agent configured to promote hemostasis. The administration of the medicant A may thus help stop bleeding and help shorten a length of the hemostasis stage 208 and, accordingly, help the inflammation stage 210 begin sooner than in typical wound healing. Examples of the medicant A include fibrin and thrombin. Also, examples of hemostatic agents configured to promote hemostasis and delivery thereof are described in U.S. Pat. Pub. No. 2013/0149343 entitled "Hemostatic Bioabsorbable Device with Polyethylene Glycol Binder" filed Dec. 13, 2011, U.S. Pat. No. 8,383,147 entitled "Reinforced Absorbable Synthetic Matrix For Hemostatic Applications" filed Aug. 22, 2012, and U.S. Pat. No. 8,329,211 entitled "Reinforced Absorbable Multi-Layered Fabric For Hemostatic Applications" filed May 17, 2010, which are hereby incorporated by reference in their entireties.

The medicant A can be administered in a variety of ways. In one example, the medicant A can be administered from a vessel. The vessel can include a bioabsorbable or dissolvable coating, e.g., a saccharide coating, etc., surrounding the medicant A. The coating can be configured to bioabsorb/dissolve relatively quickly so as to be administered to the wounded tissue within minutes of the injury, e.g., within minutes of t=0. The medicant A's hemostatic effects can thus begin prior to the start of the inflammation stage 210. As shown in FIG. 40 and FIG. 41, the dose of the medicant A can decrease over time as the agent dissipates in the tissue/the patient's body.

The medicants B, $B_1$, C, $C_1$ configured to facilitate inflammation can each have a variety of configurations. In general, the medicants B, $B_1$, C, $C_1$ can each include an inflammatory agent configured to promote inflammation. The medicants B, $B_1$, C, $C_1$ may thus help speed up the inflammatory process and, accordingly, help shorten the inflammation stage 210 as compared to typical wound healing, help the proliferation stage 212 begin sooner than in typical wound healing, help the tissue reach its minimum strength F3 sooner than when the minimum strength F4 is reached in typical wound healing, and help shorten a period of time at which the tissue is at its minimum strength F3 as compared to typical wound healing. Examples of the medicants B, $B_1$, C, $C_1$ include pro-inflammatory medicants. In some aspects, the medicants B, $B_1$, C, $C_1$ can each include the same agent. In other aspects, the medicants B, $B_1$ can each include the same agent, and the medicants C, $C_1$ can each include the same agent as each other that is a different agent than the medicants B, $B_1$. In still other aspects, the medicants B, $B_1$, C, $C_1$ can each include a different agent from one another.

The medicants B, $B_1$, C, $C_1$ can each be administered in a variety of ways. In one example, the medicant B can be administered as a vessel with the medicant $B_1$ being a coating of the medicant B vessel, and the medicant C can be administered as another vessel with the medicant $C_1$ being a coating of the medicant C vessel. The dosages of the vessel medicants B, C can be greater than the dosages of the coating medicants $B_1$, $C_1$, as shown in FIG. 40 and FIG. 42, as vessel coatings typically include less substance than the vessel that they surround.

In one example, the medicant $B_1$ can be configured to begin release prior to the medicant B, which can be configured to begin release prior to the medicant $C_1$, which can be configured to begin release prior to the medicant C. The inflammatory medicants B, $B_1$, C, $C_1$ can thus be configured to be stagger-released with each medicants' dose peaking at a different time (e.g., at a different point along the time t axis of the second graph 202). The different peak dosages of the inflammatory medicants B, $B_1$, C, $C_1$ can allow the medicants B, $B_1$, C, $C_1$ to have a cumulative inflammatory dose, shown as "BC" in FIG. 40 and FIG. 42, greater than any of their individual doses. In other words, the peak dosages of the individual medicants B, $B_1$, C, $C_1$ can be timed to contribute to an overall inflammatory dose "BC" greater than can be achieved individually with their doses. The inflammatory dose "BC" can generally have the shape of a square wave, as also shown in FIG. 40 and FIG. 42.

The inflammatory medicants B, $B_1$, C, $C_1$ can be configured to each begin release prior to the release of the other medicants effective in the inflammation stage 210, the medicants D, $D_1$ configured to inhibit MMPs. In this way, the tissue at the wound site can be allowed to be inflamed and approach its minimum tensile strength F3 a short time before day three (t=3), at which time the macrophage phase 214 of the inflammation stage 210 generally begins and during which the medicants D, $D_1$ can be administered.

The medicants D, $D_1$ configured to inhibit MMPs can each have a variety of configurations. In general, the medicants D, $D_1$ can each include an agent configured to inhibit MMP, e.g., an MMP inhibitor. The medicants D, $D_1$ can thus help less MMP be released in the inflammation stage 210, thereby allowing less of the ECM to be destroyed in the inflammation stage 210. The tissue at the wound site may thus be less torn down while still allowing the inflammatory process and, accordingly, allow the tissue to have more strength than in the typical wound healing process, e.g., F3>F4. Examples of the medicants D, $D_1$ include tissue matrix degradation inhibitors that inhibit the action of MMPs and other proteases. In one example, the medicants D, $D_1$ each include the same agent, but the medicants D, $D_1$ can differ from one another in at least some examples.

The medicants D, $D_1$ can each be administered in a variety of ways. In one example, each of the medicants D, $D_1$ can be administered via vessel. Each of the two vessels can include a coating configured to facilitate release of the medicants D, $D_1$ at the appropriate time in the wound healing process, e.g., at a time after release of the inflammatory medicants B, $B_1$, C, $C_1$, such as sometime 4 to 7 days after the injury (4<t<7). Examples of the coating include a copolymer having 90% polyglycolide (also referred to as polyglycolic acid (PGA)) and 10% polylactide (also referred to as polyactic acid (PCA)), such as Vicryl™ Rapide.

In one example, the medicant D can be configured to begin release prior to the medicant $D_1$. The MMP-inhibiting medicants D, $D_1$ can thus be configured to be stagger-released with each medicants' dose peaking at a different time (e.g., at a different point along the time t axis of the second graph 202). The different peak dosages of the MMP-inhibiting medicants D, $D_1$ can allow the medicants D, $D_1$ to have a cumulative MMP-inhibiting dose, shown as "$DD_1$" in FIG. 40 and FIG. 43, greater than their individual doses. In other words, the peak dosages of the individual medicants D, $D_1$ can be timed to contribute to an overall MMP-inhibiting dose "$DD_1$" greater than can be achieved individually with their doses.

The MMP-inhibiting medicants D, $D_1$ can be configured to each begin release prior to the release of the medicants E, F. In this way, the tissue at the wound site can be allowed to be inflamed and endure its minimum tensile strength F3 before the proliferation stage 212 begins sometime during day four.

The medicant E configured to prevent inflammation can have a variety of configurations. In general, the medicant E can include an agent configured to inhibit inflammation, e.g., an anti-inflammatory agent. The medicant E can thus be configured to help reduce inflammation at the wound site and, accordingly, help end the inflammation stage 210. Examples of the medicant E include diclofenac.

The medicant E can be administered in a variety of ways. In one example, the medicant E can be administered as a vessel. The vessel can include a coating configured to facilitate release of the medicant E at the appropriate time in the wound healing process, e.g., at a time after release of the MMP-inhibiting medicants D, $D_1$, such as at least 4 days after the injury (4<t), e.g., sometime 7 to 10 days after the injury (7<t<10). Examples of the coating include a copolymer having 90% PGA and 10% PCA and having a high molecular weight, e.g., a higher molecular weight than the coating used for the MMP-inhibiting medicants D, $D_1$ so as to be released thereafter.

The medicant F configured to facilitate tissue growth can have a variety of configurations. In general, the medicant F can include an agent configured to promote tissue growth, e.g., a growth factor. The medicant F can thus be configured to help the tissue rebuild in the proliferation stage 212. Examples of the medicant F include TGF-β.

The medicant F can be administered in a variety of ways. In one example, the medicant F can be administered as a vessel. The vessel can include a coating configured to facilitate release of the medicant F at the appropriate time in the wound healing process, e.g., at a time after release of the anti-inflammatory medicant E, such as at least 5 days after the injury (5<t), e.g., sometime 5 to 10 days after the injury (5<t<10). Examples of the coating include a copolymer having 65% PGA and 35% PCA.

Implementations

Various exemplary adjunct materials to promote tissue growth are described herein. In general, an implantable adjunct can be configured to be applied to tissue by a surgical stapler in conjunction with staples. The adjunct can have one or more medicants releasably retained therein that are effective to provide a desired effect on tissue in-growth in a predetermined manner One or more characteristics associated with the adjunct can be altered between various implementations to promote organized tissue remodeling in a desired manner during wound healing, such as by encouraging tissue growth to be in a certain direction and/or by discouraging tissue growth in a certain area and/or on a certain structure. The characteristics associated with the adjunct include construction of the adjunct (e.g., spacing of fibers forming the adjunct (e.g., density of the fibers), orientation of fibers forming the adjunct, thickness or diameter of fibers forming the adjunct, material of fibers forming the adjunct, elasticity of fibers forming the adjunct, and charge of fibers forming the adjunct), locations of where the one or more medicants are disposed within the adjunct (e.g., on a certain side of the adjunct, and within a certain region of the adjunct), and functionality of the one or more medicants (e.g., the desired effects of the medicant(s) on tissue in-growth, medicant elution rate, medicant dose amount, and medicant type). Depending on the characteristics of a particular adjunct, the adjunct can be configured to promote organized tissue remodeling, the one or more medicants can be configured to promote organized tissue remodeling, or both the adjunct and the one or more medicants can be configured to promote organized tissue remodeling.

The selection of particular characteristics associated with an adjunct may optimize effectiveness of the adjunct and the one or more medicants releasably retained therein during the process of wound healing by encouraging tissue growth in a certain way and/or by discouraging tissue growth in a certain way. The adjunct and the medicant(s) releasably retained therein may thus take advantage of the anti-isotropic nature of tissue. In other words, the adjunct and the medicant(s) releasably retained therein may take advantage of a tissue's preferred direction in which the tissue resists tearing, as opposed to the tissue's nonpreferred direction in which the tissue is prone to tearing, by encouraging tissue growth in the tissue's preferred direction. The tissue may thus be encouraged to heal in an efficient, effective way by encouraging the tissue to grow according to the tissue's natural structure, e.g., in a manner mimicking the preferred direction of the tissue's fibers. The wound may thus become stronger faster due to tissue growth corresponding to the natural tissue structure and/or the healed tissue may have a stronger resulting structure since during healing the tissue is encouraged to grow in a mimicked manner to the tissue's preferred direction. Additionally or alternatively, the selection of particular characteristics associated with an adjunct may optimize effectiveness of the adjunct and the one or more medicants releasably retained therein during the process of wound healing by helping to discourage tissue growth. For example, the construction of the adjunct, locations of where the one or more medicants are disposed within the adjunct, and/or functionality of the one or more medicants can be selected to prevent tissue in contact therewith from growing, which can help prevent unwanted tissue adhesions during wound healing, such as adhesion of adjacent organs.

The particular characteristics associated with an adjunct having one or more medicants releasably retained therein can be targeted to use of the adjunct with a particular organ, e.g., targeted to the intended stapling of the adjunct to a particular organ. Different organs have different tissue structures, as will be appreciated by a person skilled in the art, such as tissue fibers extending in different directions for different organs. As will also be appreciated by a person skilled in the art, some organs are closer to adjacent body structures than other organs such that tissue growth can be more likely to cause unwanted tissue adhesions for some organs than for other organs due to their relatively close proximity to adjacent body structures. The particular characteristics associated with the adjunct can be selected to correspond to the tissue structure of the organ to which the adjunct releasably retaining the one or more medicants is intended to be used and/or selected to reflect to the organ's proximity to other body structures. The tissue may thus be encouraged to heal in an efficient, effective way by encouraging the tissue to grow in accordance with the organ's natural tissue structure (e.g., in a manner mimicking the direction of the organ's tissue fibers) and/or by discouraging tissue growth near the adjacent body structures. The wound may thus become stronger faster due to tissue growth corresponding to the organ's natural tissue structure, the healed tissue may have a stronger resulting structure since during healing the tissue is encouraged to grow in a mimicked manner to the tissue's natural structure, and/or tissue adhesions can be prevented.

The adjunct can be in the form of a fiber lattice (also referred to herein as a "fiber-based lattice") formed from a plurality of fibers that can, as discussed above, be woven, braided, knitted, or otherwise interconnected so as to form a regular or irregular structure. One or more characteristics associated with the fiber lattice can be altered between various adjunct implementations to promote organized tissue remodeling in a desired manner, such as by encouraging tissue growth to be in a certain direction during wound healing. These characteristics can include the characteristics mentioned above, namely construction of the fiber lattice, locations of where the one or more medicants are disposed within the fiber lattice, and functionality of the one or more medicants.

The fiber lattice can have at least two distinct heterogeneous fiber lattice sections. In other words, each of the two or more fiber lattice sections can be different from one another by having different characteristics from one another, e.g., having different constructions. Each of the fiber lattice sections can be arranged in a pattern configured to promote organized tissue remodeling in a desired manner. The fiber lattice's construction can define the pattern. An adjunct having multiple heterogeneous fiber lattice sections may cause faster and/or more controlled tissue growth than an adjunct with one fiber lattice structure since the sections can be appropriately chosen for different tissue types, different tissue sizes, and/or different intended effects (e.g., encouraging tissue growth or discouraging tissue growth). A single adjunct having multiple heterogeneous fiber lattice sections may allow a single structure (the single adjunct) to affect tissue growth in multiple different ways, e.g., encourage tissue growth in different ways, discourage tissue growth in different ways, or a combination of encouraging and discouraging tissue growth. The delivery of the single structure to tissue may be faster and/or easier than delivering multiple different structures, and/or the single structure may be easier to releasably couple to a surgical stapler for delivery to tissue than multiple structures, which may not even be able to be simultaneously delivered to tissue using the stapler, unlike the single adjunct.

One or more medicants can be releasably retained in each of the fiber lattice sections and can be configured to release from the adjunct in a homogenous manner, e.g., to release uniformly therefrom. The homogenous release of the one or more medicants can help the one or more medicants all be effectively applied to the tissue at substantially the same time such that the one or more medicants all start to provide their respective desired effects at substantially the same time. A person skilled in the art will appreciate that each of the one or more medicants may not be effectively applied to the tissue at precisely the same time due to any one or more factors, such as accuracy of time measurement devices and/or small temporal differences in when medicants released from the adjunct directly contact tissue, but nevertheless be considered to be effectively applied to the tissue at substantially the same time. Additionally, as discussed herein, medicants can be timed for simultaneous release from an adjunct in a variety of ways, such as by timing of coating disintegration, timing of polymer dissolution, via application of pressure thereto, etc.

Figure 45:
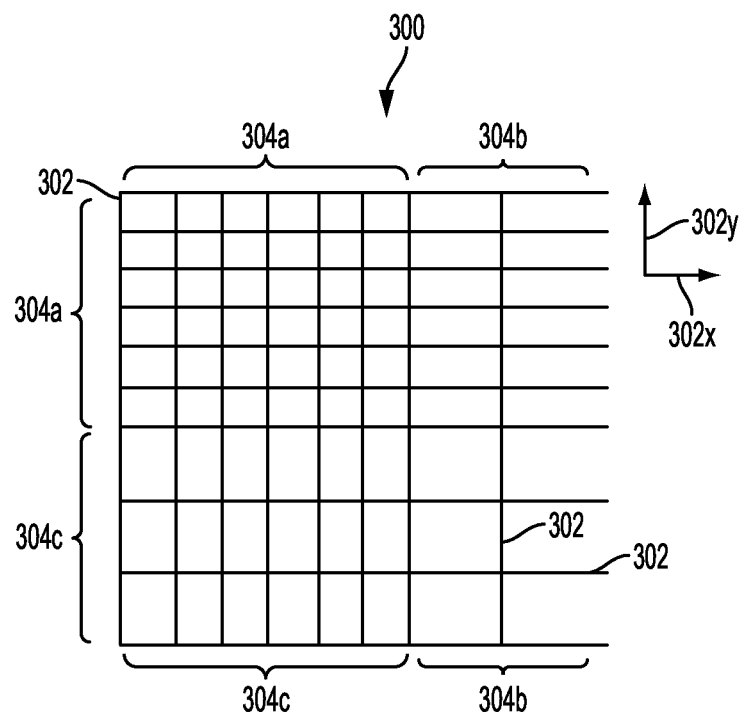
FIG. 45 is a schematic view of a portion of an implementation of an implantable adjunct formed from a plurality of fibers having different spacings.

FIG. 45 illustrates one implementation of an adjunct 300 formed from a plurality of fibers 302. Only a partial portion of the adjunct 300 is shown in FIG. 45. The fibers 302 in this illustrated embodiment have different spacing from one another in different fiber lattice sections 304a, 304b, 304c of the adjunct 300. As illustrated, the adjunct 300 includes three heterogeneous fiber lattice sections 304a, 304b, 304c but can include another plural number of sections. In general, the less space between adjacent fibers 302 (e.g., the more dense the fibers 302 or the more tightly packed the fibers 302), the more ECM growth is encouraged because there are more fibers 302 present. Cells lay down adjacent to fibers during tissue regrowth, so the more fibers that are present in a certain area, the more cells will lay down in that area, e.g., the more ECM will form in that area. The adjunct 300 can be delivered to tissue with the fiber lattice section 304a having the most closely spaced fibers 302 located in an area where the most ECM growth is desired during wound healing, such as at a central portion of a wound, e.g., along a staple line at the wound. The fiber lattice section 304c having the next most closely spaced fibers 302 and the fiber lattice section 304b having the least closely spaced fibers 302 can also be appropriately positioned relative to the wound, e.g., with the fiber lattice section 304b being positioned where ECM growth need be least strongly encouraged. The adjunct 300 can be delivered to tissue with the least-dense fiber lattice section 304b located in an area where the tissue will stretch or expand the most in the natural course of body function. Tissue growth is generally desired the least in the area where the tissue will stretch or expand the most to help prevent inhibition of the stretching or expanding, as inhibiting stretching or expanding can cause patient discomfort, reduced tissue function, and/or other adverse results. The adjunct 300 having the fiber lattice sections 304a, 304b, 304c with different fiber spacings may thus help allow tissue to grow where most needed, as encouraged by sections having more tightly spaced fibers, and help limit tissue growth where growth is least desired, as encouraged by sections having less tightly spaced fibers.

The fibers 302 in this illustrated implementation are arranged in a grid pattern with a first plurality of the fibers 302 extending in a first direction 302X and a second plurality of the fibers 302 extending in a second, opposite 302Y direction that is substantially perpendicular to the first direction 30X. A person skilled in the art will appreciate that the fibers 302 in the two directions 302X, 302Y may not be precisely perpendicular to one another due to any one or more factors, such as pliability of the fibers 302 and/or accuracy of measurement devices, but nevertheless be considered to be substantially perpendicular to one another.

As mentioned above, cells lay down adjacent to fibers during tissue regrowth, so the orientation of the fibers 302 affects how the tissue regrows. Tissue to which the adjunct 300 is applied can thus be encouraged to grow in a grid pattern, with some regrown tissue extending in the first direction 302X as encouraged by the first plurality of the fibers 302 and some regrown tissue extending in the second direction 302Y as encouraged by the second plurality of the fibers 302. The adjunct 300 having fibers 302 of different orientations may thus help encourage growth of a strong matrix of interconnected tissue fibers. Orienting fibers 302 in a certain direction may encourage tissue growth in accordance with the tissue's natural structure by encouraging tissue growth in a natural direction of the tissue by having fibers 302 extend in that natural direction. Additionally, the more fibers 302 that extend in the tissue's natural direction, the more tissue can be encouraged to grow in that direction, which can help provide stronger healed tissue and/or help provide stronger tissue during healing. For example, the first direction 302X may correspond to a target tissue's natural fiber direction, so the more closely spaced the fibers 302 that extend in the first direction 302X, the more tissue growth the adjunct 300 can encourage in a mimicked manner to the natural tissue structure.

The adjunct 300 can be releasably coupled to a stapler (e.g., to an end effector of a stapler and/or to a cartridge retainable in a stapler) so that the adjunct 300 is desirably positioned relative to tissue to which the stapler applies staples and the adjunct 300, e.g., so the fiber-dense fiber lattice section 304a is positioned where ECM growth is most desired, so fibers 302 extending in the first direction 302X extend in the tissue's natural fiber direction, etc.

Figure 46:
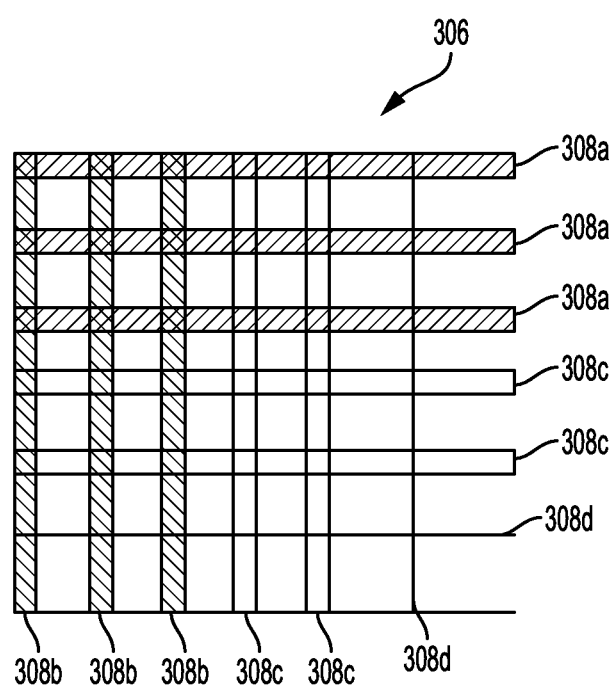
FIG. 46 is a schematic view of a portion of an implementation of an implantable adjunct formed from a plurality of fibers having different material configurations.

FIG. 46 illustrates another implementation of an adjunct 306 formed from a plurality of fibers 308a, 308b, 308c, 308d. Only a partial portion of the adjunct 306 is shown in FIG. 46. The fibers 308a, 308b, 308c, 308d in this illustrated embodiment are arranged in a grid pattern similar to the grid pattern of FIG. 45. The fibers 308a, 308b, 308c, 308d in this illustrated embodiment have different material configurations from one another. A first plurality of the fibers 308a has a first material configuration, a second plurality of the fibers 308b has a second material configuration, a third plurality of the fibers 308c has a third material configuration, and a fourth plurality of the fibers 308d has a fourth material configuration. The adjunct 306 in this illustrated implementation has four sets of fibers 308a, 308b, 308c, 308d with different material configurations, but an adjunct can have another plural number of sets with different material configurations. The material configurations can differ from one another in any one or more ways, such as any one or more of different elasticity, different thickness (e.g., different diameter), different surface finish, and different charge.

Fibers having different elasticity can help encourage tissue growth in accordance with a tissue's natural structure. Tissue tends to naturally stretch or expand in a certain direction. This direction can vary by tissue type, as mentioned herein and as will be appreciated by a person skilled in the art. Fibers having more elasticity can be aligned with a direction of a tissue's natural stretching or expansion, which can help encourage tissue growth that results in stronger healed tissue and/or stronger tissue during healing.

Fibers having different thicknesses can help encourage different amounts of tissue growth in accordance with the thicknesses. Thicker fibers, e.g., the thickest fibers 308a of FIG. 46 and the next thick fibers 308b of FIG. 46, encourage less tissue growth than thinner fibers, e.g., the thinnest fibers 308d of FIG. 46 and the next thinnest fibers 308 of FIG. 46. Accordingly, thicker fibers can be positioned where less tissue growth is desired, and thinner fibers can be positioned where more tissue growth is desired. For example, thinner fibers can be positioned at a central portion of a wound, e.g., along a staple line at the wound. For another example, thicker fibers can be in a central area of an adjunct, and thinner fibers can be in a peripheral area surrounding the central area. More tissue growth can thus be encouraged in an area at the periphery of the adjunct.

Fibers having different thicknesses can provide different amounts of structural support to a wound. Thicker fibers generally provide more structural support than thinner fibers. A portion of an adjunct including thicker fibers can accordingly be positioned at an area of a wound where structural support may be more needed than at another area of the wound, where thinner fibers of the adjunct may be positioned. Although the thicker fibers will generally encourage less tissue growth than the thinner fibers, the increased structural support provided by the thicker fibers to the wound may help improve overall structural integrity of the wound area and accordingly reduce chances of any one or more adverse effects of wound healing from developing due to the increased strength provided by the thicker fibers of the adjunct. The increased structural support can help compensate for the slower and/or smaller amount of tissue growth that may occur at the thicker fibers.

Thinner fibers can be bundled together, which may help encourage tissue growth due to the smaller diameter of the fibers while providing more structural integrity as unit than any of the individual thin fibers can individually provide. Accordingly, bundled thin fibers may help provide structural integrity to a wound while encouraging tissue growth.

Fibers having different surface finishes can help influence tissue growth in different ways in accordance with the different finishes. Smooth surface finishes generally discourage tissue growth (e.g., help prevent tissue adhesion), and non-smooth surface finishes generally encourage tissue growth (e.g., by providing a roughened surface to which cells may attach). A portion of an adjunct including fibers with smooth surface finishes can thus be positioned where tissue growth is generally unwanted, such as at an area where tissue to which the adjunct is stapled is at risk of adhering to an adjacent tissue structure, and a portion of the adjunct including fibers with non-smooth surface finishes can be positioned where tissue growth is desired, such as along a staple line. Examples of non-smooth surface finishes include micro-etched or pitted surfaces such that fibers having non-smooth surface finishes are micro-etched or pitted. Non-smooth surface finishes are further described in U.S. Pat. Pub. No. 2015/129634 entitled "Tissue Ingrowth Materials And Method Of Using The Same" filed Nov. 8, 2013, which is hereby incorporated by reference in its entirety.

Fibers having different charges (e.g., positive or negative) can help influence tissue growth in different ways in accordance with the different charges. A person skilled in the art will appreciate that blood and blood components are negatively charged. Thus, fibers being positively charged can attract inflammatory cells and blood components responsible for healing a wound (which, as mentioned, can be negatively charged), including platelets, PDGF, T-cells 1704, macrophages, and neutrophils. The positively charged fibers can thereby facilitate wound healing. Additionally, the positively charged fibers can activate tissue macrophages. As discussed herein, when activated, macrophages release growth factors and active cytokines into the wound, providing a stimulus for cell proliferation and collagen matrix deposition. The positively charged fibers may thus further enhance healing. Similarly, fiber having a negative charge can help repel inflammatory cells and blood components responsible for healing a wound, thereby discouraging tissue growth. Fibers having a positive charge can thus be positioned where tissue growth is desired, such as along a staple line, and fibers having a neutral charge (non-charge) or a negative charge can be positioned where less tissue growth is desired. Charged adjunct materials are further described in U.S. Pat. Pub. No. 2015/0133996 entitled "Positively Charged Implantable Materials And Method Of Forming The Same" filed Nov. 8, 2013, which is hereby incorporated by reference in its entirety.

The adjunct 306 can be releasably coupled to a stapler (e.g., to an end effector of a stapler and/or to a cartridge retainable in a stapler) so that the adjunct 306 is desirably positioned relative to tissue to which the stapler applies staples and the adjunct 306, e.g., so the different material configurations of the fibers 308a, 308b, 308c, 308d are positioned relative to areas where they can encourage or discourage tissue growth as desired.

Figure 47:
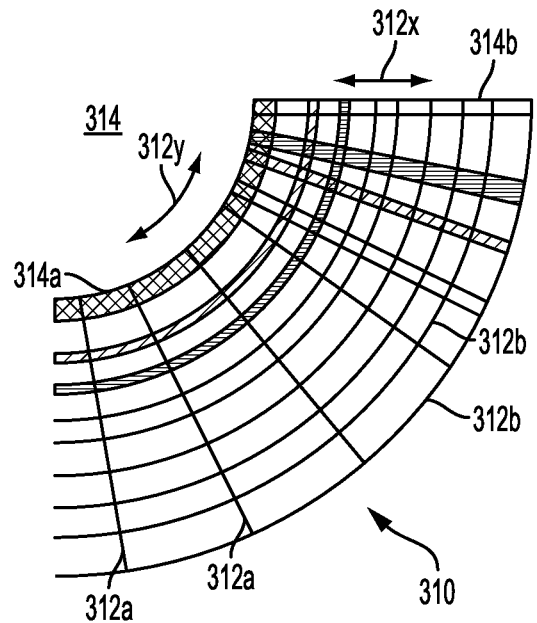
FIG. 47 is a schematic view of a portion of an implementation of an implantable adjunct formed from a plurality of radially arranged fibers.

FIG. 47 illustrates another implementation of an adjunct 310 formed from a plurality of fibers 312a, 312b. Only a partial portion of the adjunct 310 is shown in FIG. 47. Unlike the adjuncts 300, 306 of FIG. 45 and FIG. 46 that have perpendicularly arranged fibers, the adjunct 310 of FIG. 47 has radially arranged fibers 312a, 312b. Tissue to which the adjunct 310 is applied can thus encourage the tissue to grow in a radial pattern defined by the radially arranged fibers 312a, 312b. A first plurality of the fibers 312a can extend in a first direction 312X that generally extends toward/away from a radial center 314 of the adjunct 310, and a second plurality of the fibers 312b can extend in a second direction 312Y that generally extends around the radial center 314 of the adjunct 310. The radial center 314 can generally be defined by an opening of the adjunct 310, e.g., an open central portion thereof.

The first and second plurality of fibers 312a, 312b are generally more tightly spaced closer to the radial center 314. As illustrated, the terminal ends of each of the first plurality of fibers 312a closest to the radial center 314 can be closer to one another than the terminal ends of each of the first plurality of fibers 312a farthest from the radial center 314. The first plurality of fibers 312a can thus help encourage more tissue growth closer to the radial center 314. As illustrated, the second plurality of fibers 312b can be spaced closer to one another closer to the radial center 314 and farther from one another the farther the second plurality of fibers 312b are from the radial center 314. The second plurality of fibers 312b can thus help encourage more tissue growth closer to the radial center 314. Accordingly, the adjunct 310 can be positioned with the radial center 314 closest to an area of the wound where tissue growth is most desired, e.g., so the more closely spaced ones of the first plurality of fibers 312a and the more closely spaced ones of the second plurality of fibers 312b are positioned closest to an area of the wound where tissue growth is most desired.

The fibers 312a, 312b of the adjunct 310 can have different material configurations from one another. Other implementations of adjuncts described herein can also have different material configurations from one another, even if not specifically mentioned with respect thereto. For example, the first plurality of fibers 312a can have less elasticity than the second plurality of fibers 312b, which can allow the adjunct 310 to stretch or expand more in the first direction 312X than in the second direction 312Y. This configuration can facilitate expansion and retraction of the opening defined by the adjunct 310, which can facilitate passage of material (e.g., blood and/or other body matter) through the opening. The adjunct 310 attached to a colon, for example, may contract and expand in accordance with the colon's natural radial contraction and expansion with the elasticity of the second plurality of fibers 312b facilitating the contraction and expansion of the adjunct 310 with little or no restriction on the colon's natural radial expansion and contraction. For another example, as illustrated, the ones of the fibers 312a, 312b at an inner peripheral edge 314a and a side peripheral edge 314b of the adjunct 310 can be thicker than other ones of the fibers 312a, 312b. The adjunct 310 at the inner and side peripheral edges 314a, 314b can thereby be configured to provide enhanced structural support to a wound area.

The adjunct 310 can be releasably coupled to a stapler (e.g., to an end effector of a stapler and/or to a cartridge retainable in a stapler) so that the adjunct 310 is desirably positioned relative to tissue to which the stapler applies staples and the adjunct 310.

Figure 48:
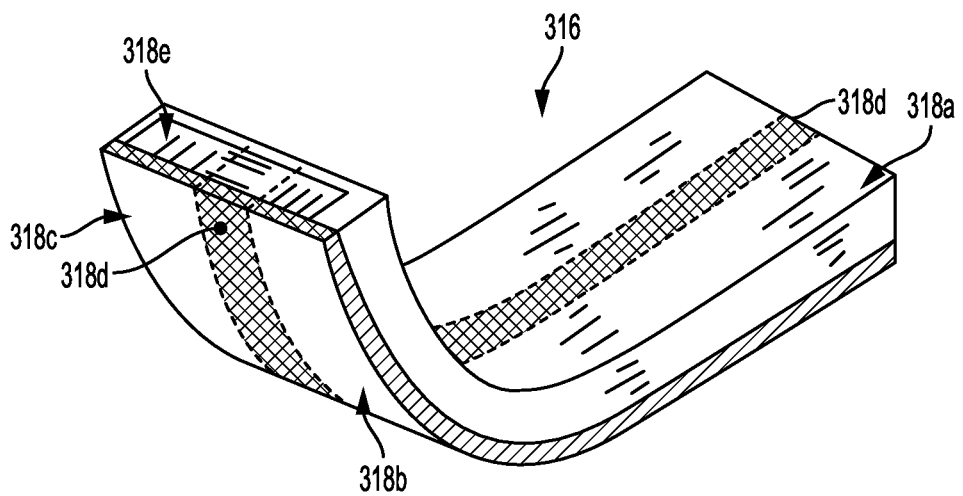
FIG. 48 is a perspective view of an implementation of an implantable adjunct formed from a plurality of fibers and including a plurality of heterogeneous fiber lattice sections.

FIG. 48 illustrates another implementation of an adjunct 316 formed from a plurality of fibers and including a plurality of heterogeneous fiber lattice sections 318a, 318b, 318c, 318d, 318e. The adjunct 316 in this illustrated implementation includes five fiber lattice sections 318a, 318b, 318c, 318d, 318e, but as mentioned herein, adjuncts can have another number of fiber lattice sections. As illustrated, the first fiber lattice section 318a is located on a top side and on opposed lengthwise sides of the adjunct 316 and is configured to discourage tissue growth, e.g., to prevent adhesion. The first fiber lattice section 318a can be configured to discourage tissue growth in a variety of ways, as discussed herein. As illustrated, the first fiber lattice section 318a has a first medicant (not shown) releasably retained therein that is configured to discourage tissue growth, such as an anti-adhesion agent.

As illustrated, the second and third fiber lattice sections 318b, 318c are each located on a bottom side of the adjunct 316 and are each configured to encourage tissue growth. The second and third fiber lattice sections 318b, 318c can be configured to encourage tissue growth in a variety of ways, as discussed herein. As illustrated, the second and third fiber lattice sections 318b, 318c each have a second medicant (not shown) releasably retained therein that is configured to encourage tissue growth, such as a growth factor. The second and third fiber lattice sections 318b, 318c have the same construction as one another and have the same medicant releasably retained therein, but in other implementations, the second and third fiber lattice sections 318b, 318c can each be configured to encourage tissue growth but differ from one another in construction and/or in retained medicant.

Between the second and third fiber lattice sections 318b, 318c on the bottom side of the adjunct 316 in this illustrated implementation is the fourth fiber lattice section 318d, which is configured to facilitate hemostasis. FIG. 48 also shows the fourth fiber lattice section 318d underlying the first and fifth fiber lattice section 318a, 318e by dotted line on the top side of the adjunct 316. As illustrated, the fourth fiber lattice section 318d extends along a central longitudinal portion of the adjunct 316, which may facilitate delivery of its hemostatic properties to tissue, as discussed further below. The fourth fiber lattice section 318d can be configured to facilitate hemostasis growth in a variety of ways, as discussed herein. As illustrated, the fourth fiber lattice section 318d has a third medicant 320 (shown in FIG. 49 and FIG. 50) releasably retained therein that is configured to facilitate hemostasis, such as a hemostatic agent.

As illustrated, the fifth fiber lattice section 318e is located in an interior area of the adjunct 316 in a cavity defined by the top side, opposed lengthwise sides, and bottom side of the adjunct 316, and is configured to space apart the top and bottom sides of the adjunct 316 to thereby space apart the tissue growth-encouraging and tissue growth-discouraging portions of the adjunct 316. In other words, the fifth fiber lattice section 318e is configured to space the second and third fiber lattice sections 318b, 318c apart from the first fiber lattice section 318a. The fifth fiber lattice section 318e can have a fourth medicant (not shown) releasably retained therein. The fourth medicant can include, for example, an anti-adhesion agent or can include ORC and/or another hemostatic agent.

The adjunct 316 can be releasably coupled to a stapler (e.g., to an end effector of a stapler and/or to a cartridge retainable in a stapler) so that the adjunct 316 is desirably positioned relative to tissue to which the stapler applies staples and the adjunct 316. In general, the desired position of the adjunct 316 relative to tissue can include the bottom side thereof facing the tissue and the top side thereof facing away from the tissue. The hemostasis-encouraging fiber lattice section 318d and the tissue growth-encouraging fiber lattice sections 318b, 318c can thus be facing the tissue so as to facilitate provision of their respective medicants thereto and accordant benefits thereof, and the tissue growth-discouraging section 318a can thus be facing away from the tissue to facilitate provision of its medicant thereto and accordant benefit thereof.

Figure 49:
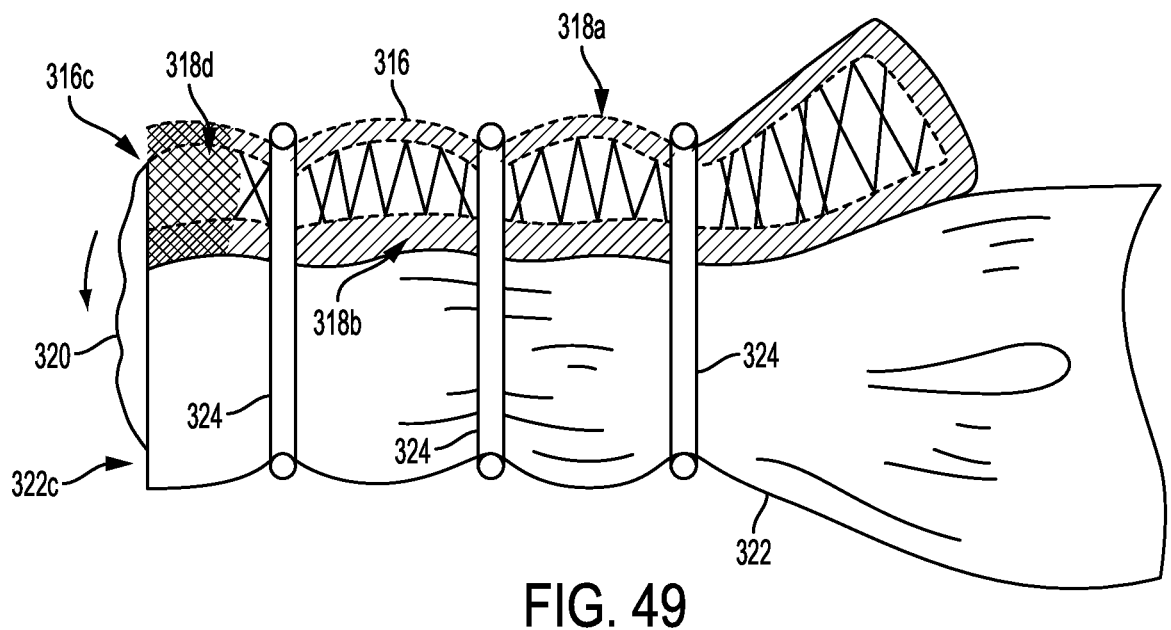
FIG. 49 is a cross-sectional side view of the adjunct of FIG. 48 stapled to tissue.
Figure 50:
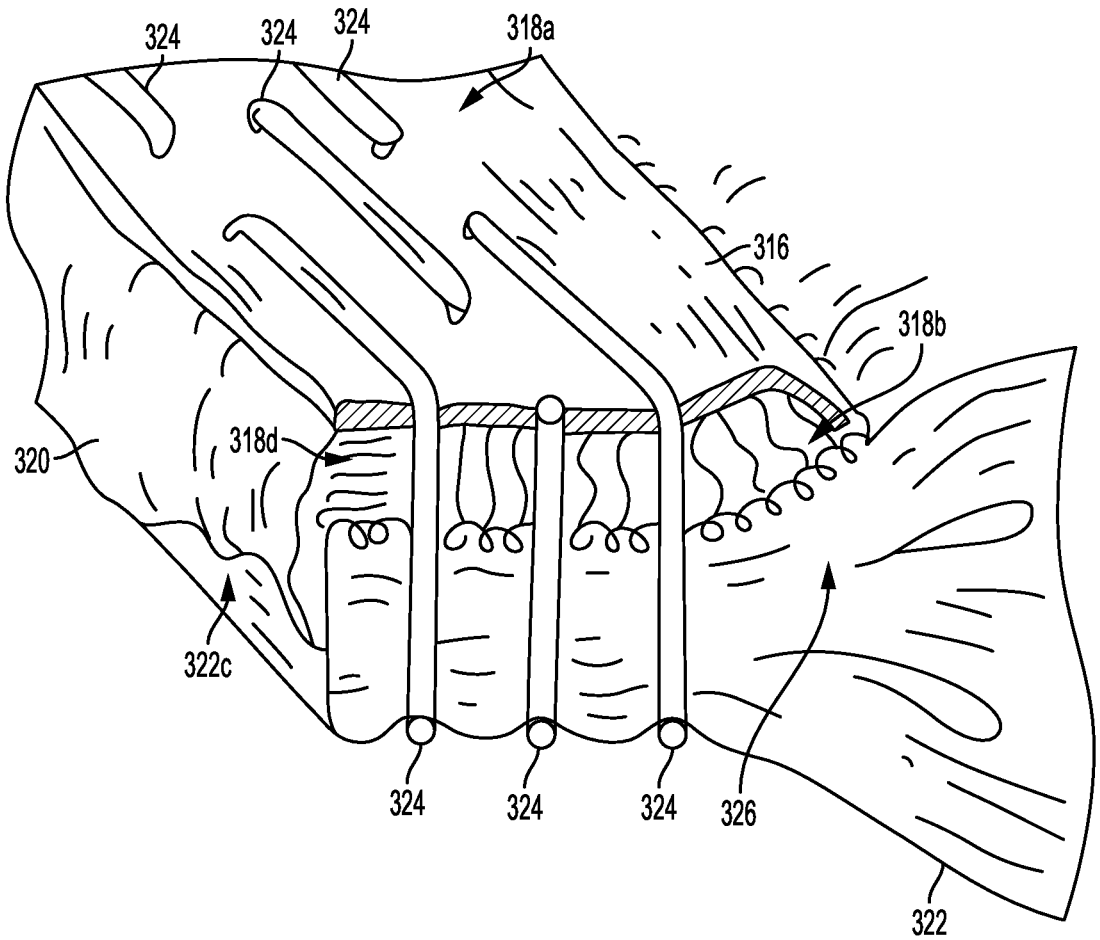
FIG. 50 is a perspective view of the adjunct and tissue of FIG. 49.

FIG. 49 and FIG. 50 illustrate an example of the adjunct 316 stapled to a tissue 322 with a plurality of staples 324. FIG. 49 and FIG. 50 show the third medicant 320 being released from the fourth fiber lattice section 318d along a cut edge 316c of the adjunct 316 and a cut edge 322c of the tissue 322, the cut edges 316c, 322c having been formed by a stapler's cutting element during the stapling process. As described herein, a stapler's cutting element can translate longitudinally along a center of a staple cartridge. The adjunct 316 can be releasably retained on the cartridge and/or on an end effector having the cartridge seated therein with the fourth fiber lattice section 318d aligned with the longitudinal path of the cutting element. The fourth fiber lattice section 318d extending along the central longitudinal portion of the adjunct 316 may facilitate such placement. Thus, when the cutting element translates along the cartridge to cut the tissue 322, the cutting element also cuts through the fourth fiber lattice section 318*d*, which may facilitate leakage, dripping, and/or other release of the third medicant 320 therefrom. In other words, the cutting of the fourth fiber lattice section 318*d* may help the third medicant 320 exit the adjunct 316. Further, the location of the fourth fiber lattice section 318*d* above the tissue 322, as shown in FIG. 49 and FIG. 50, may help the third medicant 320 drip or otherwise flow down onto the tissue 322 and, in particular, the cut edge 322*c* edge of the tissue most susceptible to bleeding and hence the area of the tissue 322 most in need of the third medicant's hemostatic properties.

As illustrated in FIG. 50, the second fiber lattice section 318*b* can be configured to unwind or fray along a side 326 thereof facing the tissue 322, e.g., the side defining part of the bottom side of the adjunct 316. In other words, fibers of the second fiber lattice sections 318*b* can be configured to "unwind." The unwinding or fraying may, as discussed herein, facilitate release of the second medicant from the second fiber lattice section 318*b*. As also discussed herein, the unwinding or fraying can be triggered by contact of the fibers with fluid, e.g., with moisture of the tissue 322. The third fiber lattice section 318*c* can be similarly configured to unwind or fray. The first fiber lattice section 318*a* can be configured to not unwind or fray, thereby facilitating antiadhesion.

Figure 51:
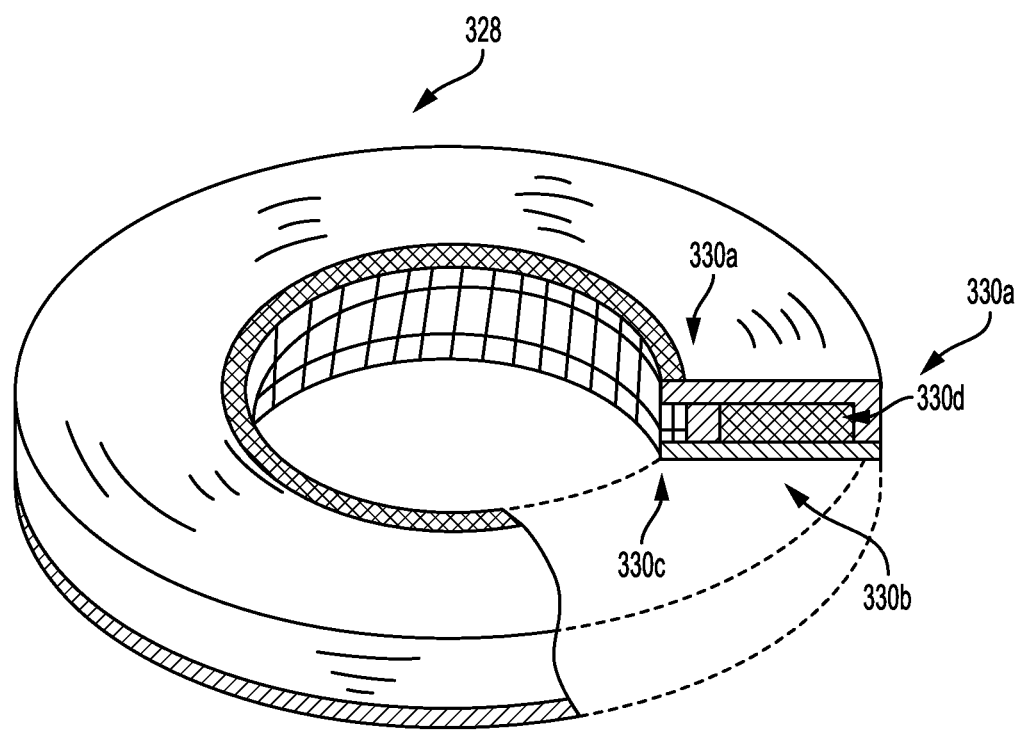
FIG. 51 is a partial cross-sectional perspective view of another implementation of an implantable adjunct formed from a plurality of fibers and including a plurality of heterogeneous fiber lattice sections.

The adjunct 316 has a generally rectangular shape to facilitate its use thereof with a linear stapler. Other adjuncts can have a different shape to facilitate use thereof with a circular stapler. FIG. 51 illustrates such an implementation of an adjunct 328.

The adjunct 328 in the illustrated implementation of FIG. 51 is formed from a plurality of fibers and includes a plurality of heterogeneous fiber lattice sections 330*a*, 330*b*, 330*c*, 330*d*. The adjunct 328 is generally configured similar to the adjunct 316 of FIG. 48 except, as mentioned above, the adjunct 328 is configured for use with a circular surgical stapler. The adjunct 328 thus has a generally circular shape. The first fiber lattice section 330*a* is similar to the first fiber lattice section 318*a* of FIG. 48 and is located on a top side and on an exterior side of the adjunct 328 and is configured to discourage tissue growth. The second fiber lattice section 330*b* is similar to the second and third fiber lattice sections 318*b*, 318*c* of FIG. 48 and is located on a bottom side of the adjunct 328 and is configured to encourage tissue growth. The third fiber lattice section 330*c* is similar to the fourth fiber lattice section 318*d* of FIG. 48 and is located on an interior side of the adjunct 328 and is configured to facilitate hemostasis. The fourth fiber lattice section 330*d* is similar to the fifth fiber lattice section 318*e* of FIG. 48 and is located in an interior area of the adjunct 328 and is configured to space apart the top and bottom sides of the adjunct 328.

An adjunct can be configured to alter its conformation in response to a load applied thereto, e.g., in response to strain, and in response to the load being removed therefrom, in response to released strain. The conformation can change by a three-dimensional (3D) size and/or shape of the adjunct changing in response to the load increasing or decreasing. The adjunct can thus be configured to remain structurally sound in the event that a load is applied thereto or removed therefrom, since the adjunct can merely conform its shape, as opposed to becoming damaged and/or completely unusable in response to the load addition/subtraction. Adjuncts configured to alter their conformations in response to a load can be particularly useful with tissues that are naturally pliable and/or squishable, such as stomach tissue. Since pliable/squishable tissue will likely change in width, length, and/or height following delivery of the adjunct thereto, the adjunct being conformable can allow the adjunct to dynamically adjust to these width, length, and/or height tissue changes without the adjunct losing its general intended functionality with respect to healing of the tissue.

Figure 52:
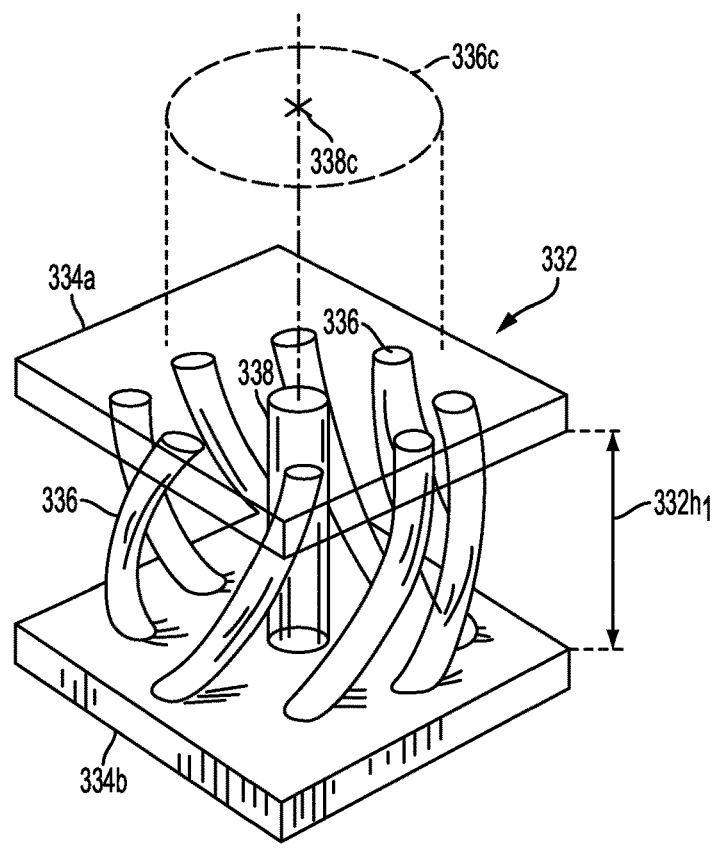
FIG. 52 is a perspective view of an implementation of an implantable adjunct formed from a plurality of fibers and configured to alter its conformation in response to a load applied thereto.
Figure 53:
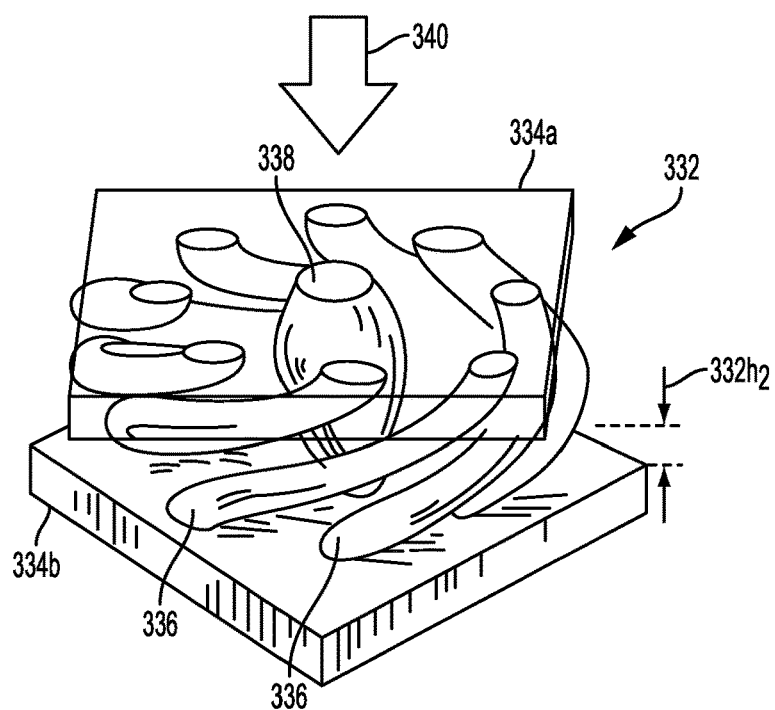
FIG. 53 is a perspective view of the adjunct of FIG. 52 having a schematic load applied thereto.

FIG. 52 and FIG. 53 illustrate an implementation of an adjunct 332 formed from a plurality of fibers and configured to alter its conformation in response to a load applied thereto. A load is illustrated schematically in FIG. 53 as an arrow 340 applying downward pressure to the adjunct 332. The adjunct 332 can be configured to move between an expanded configuration, shown in FIG. 52, in which the adjunct 332 has a maximum height $332h_1$, and a collapsed configuration, shown in FIG. 53, in which the adjunct 332 has a minimum height $332h_2$. The adjunct 332 can be configured to have multiple intermediate configurations between the expanded configuration and the collapsed configuration in which the adjunct 332 has a height between its maximum and minimum heights $332h_1$, $332h_2$.

As illustrated, the adjunct 332 includes first and second sheet-like fiber woven meshes 334*a*, 334*b* having a plurality of fibers 336 and a central fiber 338 extending therebetween. The plurality of fibers 336 can be arranged radially around the central fiber 338. The radial arrangement of the fibers 336 in this illustrated implementation is in a circle shape 336*c* with the central fiber 338 being located at a center 338*c* of the circle 336*c*. The central fiber 338 and each of the plurality of fibers 336 can be configured to deform in response to the load 340 being applied thereto, thereby altering the height of the adjunct 332. The central fiber 338 can be configured to increase in maximum thickness (maximum diameter) in response to the load 340 application, as shown in FIG. 52 in which the central fiber 338 has a maximum diameter that is less than the central fiber's maximum diameter in FIG. 53. The central fiber 338 can extend in a direction substantially perpendicular to planes containing the meshes 334*a*, 334*b*, as illustrated, to facilitate uniform thickness change of the central fiber 338. Each of the radial fibers 336 can be configured to bend radially around the central fiber 338 in response to the load 340 application. The radial fibers 336 can each be configured to bend substantially along a circumference of the circle 336*c*, as illustrated, which can help prevent the fibers 336 from tangling with each other and/or the central fiber 338 when the adjunct 332 changes its conformation. The radial fibers 336 can extend in a direction transverse to the direction in which the central fiber 338 extends and transverse to the planes containing the meshes 334*a*, 334*b*, as illustrated. In other words, the radial fibers 336 can be attached to the meshes 334*a*, 334*b* at an angle. The angling of the radial fibers 336 can urge the fibers 336 to bend (toward the collapsed configuration) and unbend (toward the expanded configuration) in a certain direction to help the fibers 336 predictably deform and not tangle.

Application of the load 340 deforms the fibers 336, 338, which may facilitate density of an ECM during wound healing since the deformed fibers may encourage growth in more disorganized directions to form a stronger matrix than with fibers extending in a more organized manner, such as the more longitudinal extensions shown in FIG. 52.

Application of the load 340 can control a rate of elution of the one or more medicants releasably retained by the adjunct 332. The greater the load 340, the more of the one or more medicants that can be released from the adjunct 332.

The adjunct 332 can have at least one medicant releasably retained therein, such as by one or both of the meshes 334*a*, 334*b* having one or more medicants disposed therein and/or by any one or more of the fibers 336, 338 having an outer coating configured to rupture in response to strain and thereby release a medicant, as discussed above with respect to FIG. 25.

The adjunct 332 can be releasably coupled to a stapler (e.g., to an end effector of a stapler and/or to a cartridge retainable in a stapler) so that the adjunct 332 is desirably positioned relative to tissue to which the stapler applies staples and the adjunct 332. In general, the desired position of the adjunct 332 relative to tissue can include the opposed meshes 334a, 334b being positioned to allow the adjunct 332 to collapse/expand in the same direction as the tissue's natural movement. Thus, when strain is applied to or removed from the tissue and/or the adjunct 332, the adjunct 332 can move in accordance with the tissue's natural movement. Additionally, when so positioned, the direction of the fibers 336, 338 will mimic the natural direction of the tissue's fibers, which can facilitate tissue growth in accordance with the tissue's natural direction.

Figure 54:
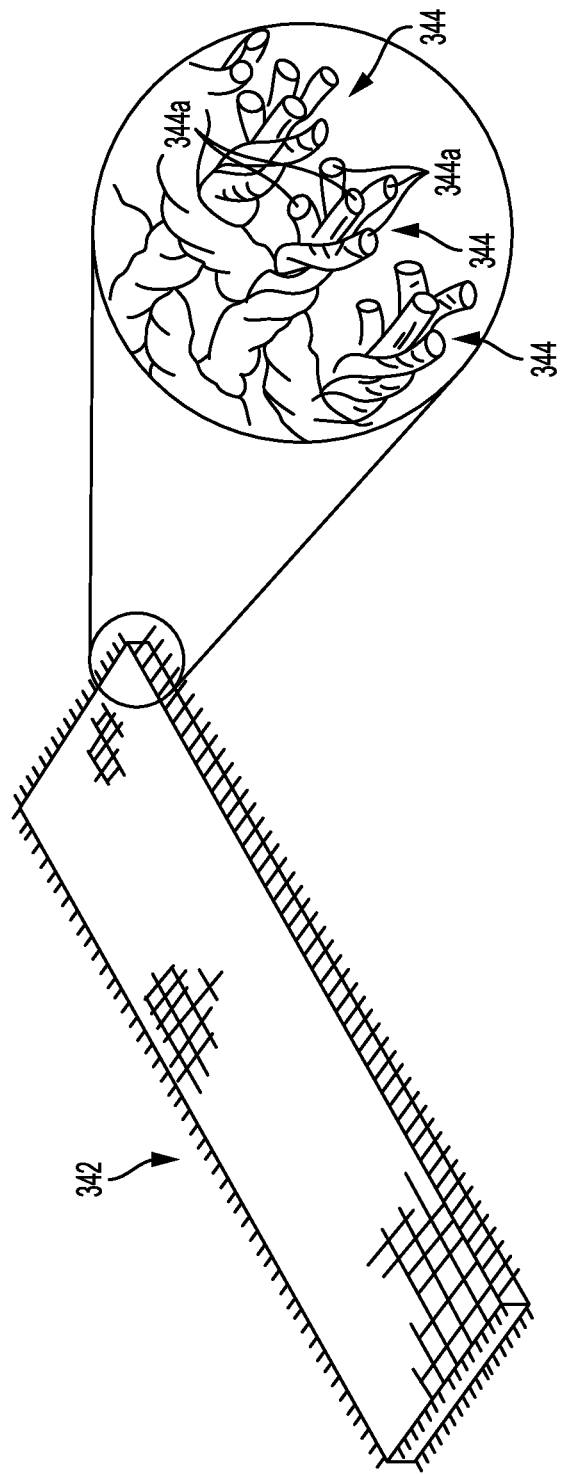
FIG. 54 is a perspective view of an implementation of an implantable adjunct formed from a plurality of fibers woven together to form a sheet-like fiber woven mesh, including an enlarged view of a portion of an edge of the adjunct.

FIG. 54 illustrates an implementation of an adjunct 342 formed from a plurality of fibers 344 woven together to form a sheet-like fiber woven mesh. The adjunct 342 can be configured to unwind or fray along a perimeter thereof. In other words, fibers 344 at the edge of the adjunct 342 can be configured to fray or unwind, which as discussed herein may encourage tissue growth by providing more fiber surface for cell interaction. The unwindable or frayable edge of the adjunct 342 can define a first fiber lattice section of the adjunct 342, and an interior of the adjunct 342 can define a second fiber lattice section of the adjunct 342. As illustrated, the fibers can be configured to fray around the adjunct's entire perimeter. As discussed herein, the unwinding or fraying can be caused by any one or more factors, such as by the adjunct 342 coming into contact with body fluid. As also discussed herein, one or more medicants can be releasably retained by the adjunct 342. The unwinding or fraying can facilitate medicant release from the adjunct 342.

Each of the fibers 344 forming the adjunct 342 include a plurality of wound fibers 344a configured to unwind or fray so as to unwind or fray their associated one of the fibers 344. Each of the fibers 344 includes five wound fibers 344a, but each can include another plural number of wound fibers, e.g., two, three, etc. A one of the wound fibers 344a can be a central core fiber around which the others of the fibers 344a are wound and about which they unwind, as illustrated. The central core fiber can help provide structural integrity to the individual fibers 344, which can help the adjunct 342 overall be more structurally stable and accordingly provide better strength to the wound during wound healing.

The adjunct 342 can be releasably coupled to a stapler (e.g., to an end effector of a stapler and/or to a cartridge retainable in a stapler) so that the adjunct 342 is desirably positioned relative to tissue to which the stapler applies staples and the adjunct 342. The adjunct 342 being unwindable or frayable around its entire perimeter may allow the adjunct 342 to encourage tissue growth regardless of how the adjunct 342 is stapled relative to the tissue.

Figure 55:
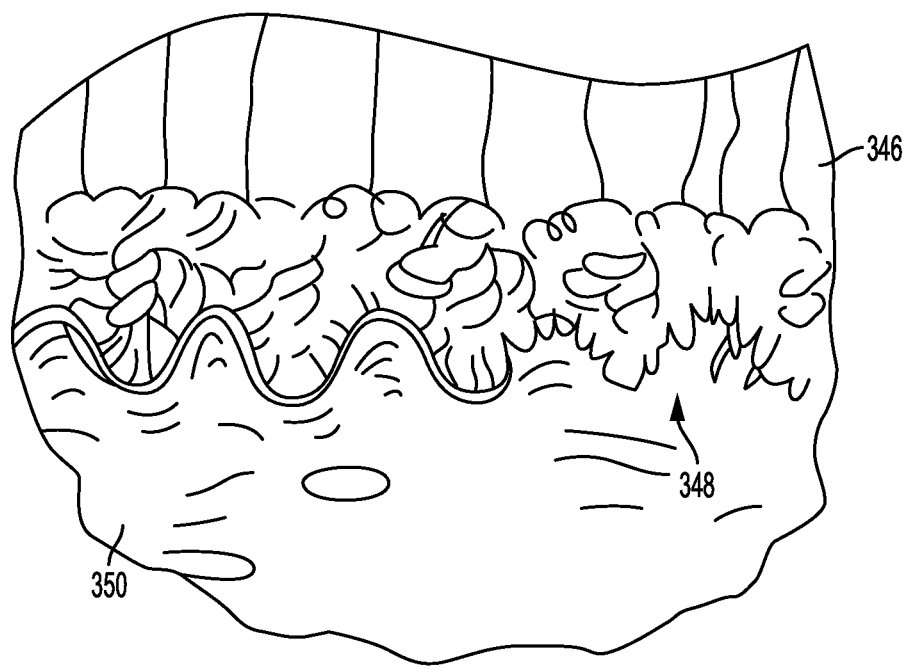
FIG. 55 is a perspective view of another implementation of an implantable adjunct formed from a plurality of fibers woven together to form a sheet-like fiber woven mesh, the adjunct applied to tissue.
Figure 56:
FIG. 56 is a perspective view of an edge portion of the adjunct of FIG. 55.

FIG. 55 illustrates another implementation of an adjunct 346 formed from a plurality of fibers woven together to form a sheet-like fiber woven mesh. Only a portion of an edge 348 of the adjunct 346 is shown in FIG. 55, which also shows the adjunct 346 delivered to tissue 350. A zoomed-in view of a portion of the edge 348 is illustrated in FIG. 56. Similar to the adjunct 342 discussed above, the adjunct 346 can be configured to unwind or fray along a perimeter thereof, e.g., along the edge 348. The entire perimeter can be unwindable or frayable. Also similar to the adjunct 342 discussed above, each of the fibers forming the adjunct 346 include a plurality of wound fibers configured to unwind or fray so as to unwind or fray their associated one of the fibers. As discussed herein, one or more medicants can be releasably retained by the adjunct 346. The unwinding or fraying can facilitate medicant release from the adjunct 346.

The edge 348 of the adjunct 346 can be non-linear, which can provide more fiber surface for cell interaction than a linear edge. As illustrated, the non-linear edge 348 can be undulating, e.g., define a wave pattern. The non-linear edge 348 can extend around the adjunct's entire perimeter, which can help encourage tissue growth around the entire adjunct 346. In contrast, the edge of the adjunct 342 of FIG. 54 has a linear edge.

The adjunct 346 can be releasably coupled to a stapler (e.g., to an end effector of a stapler and/or to a cartridge retainable in a stapler) so that the adjunct 346 is desirably positioned relative to tissue to which the stapler applies staples and the adjunct 346. The adjunct 346 being unwindable or frayable around its entire perimeter may allow the adjunct 346 to encourage tissue growth regardless of how the adjunct 346 is stapled relative to the tissue. Additionally, the edge 348 being non-linear can help the adjunct 346 encourage tissue growth along non-linear areas of the tissue, which can help the tissue become stronger faster by encouraging tissue growth in different areas of the tissue that can grow together.

Figure 57:
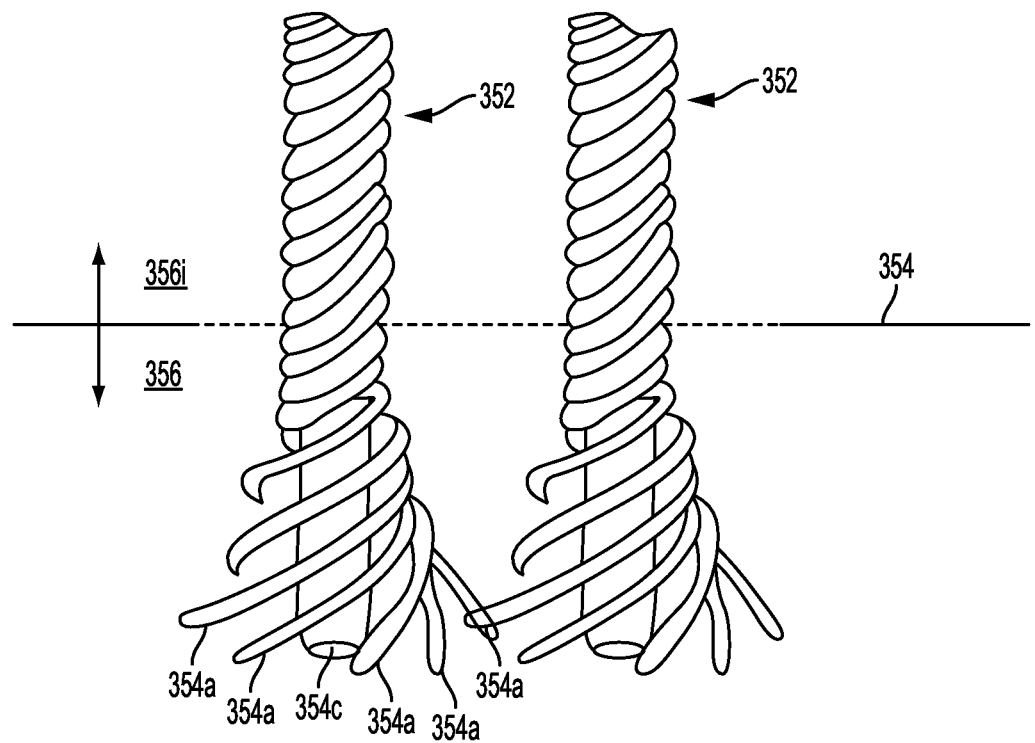
FIG. 57 is a perspective view of a portion of yet another implementation of an implantable adjunct formed from a plurality of fibers woven together to form a sheet-like fiber woven mesh.

FIG. 57 illustrates an implementation of an adjunct formed from a plurality of fibers 352 woven together to form a sheet-like fiber woven mesh. Only a portion of the adjunct is shown at an edge 354 area thereof. The fibers 352 can each be configured to fray or unwind starting from outside 356 the edge 354 of the adjunct and unwinding or fraying in a direction toward an interior 356i of the adjunct. Similar to that discussed above regarding the adjunct 342, each of the fibers 352 can include a plurality of wound fibers 354a configured to unwind or fray about a central core fiber 354c so as to unwind or fray their associated one of the fibers 352. Each of the fibers 354 includes four wound fibers 354a, but each can include another plural number of wound fibers, e.g., two, three, etc. The central core fiber 354c can have a larger diameter than each of the wound fibers 354a, which can each have a same, smaller diameter. The larger-diameter core fiber 354c can help provide the fiber 352 with strength. The wound fibers 354a can be tightly wound around the central core fiber 354c such that the core fiber 354c is completely covered by the wound fibers 354c prior to unwinding, as shown in a portion of the fibers 352 inside the edge 354. This tight winding can help provide the fibers 352, and hence the adjunct with strength, and/or can facilitate controlled medicant release, e.g., release of medicant "hidden" and unreleased prior to unwinding or fraying. As discussed herein, the unwinding or fraying can be caused by any one or more factors, such as by the adjunct coming into contact with body fluid. As also discussed herein, one or more medicants can be releasably retained by the adjunct, and the unwinding or fraying can facilitate medicant release from the adjunct. The adjunct of FIG. 57 can be releasably coupled to a stapler (e.g., to an end effector of a stapler and/or to a cartridge retainable in a stapler) so that the adjunct is desirably positioned relative to tissue to which the stapler applies staples and the adjunct.

Figure 58:
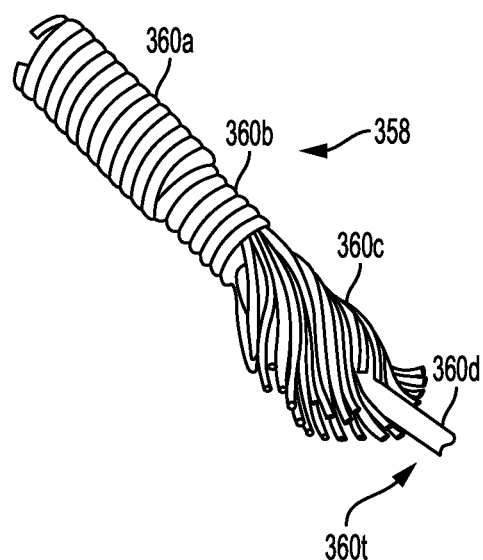
FIG. 58 is a perspective view of a fiber.

FIG. 58 illustrates an implementation of a fiber 358 that can be woven together with other fibers to form a sheet-like fiber woven mesh that can form an adjunct. As illustrated, similar to that discussed above regarding the adjunct 342, the fiber 358 can include a plurality of wound fibers 360a, 360b, 360c wound around and configured to unwind about a central core fiber 360*d*. The wound fibers 360*a*, 360*b*, 360*c* can be layered around the core fiber 360*d*, as illustrated, with an inner wound fiber 360*c* wound around the core fiber 360*d*, a middle wound fiber 350*b* wound around the inner wound fiber 360*c*, and an outer wound fiber 360*a* wound around the middle wound fiber 350*b*. As shown, each of the wound fibers 360*a*, 360*b*, 360*c* can include one or more individual fibers.

Each of the wound fibers 360*a*, 360*b*, 360*c* can terminate a different distance from a terminal end 360*t* of the core fiber 360*d*, as illustrated, or they can all terminate a same distance from the core fiber's terminal end 360*t*. Being at different distance from the core fiber's terminal end 360*t* can help control when the different wound fibers 360*a*, 360*b*, 360*c* unwind since fibers tend to unwind from their terminal end, such that in the illustrated implementation, the inner layer 360*c* would start to begin unwinding before the middle layer 360*b*, which would start to begin unwinding before the outer layer 360*a*.

Each of the wound fibers 360*a*, 360*b*, 360*c* can be the same as each other or different from each other. As illustrated, wound fibers 360*a*, 360*b*, 360*c* are each different from one another, with the inner wound fiber 360*c* having a smaller diameter than the middle wound fiber 360*b*, and the middle wound fiber 360*b* having a smaller diameter than the outer wound fiber 360*a*. The outer wound fiber 360*a* having the largest diameter among the wound fibers 360*a*, 360*b*, 360*c* can help provide structural integrity to the fiber 358 throughout its structure, e.g., from the core 360*d* to the outer fiber 360*a*. Additionally, the core fiber 360*d* can be the same as or different from any of the wound fibers 360*a*, 360*b*, 360*c*. As illustrated, the core fiber 360*d* has a larger diameter than the outer wound fiber 360*d*.

Each of the wound fibers 360*a*, 360*b*, 360*c* can be associated with a different medicant, e.g., be configured to allow release of a different medicant "hidden" therein in response to fiber unwinding or fraying. For example, each of the medicants can have a different desired effect on tissue (e.g., affect hemostasis, affect tissue growth, provide antimicrobial effect, etc.) such that different fiber unwindings provide different effects to tissue. Alternatively, any one or more of the wound fibers 360*a*, 360*b*, 360*c* can be associated with a same medicant.

An adjunct formed of a plurality of the fibers 358 can be releasably coupled to a stapler (e.g., to an end effector of a stapler and/or to a cartridge retainable in a stapler) so that the adjunct is desirably positioned relative to tissue to which the stapler applies staples and the adjunct.

Figure 59:
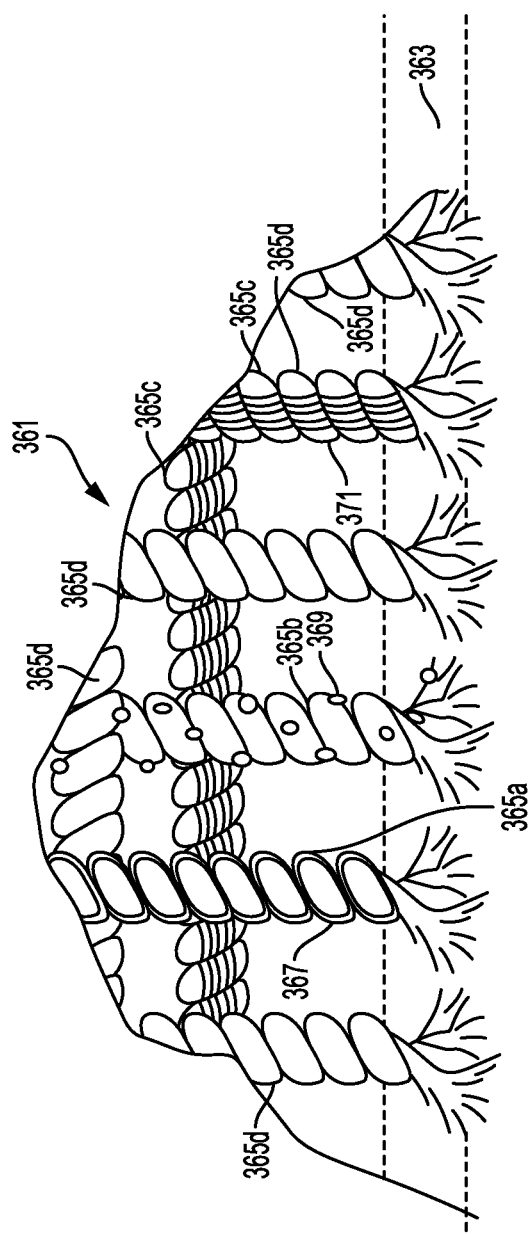
FIG. 59 is a perspective view of a portion of still another implementation of an implantable adjunct formed from a plurality of fibers woven together to form a sheet-like fiber woven mesh.

FIG. 59 illustrates another implementation of an adjunct 361 formed from a plurality of fibers woven together to form a sheet-like fiber woven mesh. Only a portion of the adjunct 361 is shown at an outer edge 363 thereof. As shown, the fibers forming the adjunct 361 include four types 365*a*, 365*b*, 365*c*, 365*d* of twisted fibers. An adjunct can include any combination of the types of fibers 365*a*, 365*b*, 365*c*, 365*d* shown in FIG. 59.

First, second, and third types of fibers 365*a*, 365*b*, 365*c* each include fibers having a certain conformation that is changeable, such as by the action of water and/or other agents that the adjunct 361 is subjected to at the treatment site, e.g., the first, second, and third types of fibers 365*a*, 365*b*, 365*c* are each configured to unwind or fray. The first type of fibers 365*a* include a coating 367 thereon that is configured to absorb, dissolve or otherwise disintegrate as discussed herein for coatings. The coating 367 can itself include a medicant, or the coating 367 can overlay a medicant on an outer surface of the fiber that is releasable from the fiber due to the coating's disintegration. The second type of fibers 365*b* has a plurality of pellets 369 attached thereto. As discussed above, the pellets 369 can each have a dissolvable coating such that, as the coating is disintegrated, the medicant can be distributed as a bolus dose or as a time release dosage. The pellets 369 can be more densely packed on the fibers 365*b* the closer the fibers 365*b* are to a center of the adjunct 361, which may allow more of the medicant to be delivered the more the fibers interact with fluid or other matter that dissolves the coating. Additionally or alternatively, the medicant of the pellets 369 can be on a progressive time release pattern in which medicant adjacent the outer edge 363 releases faster from the pellets 369 than from pellets 369 more toward the center of the adjunct 361. The third type of fibers 365*c* includes a plurality of smaller-diameter fibers 371 braided together to form the fiber. A medicant can be "hidden" within the braid and be released in response to the braid unwinding or fraying.

A fourth type of fibers 365*d* includes fibers having a certain conformation that is not changeable, e.g., the fourth types of fibers 365*d* are configured to not unwind or fray. The fourth type of fibers 365*d* form a base of the adjunct 361 so as to provide structural stability to the adjunct 361 and, hence, to provide structural stability to a wound to which the adjunct 361 is delivered.

As mentioned above, different adjuncts can have one or more medicants releasably retained therein at different locations to optimize effectiveness of the adjunct and the one or more medicants releasably retained therein during the process of wound healing. One example of such an adjunct is the adjunct 176 of FIG. 32 that includes a plurality of heterogeneous portions or layers 178*a*, 178*b*, 180*a*, 180*b* incorporating different medicants. Another example of such an adjunct is the adjunct 184 of FIG. 33 that includes top and bottom layers or portions 186, 188 that can each have different medicants therein. Yet another example of such an adjunct is the adjunct 185 of FIG. 35 that includes side-to-side portions 185*a*, 185*b* having different medicants G5, G6 disposed therein. Still another example of such an adjunct is the adjunct 187 of FIG. 36 that includes inner and outer portions 187*a*, 187*b* having different medicants G7, G8 disposed therein. Another example of such an adjunct is the adjunct 190 of FIG. 37 that includes outer and inner concentric layers 191, 192 that can each have different medicants A4, B4 therein. Yet another example of such an adjunct is the adjunct 194 of FIG. 38 that includes radially alternating portions 195, 196 having different medicants A5, B5 disposed therein. Still another example of such an adjunct is the adjunct 197 of FIG. 39 that includes outer and inner portions 198, 199 having different medicants B6, A6 disposed therein.

Figure 60:
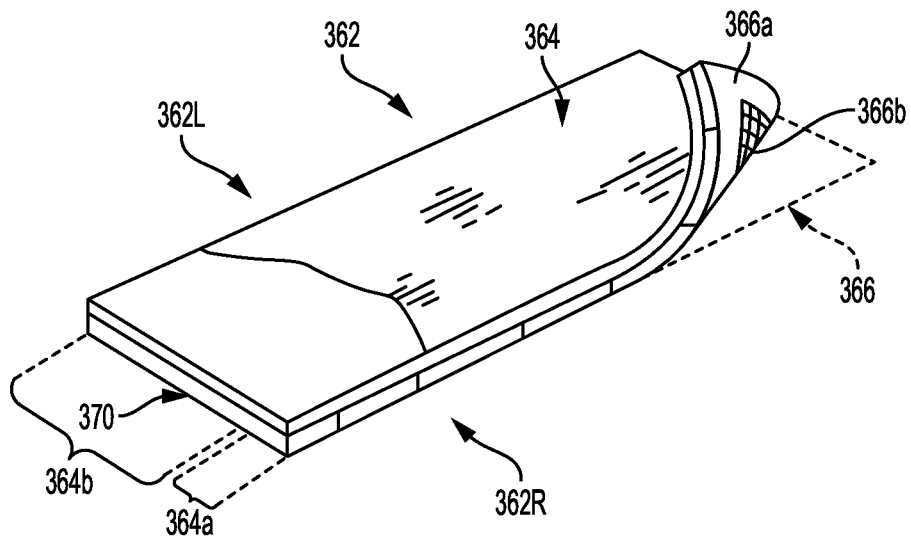
FIG. 60 is a perspective, partial cutaway view of an implementation of an implantable adjunct that includes a plurality of heterogeneous layers or portions.

FIG. 60 illustrates another example of an adjunct 362 that includes a plurality of heterogeneous layers or portions. Similar to the adjunct 176 in FIG. 32, the adjunct includes a top layer or portion 364 and a bottom layer or portion 366. In the example of FIG. 60, the top portion 364 has two portions 364*a*, 364*b* and the bottom portion 366 has two portions 366*a*, 366*b*. The top portion's two portions 364*a*, 364*b* in this example can be similar to the two top portions 178*a*, 178*b* of the adjunct 176, and the bottom portion's two portions 366*a*, 366*b* can be similar to the two bottom portions of the adjunct 184 in FIG. 33.

Figure 61:
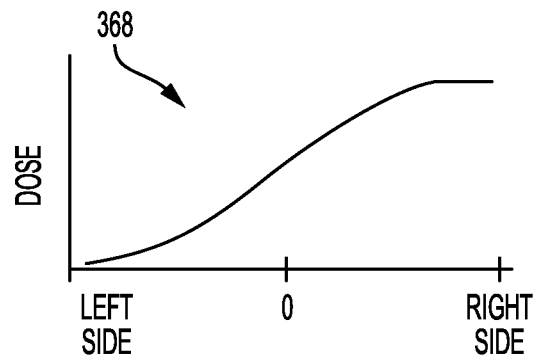
FIG. 61 is a graph showing an implementation of an elution profile of the adjunct of FIG. 60.

Each of the portions 364*a*, 364*b*, 366*a*, 366*b* can have a medicant releasably retained therein. Each of the medicants of the portions 364*a*, 364*b*, 366*a*, 366*b* can be the same as any one or more of the other medicants, or each of the medicants can be different from any one or more of the other medicants in any of one or more ways including type of medicant, dosage amount, and elution rate. Additionally, similar to that discussed above, each of the portions 364a, 364b, 366a, 366b can have degradation rates that vary in a distinct or continuous manner. The degradation rates and distribution of the medicants within one or more of the portions 364a, 364b, 366a, 366b can vary in a distinct or continuous manner such that the adjunct 362 can provide an elution profile shown in a graph 368 in FIG. 61.

The graph 368 illustrates different rates of medicant absorption across the adjunct 362 from a left side 362L thereof to a right side 362R thereof. The spatial terms "left" and "right" are used with reference to the orientation of the adjunct 362 as shown in FIG. 60 and are not intended to be limiting and absolute. The zero ("0") along the x axis of the graph 368 represents a central area 370 of the adjunct 362 centered around a mid-portion of the adjunct 362. The graph 368 represents an exemplary elution profile after the cutting of tissue (e.g., cutting by a cutting element of a surgical stapler) to which the adjunct 362 is delivered. The right side 362R of the adjunct 362 as delivered to the tissue can be positioned along the cut line or cut edge, and the left side 362L of the adjunct 362 as delivered to the tissue can be positioned along a non-cut portion of the tissue, such as a non-cut edge of the tissue, on an exterior surface of the tissue at some location within the tissue's perimeter, or on an interior surface of the tissue at some location within the tissue's perimeter. As shown, the elution rate of the one or more medicants disposed in the adjunct 362 peaks at the right side 362R and curves downward toward the left side 362L, where the elution rate is the lowest. Accordingly, a higher dose of medicant(s) is delivered the closer the medicant(s) are to the right side 362R of the adjunct 362. In this way, when the right side 362R is positioned along the cut line or cut edge of the tissue, more medicant can be delivered along the cut tissue edge, which as discussed herein, can be an area particularly susceptible to the adverse effects of wound healing. In an exemplary implementation, the one or more medicants disposed in the first portion 364a of the top portion 364 of the adjunct 362 can include a hemostatic agent, which may allow a relatively high dose of the hemostatic agent to be delivered to tissue along its cut line or edge to facilitate blood clotting therealong in accordance with the elution profile shown in the graph 368.

In the context of the adjunct 362 being delivered to a lung, the adjunct 362 can be delivered to lung tissue such that the right side 362R of the adjunct 362 is positioned along an outside edge of the lung. When stapling a lung, leakage is traditionally greatest along an outside edge of the lung. Thus, the one or more medicants eluting from the adjunct 362 according to the elution profile 368 can have a highest dose along the lung's edge and thereby help address the particular problem of leakage therealong.

Figure 62:
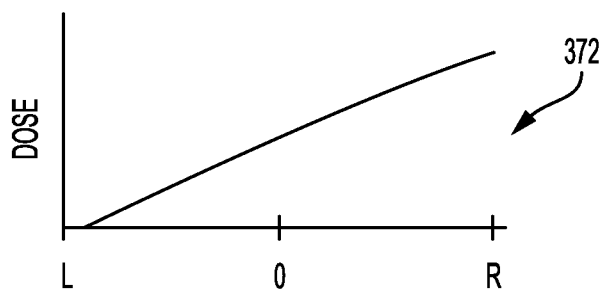
FIG. 62 is a graph showing another implementation of an elution profile of the adjunct of FIG. 60.

FIG. 62 illustrates another graph 372 showing another elution profile that the adjunct 362 can provide according to degradation rates and distribution of the one or more medicants within the portions 364a, 364b, 366a, 366b. The graph 372 is similar to the graph 368 of FIG. 61 in that the elution rate of the one or more medicants disposed in the adjunct 362 peaks at the right side 362R and slopes downward toward the left side 362L, where the elution rate is the lowest. The slope in the graph 372 is a linear line, unlike the curve in the graph 368. Similar to that discussed above regarding the graph 368, the one or more medicants disposed in the first portion 364a of the top portion 364 of the adjunct 362 can include a hemostatic agent, which may allow a relatively high dose of the hemostatic agent to be delivered to tissue along its cut line or edge to facilitate blood clotting therealong, in accordance with the elution profile shown in the graph 372, when the right side 362R of the adjunct 362 is positioned along a tissue's cut line or cut edge. Additionally, similar to that discussed above regarding the elution profile 368, the one or more medicants eluting from the adjunct 362 according to the elution profile 372 can have a highest dose along the lung's edge and thereby help address the particular problem of leakage therealong when the right side 362R of the adjunct 362 is positioned along the lung's edge.

Figure 63:
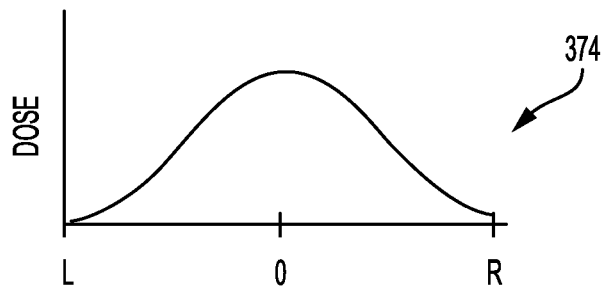
FIG. 63 is a graph showing yet another implementation of an elution profile of the adjunct of FIG. 60.

FIG. 63 illustrates another graph 374 showing another elution profile that the adjunct 362 can provide according to degradation rates and distribution of the one or more medicants within the portions 364a, 364b, 366a, 366b. The graph 374 represents an exemplary elution profile before the cutting of tissue (e.g., cutting by a cutting element of a surgical stapler) to which the adjunct 362 is delivered. The central area 370 of the adjunct 362 can be positioned along a planned cut line of tissue such that the highest dose of the one or more medicants released from the adjunct 362 can be highest along the planned cut line. In this way, when the tissue is cut along the cut line, the tissue has already begun to have delivered thereto a relatively high dose of medicant(s) along the cut line, which may help limit adverse effects of the cutting. For example, a relatively high dose of a hemostatic agent, an antimicrobial agent, an antifungal agent, and/or an antiviral agent can be delivered from the central area 370 of the adjunct 362.

Figure 64:
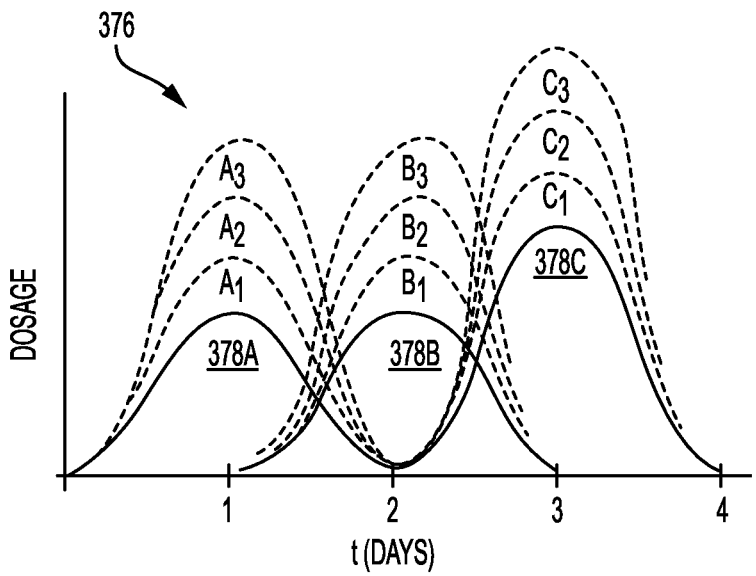
FIG. 64 is a graph showing implementations of cumulative doses of medicants.

As discussed above, multiple doses of a medicant can be released from an adjunct to achieve a cumulative dose of the medicant. FIG. 64 shows one example of a graph 376 of possible cumulative doses over time for each of three medicants 378A, 378B, 378C. The time scale in FIG. 64 is an example only. A single dose of each of the medicants 378A, 378B, 378C is shown by a solid line in the graph 376. Each additional cumulative dose released at substantially the same time as its associated single dose is shown by a dotted line, e.g., two doses of the medicant 378A shown as dotted line $A_1$, three doses of the medicant 378A shown as dotted line $A_2$, four doses of the medicant 378A shown as dotted line $A_3$, two doses of the medicant 378B shown as dotted line $B_1$, etc. In an exemplary implementation, the first medicant 378A can be configured to facilitate hemostasis in the hemostasis stage of wound healing and each of the second and third medicants 378B, 378C can be configured to facilitate inflammation in the inflammation stage of wound healing. The individual doses of the second and third medicants 378B, 378C can be configured cooperate to provide a cumulative dose (e.g., a cumulative inflammatory dose) similar to the cumulative dose "BC" in FIG. 40 and FIG. 42.

Figure 65:
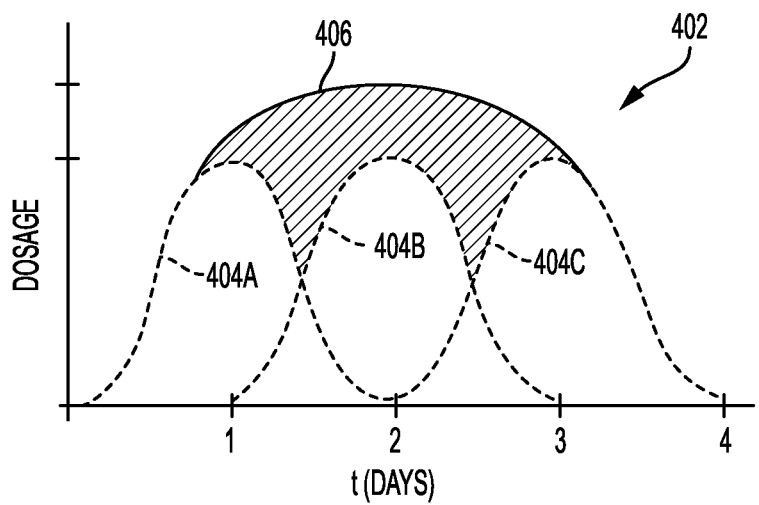
FIG. 65 is a graph showing another implementation of a cumulative dose of medicants.

FIG. 65 shows one example of a graph 402 of possible cumulative doses over time for each of three medicants 404A, 404B, 404C releasable from an adjunct. The time scale in FIG. 65 is an example only. As shown in the graph 402, the first medicant 404A begins releasing from the adjunct at a time zero of wound creation and peaks in dosage at a start of Day 1, the second medicant 404B begins releasing from the adjunct at a start of Day 1 and peaks in dosage at a start of Day 2, and the third medicant 404C begins releasing from the adjunct at a start of Day 2 and peaks in dosage at a start of Day 3. The three medicants 404A, 404B, 404C can thus have time-staggered peak dosages. Additionally, as shown, the first medicant 404A can stop releasing from the adjunct (e.g., be fully released from the adjunct) at a start of Day 3, the second medicant 404B can stop releasing from the adjunct at a start of Day 3, and the third medicant 404C can stop releasing from the adjunct at a start of Day 4. The individual doses of the three medicants 404A, 404B, 404C can be configured cooperate to provide a cumulative dose 406 similar to the cumulative dose "BC" in FIG. 40 and FIG. 42. In an exemplary implementation, the three medicants 404A, 404B, 404C can each be configured to facilitate wound healing in the inflammation stage of wound healing.

Figure 66:
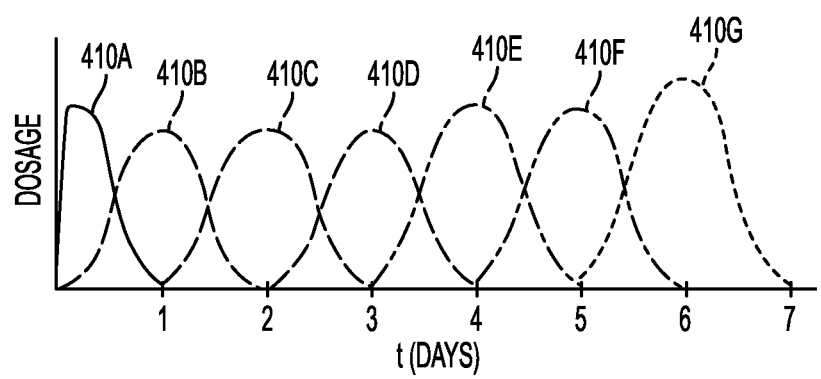
FIG. 66 is a graph showing an implementation of doses of medicants.

FIG. 66 shows one example of a graph 408 of possible cumulative doses over time for each of seven medicants 410A, 410B, 410C, 410D, 410E, 410F, 410G releasable from an adjunct. The time scale in FIG. 66 is an example only. As shown in the graph 408, the first medicant 410A begins releasing from the adjunct at a time zero of wound creation and peaks in dosage shortly after time zero, the second medicant 410B begins releasing from the adjunct at time zero and peaks in dosage at a start of Day 1, the third medicant 410C begins releasing from the adjunct at a start of Day 1 and peaks in dosage at a start of Day 2, the fourth medicant 410D begins releasing from the adjunct at a start of Day 2 and peaks in dosage at a start of Day 3, the fifth medicant 410E begins releasing from the adjunct at a start of Day 3 and peaks in dosage at a start of Day 4, the sixth medicant 410F begins releasing from the adjunct at a start of Day 4 and peaks in dosage at a start of Day 5, and the seventh medicant 410G begins releasing from the adjunct at a start of Day 5 and peaks in dosage at a start of Day 6. The seven medicants 410A, 410B, 410C, 410D, 410E, 410F, 410G can thus have time-staggered peak dosages. Additionally, as shown, the first medicant 410A can stop releasing from the at a start of Day 1, the second medicant 410B can stop releasing from the adjunct at a start of Day 2, the third medicant 410C can stop releasing from the adjunct at a start of Day 3, the fourth medicant 410D can stop releasing from the adjunct at a start of Day 4, the fifth medicant 410E can stop releasing from the adjunct at a start of Day 5, the sixth medicant 410F can stop releasing from the adjunct at a start of Day 6, and the seventh medicant 410F can stop releasing from the adjunct at a start of Day 7. In an exemplary implementation, the first medicant 410A can be configured to facilitate hemostasis in the hemostasis stage of wound healing, the second, third, and fourth medicants 410B, 410C, 410D can each be configured to facilitate inflammation in the inflammation stage of wound healing, the fifth and sixth medicants 410E, 410F can each be configured to inhibit MMP in the inflammation stage of wound healing, and the seventh medicant 410G can be configured to prevent inflammation in the proliferation stage of wound healing.

Figure 67:
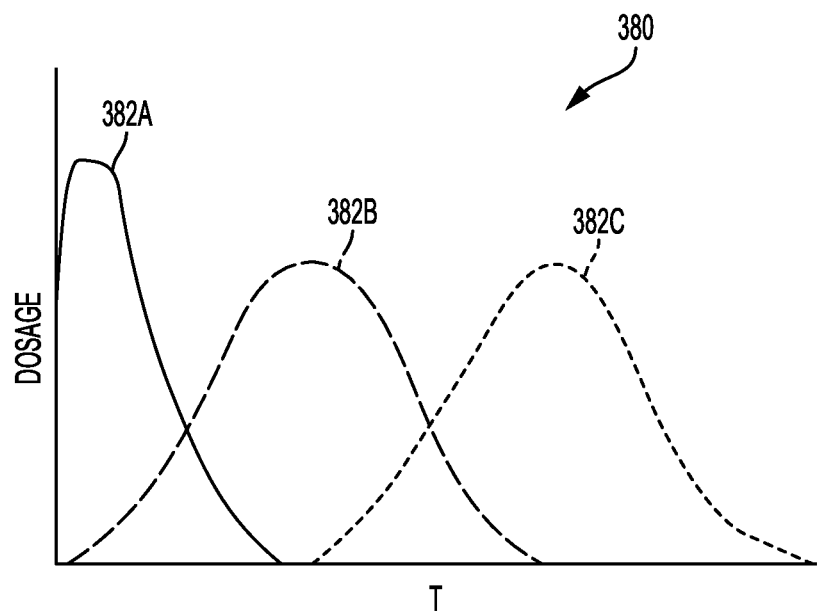
FIG. 67 is a graph showing another implementation of doses of medicants.

FIG. 67 shows one example of a graph 380 of possible doses over time for each of three medicants 382A, 382B, 382C releasable from an adjunct. Each of the doses of the medicants 382A, 382B, 382C as shown can be achieved using either a single dose or a cumulative dose. As shown in the graph 380, the first and second medicants 382A, 382B begin releasing from the adjunct at a time zero of wound creation and the third medicant 382C is released at a point in time after time zero. As shown, the first medicant 382A can achieve its peak dosage before the second medicant 382B reaches its peak dose, and the second medicant 382B can achieve its peak dosage before the third medicant 382C reaches its peak dose. The three medicants 382A, 382B, 382C can thus have time-staggered peak dosages. Additionally, as shown, the second medicant 382B can achieve its peak dosage at substantially the same time that the dose of the first medicant 382A ends and the dose of the third medicant 382C begins. In an exemplary implementation, the first medicant 382A can be configured to facilitate hemostasis in the hemostasis stage of wound healing and each of the second and third medicants 382B, 382C can be configured to facilitate wound healing in a stage following the hemostasis stage, e.g., in one or more of the inflammation, proliferation, and remodeling stages.

Figure 68:
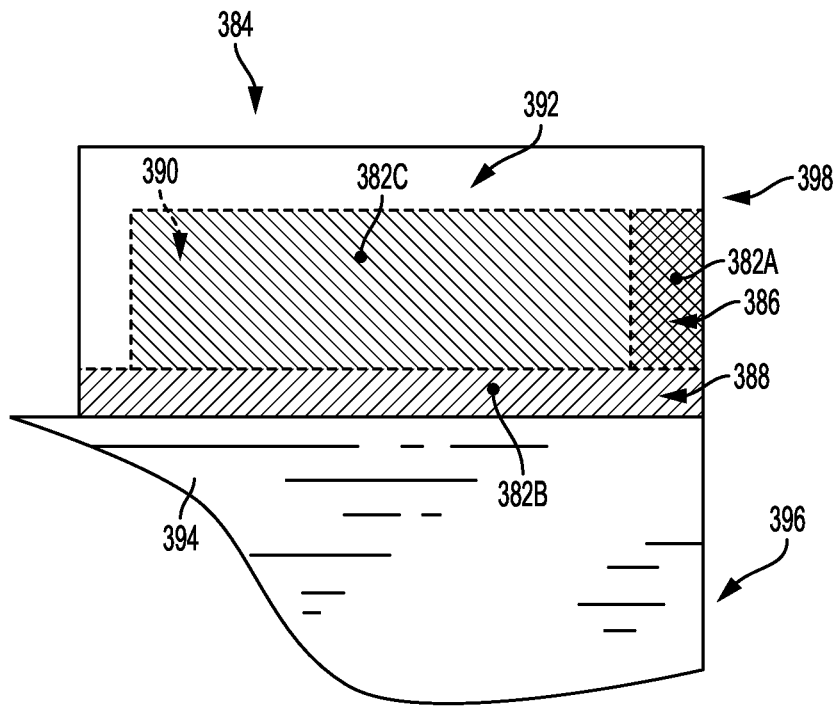
FIG. 68 is a side view of an implementation of an implantable adjunct having the medicants of FIG. 67 disposed therein, the adjunct applied to tissue.

FIG. 68 illustrates one example of an adjunct 384 that includes the three medicants 382A, 382B, 382C releasable therefrom over time in accordance with the graph 380. As shown, the first medicant 382A is releasably disposed in a first portion or layer 386 of the adjunct 384, the second medicant 382B is releasably disposed in a second portion or layer 388 of the adjunct 384, and the third medicant 382C is releasably disposed in a third portion or layer 390 of the adjunct 384. The adjunct 384 can include a fourth portion or layer 392 having no medicant disposed therein, although in other implementations, the fourth portion or layer 392 can have at least one medicant releasably disposed therein.

FIG. 68 illustrates the adjunct 384 delivered to tissue 394, such as by being delivered thereto in conjunction with staples (not shown). The adjunct 384 can be positioned relative to the tissue 394 such that, as shown, the adjunct 384 is on top of the tissue 394 with an outer edge 396 of the tissue 394 being aligned with an outer edge 398 of the adjunct 384 having at least the first portion or layer 386 exposed thereon. The first medicant 382A can thus be configured to be released from the first portion or layer 386 and leak or drip down onto the tissue's outer edge 396. The tissue's outer edge 396 can be a natural edge of the tissue 394 or can be a cut edge of the tissue 394. In the case of the tissue's outer edge 396 being a cut edge, the adjunct 384 can include two halves, with one of the halves being the portion shown in FIG. 68 and the other half of the adjunct 384 being a mirror image thereof on the other cut half of the tissue 394.

The adjunct 384 can be releasably coupled to a stapler (e.g., to an end effector of a stapler and/or to a cartridge retainable in a stapler) so that the adjunct 384 is desirably positioned relative to the tissue 394 to which the stapler applies staples and the adjunct 394, e.g., so the first portion or layer 386 of the adjunct 384 is aligned with the natural edge 396 of the tissue 394 or where the cut edge 396 of the tissue 394 will be after the stapler cuts the tissue 394.

Figure 69:
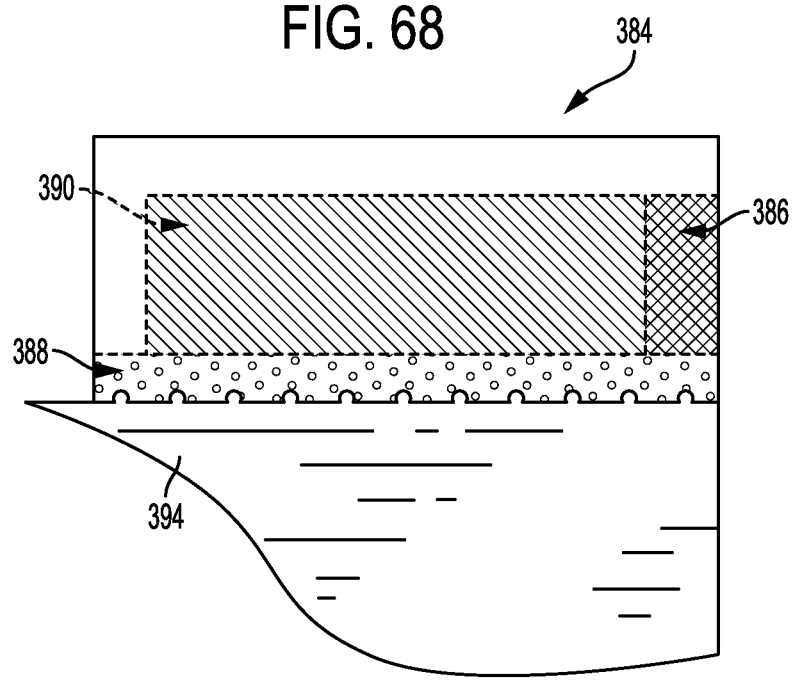
FIG. 69 is a side view of the adjunct of FIG. 68 with tissue growth started.
Figure 70:
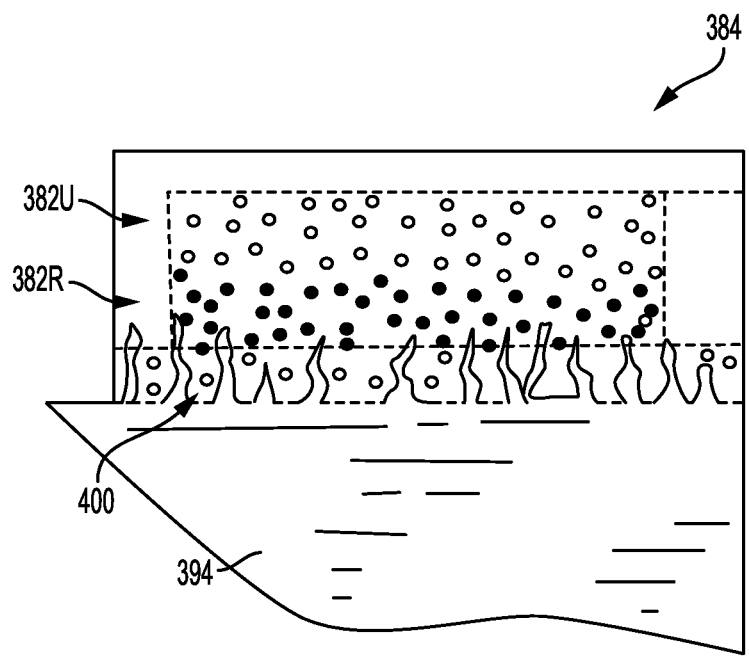
FIG. 70 is a side view of the adjunct of FIG. 69 including further tissue growth.

FIG. 69 illustrates the adjunct 384 attached to the tissue 394 with tissue growth (cell 400 migration) beginning into the second portion or layer 388. Then, as shown in FIG. 70, after an amount of time has passed, the first medicant 382A can have been fully released from the adjunct 384, the second medicant 382B can be partially released from the adjunct 384, and the third medicant 382C can begin to release from the adjunct 384 (a released portion 382R of the third medicant 382C and an unreleased or inactive portion of the third medicant 382C being shown in FIG. 70). In this illustrated implementation, the third medicant 382C begins its release from the adjunct 384 in response to interaction of cells 400 migrated thereto from the tissue 394 and through the second portion or layer 388. In other words, the third medicant 382C begins its release from the adjunct 384 in response to tissue ingrowth.

As mentioned above, the particular characteristics associated with an adjunct having one or more medicants releasably retained therein can be targeted to use of the adjunct with a particular organ, such as a colon, a stomach, a lung, and a liver. Regarding the colon, its tissue structure is generally organized to facilitate radial expansion or stretching (distension) and to limit longitudinal expansion or stretching (e.g., expansion or stretching along a longitudinal axis of the colon). Additionally, anastomosis in colectomy procedures formed using a circular stapler or a linear stapler, leaves a staple line within the colon. For colorectal procedures, leaks at the anastomosis wound site are a common and potentially life-threatening event. An adjunct having one or more medicants releasably retained therein delivered to the colon tissue at the anastomosis wound site can be configured to help prevent leaks at the anastomosis wound site and thereby improve wound healing and help prevent the adverse effects caused by leaks and by wound healing in general. The adjunct may be applied to the colon tissue along the staple line to reflect the endolumenal nature of the staple line, to provide strength along the staple line where anastomosis tissues are attached together, and/or to help focus the wound healing benefits of the adjunct and/or its associated medicant(s) along the area where leaks are most common. In exemplary implementations, the medicant(s) disposed in the adjunct delivered to the colon can be configured to perform a function of any one or more of slowing down macrophage function and/or production, increasing fibroblast activity and attraction, and reducing inflammation.

As discussed above, an adjunct having one or more medicants releasably retained therein can be delivered to tissue to focus encouraged tissue growth in a direction in accordance with the colon's natural radial expansion and contraction. This encouragement can be caused in any number of ways, as discussed above.

Figure 71:
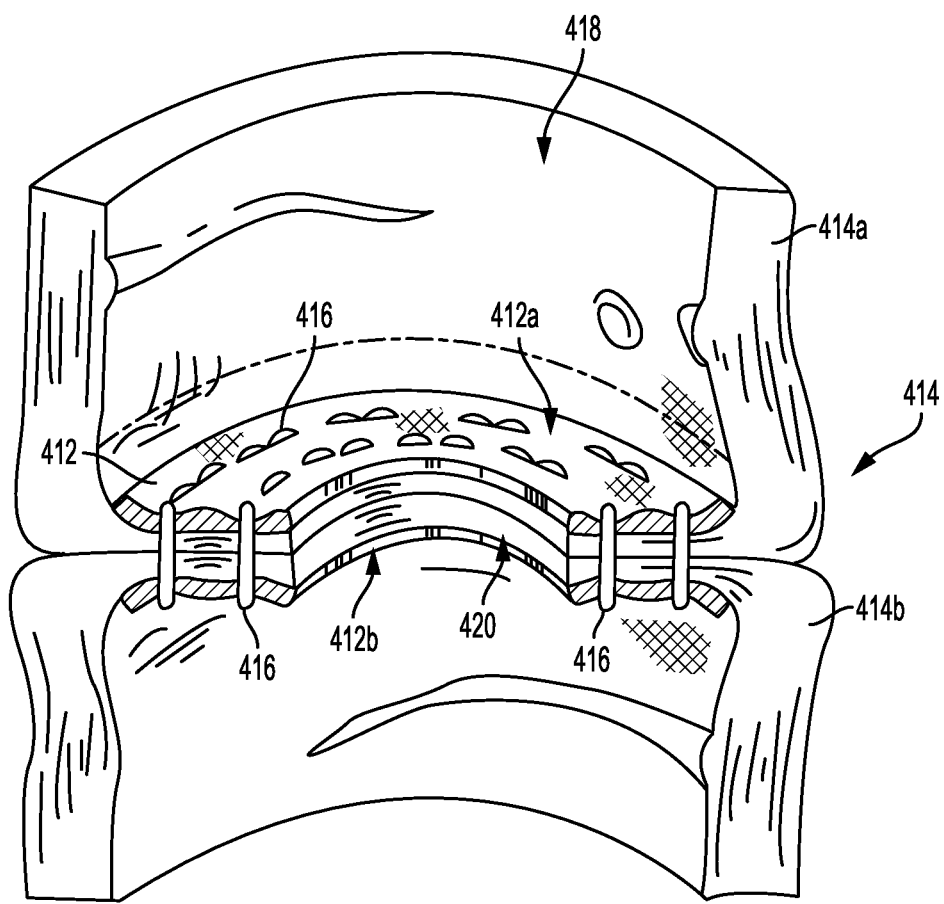
FIG. 71 is a cross-sectional perspective view of an implementation of an implantable adjunct stapled to a colon.

FIG. 71 illustrates one implementation of an adjunct 412 delivered to a colon 414 with a plurality of staples 416 in an end-to-end anastomosis procedure using a circular surgical stapler (not shown). As shown, the adjunct 412 is intralumenally placed, e.g., is located within an inner passageway 418 of the colon 414. The staple line formed by the staples 416 may extend generally transverse to the colon's natural direction of distension, as shown.

The adjunct 412 in this illustrated embodiment includes a circular-shaped fiber-based lattice with opposed sides 412a, 412b thereof positioned on opposite sides of the connected tissue 414a, 414b. An inner opening 420 of the adjunct 412 is in communication with the colon's inner passageway 418 so as to facilitate normal colon function. A circular-shaped adjunct such as the circular-shaped adjunct 412 in this illustrated example may be particularly effective in side-to-side anastomosis procedure since it may surround the entire wound area around an inner circumference of the colon 414, e.g., around a circumference of the inner passageway 418. Surrounding the entire wound area may help prevent leaks from anywhere around the wound site.

Figure 72:
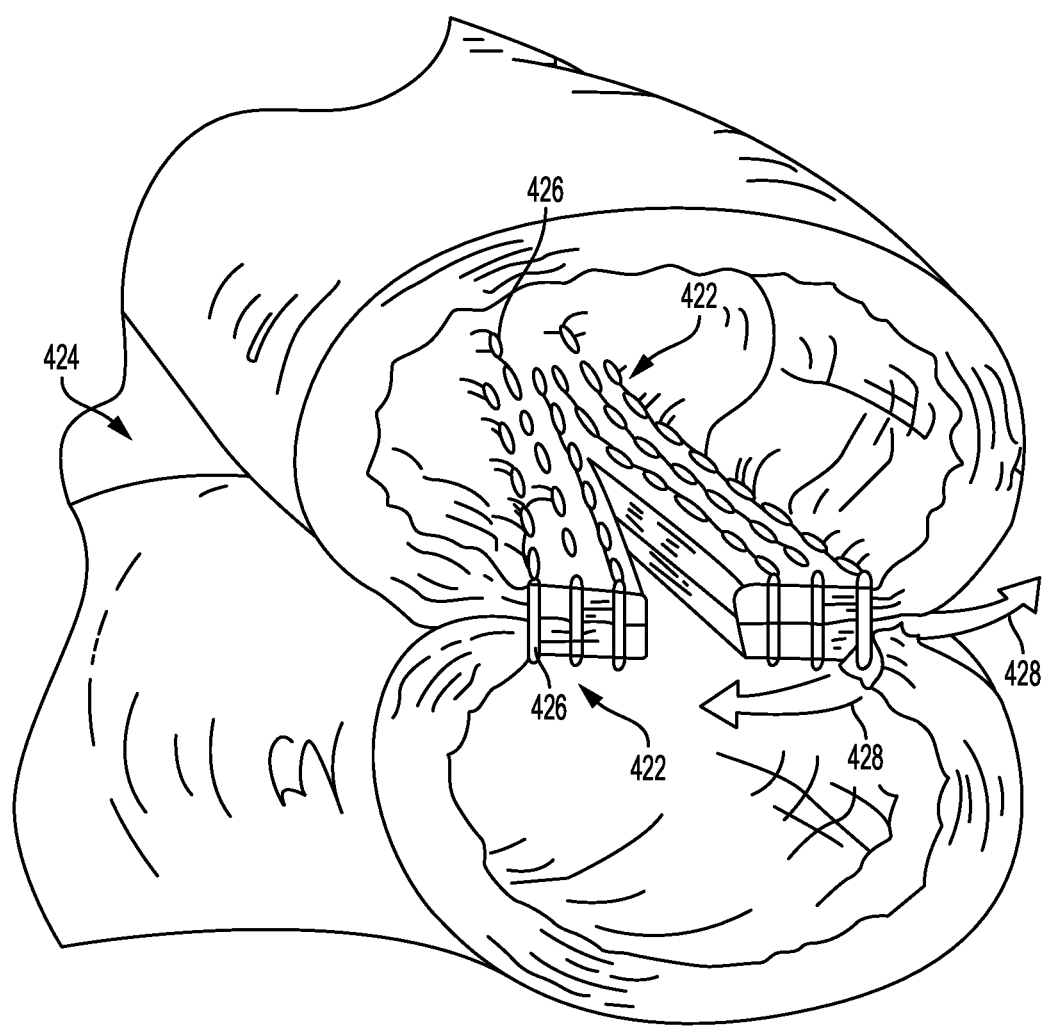
FIG. 72 is a cross-sectional perspective view of an implementation of an implantable adjunct stapled to a tubular tissue structure.

FIG. 72 illustrates one implementation of an adjunct 422 delivered to a tubular tissue structure 424 with a plurality of staples in a side-to-side anastomosis procedure. The tubular tissue structure 424 can include, for example, a colon or a tubular portion of a lung (e.g., a bronchial tubes thereof). The staple line formed by the staples may extend generally transverse to the tubular tissue structure's natural direction of distension, as shown. The adjunct 422 includes a plurality of members each having an outer layer or coating 426 encapsulating an inner layer (obscured in FIG. 72) disposed over a staple (obscured in FIG. 72), similar to the adjunct 150 of FIG. 22. The outer layer 426 and/or the inner layer can be infused with a reactive dye or reactive polymer that in the presence of a secondary agent (e.g., a swallowed pill, a suppository, etc.) can be configured to change color. The color change can allow leaks 428 to be detected by visually and/or otherwise observing the color change, such as via x-ray. Corrective action may thus be taken to address the leakage. Color-changing adjuncts are further described in U.S. patent application Ser. No. 14/840,431 entitled "Surgical Adjuncts With Medicants Affected By Activator Materials" filed on Aug. 31, 2015, which is hereby incorporated by reference in its entirety.

Instead of changing color, one or more medicants releasably retained by an adjunct, such as the adjunct 422, delivered to colon tissue can be configured to otherwise yield at least one of a signal and an effect on the adjunct, e.g., foaming or a change in conformation of the adjunct. Examples of such medicants and adjuncts are further described in above-mentioned U.S. patent application Ser. No. 14/840,431 entitled "Surgical Adjuncts With Medicants Affected By Activator Materials" filed on Aug. 31, 2015.

Regarding the stomach, its tissue structure is generally organized to facilitate radial expansion or stretching and to limit expansion or stretching along its longitudinal axis. Adjuncts having one or more medicants releasably retained therein can thus be delivered to stomach tissue to focus encouraged tissue growth in a direction in accordance with the stomach's natural radial expansion and contraction, similar to that discussed herein regarding colon tissue. Adjuncts having one or more medicants releasably retained therein can be delivered to stomach tissue in any of a variety of surgical procedures, such as procedures using a linear stapler in which a linear cut is formed in stomach tissue and procedures using a circular stapler in which an end-to-side anastomosis is formed.

It may be beneficial to deliver to the stomach an adjunct having disposed therein one or more medicants configured to prevent tissue in contact therewith from growing. The stomach is near various other tissue structures, e.g., the esophagus, the intestine, etc., to which adhesion of the stomach is generally not be desired. The one or more medicants configured to prevent tissue in contact therewith from growing can be configured to be released from the adjunct, in any of various ways described herein, in area(s) adjacent the tissue(s) to which the stomach should not be adhered.

Examples of adjuncts and medicants deliverable to the stomach are further described in U.S. patent application Ser. No. 14/841,074 entitled "Adjunct Material For Delivery To Stomach Tissue" filed on Aug. 31, 2015, which is hereby incorporated by reference in its entirety.

Regarding the lungs, its tissue structure is generally organized to facilitate radial expansion or stretching and to limit expansion or stretching along its longitudinal axis. Adjuncts having one or more medicants releasably retained therein can thus be delivered to lung tissue to focus encouraged tissue growth in a direction in accordance with the lung's natural radial expansion and contraction, similar to that discussed herein regarding colon tissue. Adjuncts having one or more medicants releasably retained therein can be delivered to lung tissue in any of a variety of surgical procedures, such as procedures using a linear stapler in which a linear cut is formed in lung tissue. It may be beneficial to allow distension of lung tissue along a length of a staple line applied to the lung tissue. The natural direction of the tissue that encourages the distension, and hence the direction that an adjunct may be configured to encourage tissue growth in any of a variety of ways described herein, may thus be along a longitudinal axis of the staple line. Examples of adjuncts and medicants deliverable to the lung are further described in U.S. patent application Ser. No. 14/840,878 entitled "Surgical Adjuncts And Medicants For Promoting Lung Function" filed on Aug. 31, 2015 and U.S. patent application Ser. No. 14/841,147 entitled "Inducing Tissue Adhesions Using Surgical Adjuncts And Medicants" filed on Aug. 31, 2015, which are hereby incorporated by reference in their entireties.

Regarding the liver, its tissue structure is generally organized to facilitate radial expansion or stretching and to limit expansion or stretching along its longitudinal axis. Adjuncts having one or more medicants releasably retained therein can thus be delivered to liver tissue to focus encouraged tissue growth in a direction in accordance with the liver's natural radial expansion and contraction, similar to that discussed herein regarding liver tissue. Adjuncts having one or more medicants releasably retained therein can be delivered to liver tissue in any of a variety of surgical procedures, such as procedures using a linear stapler in which a linear cut is formed in liver tissue. Examples of adjuncts and medicants deliverable to the liver are further described in U.S. patent application Ser. No. 14/841,180 entitled "Adjunct Material For Delivery To Live Tissue" filed on Aug. 31, 2015, which is hereby incorporated by reference in its entirety.

As discussed above, the adjunct material can have a variety of configurations and be formed from any number of materials. Various exemplary composite adjunct materials for delivering medicants are provided. In general, the adjunct material can be configured to be delivered to tissue by deployment of staples from a cartridge body of a surgical stapler. The adjunct material includes a conformable region and a distinct reinforcing region that form the composite structure. The conformable region can be any material that can conform to an irregular surface, and it can be a viscous or flowable material as explained in more detail below. The reinforcing region is non-conformable and can be any structural component or material that provides reinforcement to the adjunct material. The reinforcing region can be in various forms such as a foam, one or more fibers, a mesh, or a scaffold or any other relatively non-conformable structure. An effective amount of at least one medicant can be disposed within and releasable from at least one of the conformable region and the reinforcing region and can provide a desired effect on tissue in-growth in a predetermined manner.

In an exemplary implementation, the conformable region can be any material that is viscous and flowable. The material can vary depending on the viscosity. For example, a more viscous conformable region will be more flowable and a less viscous conformable region will be less flowable. The conformable region can vary in a number of ways. One or more conformable regions can be positioned in the adjunct material in any desired pattern and configuration. Each conformable region can have any desired properties.

The conformable region can have properties that vary under different conditions. In one aspect, the properties of the conformable region can change when the conformable region contacts liquids. For example, when the conformable region includes a polymer, the interaction of the polymer with water and hydrolysis of the polymer can enhance the flowability of the polymer. In one implementation, the conformable region can include a somewhat cross-linked polymer such as a hydrogel that can swell upon contact with water, causing a decrease in its viscosity and an increase in its flowability.

In one aspect, the properties of the conformable region can change in response to exposure to temperatures in certain ranges. For example, when temperature increases (e.g., from room temperature to body temperature), the conformable region can become more flowable. The conformable region can initially be in the form of a somewhat hard material, such as a wax, but then become a softer and more flowable material when the temperature increases.

The conformable region can be made from a variety of materials. Any number of polymers can be suitably used to form the conformable region. The conformable region can be, for example, a low glass transition temperature (e.g., below about 10° C., such as below about 4° C.) absorbable polymer or a low molecular weight, or a low inherent viscosity polymer (e.g., in a range of about 1.0 dL/g to about 2.0 dL/g). Examples of conformable region compositions are also described in U.S. patent application Ser. No. 14/667,874 entitled "Malleable Bioabsorbable Polymer Adhesive For Releasably Attaching A Staple Buttress To A Surgical Stapler" filed Mar. 25, 2015, which is hereby incorporated by reference in its entirety. The conformable region can be a hydrogel. Non-limiting examples of materials for the conformable region include hyaluronic acid, carboxymethylcellulose (CMC), polyvinyl alcohol, polyvinyl acetate, higher molecular weight (PEG) (solid form), and higher molecular weight polypropylene glycol (PPG) (solid form). The conformable region can include liquids such as, for example, glycerin, low molecular weight PEG (liquid form), and low molecular weight PPG (liquid form). In one aspect, the conformable region can be a slow flowing absorbable polymer, such as a PEG with a molecular weight in the range of about 50 to about 20,000 Daltons. In one aspect, the conformable region can be PEG or a pressure sensitive adhesive (PSA) which dissolves quickly in the body within minutes of delivery, leaving any medicant to be delivered to the tissue.

The conformable layer can have adhesive properties or be tacky enabling the adjunct material to attach to the cartridge body, an anvil, or staples. In one aspect, the conformable layer can be a PSA with short oxidized regenerated cellulose (ORC) fibers. The ORC fibers are a hemostatic agent that forms a gel when in contact with water.

The conformable region can include a pressure sensitive adhesive (PSA) such as those disclosed in previously mentioned U.S. patent application Ser. No. 14/667,874 entitled "Malleable Bioabsorbable Polymer Adhesive For Releasably Attaching A Staple Buttress To A Surgical Stapler" filed Mar. 25, 2015.

As stated above, one or more medicants can be included in the conformable region. The medicant(s) can be incorporated into the conformable region in any desired manner for any desired effect as described above. The one or more medicants can have different release or absorption profiles as discussed above. For example, the medicant can dissolve or absorb into tissue upon delivery or be released over time. The medicant can be formulated in a number of ways as described above. In one example, the medicant can be contained in spheres that are incorporated into a flowable conformable region.

The medicant(s) can be placed in different areas of the adjunct material. The conformable region(s) within the same adjunct material can deliver the same or different medicants in the same or different manners. The medicant(s) can be disposed within and releasable from the reinforcing region. Medicant(s) in the conformable region can be the same or different than any medicant(s) in the reinforcing region.

As discussed above in more detail, medicants include, but are not limited to, drugs or other agents included within, or associated with, the adjunct material that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The medicant can be any desired medicant or combination of the medicants described above. For example, the medicant can be a drug, hemostat, or sealant, or any other desired substance described above that elutes from the adjunct material after deployment to tissue. In one aspect, the conformable region can be in the form of a flowable polymer and a medicament such as ORC can be embedded in the conformable region.

The conformable region can be made in a variety of ways. For example, the conformable region can be encapsulated within a vessel as described above. The vessel can be a pellet which can be in the form of microcapsules, microbeads, or any other desired vessel for containing flowable material and a medicant. In one aspect, the conformable region can be formed from a dry polymer (powdered) of a water soluble polymer (such as carboxymethyl cellulose (CMC)) that is mixed with a water soluble liquid such as glycerin. When mixed, such substances can form a tacky/sticky/viscous compound such as a gel. This compound remains tacky and can adhere to dry surfaces or substances, but not adhere to wet or hydrated substances. When this compound comes into contact with water or a wet surface, the compound becomes slippery and lubricious. This compound will also go into complete solution when added to water more rapidly than the dry polymer powder alone.

The conformable region(s) and the reinforcing region(s) of the adjunct material can be configured in a variety of different manners to achieve any desired purpose or effect. For example, the conformable region can be configured to facilitate application of the adjunct material to tissue. The adjunct material can be configured to release a medicant in a desired manner. To achieve these desired results, the conformable region can be in different positions in the adjunct material. Also, the reinforcing region can be in various forms. The conformable region can be attached to, disposed on, or incorporated into the reinforcing region in any number of configurations.

The conformable region can be configured to act as a sealing component, an attachment means to a surgical device, or an attachment means to another portion of the adjunct material such as a laminate of the scaffold. For example, the conformable region can be used to adhere the adjunct material to a cartridge body or an anvil or other mechanism for delivering the adjunct material to tissue. The adjunct material can be releasably retained on at least one of the tissue-facing surfaces of the first and second jaws of an end effector.

In one aspect, the conformable region or a portion thereof can be the part of the adjunct material that adheres to a cartridge body. The conformable region can be incorporated into the reinforcing layer while also having a portion disposed on a surface of the adjunct material that contacts the cartridge body, or the conformable region can be a separate layer of the adjunct material.

Figure 73:
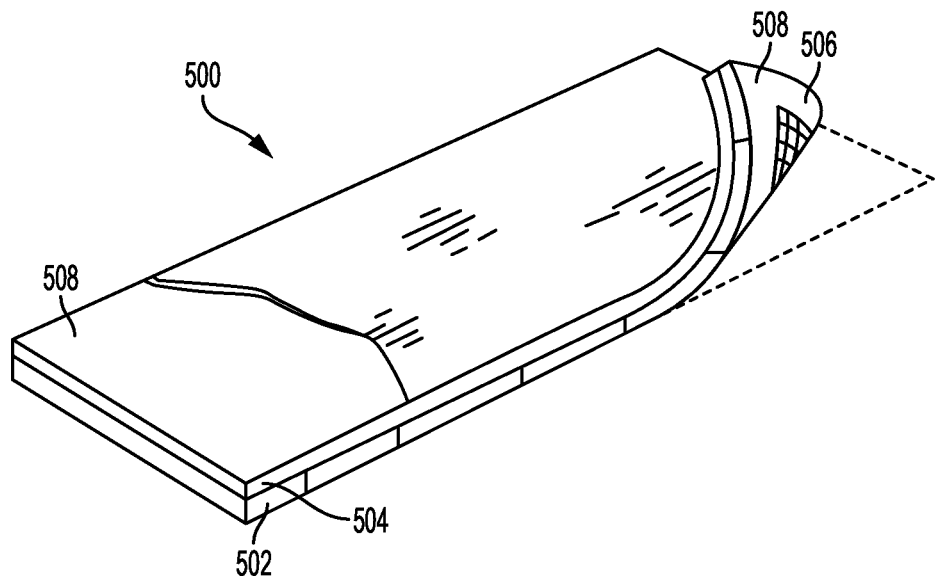
FIG. 73 is a perspective, partial cutaway view of an example of an adjunct material in the form of a composite having a reinforcing layer and a conformable layer.

FIG. 73 shows a perspective partial cutaway view of an example of a composite adjunct material 500 having a conformable region 502 and a distinct reinforcing region 504. The reinforcing region 504 is in the form a reinforcing layer that is the top layer, as oriented in FIG. 73. The conformable region 502 is in the form of a conformable layer that is the bottom layer, as oriented in FIG. 73. The conformable layer has a bottom surface 506 that can be adhered to the cartridge body, for example. One or more medicants 508 can be included in any portion of the adjunct material 500. For example, in the illustrated example, the conformable region 502 and the reinforcing region 504 include a medicant 508. In some aspects, the medicant(s) can have different absorption rates or elution profiles in different regions of the adjunct material. The medicant(s) can be the same or different in the different regions of the adjunct material.

In another aspect, the adjunct material can be configured to be attached to a surgical staple. For example, the adjunct material can be a coating on the staple legs. The conformable region can adhere to the staple legs at any desired position thereon. The adjunct material can also be configured to swell to fill the holes created by the staples as they pass through tissue. The conformable region can release medicant into the holes created by the staple legs upon deployment in tissue. For example, the conformable region can swell to release a medicant or to treat the area in which the conformable region has swelled or both.

Figure 74:
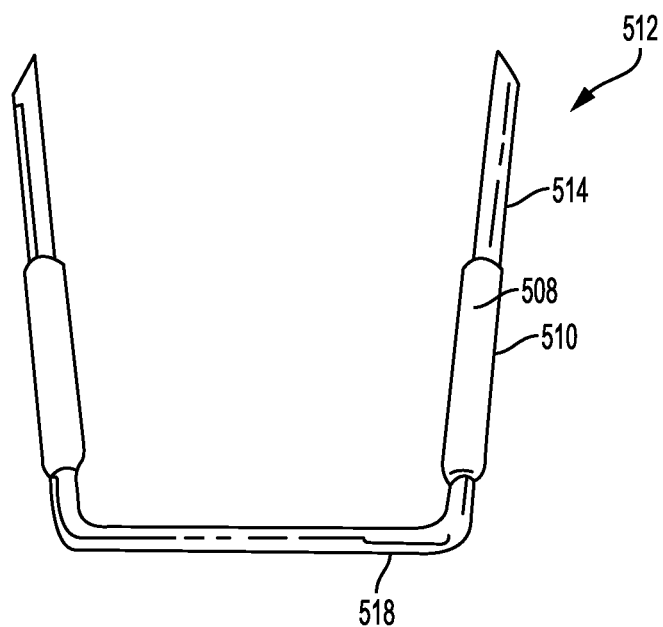
FIG. 74 is a side view of an example of an adjunct material disposed on the legs of a surgical staple.
Figure 75:
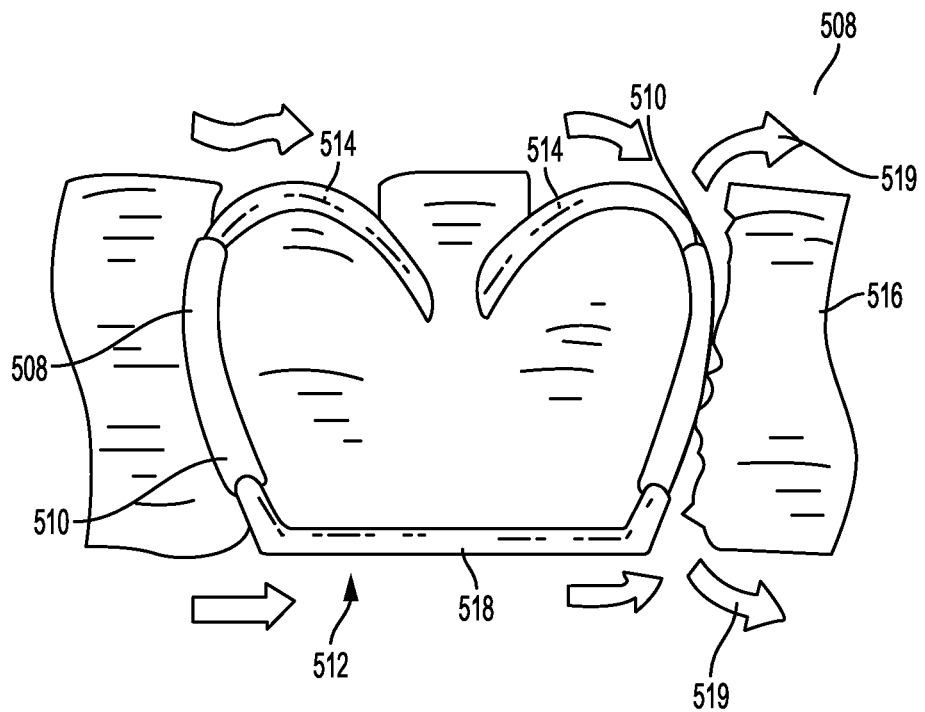
FIG. 75 is the adjunct material of the surgical staple of FIG. 74 delivered to tissue.

FIG. 74 shows a side view and FIG. 75 show a cross-sectional side view of an example of an adjunct material 510 disposed on a surgical staple 512. In this implementation, the adjunct material 510 is a coating on the legs 514 of the staple 512. The adjunct material can include a medicant 508. FIG. 74 shows the adjunct material 510 coated on the staple legs 514 before insertion into tissue 516. FIG. 75 shows the adjunct material 510 on the staple legs 514 after being fired into tissue.

As shown in the illustrated figures, the adjunct material 510 is adhered to the staple legs 514 at a position closer to the crown 518 of the staple 512. Thus, when the staple 512 is deployed in tissue 516 and the ends of the staple legs 514 bend towards each other, the portion of the staple legs 514 coated with adjunct material 510 is minimally disrupted. The adjunct material 510 is thus positioned on the staple legs 514 where it will be subjected to less strain during insertion into tissue so as minimize the possibility of the medicant being released too soon due to, for example, cracking or destruction of the coating. For example, the adjunct material 510 can be positioned so that it will be within the tissue when the staple is fully deployed in tissue. The medicant can be configured to be released once it is positioned within the tissue. The medicant can be released into holes formed by deployment of the staple 512 in the tissue.

FIG. 75 schematically illustrates the adjunct material 510 when first deployed in tissue 516 (staple leg 514 on the left side) and after a period of time when the medicant 508 is released into the gaps or holes formed by insertion of staple leg 514 into the tissue 516 (staple leg 514 on the right side). The flow of the medicant 508 is shown by reference number 519. The conformable region of the adjunct material or the medicant or both can plug the holes created by the staples.

In one aspect, the conformable region can be flowable and the reinforcing region can be non-flowable. The conformable region can be in a non-flowable state prior to use and deployment within a patient and can be in a flowable state upon deployment in the patient. When in a non-flowable state prior to deployment, the conformable region can be attached to the reinforcing region in a variety of ways to achieve a desired effect when inserted into tissue. In one aspect, the conformable region can be material that is lyophilized or in a powder form and then applied to the reinforcing region. The conformable region can be configured to flow or swell or release the medicant in a certain manner upon staple deployment. Examples of flowable conformable regions are also described in U.S. Pat. Pub. No. 2013/0149343, entitled "Hemostatic Bioabsorbable Device with Polyethylene Glycol Binder" filed Dec. 13, 2011, U.S. Pat. No. 8,383,147 entitled "Reinforced Absorbable Synthetic Matrix For Hemostatic Applications" filed Aug. 22, 2012, U.S. Pat. No. 8,329,211 entitled "Reinforced Absorbable Multi-Layered Fabric For Hemostatic Applications" filed May 17, 2010, and U.S. Pat. No. 8,273,369 entitled "Reinforced Absorbable Synthetic Matrix For Hemostatic Applications" filed May 17, 2010, which are hereby incorporated by reference in their entireties.

FIG. 76 through FIG. 79 show examples of adjunct materials where the conformable region can be in a non-flowable state prior to deployment within a patient and can be in a flowable state upon deployment in the patient.

FIG. 4 shows an example of an adjunct material 520 including a reinforcing region that is in the form of a scaffold made of a plurality of fibers 522. The conformable region can be in the form of beads 524a, 524b, 524c of various sizes anchored to various fibers 522 in the reinforcing region. The beads 524a, 524b, 524c can be a powder or lyophilized material that is capable of swelling upon delivery to tissue. One or more medicants can be included in the beads 524a, 524b, 524c.

Figure 76:
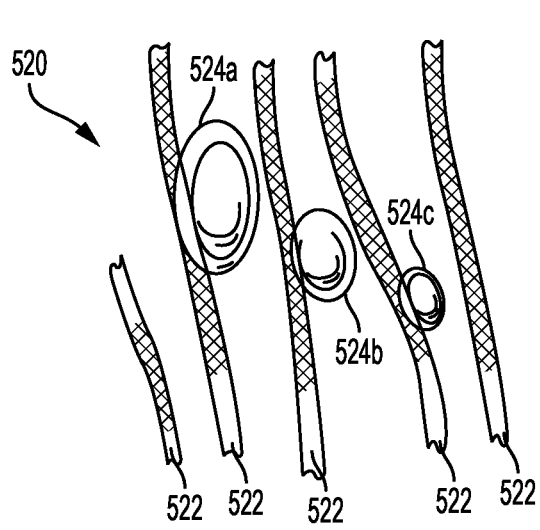
FIG. 76 is a cross-sectional side view of an example of a portion of an adjunct material where the reinforcing region is in the form of fibers and the conformable regions are in the form of bead disposed on the fibers.
Figure 77:
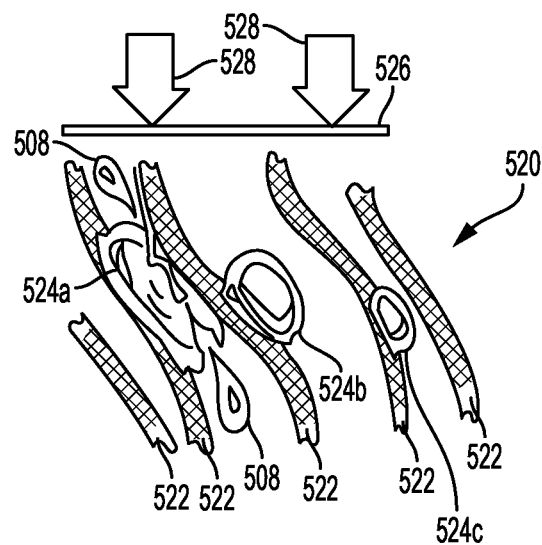
FIG. 77 represents the adjunct material of FIG. 76 delivered to tissue.

FIG. 77 shows the adjunct material 520 of FIG. 76 when a staple 512 is inserted and a force is applied to the fibers 522 during deployment in tissue. When force is applied during deployment of the staples 512 (as shown by the downward facing arrow 528), the conformable regions or beads 524a, 524b, 524c compress or deform. As shown, bead 524a has been deformed to the point of rupture, thereby releasing the medicant 508. In some aspects, the beads 524a, 524b, 524c can be configured to rehydrate when in contact with the tissue so as to expand to the point of rupture, thereby releasing the medicament 508 from the adjunct material 520. The beads 524a, 524b, 524c can be configured to break, in any manner, at different times.

Figure 78:
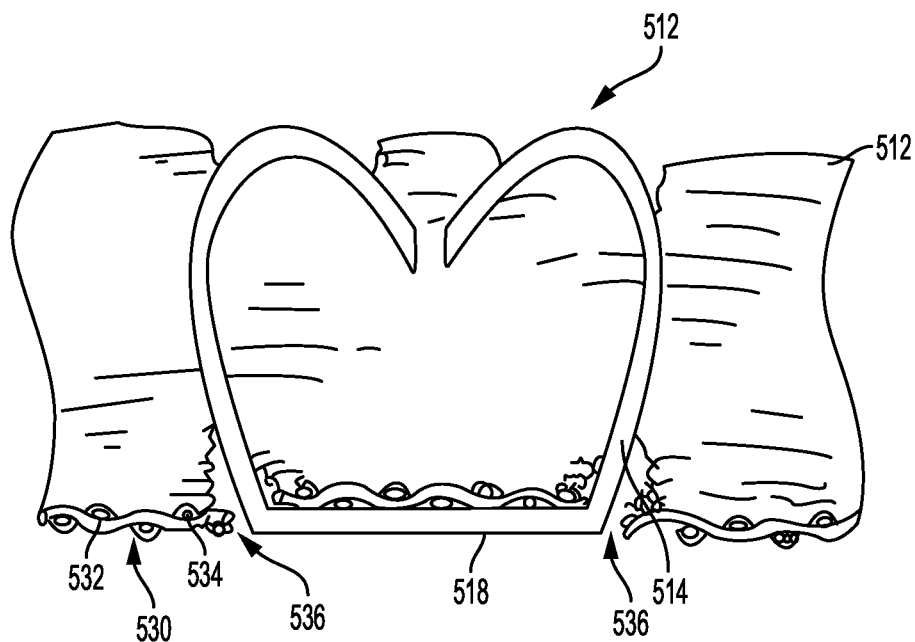
FIG. 78 is a cross-sectional side view of an example of an adjunct material applied to a staple crown and delivered to tissue, where the adjunct material includes a reinforcing region in the form of a fiber and the conformable region is attached to the fibers.
Figure 79:
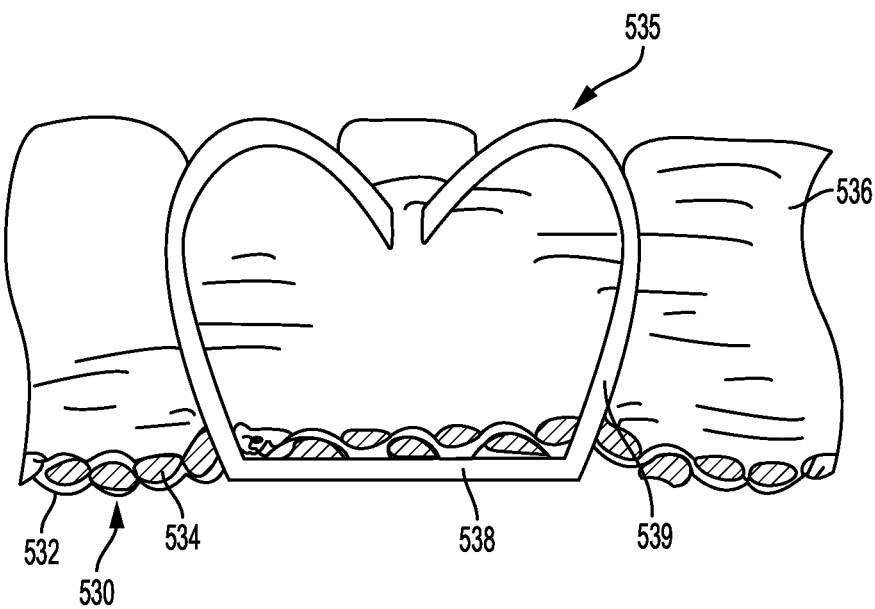
FIG. 79 is the adjunct material of FIG. 78 where the conformable region has swelled after a period of time in the tissue.

FIG. 78 and FIG. 79 show an example of an adjunct material 530 in which the reinforcing region 532 is in the form of a fiber and the conformable region 534 is a material that is bonded to the fiber. The conformable region 534 can be a dry substance that is swellable upon delivery to tissue. For example, the conformable region can be a lyophilized polymer or a powder. FIG. 78 shows the adjunct material 530 upon deployment of staple 512 in the tissue 516. Gaps 536 and tears in the reinforcing region 532 near the junction of the crown 518 of the staple and the staple legs 514 can be seen in FIG. 78. After a period of time, the conformable region 534 can swell, as shown in FIG. 79, such that the conformable region fills the gaps 536 formed by insertion of the staple 512. The conformable region 534 can have at least one medicant that is released from the conformable region 534. The medicant(s) can be released into the gaps 536.

The magnitude of force applied to an adjunct material during application to tissue can control elution rates of various medicants to attract different cellular constructs. Higher forces can increase the elution rate. For example, higher elution rates can occur when fiber coatings crack under high pressure to release inner layers of medicant. The coatings can crack due to the bending of the fibers at extreme angles, or due to interference between and abrasion of one fiber on another under high stress. Low pressures can maintain the reinforcing region or scaffold and result in nominal elution rates. Thus, the adjunct materials, such as those shown in FIG. 77 and FIG. 79, can have higher elution rates of medicants when subjected to pressure during deployment of staples.

In one implementation, the conformable region can be disposed in tubes or channels formed in the reinforcing region. For example, the conformable region can be a hydrogel or other swellable, absorbable material that is injected into such tubes or channels within the reinforcing region. The reinforcing region can be in the form of a film or a substrate having channels therein. A medicant can be included in the channel.

When the conformable region swells the medicant can elute from the tube or channel. The tube or channel can be designed such that the outer diameter is constrained. For example, the outer diameter can be constrained by a wound fiber, by proximity to other fibers in a tight mesh, or any other desired manner. In one example, the tube walls can swell in the presence of moisture but due to the constraints on the outward expansion, the inner diameter can be reduced and any material in the tube can be squeezed out of the tube.

Figure 80:
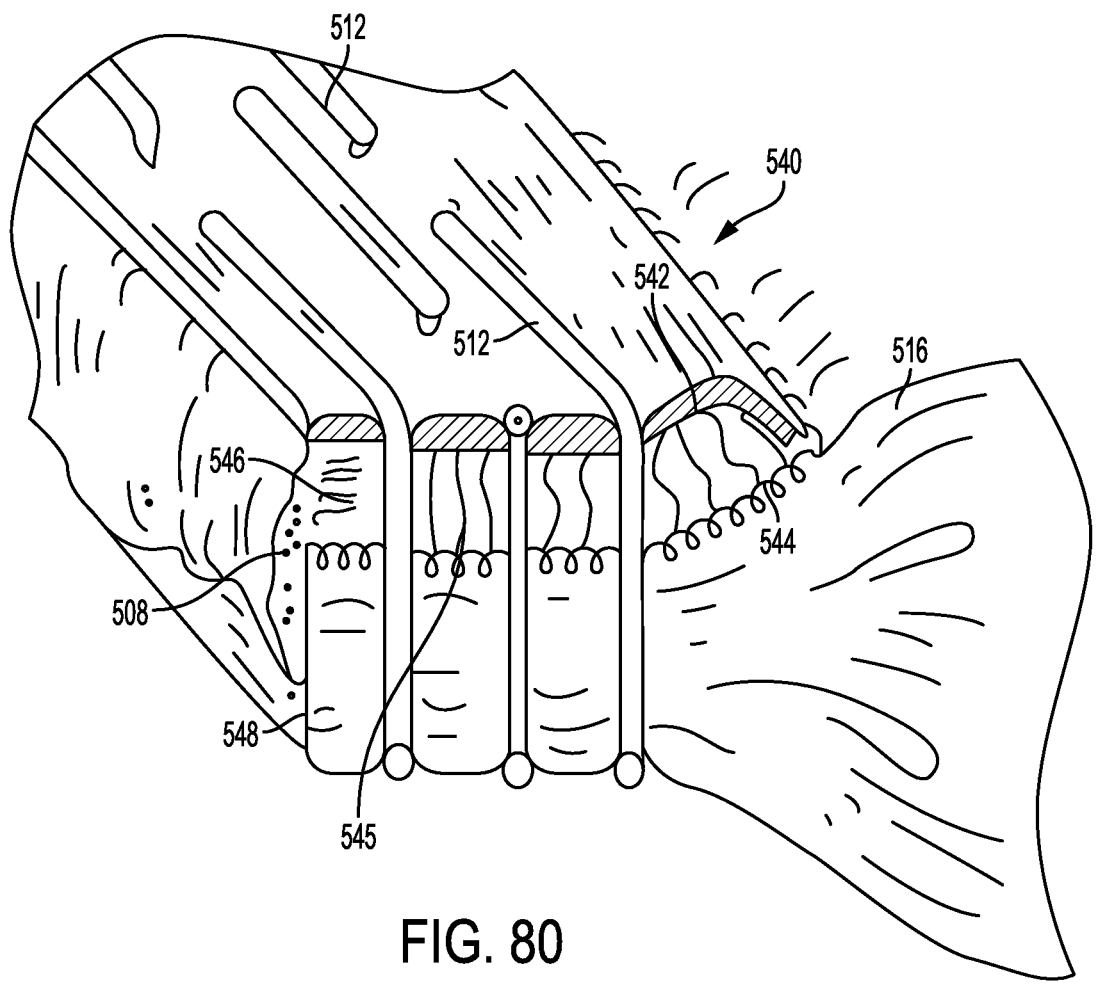
FIG. 80 is a perspective view of an example of an adjunct material and staples delivered to tissue where the reinforcing region is in the form of a spacer fabric with the conformable region contained therein.

FIG. 80 shows a cross-sectional perspective side view of an example of an adjunct material 540 secured to tissue 516 by staples 512. The adjunct material includes a top barrier layer 542 and a bottom barrier layer 544. In one aspect, the bottom layer can be a reinforcing layer instead of a barrier layer. In the illustrated adjunct material, the top barrier layer 542 and the bottom barrier layer 544 enclose the reinforcing region 545. The barrier layers 542, 544 can be non-porous and can include a densely woven material. The reinforcing region 545 can be in the form of a spacer scaffold. In one implementation, the reinforcing region can be constructed of fibers and a woven pattern that provides a predefined (such as multiaxial) lattice along an intraluminal (circular or linear) staple line. The conformable region 546 can be a gel or other flowable material within tubes or channels within the reinforcing region 545. The conformable region 546 can also include at least one medicant 508. The conformable region 546 can be a semi-solid that becomes flowable upon delivery to tissue and can then release medicant. The left side of the tissue 516 shown in this figure has a cut edge 548. The right side of the adjunct material 540 shown in FIG. 80 is closed where the top barrier layer 542 and the bottom barrier layer 544 are connected. Because the right side of the adjunct material 540 is closed, the medicant 508 flows out of the left side of the adjunct material and can treat the cut edge of the tissue 516. The adjunct material can absorb water upon delivery to the body and then the conformable region can become flowable and release medicant such as a sealant or hemostat along the cut edge. The adjunct material can contain one or more medicants that can direct or encourage in-growth from the sides and through the thickness of the adjunct material.

Figure 81:
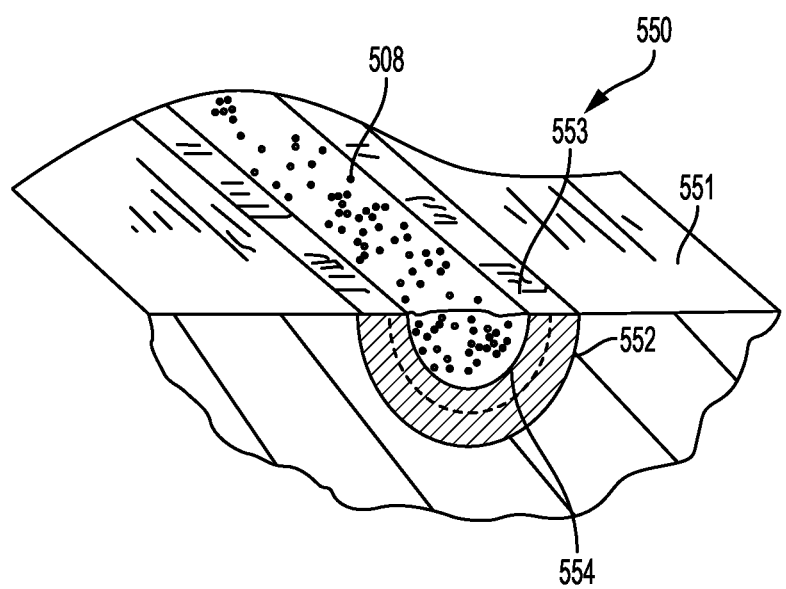
FIG. 81 is a perspective view of an example of an adjunct material in which the conformable region is in the form of a channel disposed within the reinforcing region.
Figure 82:
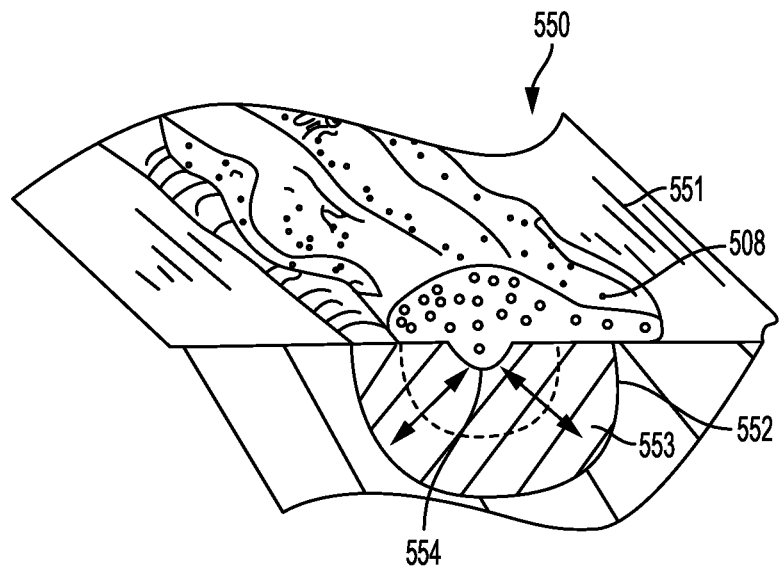
FIG. 82 is the adjunct material of FIG. 81 in which the conformable region has swelled so as to release medicant contained in the conformable region.

FIG. 81 and FIG. 82 show another example of an adjunct material 550 in which the reinforcing region 551 is formed as a substrate containing a channel 552 therein. A conformable region 553 is contained within the channel 552 in the reinforcing region 551. The reinforcing region 551 can have more than one channel formed therein. The channel 552 can contain a medicant 508 arranged in a number of configurations in the conformable region 553. For example, the medicant can be mixed or dispersed within the conforming region. In one aspect, one or more channels can be formed in the conformable region for containing the medicant. In FIG. 81, the conformable region 553 itself forms an additional channel 554 containing the medicant 508. The conformable region 553 can include a swellable material such as a hydrogel. The conformable region can swell upon contact with tissue to release the medicant. In addition or alternatively, as the conformable region swells, the medicant can treat the area into which the conformable region swells. As shown in FIG. 82, when the conformable region 553 (such as a hydrogel) swells once inside the body, the medicant 508 can elute out of the channel 554 formed in the conformable region 553.

In one aspect, the conformable region can be flowable and the reinforcing region can be non-flowable. In such implementation, the conformable region is not anchored to the reinforcing region. For example, the conformable region can be a hydrogel or other swellable material and the reinforcing region can include a spacer fabric. The hydrogel can be injected into the spacer fabric. In some aspects, the conformable region can be designed to fill holes in the reinforcing region that are created by staples.

Figure 83:
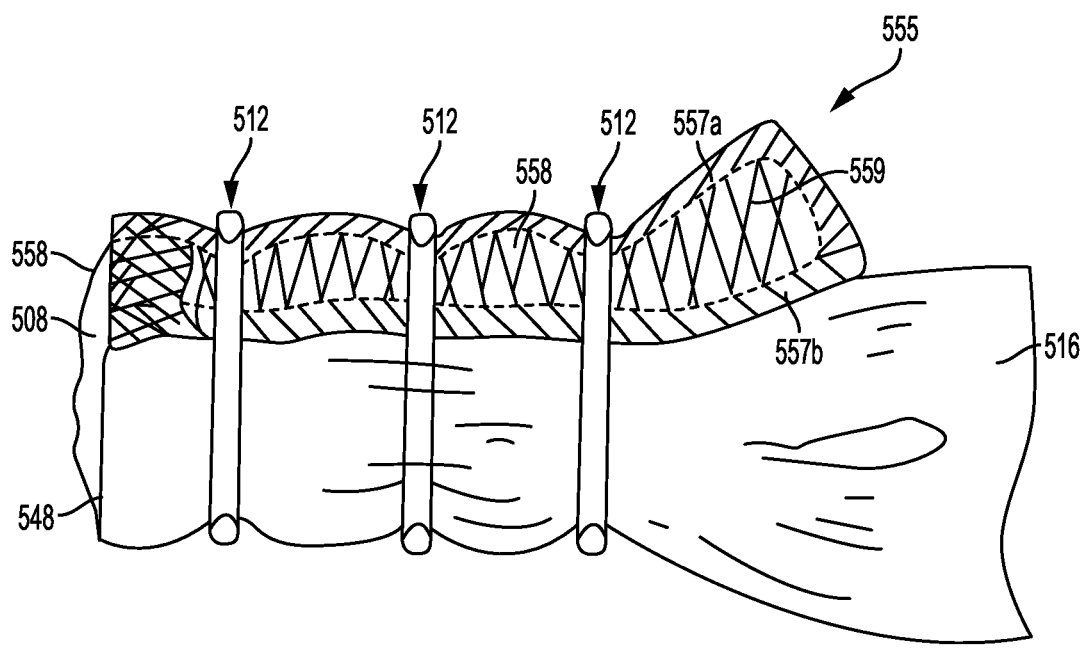
FIG. 83 is a cross-sectional side view of another example of an adjunct material disposed on tissue, where the adjunct material includes a first reinforcing region and a second reinforcing region and a conformable region contained between the first reinforcing region and the second reinforcing region.

FIG. 83 shows an example of an adjunct material 555 disposed on tissue 516 and secured with staples 512, where the conformable region is not anchored to the adjunct material 555. In the illustrated example, the adjunct material 555 includes a first reinforcing region 557a and a second reinforcing region 557b and a conformable region 558 is contained therebetween. The first reinforcing region 557a can be a top layer and the second reinforcing region 557b can be a bottom layer. A spacer fabric 559 or reservoir can be contained between the layers and include a conformable region 558 therein. In this figure, the top layer and bottom layer are connected at the right side of FIG. 83. The conformable region 558 can be in the form of a swellable material such as a hydrogel that is not anchored to the adjunct material 555. Instead, the conformable region 558 can be injected into the spacer fabric 559.

The spacer fabric 559 containing the swellable material can fill the reservoir formed between the top layer and the bottom layer or it can fill a portion of the reservoir. For example, the swellable material can be positioned in a portion of the spacer fabric 559 closest to the staple 512 hole or cut edge 548. In one aspect, the area of the reinforcing region or scaffold designed for tissue contact can have a different pattern to the weave, a different density of the fibers, a different "tightness" of the woven fibers, different diameter of fibers, even end terminations, or an intermittent wound fiber to create lots of ends of the fibers with which the tissue can interact, or any combination of these features. When the staples are deployed and the adjunct is in contact with tissue, the conformable region 558 swells and fills the hole formed by a cut edge 548 on the left side of FIG. 83. The swellable material of the conformable region 558 can also fill holes formed by the staples. In one aspect, the portion of the conformable region that swells along the cutline can elute a medicant 508 such as a sealant.

As discussed above, in a multi-layered adjunct material, the conformable region can be attached to the reinforcing region in a number of ways. In one aspect, the conformable region can be laminated to the bottom of a solid reinforcing region. FIG. 73, discussed above, shows an adjunct material 500 having a conformable region 502 as the bottom layer and a reinforcing region 504 as the top layer. The conformable layer can be laminated to a planar surface of the reinforcing layer.

In some implementations, the composite adjunct material can be a laminated or multi-layered structure that includes one or more conformable layers and one or more reinforcing layers. These layers can be in any desired configuration. One or more layers can deliver medicant(s) in different manners.

Figure 84:
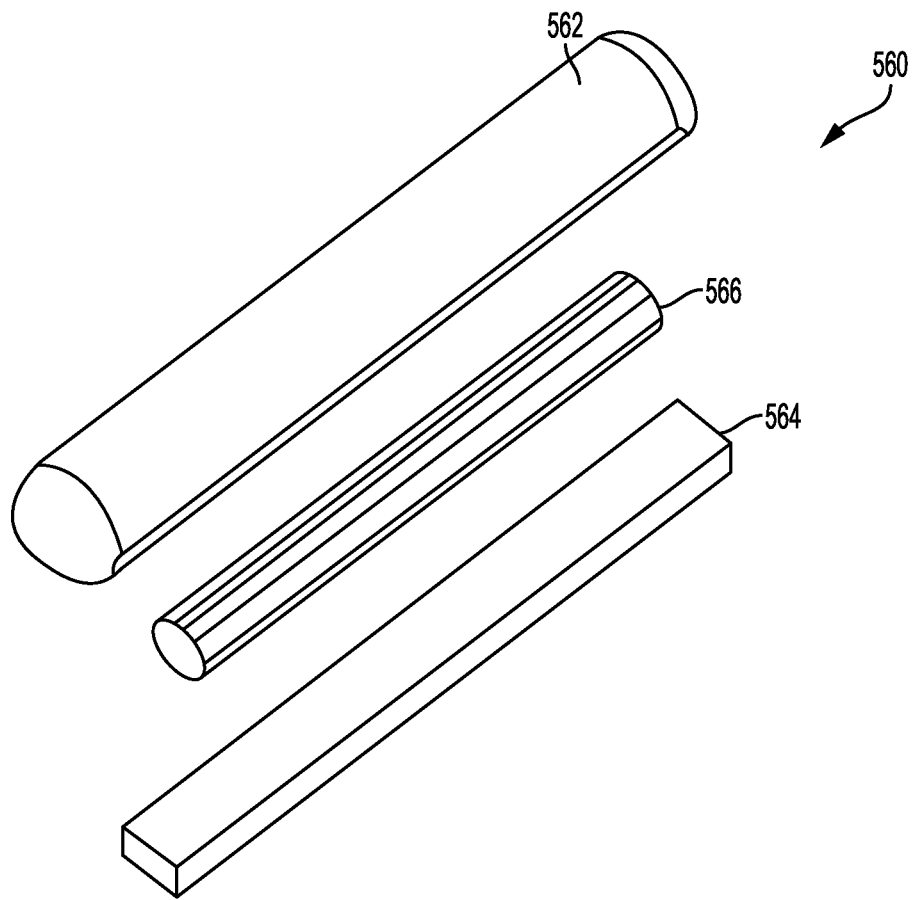
FIG. 84 is an exploded perspective view of an example of an adjunct material having a first reinforcing layer and a second reinforcing layer with a conformable layer containing a medicant disposed therebetween.

FIG. 84 is an exploded perspective view of an example of an adjunct material 560 having multiple layers. As shown, the adjunct material has a top reinforcing layer 562 that is in the form of a cap and a bottom reinforcing layer 564. A conformable layer 566 is disposed between these reinforcing layers 562, 564. The conformable layer 566 can be flowable. When these layers are assembled, they form a capsule that contains the conformable layer 566. The layers can be made from any desired materials including those discussed above to achieve desired results. For example, the top reinforcing layer 562 can be a low molecular weight polyethylene glycol (PEG), polyethylene oxide (PEO), or a starch-based poly-vinyl alcohol (S-PVA-C) thermoplastic gelatin cover. This reinforcing layer can be designed to dissolve or degrade within a desired amount of time. For example, the top reinforcing layer 562 can be in the form of a cap or capsule that protects the materials therein from activation prior to implantation and then degrades within about 2 hours after implantation. The bottom reinforcing layer 564 can be any non-conformable rigid material. For example, the bottom reinforcing region 564 can be an electrospun nano-fiber material such as poly(glycolide-co-lactide) at a ratio of LA10/GA90, electrospun nano-fiber scaffold. The conformable layer can be a hydrogel or other flowable material such as a high molecular weight hyaluronic acid-hydrogel filler. The conformable region can also include one or more medicants as described above. The medicant can be released after the top reinforcing layer 562 degrades and/or when the adjunct material 560 is punctured by a staple leg. The conformable layer 566, such as a hydrogel, can therefore seal the puncture site and also contain medicants to be released.

Thus, the multi-layered adjunct material can have various configurations. In one implementation, the adjunct material can include a hydrogel conformable region disposed on or impregnated into the bottom reinforcing region and covered by a reinforcing region in the form of a degradable capsule. In one aspect, the adjunct material can be a planar adjunct material protected by a degradable capsule. The adjunct material can be figured to provide a hemostatic barrier and release at least one medicant to reinforce or inhibit at least one stage of the wound healing process described above.

In one aspect, the multi-layer composite adjunct material can include a barrier layer in addition to one or more conformable layers and one or more reinforcing layers. The barrier layer can prevent materials of the conformable region or any medicants from passing therethrough prior to or as the adjunct material is stapled to tissue. The barrier layer can be impermeable to the materials of the conformable layer, such as a flowable substance, or impermeable to one or more medicants in the conformable layer. The barrier layer can be in any desired configuration. In one aspect, the barrier layer can be disposed between the conformable layer and the reinforcing layer. In another aspect, the barrier layer can be on an outer surface of the adjunct material.

The barrier layer can include any desired materials. The barrier layer can include one or more different sealants or coating layers, as described above, which can include absorbable or non-absorbable polymers. Non-limiting examples of materials for the barrier layer include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

Figure 85:
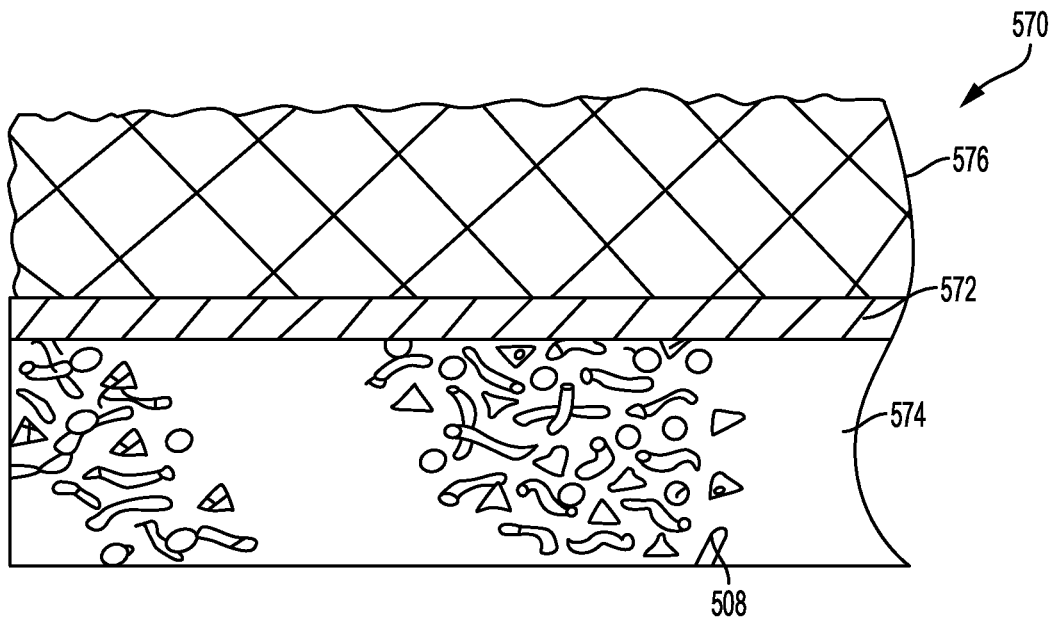
FIG. 85 is a cross-sectional side view of an example of an adjunct material having a reinforcing a layer disposed on a barrier layer which is disposed on a conformable layer containing a medicant therein.
Figure 86:
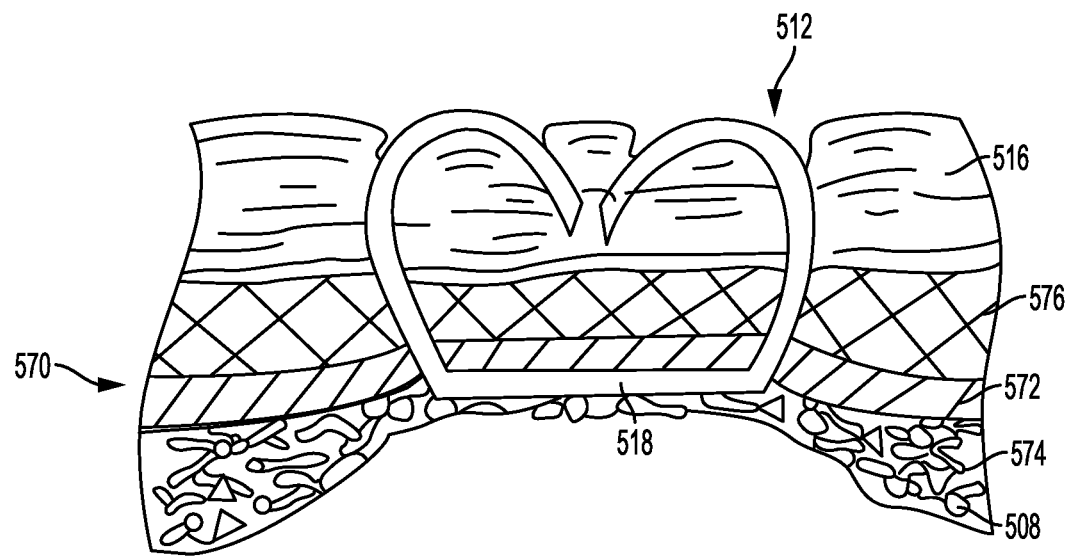
FIG. 86 is the adjunct material of FIG. 85 secured to tissue with a staple.

FIG. 85 and FIG. 86 show an example of an adjunct material 570 having multiple layers including a barrier layer 572. FIG. 85 is a cross-sectional side view of an adjunct material 570 having a barrier layer 572 disposed between a conformable layer 574 and a reinforcing layer 576. The conformable layer 574 can be any desired material including, for example, a liquid or any flowable material. In one aspect, the conformable layer 574 can be PSA with short ORC fibers. The conformable layer 574 can also contain a medicant 508. The PSA or other adhesive material of the conformable layer 574 can be the vehicle for delivery of the medicant 508. The barrier layer 572 can act to prevent the materials of the conformable layer 574 or any medicant 508 therein from flowing into or permeating the reinforcing layer 576.

FIG. 86 shows the adjunct material 570 of FIG. 85 secured to tissue 516 with a staple 512. The conformable layer 574 is compressed by the force resulting from the deployed staple 512. As shown, the medicant 508 is not eluting out of the conformable layer 574 and into the reinforcing layer 576 due to the barrier layer 572. But the medicant is shown eluting laterally away from the staple crown 518. In one aspect, the conformable layer can also dissolve quickly and be released into the body.

Figure 87:
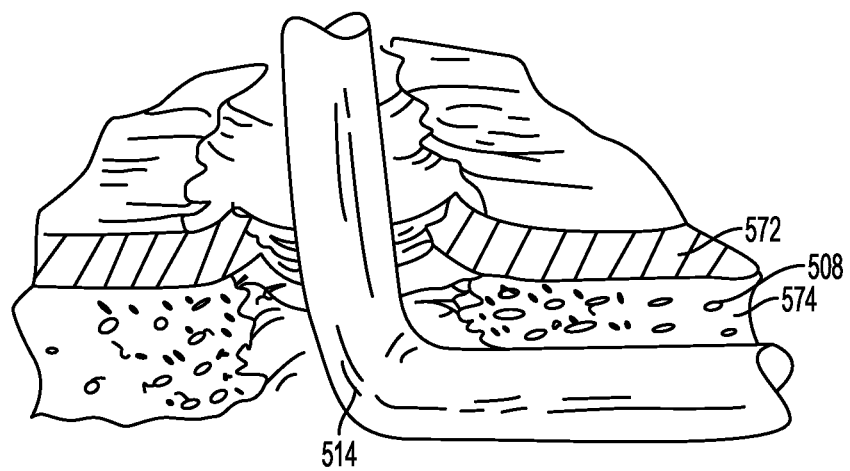
FIG. 87 is a detailed view of a portion of the adjunct material of FIG. 86 showing the staple deployed in the adjunct material and the tissue.
Figure 88:
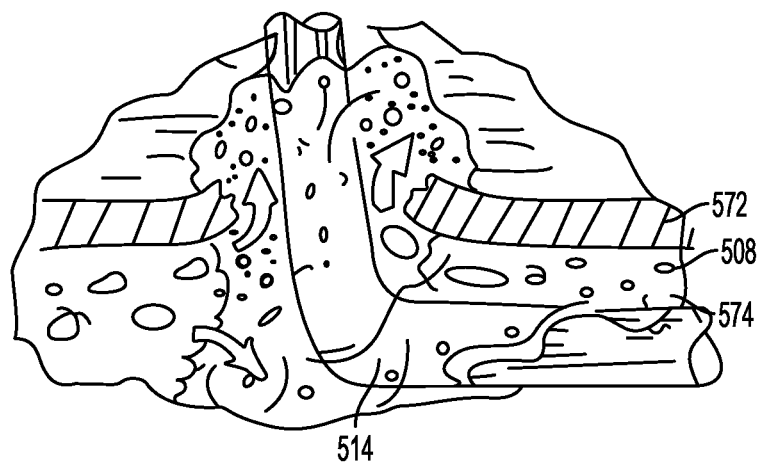
FIG. 88 is a detailed view of a portion of the adjunct material of FIG. 87 showing the staple deployed in the adjunct material and the tissue and the flow of medicant from the conformable layer.

FIG. 87 and FIG. 88 show more detailed views of the adjunct material 570 of FIG. 86. In particular, FIG. 87 is a detailed view of a portion of the adjunct material 570 of FIG. 86 showing the staple 512 deployed in the adjunct material 570 and tissue 516. FIG. 88 is a detailed view of a portion of the adjunct material 570 of FIG. 87 after the staple 512 has been deployed in the adjunct material 570 and tissue 516 for a period of time and the adjunct material 570 has contacted fluid in the body. In FIG. 88, the medicant 508 is shown flowing from the conformable layer 574 along the hole formed by the staple leg 514. When the conformable region is a flowable material such as a hydrogel, the conformable region may not be anchored to the reinforcing region and the conformable region can also flow to fill in holes created by a staple leg. In one aspect, the reinforcing region can be configured to dissolve after a period of time in the patient. In FIG. 87 and FIG. 88, the reinforcing layer dissolved after a period of time.

In one aspect, the adjunct material includes a conformable region that is incorporated into the adjunct material in a dry form and then becomes flowable upon delivery to tissue. For example, the adjunct material can include a conformable region that includes a lyophilized material that is delivered dry and then rehydrated upon delivery to tissue to become flowable. The lyophilized material can be impregnated into a reinforcing layer. In one aspect, the conformable region is a lyophilized hydrogel impregnated into a reinforcing layer. A non-limiting example is a vicryl mesh reinforcing layer and a conformable layer including fibrin and thrombin that are lyophilized on a mesh reinforcing layer (see, e.g., EVARREST® Fibrin Sealant Patch by Ethicon Biosurgery Division of Ethicon, Inc., and U.S. Pat. Pub. No. 2013/0149343 entitled "Hemostatic Bioabsorbable Device With Polyethylene Glycol Binder" filed Nov. 13, 2011, U.S. Pat. No. 8,383,147 entitled "Reinforced Absorbable Synthetic Matrix For Hemostatic Applications" filed Aug. 22, 2012, U.S. Pat. No. 8,319,211 entitled "Reinforced Absorbable Multi-Layered Fabric For Hemostatic Applications" filed May 17, 2010, U.S. Pat. No. 8,273,369 entitled "Reinforced Absorbable Synthetic Matrix For Hemostatic Applications" filed May 17, 2010, and U.S. patent application Ser. No. 14/300,954 entitled "Adjunct Materials And Methods Of Using Same In Surgical Methods For Tissue Sealing," filed Jun. 10, 2014, which are hereby incorporated by reference in their entireties).

In some implementations, the composite adjunct material can be designed to distribute force exerted on the adjunct material from tissue of variable thickness and density when the adjunct material is secured to the tissue by the staples. For example, the adjunct material can include a conformable layer that can swell and conform to the varying tissue thickness. Medicants can pass through the swellable material of the conformable layer. In this aspect, the reinforcing layer can be solid to support and withstand the varying pressure distribution. The conformable layer can be a fibrous layer that contains a hydrogel. The hydrogel can be applied as a coating to fibers of the fibrous layer. In one example, the fibrous layer can be a spacer fabric. In another example, the conformable layer can include a spacer fabric or one or more layers that are filled with a viscous fluid.

Figure 89:
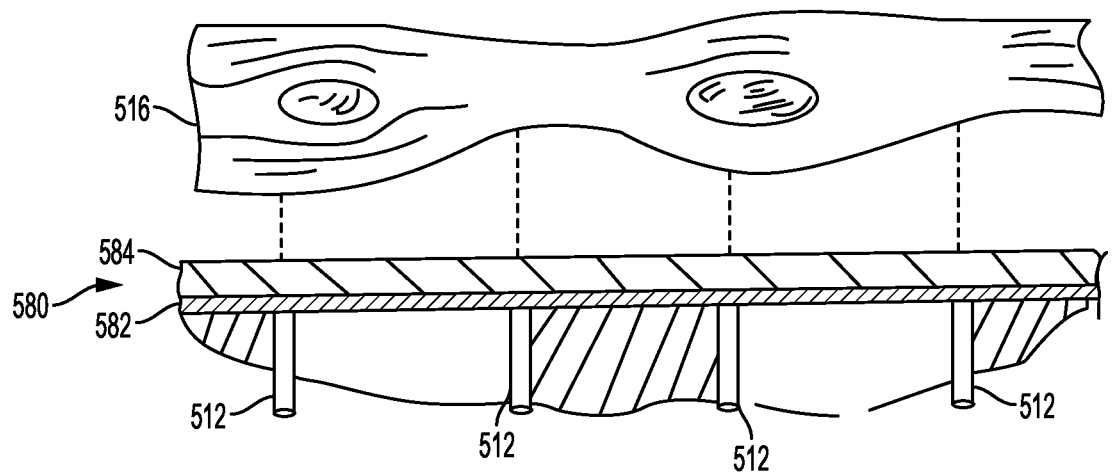
FIG. 89 is a cross-sectional side view of an example of an adjunct material having a conformable layer and a reinforcing layer and the legs of staples prior to insertion into the adjunct material and tissue having variable thickness and density.
Figure 90:
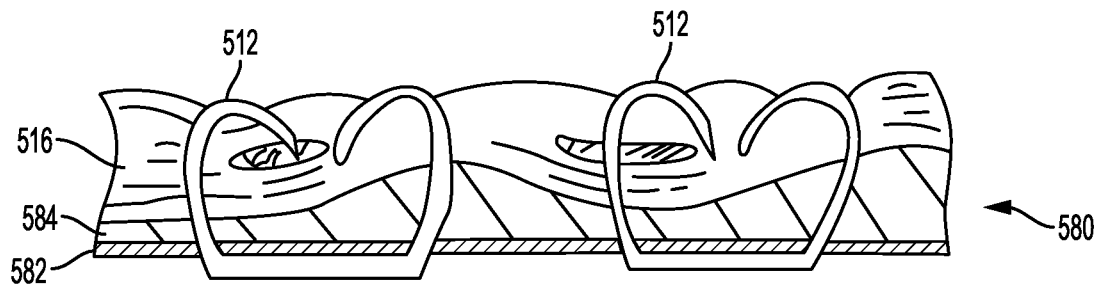
FIG. 90 is the adjunct material of FIG. 89 after deployment of the staples in the adjunct material and the tissue.

FIG. 89 and FIG. 90 show an example of an adjunct material 580 designed for pressure distribution upon delivery to tissue 516 having variable thickness and density. FIG. 89 shows the adjunct material 580 before application to the tissue 516. FIG. 90 shows the adjunct material 580 after deployment of the staples 512 and application of the adjunct material 580 to the tissue 516. In this illustrated example, the reinforcing layer 582 is the bottom layer that contacts the cartridge body and the conformable layer 584 is the top layer that contacts tissue 516. The conformable layer 584 can include any swellable, viscous material. Once the conformable layer 584 contacts the tissue, the conformable layer swells and conforms to the variable thickness of the tissue 516, as shown in FIG. 90.

In one aspect, the multi-layer adjunct material can include a coating. The coating can be an outer coating that acts as a barrier layer, a reinforcing layer, or a conformable layer having any desired properties including those discussed above. For example, the coating can be a barrier layer that can control the release of the medicant and act as a barrier to the flowable material of a conformable layer.

In one aspect, the adjunct material itself can be a coating on a cartridge body.

Figure 91:
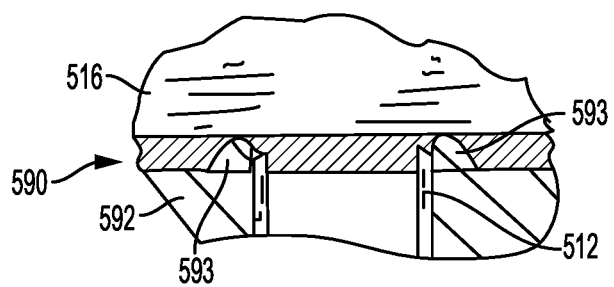
FIG. 91 is a cross-sectional side view of an example of an adjunct material in the form of a film that is disposed on a cartridge body and covers surface features protruding from the cartridge body.

FIG. 91 is a cross-sectional side view of an example of an adjunct material 590 that is in the form of a coating or film on a cartridge body 592. The cartridge body 592 has surface features 593 (such as GST (gripping surface technology) features or bumps) protruding from the cartridge body 592. The adjunct material 590 coating can be applied to the surface of the cartridge body 592 containing the surface features 593 to protect tissue 516 from rubbing against these surface features 593 when compressed during staple deployment. The coating can be applied in a thickness that is the same or greater than the height of the surface features 593 in order to cover the surface features 593. The adjunct material 590 can include layers of one or more conformable regions and one or more reinforcing regions. The adjunct material 590 can also include one or more medicants.

Figure 92:
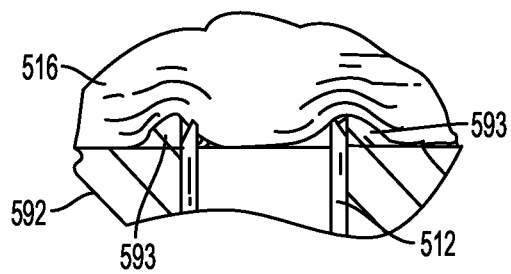
FIG. 92 is the adjunct material of FIG. 91 in which the adjunct material has dissolved after a period of time leaving the surface features in contact with the tissue.

FIG. 92 is a cross-sectional side view of the cartridge body 592 and the surface features 593 of FIG. 91 in which the adjunct material 590 has dissolved after a period of time leaving the surface features 593 and the surface of the cartridge body 592 in direct contact with the tissue 516. In some implementations, the reinforcing region and the conformable region can dissolve at the same or different rates after delivery.

Figure 93:
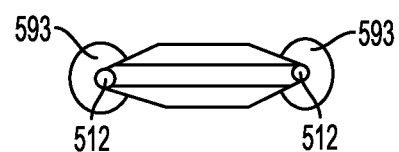
FIG. 93 is a top plan view of the surface features on the cartridge body and the staples shown in FIG. 92.
Figure 94:
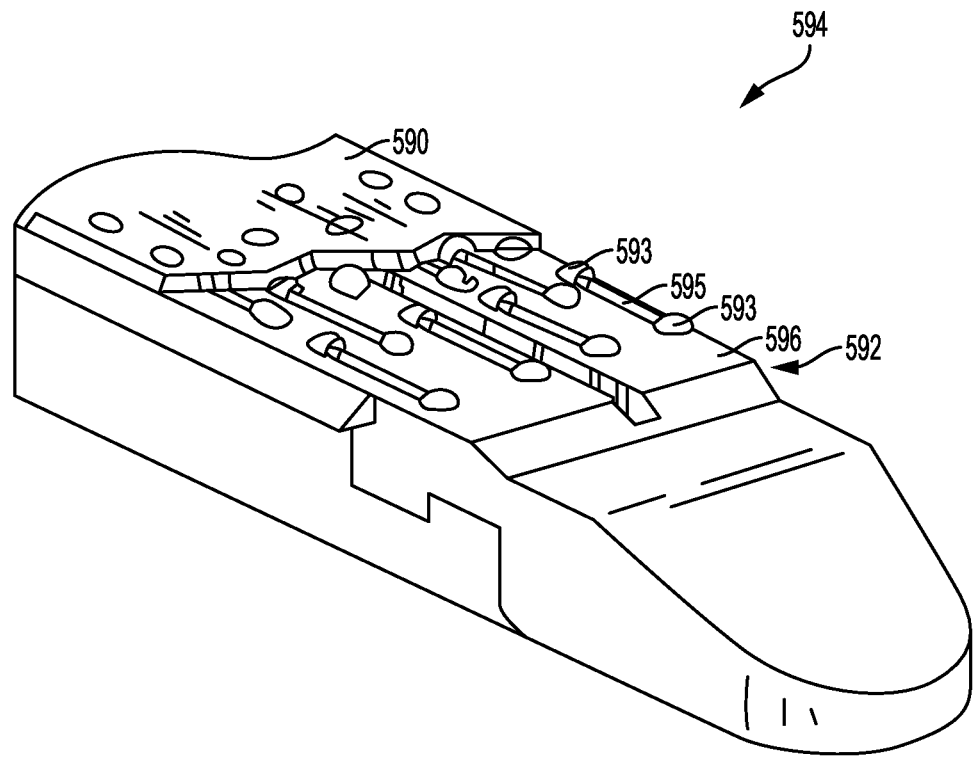
FIG. 94 is a perspective partial cutaway view of the adjunct material of FIG. 91 disposed on the cartridge body having surface features and recesses for staples.

FIG. 93 and FIG. 94 show additional views of the cartridge body shown in FIG. 91 and FIG. 92. FIG. 93 is a top view of surface features 593 on the cartridge body 592 and the staples 512 shown in FIG. 92. FIG. 94 is a perspective cutaway view of a staple cartridge assembly 594 including the adjunct material 590 of FIG. 91 disposed on the cartridge body 592 having surface features 593. As shown in FIG. 94, the cartridge body has a plurality of staple cavities 595 with each staple cavity 595 having a staple disposed therein. The adjunct material 590 is disposed over the tissue-facing surface 596 containing the staple cavities 595 and staples. The adjunct material 590 is shown covering the surface features 593 protruding from the tissue-facing surface 596. The adjunct material 590 can be releasably retained on the cartridge body 592 and configured to be delivered to the tissue by the deployment of the staples positioned in the cavities 595.

In one aspect, the outer coating of the adjunct material can prevent premature gelling of the conformable region or other reactions but can dissolve within a short amount of time after delivery. The outer coating can be smooth, non-sticky, or lubricated so that it does not interfere with tissue positioning. The surface characteristics of the coating can change when introduced into patient. Exposure to liquid or elevated temperature (e.g., body temperature) can change the properties of the coating. In one aspect, the cartridge with GST features has a coating that prevents premature interaction of the cartridge atraumatic pocket extensions (APES) with tissue. The conformable layer can dissolve prior to firing because pressure from clamping and moisture can cause the layer to flow away from its location. The dissolved conformable region can elute a medicant or can plug holes formed by staples or treat cuts in tissue. For additional non-limiting examples regarding GST features, see U.S. patent application Ser. No. 14/318,996 entitled "Fastener Cartridges Including Extensions Having Different Configurations" filed on Jun. 30, 2014, which is hereby incorporated by reference in its entirety.

In one aspect, the adjunct material coating can be a fibrous based scaffold for staple line reinforcing where at least two of the fibers are made of different fibers with different absorption rates and different medicants. The medicants can be released at different rates over time. One or more of the fibers can include absorbable co-polymers. The fibers can be helically wrapped. The fibers can be synthetic, natural or a combination thereof.

In one aspect, the adjunct material can include multiple regions of medicants. The medicants can be infused into a reinforcing region with any desired conformable region material such as, for example, a gel. The multiple regions of medicants can include a single medicant with different release rates or other properties. Additionally or alternatively, the multiple regions can include more than one medicant with the same or different release profiles or other properties.

The composite adjunct material can include one or more of the features described above. For example, the composite adjunct material can include multiple layers and a coating. The adjunct material can include a region with microspheres and another region with laminated planar layers. The adjunct material can include fibers that are formed from a medicant or be a coated structure.

In exemplary implementations described herein, a biocompatible adjunct can be releasably retained on a surgical device and can be configured to be delivered to tissue by deployment of staples in a cartridge body. The biocompatible adjunct can be releasably retained on one or both of a tissue-facing surface of the cartridge body or a tissue-facing surface of the anvil. The adjunct can have a plurality of distinct regions having one or more medicants incorporated therein. Each of the regions can be at a different location on the adjunct and each region can have a different adjunct construction. In this way, the medicants are configured to release from the regions in various spatial and/or temporal manners. Such non-homogeneous release of the medicants with respect to at least one of time of release and location of release can allow providing a desired therapeutic effect in a more controlled and targeted manner.

The adjunct and distinct regions thereof can be constructed in a variety of different ways so as to deliver retained medicants into desired locations at a treatment site in manner that facilitates tissue in-growth or provide other effects to a wound. Different portions of the adjunct can be configured to deliver different treatment effects to various locations in the wound. For example, the adjunct can be configured to release certain medicant(s) near a tissue cut line or edge to promote hemostasis, portions of the adjunct disposed away from the cut line on a top side of the adjunct can deliver medicants to prevent adhesion, and portions of the adjunct disposed on a bottom side of the adjunct also away from the cut line can deliver medicants to promote tissue growth. Any types of medicants can be delivered in this manner in a number of desired dosages. In this way, different portions of the same adjunct can provide heterogeneous effects on wound healing.

In general, one or more medicants can be released in various spatial and temporal patterns to promote one or more stages of wound healing, such as hemostasis, inflammation, proliferation, and remodeling. FIG. 40 above depicts wound healing over time. Various medicants can be releasable from an adjunct to be administered to tissue at a treatment site to facilitate the wound healing stages. The timing of the release can allow the medicants to be administered to tissue at the appropriate time in the wound healing process to achieve the desired effects, as discussed above in connection with FIG. 40.

At least one medicant can be released from an adjunct as a bolus dose such that the medicant is released substantially immediately upon delivery of the adjunct to tissue. Alternatively, the at least one medicant can be released from the adjunct over a certain duration of time, as a time release dosage. An adjunct in accordance with the described techniques can release medicants as various combinations of bolus doses and time release dosages, depending on a type of the wound, desired effects on the wound healing, patient's conditions, and other factors.

An adjunct in accordance with the described techniques can have a variety of different structures that form regions configured to elute medicants therefrom in a heterogeneous manner. The regions can be layered, overlapped, intertwined, or otherwise structured. For example, the adjunct can be in the form of a fiber lattice and it can releasably retain medicants in various ways—e.g., the medicants can be adhered to fibers in the fiber lattices, coated on the fibers, incorporated within the fibers, etc. Any other adjunct structures can be used additionally or alternatively. A structure of an adjunct can be heterogeneous in a number of different ways, including number, location, and position of regions, manners in which medicants are releasable from the regions, types, number, dosages and effects provided by the medicants, and in any other suitable ways.

Figure 95:
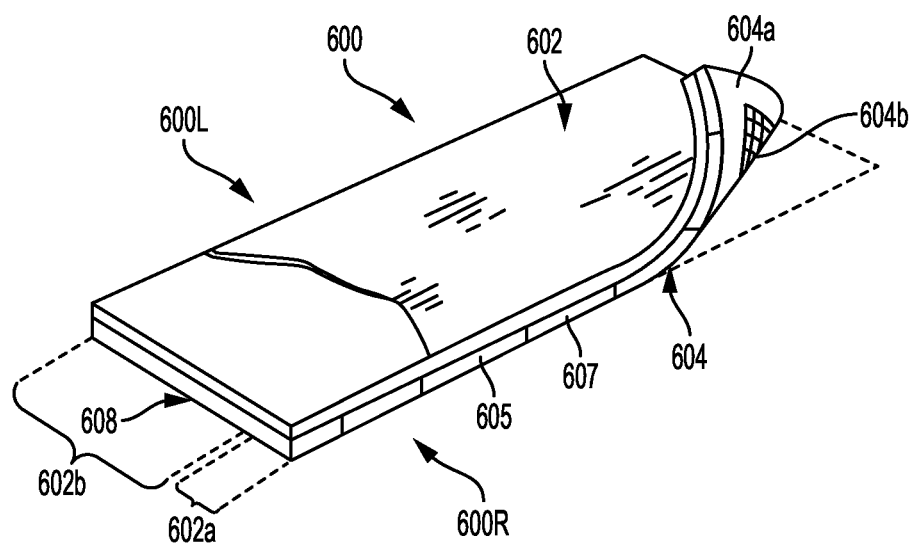
FIG. 95 is a perspective, partial cutaway view of an implementation of an implantable adjunct that includes a plurality of heterogeneous layers or portions.

FIG. 95 illustrates an example of an adjunct 600 that includes a plurality of layers or portions that can provide various medicant elution profiles. Similar to the adjunct 176 in FIG. 32, the adjunct 600 includes a top layer or portion 602 and a bottom layer or portion 604. In the example of FIG. 95, the top portion 602 has two regions 602*a*, 602*b* and the bottom portion 604 has two regions 604*a*, 604*b*. The top portion's two regions 602*a*, 602*b* in this example can be similar to the two top portions 178*a*, 178*b* of the adjunct 176, and the bottom portion's two regions 604*a*, 604*b* can be similar to the two bottom portions of the adjunct 184 in FIG. 33. Furthermore, one or both regions 604*a*, 604*b* of the bottom portion 604 can further include various sub-regions, two of which are shown in FIG. 95 with reference numbers 605, 607. Thus, the adjunct 600 can release medicants therefrom in a number of different patterns.

Each of the regions 602*a*, 602*b*, 604*a*, 604*b* can have at least one medicant releasably retained therein, which may or may not be in the form of a vessel. Each of the medicants of the regions 602a, 602b, 604a, 604b can be the same as any one or more of the other medicants, or each of the medicants can be different from any one or more of the other medicants in any of one or more ways including type of medicant, dosage amount, and elution rate. Each of the regions 602a, 602b, 604a, 604b can have degradation rates and/or other properties affecting medicant release that vary in a distinct or continuous manner. In this way, the medicants disposed within these regions can be releasable from one or more of the regions in a non-homogeneous manner with respect to at least one of time of release and location of release. The degradation rates and distribution of the medicants within one or more of the regions 602a, 602b, 604a, 604b can vary in a distinct or continuous manner such that the adjunct 600 can provide an elution profile shown in a graph 606 in FIG. 96.

Figure 96:
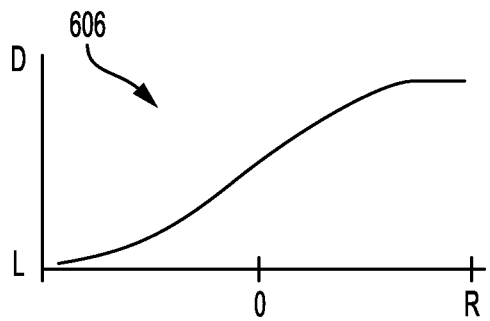
FIG. 96 is a graph showing an implementation of an elution profile of the adjunct of FIG. 95.

The graph 606 of FIG. 96 illustrates different rates or doses ("D") of medicant release across the adjunct 600 from a left side 600L thereof to a right side 600R thereof. The spatial terms "left" and "right" are used with reference to the orientation of the adjunct 600 as shown in FIG. 96 and are not intended to be limiting and absolute. The zero ("0") along the x axis of the graph 606 represents a central area 608 of the adjunct 600 centered around a mid-portion of the adjunct 600. The graph 606 represents an exemplary elution profile that can represent release of the medicants, for example, after the adjunct 600 is delivered to tissue and the tissue to which the adjunct is delivered is cut (e.g., by a cutting element of a surgical stapler).

As shown, the elution rate of the one or more medicants disposed in the adjunct 600 peaks at the right side 600R and curves downward toward the left side 600L, where the elution rate is the lowest. Accordingly, a higher dose of medicant(s) is delivered the closer the medicant(s) are to the right side 600R of the adjunct 600. In this way, when the right side 600R is positioned along the cut line or cut edge of the tissue, more medicant can be delivered along the cut tissue edge. In an exemplary implementation, the one or more medicants disposed in the first portion 602a of the top portion 602 of the adjunct 600 can include a hemostatic agent, which may allow a relatively high dose of the hemostatic agent to be delivered to tissue to facilitate blood clotting therealong in accordance with the elution profile shown in the graph 606.

Figure 97:
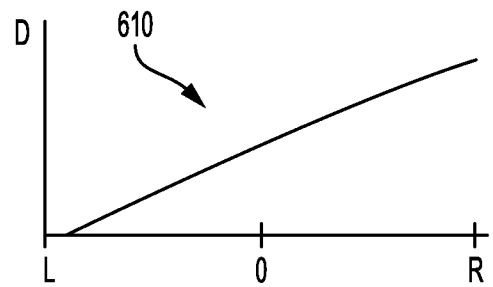
FIG. 97 is a graph showing another implementation of an elution profile of the adjunct of FIG. 95.

FIG. 97 illustrates another graph 610 showing another elution profile (a dose D versus a location within the adjunct 600) that various regions of the adjunct 600 can provide together, in accordance with degradation rates of polymers and distribution of the one or more medicants within the regions 602a, 602b, 604a, 604b. The graph 610 is similar to the graph 606 of FIG. 96 in that the elution rate of the one or more medicants disposed in the adjunct 600 peaks at the right side 600R and slopes downward toward the left side 600L, where the elution rate is the lowest. The slope in the graph 610 represents a linear function, unlike the curve in the graph 606.

Figure 98:
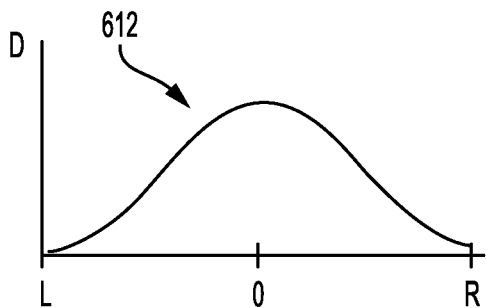
FIG. 98 is a graph showing yet another implementation of an elution profile of the adjunct of FIG. 95.

FIG. 98 illustrates another graph 612 showing another elution profile that the adjunct 600 can provide according to degradation rates and other properties of the regions 602a, 602b, 604a, 604b. As shown in the graph 612, the central area 608 of the adjunct 600 can have the highest elution rate. This area configured to release the highest dosage of one or more medicants can be disposed, for example, along a planned cut line of tissue such that the highest dosage of the one or more medicants is delivered to the cut line created by a cutting element of a surgical stapler. For example, a relatively high dose of a hemostatic agent, an antimicrobial agent, an antifungal agent, and/or an antiviral agent can be delivered from the central area 308 of the adjunct 600. Examples of applications where it can be advantageous to deliver the highest dosage of one or more medicants along the cut line are further described in U.S. patent application Ser. No. 14/840,255 entitled "Adjunct Material To Promote Tissue Growth" filed on Aug. 31, 2015, which is hereby incorporated by reference in its entirety. As shown in FIG. 98, the elution rate decreases from the central area 608 towards both the left and right sides 600L, 600R of the adjunct 600.

Multiple doses of a medicant can be released from one or more regions of an adjunct at different times and over different periods of time to achieve a cumulative dose of the medicant. Examples of graph of cumulative doses of various medicants are described in above-mentioned U.S. patent application Ser. No. 14/840,255 entitled "Adjunct Material To Promote Tissue Growth" filed on Aug. 31, 2015.

In some exemplary implementations, adjuncts configured to release at least one medicant therefrom in a variety of temporal and spatial patterns can be in the form of matrix metalloproteinase (MMP) inhibiting adjuncts for surgical devices. As discussed above, in the inflammation stage of the four wound healing stages (hemostasis, inflammation, proliferation, and remodeling), MMPs can be released to facilitate destruction of the ECM in the proliferation stage. As also discussed above, during the proliferation stage, an epithelialization process occurs in which parts of the ECM are destroyed to facilitate the migration of epithelial cells over the wound, and fibroblasts differentiate into myofibroblasts to form a protective outer layer over the wound. In the case of a patient's tissue being wounded by having staples applied thereto, the epithelialization process generally occurs at the tissue along the one or more lines of staples applied to the tissue. The more of the ECM that is destroyed and the longer the epithelialization process lasts, the more likely the patient will experience one or adverse effects of wound healing, e.g., infection, scarring, pain, etc. It may therefore be advantageous to reduce an amount of the ECM that is destroyed and/or to a length of the epithelialization process. In other words, it may be advantageous to accelerate the start of the proliferation stage and to reduce its duration and, consequently, reduce an amount of time before the remodeling stage begins. The patient can thus be less likely to experience complications resulting from the wound.

Thus, an implantable adjunct can be configured to releasably retain at least one medicant, such as a tissue matrix degradation inhibitor, that can accelerate the inflammation stage and/or the proliferation stage and, accordingly, reduce an amount of time before the remodeling stage begins. The at least one medicant can be configured to be released along a staple line defined by staples, which may help target the at least one medicant's desired functionality to where MMPs are released and where the epithelialization process generally occurs at the wounded tissue. The adjunct and the at least one medicant releasable therefrom may thus help prevent the tissue along the staple line from becoming too weak during the wound healing process.

The tissue matrix degradation inhibitor can be configured to inhibit MMP and, hence, be configured to allow less of the ECM to be destroyed. The MMP inhibitor can be introduced to the tissue via the adjunct and thereby limit the enzymatic destruction of the underlying collagen matrix, which as discussed above can be overly accelerated by an overactive inflammation response and by macrophages. The MMP inhibitor can thus delay the destruction and therefore delay strength loss at the wound along the staple line long enough for the new collagen being laid down to reinforce the staple line and thereby help prevent staple failure.

Examples of adjuncts that can release at least one medicant in various spatial and temporal patterns include adjunct 108 in FIG. 9. As shown in FIG. 9, the adjunct 108 has multiple reservoirs or regions formed in different location within the adjunct 108, five of which are shown as regions 109a, 111a, 113a, 109b, 111b that carry respective vessels 110, 112, 114, 110, 112. The vessels 110, 112, 114 can releasably retain therein first, second, and third medicants, respectively. Thus, the regions 109a, 109b can be configured to release the first medicant, the regions 111a, 111b can be configured to release the second medicant, and the region 113a can be configured to release the third medicant. Each of the regions 109a, 109b can be configured to commence release of the first medicant substantially immediately upon delivery of the adjunct 108 to tissue, each of the regions 111a, 111b can be configured to commence release of the second medicant after release of the first medicant, and the region 113a can be configured to commence release of the third medicant after release of the second medicant. In this way, different medicants can be delivered at appropriate times to desired locations in tissue being treated.

In some implementations, the 109a, 109b regions can be configured to complete delivery of the first medicant within about one day after delivery of the adjunct 108 to tissue, the regions 111a, 111b can be configured to deliver of the second medicant within a period of about one day after delivery of the adjunct 108 to tissue to about three days after delivery of the adjunct material to tissue, and the region 113a can be configured to initiate delivery of the third medicant within about three days after delivery of the adjunct 108 to tissue. In such implementations, for example, the first medicant configured to commence its release substantially immediately upon delivery of the adjunct 108 to tissue can be a hemostatic agent or other agent that is released at an acute dose (bolus release). The second medicant can be an anti-inflammatory agent. Also, at least one of the second and third medicants can be at least one medicant such as, for example, MMP inhibiting agent configured to reduce a length of the epithelialization process, with the coating associated therewith being on the side 108a, 108b of the adjunct 108 facing a staple line.

Other examples of adjuncts that can spatially and temporary release at least one medicant to provide a desired therapeutic effect include adjunct 100 of FIG. 40, adjunct 122 of FIG. 15, adjunct 116 of FIG. 12, adjunct 162 of FIG. 26, and adjunct 176 of FIG. 32. Examples of MMP inhibiting adjuncts are described in U.S. patent application Ser. No. 14/840,406 entitled "Matrix Metalloproteinase Inhibiting Adjuncts For Surgical Devices" filed on Aug. 31, 2015, which is hereby incorporated by reference in its entirety.

In some implementations, an adjunct can be configured to releasably retain at least one medicant as described, for example, in U.S. Pat. Pub. No. 2013/0149343 entitled "Hemostatic Bioabsorbable Device With Polyethylene Glycol Binder" filed Nov. 13, 2011, U.S. Pat. No. 8,383,147 entitled "Reinforced Absorbable Synthetic Matrix For Hemostatic Applications" filed Aug. 22, 2012, U.S. Pat. No. 8,319,211 entitled "Reinforced Absorbable Multi-Layered Fabric For Hemostatic Applications" filed May 17, 2010, U.S. Pat. No. 8,273,369 entitled "Reinforced Absorbable Synthetic Matrix For Hemostatic Applications" filed May 17, 2010, which are hereby incorporated by reference in their entireties. The entire adjunct or a portion thereof can be in a form of EVARREST™ Fibrin Sealant Patch manufactured by Ethicon Biosurgery, Division of Ethicon, Inc. In at least some of such implementations, the adjunct can include at least one medicant, such as a hemostatic or other agent, in a form of powder that is coupled to an absorbable film configured to elude an MMP inhibitor which starts on day one after the adjunct is delivered to tissue and can end until the end of day three. In some implementations, an adjunct can include multiple layers releasably retaining at least one medicant. Each of the layers can be formed from respective one or more bioabsorbable polymer and can retain a medicant that is different from medicants retained by other layers. Depending on degradation rates of the bioabsorbable polymer and other factors, the adjunct can release the medicants in various patterns. For example, adjunct release pattern can include multiple mini-boli of different medicants released at different times. As another example, medicants can be released at different times over longer time periods such that release of two or more medicants can overlap in time. Furthermore, the medicants can be disposed at different locations within an adjunct and two or more medicants can release at different locations of the adjunct as bolus doses or time release dosages. Examples of adjuncts that include multiple layers retaining at least one medicant include adjunct 108 in FIG. 9 through FIG. 11 and adjunct 116 in FIG. 12 through FIG. 14.

In some exemplary implementations, an adjunct can be in the form of a fiber lattice including multiple fibers formed from a biodegradable polymer. The fiber lattice can retain one or more medicants therein such that the medicants are releasably coupled to fibers of the fiber lattice by being "trapped" within the fibers. For example, the adjunct can retain the medicant due to a conformation of the fibers (e.g., the fibers can be wound together or woven into a sheet mesh or other structures). The medicant can be located within pores or other reservoirs formed in the adjunct. Also, the fibers can be tightly wound, woven, knitted, or otherwise interconnected such that medicant(s) can be retained in the adjunct by being held within the tightly interconnected fibers.

Degradation of the fiber lattice causes the adjunct to change its conformation, such as by the action of water and/or other agents that the adjunct is subjected to at a treatment site. The change of the conformation can involve, for example, one or more of degradation of one or more layers of the adjunct, opening of pores, loosening of the fibers' interconnection, unwinding of the fibers, or other changes in the adjunct relative to its original conformation. As the adjunct changes its conformation, release of one or more medicants can be released from one or more locations within the adjunct that become exposed to water and/or other agents present at an environment around the adjunct in the treatment site. Examples of adjuncts that can releasably retain one or more medicants in the above-described manner include adjunct 162 in FIG. 26 and FIG. 27 and adjunct 166 in FIG. 28 and FIG. 29. An adjunct such as the adjunct 162 or adjunct 166 can include a plurality of regions includes a fiber lattice region that is water soluble and degrades more quickly than a second one of the regions.

In some exemplary implementations, an adjunct can include a copolymer or multiple bioabsorbable copolymers that can carry an effective dose of at least one medicant. The polymers can be different polymers or different versions of the same bioabsorbable polymer. For example, an adjunct can include both lower and higher molecular weight versions of the same bioabsorbable polymer. The at least one medicant can be incorporated into the one or more copolymers such that, when the copolymer(s) degrade, the at least one medicant is being released under control of the copolymers' degradation rate and other factors. The copolymer(s) can be in the form of two or more layers formed such that the layers have different degradation rates and retain different concentrations of the same or different medicant(s). The layers of an adjunct can be formed from the same type of a bioabsorbable polymer that is treated such that each of the layers has degradation rate different from that of one or more of other layers. In general, the at least one medicant can be dispersed within one or more copolymers in a number of different ways. For example, the at least one medicant can be dispersed within one or more copolymers in a substantially homogeneous manner across the adjunct. Alternatively, the at least one medicant can form one or more higher-concentration areas within the adjunct—e.g., some of the locations of the adjunct can release more medicants than other areas.

Examples of adjuncts that can releasably retain at least one medicant within layers of one or more copolymers include adjunct 116 in FIG. 12 through FIG. 14. As described above, the adjunct 116 has first (top) and second (bottom) layers 118, 120 formed from absorbable polymers having different degradation rates. The first layer 118 can be a low molecular weight absorbable polymer that absorbs during a first time period after the adjunct 116 is delivered to tissue and the second layer 120 can be a high molecular weight absorbable polymer that absorbs during a second time period after the first time period is completed. As the first and second layers 118, 120 absorb in accordance with their degradation rates, they release respective medicant(s) incorporated therein. Examples of implantable medical devices formed of block co-polymers are described in U.S. Pat. No. 8,652,506 entitled "Bio-degradable Block Co-polymers For Controlled Release" filed on Jun. 5, 2008, which is hereby incorporated by reference in its entirety.

As mentioned above, an adjunct in accordance with the described techniques can retain medicants at different locations throughout the adjunct. The spatial distribution of the medicants can vary in different ways to provide different patterns of medicant release to achieve desired effect. Various medicants can be disposed at different locations within the adjunct and targeted delivery of the medicants can be accomplished in a number of different ways. For example, FIG. 9 through FIG. 11 illustrate adjunct 108 having multiple reservoirs or regions 109a, 111a, 113a, 109b, 111b disposed at different locations and releasably retaining therein different medicants. The regions are covered by coatings A1, B1, C1 have different degradation or absorption rates that control release of the medicants from different locations of the adjunct 108 at different times. Opposite sides 108a, 108b of the adjunct 108 are configured to release one or more medicants in different patterns such that the medicants can be delivered at appropriate times to desired locations in tissue being treated. For example, in some implementations, at least one first medicant released from regions 109a, 109b on the first side 108a of the adjunct 108 can be at least one agent that promotes healing, whereas at least one second medicant released from regions 111a, 111b on the second side 108b of the medicant can be at least one medicant that prevents adhesion of tissue to the adjunct 108. In such implementations, the first side 108a can be a tissue contacting surface.

An adjunct can be configured such that at least one medicant is released therefrom at a cut line formed, e.g., by a stapler's cutting element, and different medicants are released at locations in the adjunct away from the cut line. Also, similar to the adjunct 108 of FIG. 9 through FIG. 11, different sides of an adjunct can be configured to deliver different medicants therefrom, to provide a desired location-specific effect on tissue.

In some implementations, a tissue cutting element of a surgical stapling device can be configured to pass through a slot formed along a longitudinal axis thereof of a cartridge body. An adjunct can include first, second, and third portions releasably retaining first, second, and third medicants, respectively. The first region can be positioned within a central portion of the adjunct on either side of the slot and it can be configured to be separated by passage of the tissue cutting element through the slot such that release of the first medicant commences substantially simultaneously upon passage of the cutting element through the first region. The second region can be in contact with a surface of the cartridge body, and the second medicant can be effective to inhibit tissue growth adjacent the second region. The third region can be opposite the second region and it can be effective to promote tissue growth.

Figure 99:
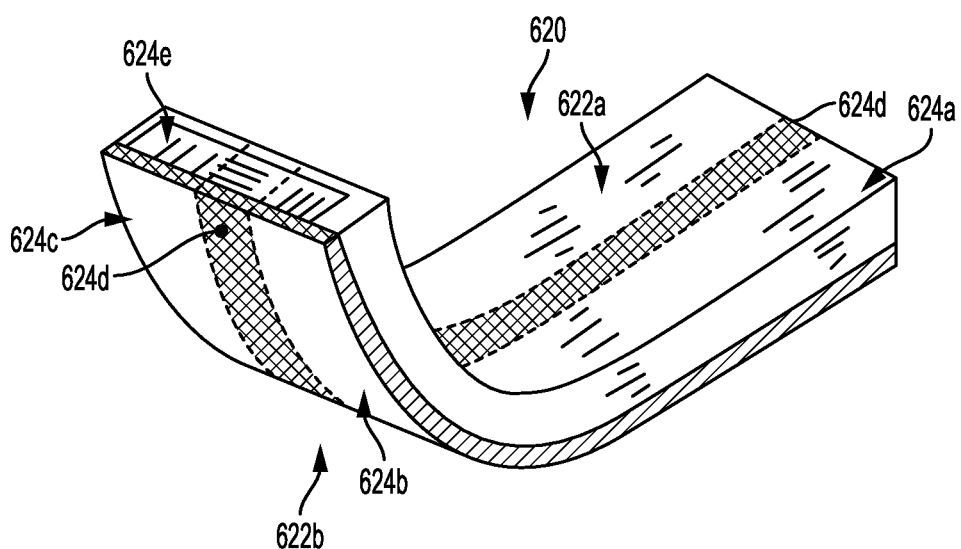
FIG. 99 is a perspective view of an implementation of an implantable adjunct including a plurality of heterogeneous regions.

FIG. 99 illustrates an implementation of an adjunct 620 formed from a plurality of fibers and including a plurality of heterogeneous sections or regions 624a, 624b, 624c, 624d, 624e. It should be appreciated, however, that adjuncts can have another number of heterogeneous regions. In the example illustrated, the first region 624a is located on a top side 622a and on opposed lengthwise sides of the adjunct 620 and is configured to discourage tissue growth, e.g., to prevent adhesion. The first region 624a can be configured to discourage tissue growth in a variety of ways. Examples of ways in which tissue growth can be discouraged are discussed in mentioned-above U.S. patent application Ser. No. 14/840,255 entitled "Adjunct Material To Promote Tissue Growth," filed on Aug. 31, 2015. The first region 624a can have at least one first medicant (not shown) releasably retained therein that is configured to discourage tissue growth, such as an anti-adhesion agent.

The second and third regions 624b, 624c are each located on a bottom side 622b of the adjunct 620 and are each configured to encourage tissue growth. The second and third regions 624b, 624c can be configured to encourage tissue growth in a variety of ways, as discussed, for example, in U.S. patent application Ser. No. 14/840,255 entitled "Adjunct Material To Promote Tissue Growth," filed on Aug. 31, 2015. The second and third regions 624b, 624c can have at least one second medicant (not shown) releasably retained therein that is configured to encourage tissue growth, such as a growth factor. Further, the second and third regions 624b, 624c can have the same structure as one another and can have the same medicant releasably retained therein, but, in other implementations, the second and third regions 624b, 624c can each be configured to encourage tissue growth but differ from one another in structure and/or in retained medicant(s).

As illustrated, a fourth region 624d is disposed between the second and third regions 624b, 624c on the bottom side 622b. In this illustrated implementation, the fourth region 624d is configured to facilitate hemostasis. FIG. 99 also shows the fourth region 624d underlying the first and fifth regions 624a, 624e by a dotted line on the top side 622a of the adjunct 620. As illustrated, the fourth region 624d extends along a central longitudinal portion of the adjunct 620, which facilitates delivery of its hemostatic properties to tissue. The fourth region 624d can be configured to facilitate hemostasis growth in a variety of ways, as discussed, for example, in U.S. patent application Ser. No. 14/840,255 entitled "Adjunct Material To Promote Tissue Growth," filed on Aug. 31, 2015. The fourth region 624d has a third medicant 626 (shown in FIG. 100 and FIG. 101) releasably retained therein that is configured to facilitate hemostasis, such as a hemostatic agent.

As shown in FIG. 99, the fifth region 624e is located in an interior area of the adjunct 620 in a cavity defined by the top side 622a, opposed lengthwise sides, and bottom side 622b of the adjunct 620, and is configured to space apart the top and bottom sides of the adjunct 620 to thereby space apart the tissue growth-encouraging and tissue growth-discouraging portions of the adjunct 620. In other words, the fifth region 624e is configured to space the second and third regions 624b, 624c apart from the first region 624a. The fifth region 624e can have a fourth medicant (not shown) releasably retained therein. The fourth medicant can include, for example, an anti-adhesion agent such as, for example, oxidized regenerated cellulose (ORC), and/or another hemostatic agent.

The adjunct 620 can be releasably coupled to a stapler (e.g., to an end effector of a stapler and/or to a cartridge retainable in a stapler) so that the adjunct 620 can be positioned relative to tissue to which the stapler applies staples and the adjunct 620. In general, the position of the adjunct 620 relative to tissue can include the bottom side 622b thereof facing the tissue and the top side 622a thereof facing away from the tissue. The hemostasis-encouraging region 624d and the tissue growth-encouraging regions 624b, 624c can thus be facing the tissue so as to facilitate delivery of their respective medicants to the tissue, and the tissue growth-discouraging section 318a can thus be facing away from the tissue to this deliver its medicant thereto.

In some implementations, the second and third tissue growth-encouraging regions 624b, 624c can include a plurality of medicants configured to evoke healing processes at portions of the regions 624b, 624c disposed at both sides of and away from the fourth region 624d. Thus, while the third medicant 626 released from the fourth region 624d is configured to facilitate hemostasis, the plurality of medicants can be released from different locations of the second and third regions 624b, 624c at different times. The medicants can be retained within the second and third regions 624b, 624c in a number of different ways as described herein, and one or more of the medicants can be carried within vessels. For example, the medicants can be located in pores or reservoirs distributed throughout the second and third regions 624b, 624c in a desired pattern. In some aspects, the reservoirs can be formed in a similar manner as in the adjunct 108 of FIG. 9 through FIG. 11. The pattern of the reservoirs and the way in which the medicants are configured to be released from the reservoirs can be such that, for example, medicants facilitating subsequent wound healing stages are released at times and for time periods that facilitate progression of the wound healing stages. The reservoirs can be located within the adjunct to as to allow release of appropriate medicants at locations of the wound where those medicants are beneficial. The medicants can be released from the reservoirs in a variety of ways, e.g., as one or more coatings of the reservoirs rupture, as adjunct's portions (e.g., fibers, fiber lattices, fiber meshes, etc.) retaining the medicant(s) disintegrate and/or change their conformation, and in other manners as described herein.

Figure 100:
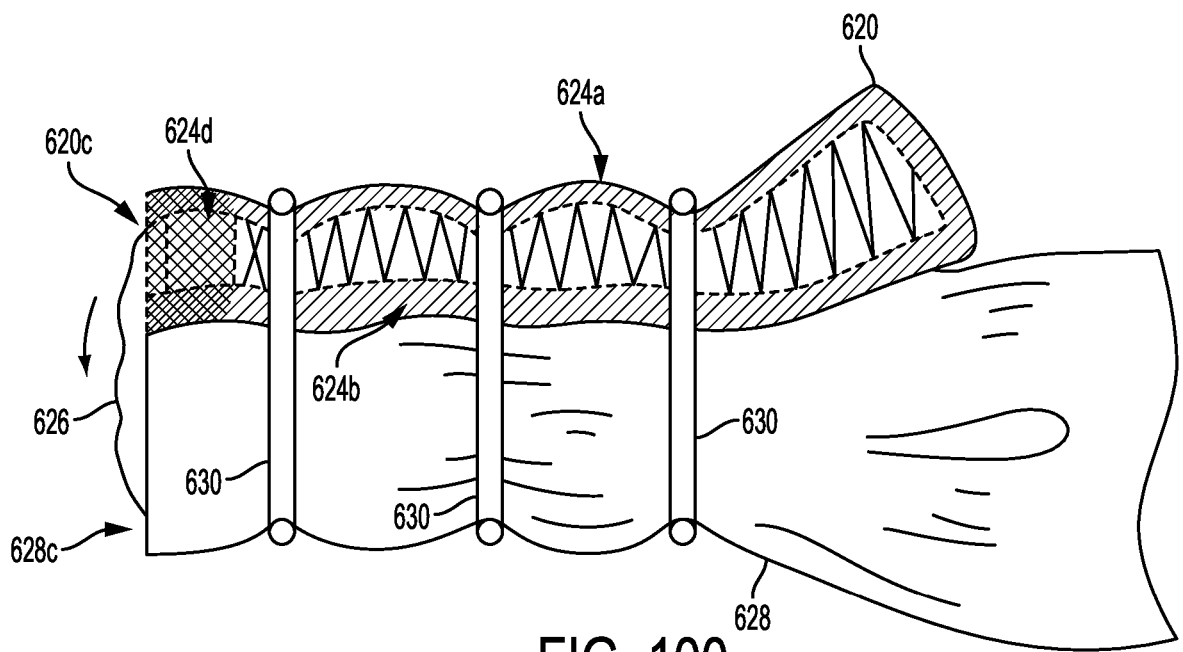
FIG. 100 is a cross-sectional side view of the adjunct of FIG. 99 stapled to tissue.
Figure 101:
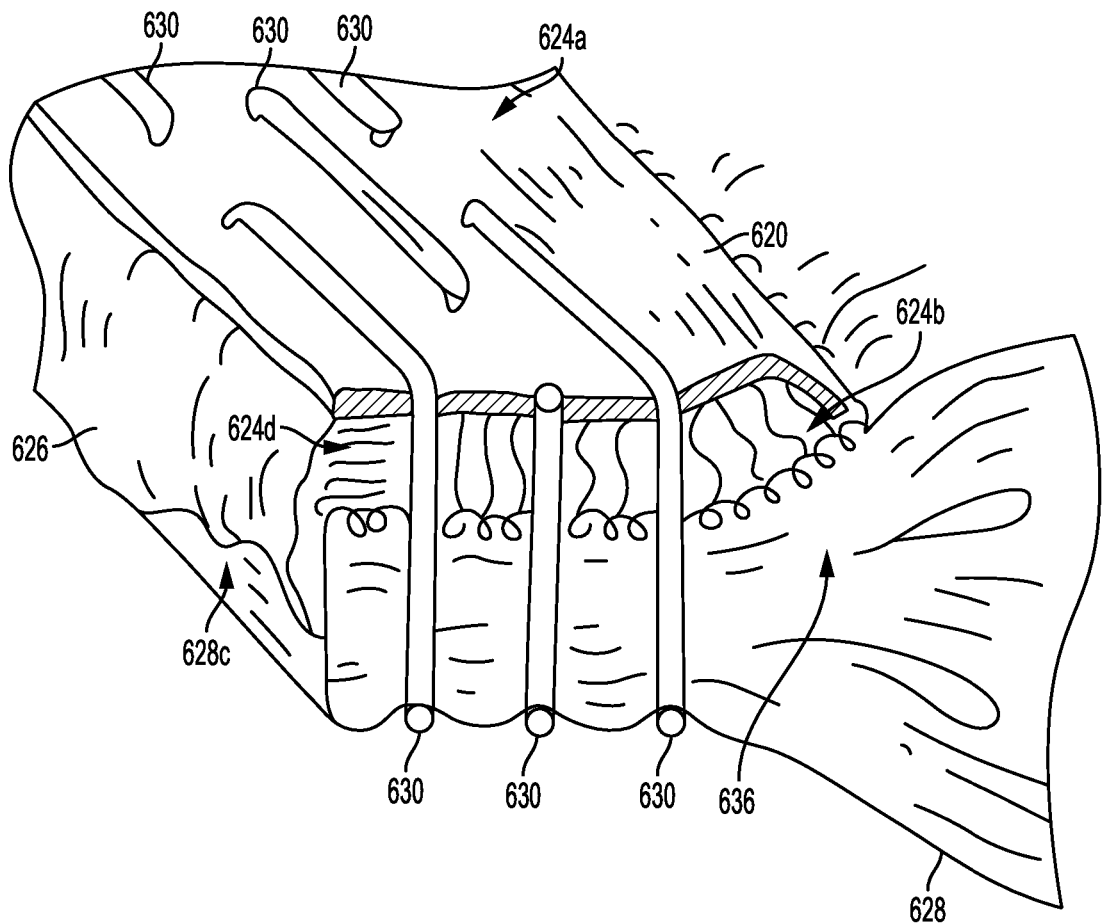
FIG. 101 is a perspective view of the adjunct and tissue of FIG. 100.

FIG. 100 and FIG. 101 illustrate an example of the adjunct 620 stapled to a tissue 628 with a plurality of staples 630. FIG. 100 and FIG. 101 show the third medicant 626 being released from the fourth region 624d along a cut edge 620c of the adjunct 620 and a cut edge 628c of the tissue 628, the cut edges 320c, 628c having been formed by a stapler's cutting element during the stapling process. In the illustrated implementation, a stapler's cutting element can translate longitudinally along a center of a staple cartridge. The adjunct 620 can be releasably retained on the cartridge and/or on an end effector having the cartridge seated therein with the fourth region 624d aligned with the longitudinal path of the cutting element. The fourth region 624d extending along the central longitudinal portion of the adjunct 620 may facilitate such placement. Thus, when the cutting element translates along the cartridge to cut the tissue 628, the cutting element also cuts through the fourth region 624d, which may facilitate leakage, dripping, and/or other release of the third medicant 626 from the fourth region 624d. In other words, the cutting of the fourth the fourth region 624d can help the third medicant 626 exit the adjunct 620. Further, the location of the fourth region 624d above the tissue 628, as shown in FIG. 100 and FIG. 101, can help the third medicant 626 to drip or otherwise flow down onto the tissue 628. In particular, the third medicant 626 can be advantageously delivered to the cut edge 628c of the tissue 628 which is an area that is most susceptible to bleeding and hence is most in need of the hemostatic properties provided by the third medicant.

As illustrated in FIG. 101, the second region 624b can be configured to unwind or fray along a side 636 thereof facing the tissue 628, e.g., the side defining part of the bottom side 622b of the adjunct 620. In other words, fibers of the second region 624b can be configured to "unwind." The unwinding or fraying can facilitate release of the second medicant from the second region 624b. The unwinding or fraying can be triggered by contact of the fibers with fluid, e.g., with moisture of the tissue 628. The third region 624c can be similarly configured to unwind or fray, whereas the first region 624a can be configured to not unwind or fray, thereby facilitating anti-adhesion.

In the examples of FIG. 99, FIG. 100, and FIG. 101, the adjunct 620 has a generally rectangular shape to facilitate its use with a linear stapler. However, an adjunct that can facilitate anti-adhesion and encourage tissue in-growth and hemostasis can have other different shapes, for example, shapes that allow use of the adjunct with a circular stapler.

In some implementations, an adjunct configured to release at least one medicant therefrom in a heterogeneous manner can be structured such that, when a cutting element (e.g., knife) translates along a cartridge and cuts tissue and a portion of an adjunct (e.g., its central portion), the cutting activates release of multiple medicants from the adjunct. The medicants can be released such that two or more of the medicants are blended together. In the blend, the medicants (e.g., fibrin and thrombin, etc.) can enhance one another's activation raters. The cutting element (e.g., knife and/or staples) can have features that enhance the distribution and/or mixing of the medicants.

Examples of adjunct materials that can release a plurality of medicants are described in U.S. Pat. Pub. No. 2013/0256367 entitled "Tissue Thickness Compensator Comprising A Plurality of Medicaments" filed on Mar. 28, 2012, which is hereby incorporated by reference in its entirety. As described in U.S. Pat. Pub. No. 2013/0256367, a material can be provided that is configured to be disposed on a cartridge and that can include an outer layer encompassing an inner layer that includes medicants, such as freeze-dried thrombin and/or fibrin. When the outer layer, which can be water impermeable, is punctured by staples, water and/or other agents in the external environment at a treatment site can infiltrate the inner layers and cause the medicant to release from the adjunct. Furthermore, in some implementations, the staples inserted into the inner and outer layers can be disposed around the inner layer and the staples and can be sealed. Another example of an adjunct that can release a plurality of medicants is described in U.S. Pat. No. 7,708,180 entitled "Surgical Fastening Device With Initiator Impregnation Of A Matrix Or Buttress To Improve Adhesive Application" filed on Nov. 9, 2006, which is also hereby incorporated by reference in its entirety.

In some implementations, at least one medicant can be releasably disposed in a dispenser in an elongate shaft of a surgical instrument. Examples of such surgical instruments are described in U.S. Pat. No. 8,905,977 entitled "Surgical Stapling Instrument Having An Electroactive Polymer Actuated Medical Substance Dispenser" filed on Jun. 1, 2005, and U.S. Pat. No. 8,215,531 entitled "Surgical Stapling Instrument Having A Medical Substance Dispenser" filed on Jan. 29, 2010, which are hereby incorporated by reference in their entireties. Movement of a cutting element, such as knife, can release the at least one medicant contained in the shaft of the surgical instrument. If the surgical instrument is a multi-fire device, the at least one medicant can be reloaded into the instrument after each application to tissue. Alternatively, a dispenser (e.g., syringe or other device) releasably carrying the medicant and disposed within a shaft of a surgical instrument can be replaced after each use.

The techniques described in the above-mentioned references can be used in conjunction with the adjunct 620 shown in FIG. 99, FIG. 100, and FIG. 101. In this way, a surgical instrument can include a biocompatible adjunct releasably retained on a cartridge body retaining at least one first medicant, and the surgical instrument can further include at least one second medicant disposed within an elongate shaft. Actuation of a tissue cutting element of the surgical instrument can cause both the first and second medicants to be delivered to tissue. In some implementations, one of the first and second medicants can affect activity of another of the first and second medicants.

In some implementations, as mentioned above, an adjunct can retain therein a plurality of medicants at different locations thereof, such that the medicants are configured to release from the adjunct in spatially heterogeneous patterns. For example, the adjunct can include a plurality of layers (e.g., concentric and/or stacked layers, or otherwise structured layers) that can each releasably retain at least one medicant therein. In some aspects, each of the layers can retain a different medicant. Regardless of the specific configuration of the adjunct, different medicants retained therein can be delivered to desired locations in tissue being treated. Examples of such adjuncts include adjunct 176 in FIG. 32, adjunct 190 in FIG. 37, adjunct 194 in FIG. 38, and adjunct 197 in FIG. 39. In these adjuncts, and any other adjuncts in accordance with the techniques described herein, the plurality of medicants being released from one or more portions of the adjuncts in a non-homogeneous manner with respect to at least one of time of release and location of release can deliver various effects to tissue. For example, the medicants can upregulate anti inflammation or pro-healing agents. As another variation, one medicant can upregulate pro-healing response such as VEGF, FGF, or TGF, and another medicant can down regulate anti-healing response such as specific MMPs, IL, or TNFa. Any other desired effects can be provided to tissue being treated.

At least one medicant can be incorporated into an adjunct at locations within the adjunct that facilitate delivery of the at least one medicant to a desired tissue location. As mentioned above, a medicant releasably retained by an adjunct can elute from the adjunct when a tissue cutting element passes through a slot in a cartridge body of a surgical instrument and thereby cuts tissue and a region of the adjunct positioned within a central portion of the adjunct on either side of the slot. Additionally or alternatively, staples configured to deliver an adjunct to tissue can be configured to thereby cause at least one medicant retained by the adjunct to be released from one or more portions of the adjunct. Furthermore, the at least one medicant can be associated with the staples. Examples of surgical staples associated with at least one medicant are described, for example, in U.S. patent application Ser. No. 14/840,716 entitled "Adjunct Material To Provide Controlled Drug Release," filed on Aug. 31, 2015, which is hereby incorporated by reference in its entirety.

Figure 102:
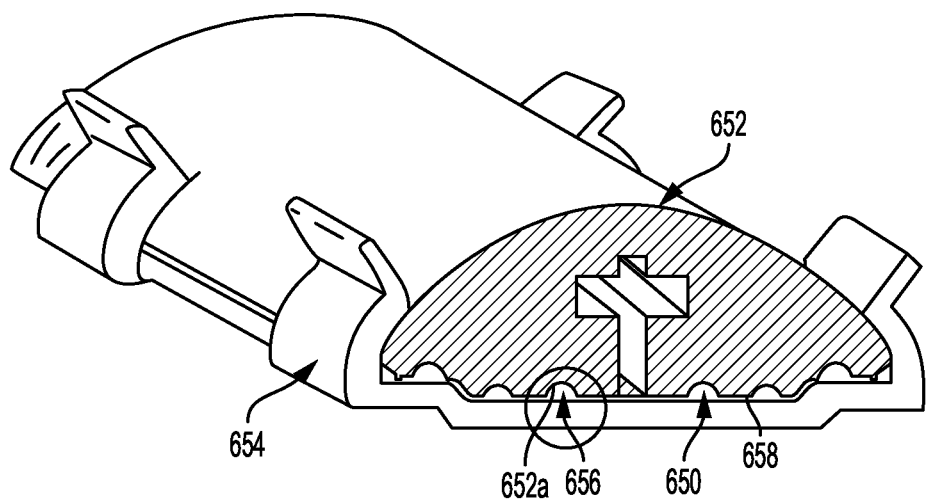
FIG. 102 is a cross-sectional perspective view of an anvil of a surgical instrument releasably associated with an adjunct containing at least one medicant.
Figure 103:
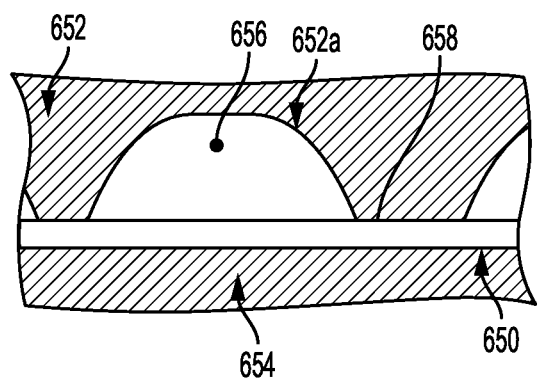
FIG. 103 is a cross-sectional view of a portion of the anvil of FIG. 102.

FIG. 102 and FIG. 103 illustrate an exemplary adjunct 650 that can be configured to be disposed over an anvil 652 of a surgical instrument. The adjunct 650 can be retained on the anvil 652 using a retainer component 654 which can have a variety of different configurations. However, in some implementations, the retainer component 654 may not be used. As shown, the adjunct 650 can include different doses of first and second medicants 656, 658 that can be released therefrom when the adjunct 650 is delivered to tissue. As also shown, the adjunct 650 can be configured such that regions with the first medicant 656 are disposed in staple forming pockets 652a formed on the surface of the anvil 652 and regions with the second medicant 658 are disposed in areas of the anvil 652 between the staple forming pockets 652a. Thus, the first medicant 656 is disposed a larger amount than the second medicant 658. When staples (not shown) are fired from a staple cartridge of the surgical instrument and are formed in the staple forming pockets 652a, the staples can puncture the adjunct 650 at its areas disposed over the staple forming pockets 652a and thereby release the first medicant 656 disposed at those areas. The second medicant 658 can be configured to be released in a variety of other manner as described herein. Furthermore, in some cases, release of the first medicant 658 from the adjunct 650 can affect release of the second medicant 658 therefrom.

It should be appreciated that the first and second medicants 656, 658 can be releasably disposed directly on the anvil 652 such that they are not retained by any adjunct. In such implementations, the retainer component 654 as shown in FIG. 102 and FIG. 103, or any other type of a retainer, can releasably retain the first and second medicants 656, 658 on the surface of the anvil 650.

At least one medicant can be disposed within an adjunct at locations thereof corresponding to various locations on a surface of an anvil or a cartridge. For example, patterns in which the at least one medicant is releasably retained in the adjunct can correspond to a pattern of staples to be delivered from the cartridge. At least one medicant can be disposed in areas of the adjunct to be punctured by staples and at least one other medicant can be disposed in areas of the adjunct disposed between the areas to be punctured by staples. Also, the at least one medicant to be delivered to tissue by deployment of staples can be disposed within the adjunct in patterns corresponding to a shape of staple forming pockets. Examples of such adjuncts are described in U.S. patent application Ser. No. 14/498,145 entitled "Method For Creating A Staple Line" filed on Sep. 26, 2014, which is hereby incorporated by reference in its entirety.

In general, surgical adjuncts having medicants controllably releasable therefrom are provided. In an exemplary implementation, an adjunct having one or more medicants controllably releasable therefrom can be used with a staple cartridge assembly and/or an end effector of a surgical instrument designed to be deployed within an interior of a patient.

As an exemplary implementation, an adjunct retaining at least one medicant controllably releasable therefrom can be configured to be responsive to one or more physiological triggers. The adjunct can be provided with the at least one medicant releasably retained within the adjunct. In general, the one or more physiological triggers can each include an environmental condition to which the adjunct is exposed, such as when the adjunct is positioned within a body, such as by being stapled to tissue. Various physiological triggers can affect the adjunct, causing the adjunct to release the at least one medicant to the surrounding tissue in a selectable elution profile depending on the physiological trigger(s) that affect a particular adjunct. The amount of medicant delivered to tissue of a patient and/or a timing of when the medicant is delivered to the tissue of the patient can therefore vary depending on one or more physiological triggers. A response of the adjunct to the physiological trigger(s) may allow more medicant(s) to be used to treat a potentially harmful physiological condition as the physiological condition increases in severity, may allow less medicant(s) to be used to treat the condition as the physiological condition decreases in severity, and/or allow for more effective and localized treatment for individual harmful physiological conditions by delivering medicant(s) locally to a site of the harmful physiological condition.

An adjunct can be configured to respond to a physiological trigger in a variety of ways. In at least some implementations, the adjunct can be formed at least partially from a biocompatible polymeric material configured to be responsive to the physiological trigger. The adjunct's response to the physiological trigger can be configured to change an elution profile of the one or more medicants releasably retained by the adjunct. The adjunct's response to the physiological trigger can include the polymeric material absorbing, dissolving, and/or otherwise disintegrating at a different rate in response to the physiological trigger, e.g., increasing from no disintegration to some amount of disintegration, increasing from a first non-zero rate of disintegration to a second non-zero rate of disintegration, decreasing from some amount of disintegration to zero disintegration, or deceasing from a first non-zero rate of disintegration to a second non-zero rate of disintegration. An adjunct can be configured to respond to only one physiological trigger or to a plurality of physiological triggers.

One example of physiological trigger for an adjunct includes an environmental condition of a physical condition such as temperature. The environmental condition including temperature may allow more medicant(s) to be released from the adjunct to tissue as temperature to which the adjunct is exposed increases and less medicant(s) to be released from the adjunct as the temperature to which the adjunct is exposed decreases. When an adjunct is configured to respond to temperature, the one or more medicants releasably retained therein can include one or more medicants configured to reduce a temperature in a patient (e.g., an anti-inflammatory agent, an antimicrobial agent, etc.), such that the higher the temperature the adjunct is exposed to, the more medicant(s) can be released to combat the relatively high temperature. This temperature responsiveness of the adjunct may allow an increasing amount of medicant(s) to be released from the adjunct to treat the patient while the patient's temperature increases and may allow a decreasing amount of medicant(s) to be released from the adjunct as the temperature decreases, thereby allowing more effective and localized treatment of any harmfully high temperature in the patient. As an example, an infection at a tissue site, such as one arising before or during wound healing, can cause the patient's temperature to increase. The adjunct being responsive to temperature may thus allow for prompt and effective treatment of the infection at the tissue site.

Figure 104:
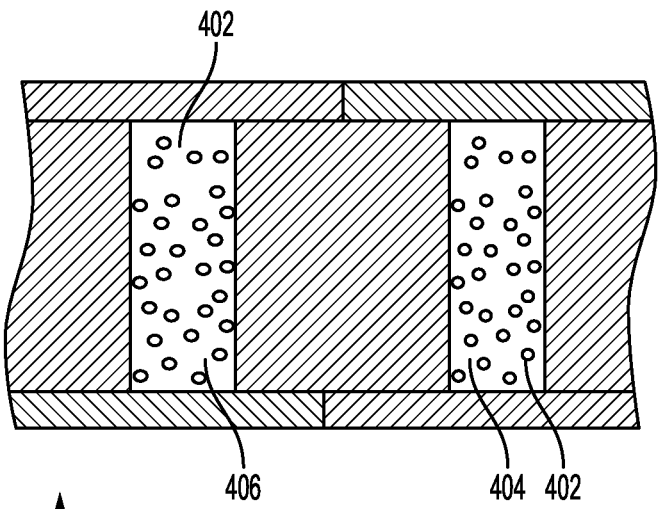
FIG. 104 is a partial, cross-sectional view of an implementation of an adjunct retaining a medicant.

FIG. 104 illustrates one implementation of an adjunct 400 configured to respond to an environmental condition of temperature and having at least one medicant 402 releasably retained therein. The adjunct 400 can generally be configured similar to the adjunct 128 of FIG. 18. As shown in FIG. 104, the adjunct 400 has at least two porous regions 404, 406 formed therein that each carry the at least one medicant 402 therein. The at least one medicant 402 can be the same in each of the regions 404, 406 or different in each of the regions 404, 406. Any number of medicants and/or regions can be used. the adjunct 400 can include first and second coatings 408, 410 such that the first coating 408 on one side of the adjunct 400 seals the porous region 404 and the second coating 410 on an opposite side of the adjunct 400 seals the porous region 406. In the illustrated example, the coatings 408, 410 create a barrier that affects release of the at least one medicant according to the environmental condition of temperature.

Figure 105:
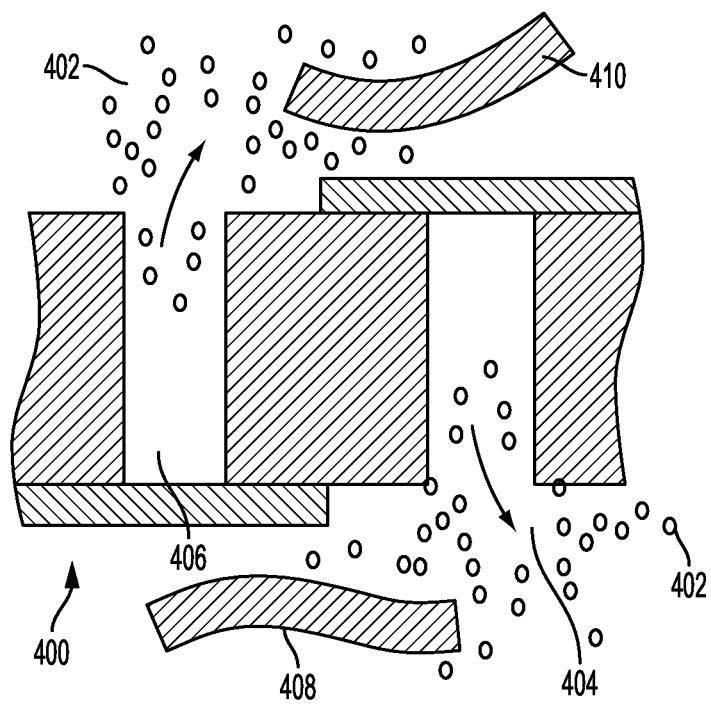
FIG. 105 is a partial, cross-sectional view of the adjunct of FIG. 104 releasing the medicant.

As shown in FIG. 105, the polymeric materials of the coatings 408, 410 can be configured to exhibit thermo-responsive properties by changing conformation and can thus be responsive to a change in temperature conditions. As a temperature increases, the coatings 408, 410 of the regions 404, 406 can be configured to soften and thereby allow release of the at least one medicant 402 from the regions 404, 406. As discussed above, the coatings 408, 410 can be selected such that they respond in a same way, e.g., respond in a same to temperature changes, so as to release the at least one medicant 402 from the regions 408, 410 in a same manner. Alternatively, the coatings 408, 410 can be selected such that they respond in a different way, e.g., respond differently to changes in temperature such that the at least one medicant 402 is released from the regions 408, 410 in different ways, such as in response to different extents of temperature change.

In use, the adjunct 400 can be coupled to a surgical stapler, e.g., to a staple cartridge thereof, and delivered to tissue of a patient when the surgical stapler delivers staples to the tissue, e.g., when the staples are ejected from the staple cartridge. The adjunct 400 can be subjected to temperature conditions within the patient and release the at least one medicant 402 from the at least two regions 404, 406 in accordance with the temperature.

Another example of a physiological trigger for an adjunct includes an environmental condition of a chemical condition such as pH. The adjunct can be configured to disintegrate at a faster rate when there is a change in the pH level to which the adjunct is exposed. For example, depending on a material composition of the adjunct (e.g., a material composition throughout the adjunct or in different distinct regions thereof), a higher pH level in tissue to which the adjunct has been applied can be configured to cause the faster rate of disintegration, and as the pH level lowers, the adjunct can be configured to disintegrate at a slower rate. Alternatively, a lower pH level in tissue to which the adjunct has been applied can be configured to cause the faster rate of degradation, and as the pH level rises, the adjunct can be configured to disintegrate at a slower rate. In this way, depending on the adjunct's construction, the pH level to which the adjunct is exposed can accelerate and/or retard a breakdown of the adjunct and therefore control a metered rate of release of the one or more medicants releasably retained by the adjunct. For example, at least one medicant retained by an adjunct can include an antimicrobial agent and/or other medicant(s) configured to combat infection. The adjunct can be formed at least partially from a pH sensitive low molecular weight absorbable polymer. When an infection affects tissue, the pH level goes down. Disintegration of the adjunct's pH sensitive polymer can thus accelerate, and the accelerated disintegration can release more of the medicant(s) retained by the adjunct to fight the infection.

The material composition of the adjunct can include any material susceptible to variations in the pH levels and can be varied depending on a desired metered rate of release of the one or more medicants releasably retained by the adjunct. For example, a polymer can be used that at least partially includes a high molecular weight polyanhydrides microsphere encapsulation (e.g., p-carboxyphenoxypropane (pCPP)), which has an approximately three year absorption period under normal pH conditions but has an absorption period of approximately 100 days with a pH level at 10.0. As another example, Poly carboxyphenoxyacetic acid (PCPA) can be used, which has a ten day degradation cycle that is affected by pH level.

In addition and/or alternatively to pH level regulating disintegration of the adjunct, the pH level can self-regulate. For example, lower pH levels can cause breakdown of pH sensitive polymer(s) that at least partially form the adjunct, which can release buffer or neutralizing agent(s) to raise pH to levels. The rising pH levels may be beneficial for improving healing of wounded tissue to which the adjunct has been applied.

Figure 106:
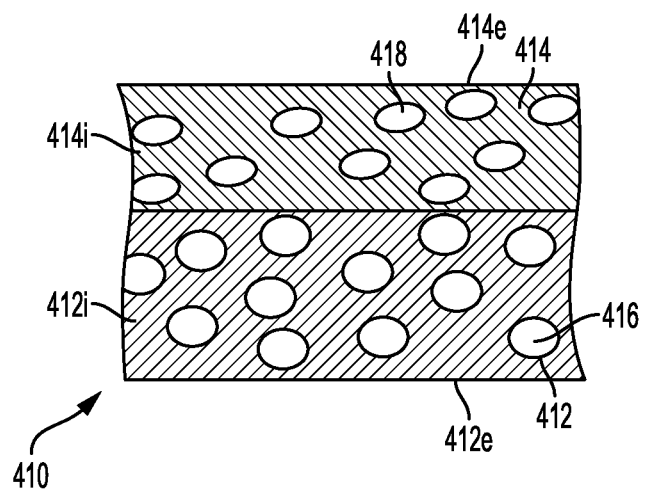
FIG. 106 is a partial, cross-sectional view of another implementation of an adjunct retaining first and second medicants.

FIG. 106 illustrates one implementation of an adjunct 410 configured to respond to an environmental condition of a chemical condition. The adjunct 410 can be configured to be responsive to a chemical trigger at a tissue site of the patient. A variety of different chemical triggers can be used, such as surface and bulk water mediated degradation and pH levels.

The adjunct 410 can generally be configured similar to the adjunct 116 of FIG. 12. In this illustrated implementation illustrative of surface and bulk water mediated degradation, the adjunct 410 has first and second distinct layers or regions 412, 414 formed from absorbable polymers having, first and second medicants 416, 418 disposed therein, respectively. As discussed above, the first and second layers 412, 414 can be formed from different polymers or from the same type of polymer that is treated so as to form layers or other structures having different degradation properties, which in this example include different responses to the chemical condition.

Figure 107:
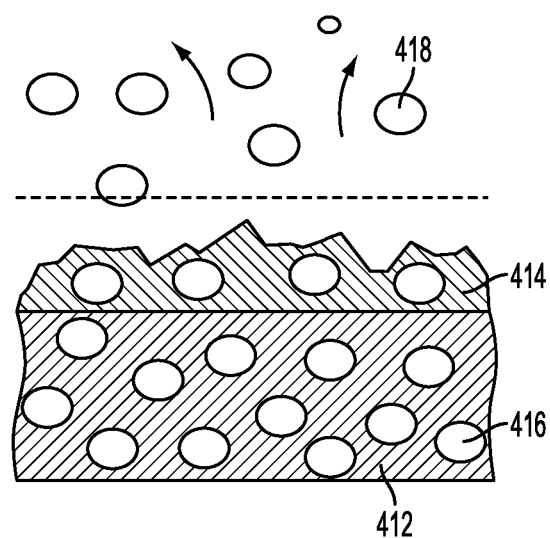
FIG. 107 is a partial, cross-sectional view of the adjunct of FIG. 106 as the adjunct experiences degradation and releases the first medicant.
Figure 108:
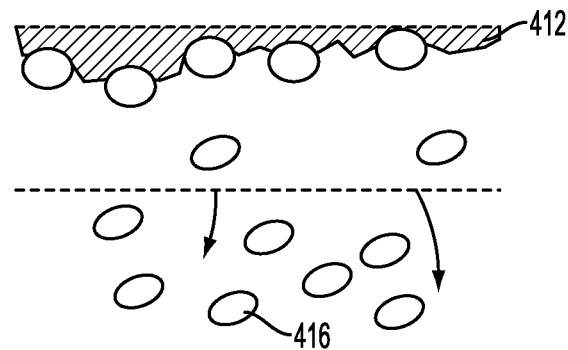
FIG. 108 is a partial, cross-sectional view of the adjunct of FIG. 107 as the adjunct experiences degradation and releases the second medicant.

The adjunct 410 can be configured to be subjected to water conditions within a patient at a tissue site. The regions 412, 414 can each be configured to experience heterogeneous disintegration where the water degrades exterior surfaces 412e, 414e of the regions 412, 414, respectively, faster than the water penetrates interiors 412i, 414i of the regions 412, 414, respectively. This disintegration of the exterior surfaces 412e, 414e can allow release of the medicants 416, 418 to surrounding tissue from their respective regions 412, 414. The regions 412, 414 can vary in composition such that each region's external surface disintegrates at a different rate, thereby allowing for a selectable release of each medicant 416, 418 disposed therein. For example, as shown in FIG. 106, no disintegration has yet occurred in either the first or second regions 412, 414. FIG. 107 shows that the second region 414 can be configured to disintegrate at a faster rate than the first region 412, thereby resulting in a faster release of the second medicant 418 compared to the first medicant 416. As shown in FIG. 108, in this example the second region 414 can thus be configured to entirely disintegrate and the second medicant 418 can be configured to be entirely released while the first region 412 can be configured to first begin to disintegrate and the first medicant 416 can be configured to first begin to be released. Because of the surface disintegration of the exterior surfaces 412e, 414e, the medicants 416, 418 can be configured to be released from the adjunct 410 in selectable directions, where the second medicant 418 is configured to be released upward as seen in FIG. 107 and the first medicant 416 is configured to be released downward as seen in FIG. 108.

Alternatively and/or additionally, the regions 412, 414 can include hydrogels. As water penetrates the interiors 412i, 414i of the regions 412, 414, the water can be configured to cause the hydrogel-including regions 412, 414 to swell and thereby release their respective medicants 416, 418.

Another example of a physiological trigger for an adjunct includes an environmental condition of a mechanical condition such as strain and rate of change in strain. Various mechanical conditions can be configured to affect the adjunct, causing the adjunct to release at least one medicant retained therein to surrounding tissue in a selectable elution profile depending on the mechanical condition. The amount of medicant(s) delivered from the adjunct can therefore vary depending on a mechanical condition and a physical interaction between the adjunct and tissue to which the adjunct has been applied. This responsiveness of the adjunct to the mechanical condition may allow more medicant(s) to be used to treat a potentially harmful condition as the potentially harmful condition increases in severity, may allow less medicant(s) to be used to treat the potentially harmful condition as it decreases in severity, and/or may allow for more effective and localized treatment for individual potentially harmful conditions by delivering medicant(s) locally to a site of the potentially harmful condition.

An adjunct can be configured to respond to a mechanical condition in the form of strain. In at least some implementations, the adjunct can include an anisotropic mechanical scaffold that can be configured to be affected by the strain. The adjunct including the anisotropic mechanical scaffold can be configured to change a release rate of at least one medicant retained in the adjunct based on the strain experienced by the scaffold. The adjunct can be configured to increase an expulsion rate of the at least one medicant based on the strain applied to the adjunct. The adjunct can be configured to contain one or more thin membrane walls containing micro pores that are strain sensitive. Strain can be configured to cause release of the medicant(s) at a specific moment and/or over time. For example, a continually-applied force can be configured to cause an adjunct including the anisotropic mechanical scaffold that includes mesh to stretch over time such that mesh of the adjunct slowly gives way and results in a strain rate over time. As the adjunct experiences strain and a pore size of the mesh increases, the adjunct can release a medicant of a specific size as the pore size reaches the specific size of the medicant. A plurality of medicants with varying sizes can be interwoven with an adjunct and released at varying times as the pore size changes.

In at least some implementations of an adjunct configured to respond to a mechanical condition in the form of strain, the adjunct can be formed of a material capable of retaining at least one medicant and increasing or decreasing a release rate due to strain. For example, the adjunct can be formed of a fast-degrading stiff copolymer and a slower-degrading elastomeric polymer, thereby allowing variation of release of the medicant(s) and causing a strain rate over time to control the release of the medicant(s) from the adjunct. The stiff copolymer and the elastomeric polymer can each include any one or more materials having stiff properties and elastomeric properties, respectively. The fast-degrading stiff polymer can be configured to release a bolus of one or more medicants retained by the adjunct rapidly as the stiff polymer degrades. The bolus can be used, for example, to reduce inflammation upon an initial surgery. As a healing process proceeds and the stiff polymer degrades, the elastomeric polymer can be configured to deform to a greater extent, increasing the pore size of the adjunct and releasing one or more additional medicants to aid in a later period of the healing process. For example, the stiff material can include an oriented Poly(glycolic acid) (PGA) scaffold that is woven or non-woven with the elastomeric polymer, which can include poly(etherurethane urea) (PEUU). As the PGA stiff copolymer degrades, the PEUU elastomeric polymer can be configured to deform more, which can increase the pore size in the adjunct and can increase release of the medicant(s). Thereby a plurality of medicants can be selectively released at varying times based on the strain rate over time.

In at least some implementations of an adjunct configured to respond to a mechanical condition in the form of strain, the adjunct can be configured to become increasingly elastic with hydration, influencing a rate of release of one or more medicant(s) as the adjunct experiences strain. As a mesh of the adjunct is exposed to water and the strain applied to the adjunct increases over time, the adjunct can be configured to experience greater pore sizes due to increasing elasticity, which can allow release of the medicant(s).

An adjunct can be configured to be responsive to multiple environmental conditions. For example, an adjunct can be configured to have intersecting fibers bound together and configured to be responsive to one or more selectable environmental conditions. The fibers can be configured to respond to any of temperature, moisture, pH levels, etc., as discussed above. The adjunct can be configured to release at least one medicant based on both strain applied to the adjunct and one or more selectable environmental conditions in the surrounding tissue. The adjunct can thus use a physiologically sensitive degradation profile in addition to any strain applied to the adjunct to control a release rate of the medicant(s). The fibers of the adjunct can also increase in length in response to the environmental conditions in tissue to which the adjunct is attached. For example, the fibers can increase in length based on temperature, moisture, etc.

Figure 109:
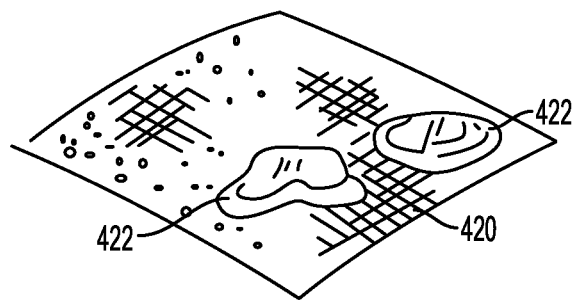
FIG. 109 is a perspective view of an implementation of an adjunct responsive to a strain and retaining a medicant.
Figure 110:
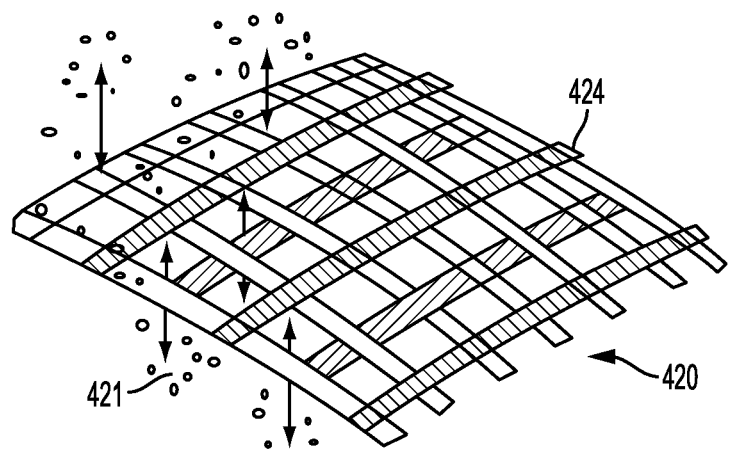
FIG. 110 is an enlarged perspective view of the adjunct of FIG. 109 experiencing a strain and releasing the medicant.

FIG. 109 illustrates one implementation of an adjunct 420 configured to respond to a mechanical condition including strain, e.g., strain of tissue to which the adjunct 420 is applied. The adjunct 420 can generally be configured similar to the adjunct 166 of FIG. 28. The adjunct 420 can include a mesh of individual fibers 424 with at least one medicant 421 interwoven therewith. Similar to that discussed above, when the adjunct 420 is delivered at the treatment site, water and/or other agents, shown schematically as drops 422 in FIG. 109, can cause the fibers 424 to experience strain and thereby swell and elongate such that the distances between the fibers 424 increase, as shown in FIG. 110. In this way, the at least one medicant 421 is released from the adjunct 420, as also shown in FIG. 110. The adjunct 420 can be configured to become increasingly elastic with hydration. As the mesh is exposed to the water and/or other agents over time, the adjunct 420 can be configured to experience greater pore sizes due to increasing elasticity, thereby allowing a more rapid release of the at least one medicant 421.

Figure 111:
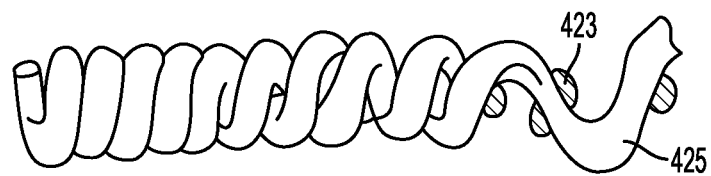
FIG. 111 is a perspective view of a fiber of the adjunct of FIG. 109.
Figure 112:
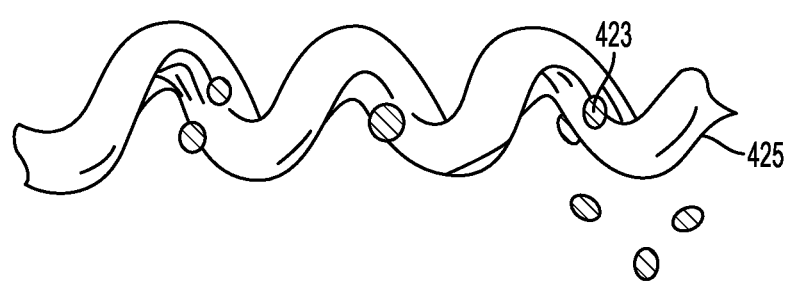
FIG. 112 is a perspective view of the fiber of FIG. 111 experiencing a strain and releasing the medicant.

FIG. 111 illustrates another implementation of an adjunct 425 configured to respond to a mechanical condition including strain, e.g., strain of tissue to which the adjunct 425 is applied. The adjunct 425 can generally be configured similar to the adjunct 162 of FIG. 27. Similar to that discussed above, the adjunct 425 can have a shape of a tightly wound spiral can retain therein one or more vessels carrying at least one medicant 423. In response to strain, e.g., strain experienced at a tissue site to which the adjunct 425 has been stapled, the wound fibers thereof can be configured to swell and increase in length, or elongate, such that the distances between the fibers increase and the adjunct 425 "unwinds" and releases the medicant 423 "trapped" within the adjunct 425, as shown in FIG. 112.

In at least some implementations, the adjunct can include an anisotropic mechanical scaffold that can be configured to respond based on stress experienced, by changing a release rate of at least one medicant retained in the adjunct based on stress experienced by the scaffold. The adjunct can be configured to change the release rate in situations, for example, of highly non-linear moduli. The adjunct can be configured to experience low forces that are capable of causing significant deformation of the adjunct. Such deformation of the adjunct can cause unintended release of the one or more medicants if the adjunct releases medicant(s) in response to strain. However, the adjunct releasing medicant(s) in response to stress experienced can be configured to release medicant(s) when tissue to which the adjunct is fixed bears a certain load rather than deforms. An adjunct can be configured to contain, for instance, microcapsules, microbeads, or any other vessels that release medicant(s) based on stress transmitted through the adjunct as stress increases to a level to which the microcapsules, microbeads, or any other vessels cannot maintain attachment to the adjunct and/or cannot maintain structural integrity.

In at least some implementations, an adjunct configured to respond to a mechanical condition in the form of experienced stress can be configured to contain micro-cavities with walls having varying thicknesses. At least one medicant can be retained within the micro-cavities. Increasing stress on the adjunct can be configured to cause select walls to fail, thereby rupturing the microcavities and releasing the contained medicant(s).

Figure 113:
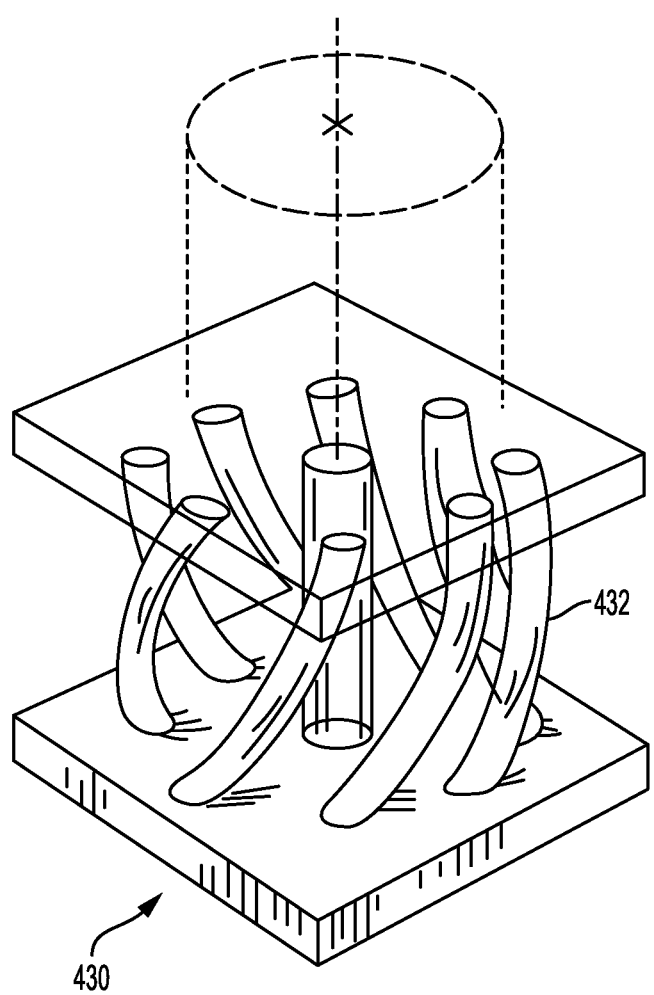
FIG. 113 is a perspective view of another implementation of an adjunct responsive to a strain and retaining a medicant.
Figure 114:
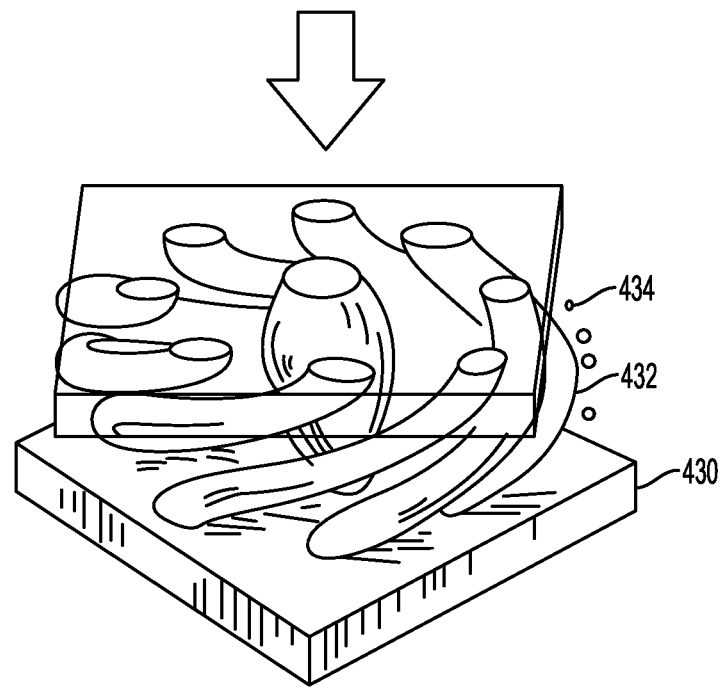
FIG. 114 is a perspective view of the adjunct of FIG. 113 experiencing a strain and releasing the medicant.

FIG. 113 illustrates one implementation of an adjunct 430 configured to respond to stress, e.g., to stress on tissue to which the adjunct 430 is delivered. The adjunct 430 can be formed from a plurality of fibers and be configured to alter its conformation in response to a load applied thereto. A load is illustrated schematically in FIG. 114 as an arrow applying downward pressure to the adjunct 430. In general, the adjunct 430 can include a plurality of individual fibers 432 with at least one medicant 434 retained on the fibers 432. For example, the fibers 432 can be configured to contain microbeads that contain the medicant 434. As stress on the scaffold of the adjunct 430 causes the fibers 432 to compress, as shown in FIG. 114, a release rate of the medicant 434 can be configured to increase based on the stress applied to the adjunct 430. Adjuncts formed from a plurality of fibers and be configured to alter its conformation in response to a load applied thereto are further described in U.S. patent application Ser. No. 14/840,255 entitled "Adjunct Material To Promote Tissue Growth" filed on Aug. 31, 2015, which is hereby incorporated by reference in its entirety.

FIG. 24 illustrates an implementation of a vessel 158 configured to respond to stress, e.g., to stress on tissue to which the vessel 158 is delivered. As discussed above, when a strain is applied to the vessel 158 as schematically shown by the arrow 161, the outer coating 159 can break or rupture such that its contents in the form of the at least one medicant 160 are released.

FIG. 22 illustrates another implementation of an adjunct 150 configured to respond to stress, e.g., to stress on tissue to which the adjunct 150 is delivered. As discussed above, when strain is applied to the adjunct 150 (e.g., when the staple 151 is deformed), as schematically shown by the arrow 153, the outer coating 152 can be caused to also deform and rupture.

Some aspects of the present disclosure relate to an adjunct releasably retained on a cartridge body of a staple cartridge assembly of a surgical device and configured to be delivered to tissue by deployment of staples in the cartridge body. The adjunct can have at least one first medicant component or medicant configured to be released from the adjunct as a bolus dose substantially immediately upon delivery of the adjunct to tissue a treatment site. The adjunct can also have at least one second medicant component or medicant configured to release from the adjunct such that release of the second medicant to tissue is regulated by the release of the first medicant. In other words, presence of the first medicant and/or other effects provided by the first medicant (e.g., its release from an adjunct or other structure) affect a manner in which the second medicant is released from the adjunct.

The second medicant can be associated with a component of the staple cartridge assembly in a manner that facilitates regulation of its release to tissue by release of the first medicant component. For example, the second medicant can be disposed in the same adjunct as the first component and, in some cases, in the vicinity of a location of the first component in the adjunct. The second medicant can be configured to be released to tissue at a time after the release of the first medicant component.

The first and second medicants can be disposed in an adjunct at locations that facilitate their release therefrom such that the first medicant commences release before the second medicant and then affects the release of the second medicant. For example, the first medicant can be disposed at a portion of an adjunct along a cut line to be formed, e.g., by a stapler's cutting element. The second medicant can be disposed at one or more portions of the adjunct that are disposed away from the cut line. However, the second medicant can be disposed at the same location as the first medicant while release of the second medicant is still regulated by release of the first medicant. Specifically, release of the first medicant can be triggered by activation of a stapler, whereas release of the second medicant is controlled by the release of the first medicant.

In some implementations, the first medicant can be configured to release as a bolus dose. The second medicant can then release as a time release dose, or in some cases, as a bolus dose. Furthermore, in some implementations, an adjunct can include two or more portions configured such that in some of the portions the second medicant is released as a bolus dose whereas in others it is released as a time-release dose.

In some implementations, the bolus dose of the first medicant can include the second medicant. In such implementations, the second medicant can be disposed within vessels which are disposed in the same location in an adjunct as the first medicant. The first medicant can also be incorporated into vessels such that the adjunct can have both vessels including the first medicant and vessels including the second medicant. The vessels with the second medicant, which can include one or more of second medicants, can be configured to release the second medicant therefrom at a slower rate than the vessels carrying the first medicant release the first medicant. In this way, a bolus dose release of the first medicant is followed by release of the second medicant over a longer period of time. In some aspects, the first and second medicants can be the same or they can include the same active agent. In other aspects, the first and second medicants can contain different active agents.

In some implementations, the second medicant can be included in the same vessel (e.g., a pellet, capsule, bead, etc.) as the first medicant. The vessel can be formed from at least one bioabsorbable polymer and the first medicant can be in the form of a layer (e.g., an outer layer) of the vessel. The second medicant can be an active agent and it in the form of one or more of inner layers of the vessel such that the second medicant is configured to be released to tissue from the first medicant in the form of the outer layer upon degradation of the bioabsorbable polymer forming the outer layer. In such implementations, release of the second-medicant containing first medicant in the form of multiple vessels from an adjunct (e.g., from one or more reservoirs or other portions thereof) regulates the release of the second medicant from the first medicant. As described above, the vessel can include multiple layers and it can thus have more than one second medicants releasably disposed therein.

Furthermore, an adjunct can be in the form or a fiber lattice or a fiber mesh or other structure, as described herein, that releasably retains at least one second medicant containing an active agent. Degradation of at least one bioabsorbable polymer forming such a structure can control release of the at least one second medicant therefrom.

Release of the first medicant from the vessel (e.g., from an outer layer thereof) can allow the second medicant to release from the vessel (e.g., from one or more inner layers thereof) as well. As described above, the vessel can include multiple layers and, in some implementations, release of the first medicant from the vessel can control release of multiple other medicants therefrom.

In some implementations described herein, a bolus dose of the first medicant can be released from a cartridge body. An adjunct releasably retaining the first medicant can be associated with the cartridge body in a number of ways. For example, a staple channel or cavity that holds the staples can also retain at least one medicant therein. The medicants can be included in the adjunct or the adjunct (e.g., in a form of a film) can be used to retain the medicants within one or more staple cavities, in which case the adjunct itself can also include one or more medicants. Deployment of staples can cause the medicant to release from the staple cavity in a manner that can affect release of other medicant(s) from the adjunct.

Figure 115:
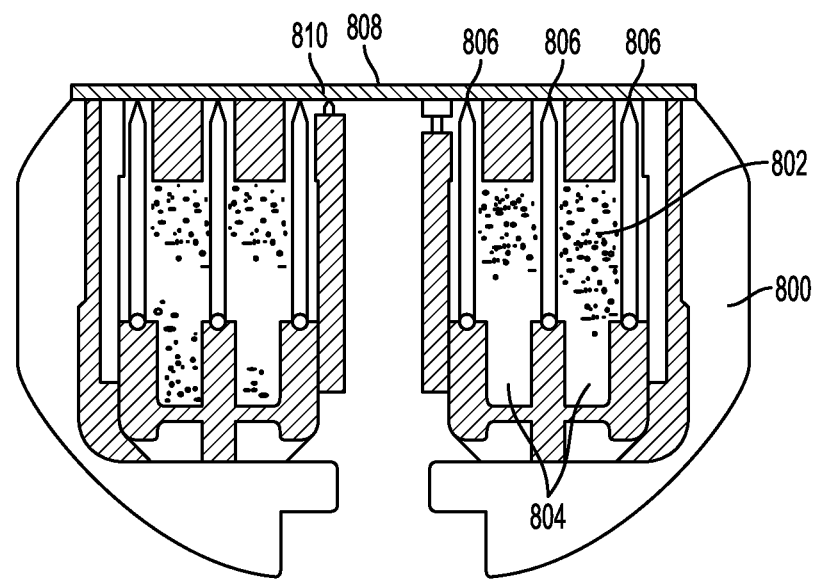
FIG. 115 is a perspective view of an adjunct disposed in a cartridge body.

FIG. 115 illustrates an example of a cartridge body 800 of a staple cartridge of a surgical device having a least one first medicant 802 retained in staple cavities 804 of the cartridge body 800. Each staple cavity 804 has a surgical staple 806 disposed therein. As shown, an adjunct 808 can be configured to releasably retain the at least one first medicant 802 within the staple cavities 804. The adjunct 808 can have at least one second medicant 810 disposed therein, which can be disposed within the adjunct 808 in any suitable way. The first and second medicants 802, 810 can be the same or different medicants.

The adjunct 808 can have a number of different structures and it can be formed from various materials. In the example of FIG. 115, the adjunct 808 can be in the form of a film or other structure. The film can be formed from at least one bioabsorbable polymer having certain elution characteristics (e.g., degradation rate, etc.). An exemplary structure of the adjunct 808 includes a poly-p-dioxanone (PDS) film attached to a woven construct made of oxidized regenerated cellulose (ORC) or other material. The PDS film can be attached to the ORC construct using heat as described, for example, in U.S. patent application Ser. No. 14/667,874 entitled "Malleable Bioabsorbable Polymer Adhesive For Releasably Attaching A Staple Buttress To A Surgical Stapler" filed Mar. 25, 2015, and U.S. Pat. No. 7,601,118 entitled "Minimally Invasive Medical Implant And Insertion Device And Method For Using The Same" and filed Sep. 12, 2007, which are hereby incorporated by reference in their entireties.

Regardless of the specific configuration of an adjunct in accordance with the described subject manner, such as adjunct 808 in FIG. 115, the adjunct can be configured to be penetrated by staples such that content of the adjunct (e.g., at least one second medicant) can be released. Additionally or alternatively, upon delivery of the adjunct to a treatment site, the adjunct can commence to degrade due to moisture and other agents or factors in an external environment at the treatment site.

Figure 116:
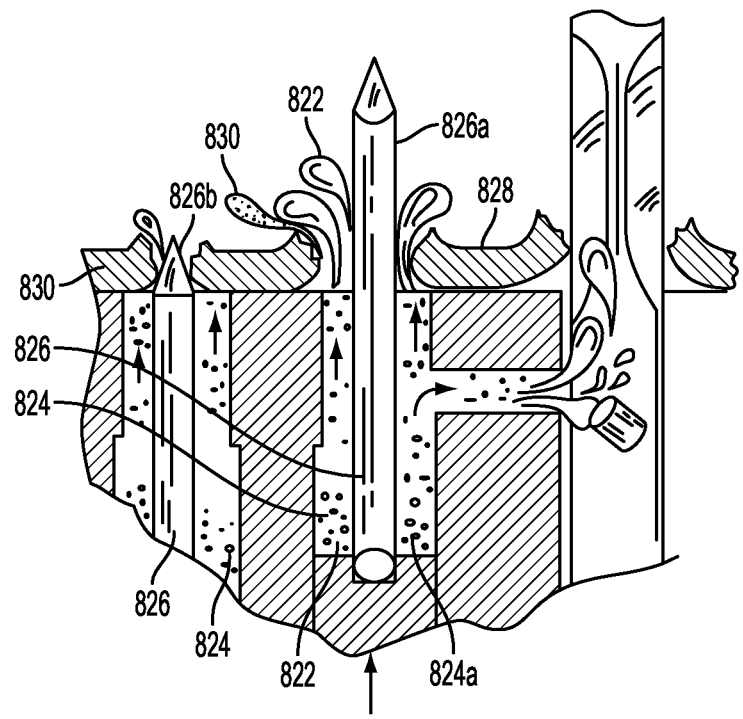
FIG. 116 is a perspective view of a portion of an adjunct disposed in a cartridge body, showing the adjunct penetrated by staples delivered by the cartridge body.

FIG. 116 illustrates an example of a cartridge body 820 similar to cartridge body 800 in FIG. 115. As shown in FIG. 116, the cartridge body 820 has at least one first medicant 822 retained in staple cavities 824 thereof. Each staple cavity 824 has a surgical staple 826 disposed therein, and, in the illustrated example, the surgical staples 826 can be configured to deployed such that they emerge from a tissue-facing surface of the cartridge body 820 at different times. As shown, the cartridge body 820 has an adjunct 828 disposed thereon that is configured to releasably retain the at least one first medicant 822 within the staple cavities 824. The adjunct 828 can be similar to adjunct 808 in FIG. 115 and it can include at least one second medicant 830 releasably disposed therein.

As further shown in FIG. 116, upon deployment of the staples 826, the first medicant 822 can be released from the staple cavities 824 as a bolus dose. As mentioned above, in the example of FIG. 116, the surgical staples 826 can penetrate the adjunct 828 disposed on the tissue-facing surface of the cartridge body 820 at different times. Thus, as shown in FIG. 116, a staple 826a can penetrate the adjunct 828 first after which staple 826b penetrates the adjunct 828. As also shown, penetration of the adjunct 828 by the staple 826a causes the first medicant 822 to be released from a respective staple cavity 824a. Also, the second medicant 830 can be released from the adjunct 828, which can be regulated by release of the first medicant 822 from the staple cavity 824a. In aspects in which different staple cavities or rows carry respective different medicants, deployment of the staple 826b after the staple 826a is deployed can cause another medicant to release from the respective staple cavity. The adjunct 828 can include more than one second medicant that can be affected by release of one or more different first medicants from the staple cavities.

In addition, in some implementations, as mentioned above, one or more of the staple cavities can include both the first and second medicant that are releasable from the cavities such that release of the first medicant controls or affects release of the second medicant.

In the examples of FIG. 115 and FIG. 116, a first medicant can be disposed in a cartridge body in a number of different ways. For example, one or more row of staples (linear or circular) in the cartridge body can be dedicated to medicant delivery. Thus, the staple cavities in the row(s) will carry the first medicant 802. Furthermore, in some implementations, one or more staples can be removed from a staple row dedicated to medicant delivery (not shown). In this way, one or more of the staple cavities (e.g., the staple cavities 804 or 824) can retain a dose of the first medicant that can be released when an end effector of the surgical device is deployed. Each of the staple cavities, whether with a staple or having a staple removed, can be associated with one medicant or with a blend of different medicants. Also, each of the staple cavities can be associated with a different medicant. In some aspects, a staple row can be associated with a different medicant such that each staple row in a cartridge body carries a medicant that is different from medicants carried by other staple rows. It should be appreciated that only some of the staple cavities and/or only some of the staple rows in a cartridge body can be associated with one or more medicants.

As mentioned above, an adjunct in accordance with the described techniques can be configured such that release of a first medicant can be triggered by mechanical disruption of a carrier for the first medicant. For example, as described above, the first medicant can be disposed within a coating formed on the staples, and the coating can be disrupted by deformation of the staples. The first medicant can also be disposed within a staple line of the cartridge body, and puncture of a film retaining the first medicant within the staple line can result in release of the first medicant. As another example, the first medicant can be disposed at a cut line to be cut by a tissue cutting instrument of a surgical stapling device.

In some implementations, an adjunct can be configured to incorporate at least one first medicant at a portion thereof to be cut by a tissue cutting instrument, and at least one second medicants at other locations of the adjunct. Examples of such adjuncts are described in U.S. patent application Ser. No. 14/840,659 entitled "Adjunct Material To Provide Heterogeneous Drug Elution" filed on Aug. 31, 2015, which is hereby incorporated by reference in its entirety. The first and second medicants can be released from such an adjunct in various patterns and release of the first medicant can influence release of the second medicant.

An environment created by a first medicant when it is released or as it is being released can affect a rate of release of the second medicant. Staple penetration of an adjunct can result in a bolus dose release of the first medicant whereas a long-term degradation of material forming the adjunct uses release of the second medicant. Examples of components that can release at least one drug upon being cut with a tissue cutting instrument are described in U.S. Pat. Pub. No. 2013/0256367 entitled "Tissue Thickness Compensator Comprising A Plurality Of Medicaments" filed on Mar. 28, 2012, which is hereby incorporated by reference in its entirety.

In some implementations, an adjunct can be configured to incorporate at least one first medicant at locations thereof to be punctured by the staples and at least one second medicants at other locations thereof that are between the locations to be punctured by staples. Examples of such adjuncts are described in U.S. patent application Ser. No. 14/840,659 entitled "Adjunct Material To Provide Heterogeneous Drug Elution" filed on Aug. 31, 2015.

In some implementations, at least one medicant can be releasably disposed in a dispenser in an elongate shaft of a surgical instrument. Examples of such surgical instruments are described in U.S. Pat. No. 8,905,977 entitled "Surgical Stapling Instrument Having An Electroactive Polymer Actuated Medical Substance Dispenser" filed on Jun. 1, 2005, and U.S. Pat. No. 8,215,531 entitled "Surgical Stapling Instrument Having A Medical Substance Dispenser" filed on Jan. 29, 2010, which are hereby incorporated by reference in their entireties. Movement of as a cutting element, such as knife, can release the at least one medicant contained in the shaft of the surgical instrument. In these implementations, the medicant configured to be released from a shaft of the surgical instrument can be at least one first medicant that affects release of at least one second medicant, as described herein. The at least one second medicant can be releasably disposed in an adjunct that can be releasably retained on a cartridge body of that surgical instrument.

As mentioned above, a staple can be associated with at least one medicant which, in the illustrated implementations, can act as a first medicant affecting release of another medicant. Also, in some cases, the staple leg can include both a first medicant and a second medicant, which can be released independent of the first medicant. The at least one medicant can be disposed in an adjunct associated with the staple. As disused above, the adjunct can be in the form of a film, fiber lattice, and/or foam. The staple can carry the adjunct thereon such that at least one medicant disposed in the adjunct can release when the staple is deformed upon staple deployment. One example of such an implementation is adjunct 150 in FIGS. 22 and 23 above. As discussed above, when the staple carrying an adjunct is deformed upon its deployment, an outer surface of the adjunct ruptures and thereby causes at least one retained medicant to release. Also, deformation of the staple can cause the outer surface of the adjunct to deform, which exposes inner coating(s) including at least one medicant (e.g., an anti-microbial agent or antibiotic). As another example, the least one medicant can release from the adjunct associated with a staple due to moisture and other agents to which the adjunct is exposed in tissue of a wound. When a staple is coated with an adjunct in the form of one or more biodegradable layers, the layers can gradually absorb or degrade and thus release at least one medicant under control of the degradation rate. As one example, a non-cross linked coating can swell and become a polymer gel before it begins to break down.

At least one medicant can be directly coated over a staple leg with one or more layers of the medicant coating the staple leg. The staple leg can also be coated with a layer including at least one agent that prevents bio-film formation. The coated medicant may or may not be encapsulated within an outer shell which can be at least one bioabsorbable polymer and/or that can be ruptured in a number of different ways.

Further, staple coating technologies for medicant delivery in accordance with the described techniques can include braiding multiple fibers around a staple wire, as described, for example, in U.S. Pat. No. 8,663,277 entitled "Braided Barbed Suture" filed on Jun. 29, 2005, which is hereby incorporated by reference in its entirety. The fibers can be disposed over the staple wire before the staple is formed and loaded into a cartridge. One or more of the fibers can contain medicants, as discussed herein. Examples of staples carrying multiple layers at least one of which retains one or more medicants are discussed in U.S. patent application Ser. No. 14/841,139 entitled "Adjunct Material To Provide Controlled Drug Elution" filed on Aug. 31, 2015, which is hereby incorporated by reference in its entirety.

Figure 117:
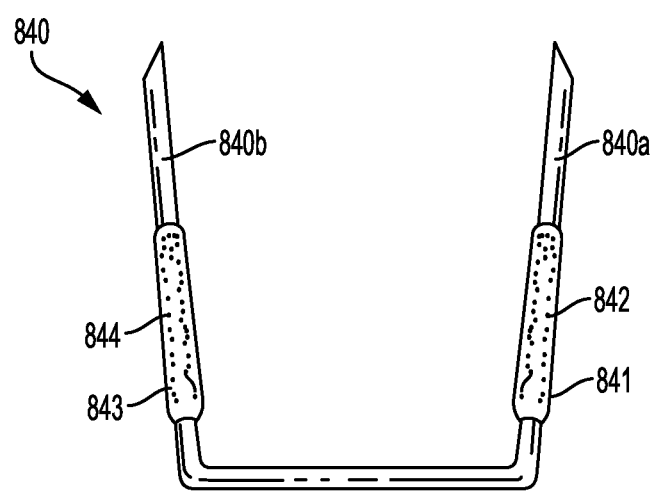
FIG. 117 is a perspective view of a staple with medicants.

FIG. 117 illustrates an exemplary implementation of a surgical staple 840 that can be used in conjunction with the described subject manner. As illustrated, the staple 840 has first and second medicants 842, 844 disposed on legs 840a, 840b thereof. The first and second medicants 842, 844 can be the same or different medicants. In the example illustrated, the first and second medicants 842, 844 can be disposed within respective adjuncts 841, 842 formed of at least one bioabsorbable polymer and disposed over the staple legs 840a, 840b. As the polymer disintegrates, the medicants can be released therefrom. The adjunct can be configured to be disrupted and thereby release its content when strain is applied thereto, as discussed above. However, it should be appreciated that the medicants 842, 844 can be associated with the staple legs in a number of different ways, including ways that differ among the legs. For example, the medicants 842, 844 can be coated over at least a portion of the staple legs in their pure form or as incorporated into at least one bioabsorbable polymer, at least partially impregnated into the portion(s) of the staple legs, or otherwise releasably associated with the staple legs 840a, 840b.

Figure 118:
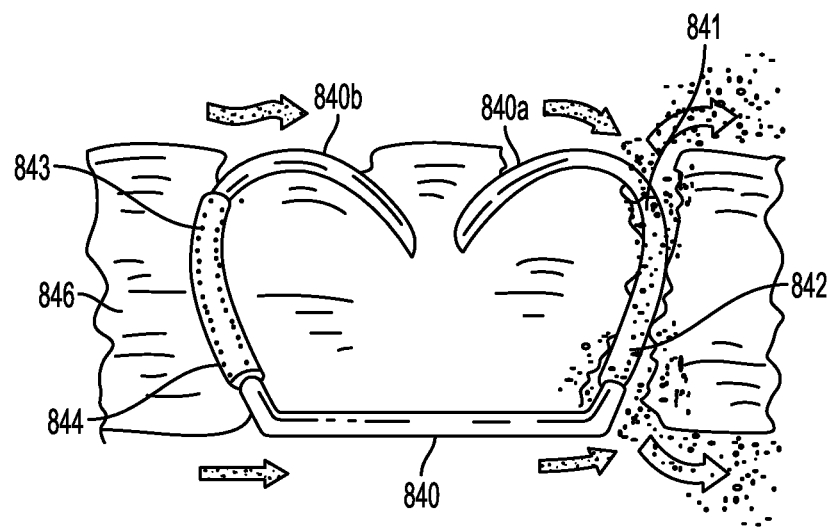
FIG. 118 is a cross-sectional view of tissue with the staple of FIG. 117 inserted therethrough.

When the staple 840 is delivered to a tissue 846 such that the legs 840a, 840b bend towards each other, as shown in FIG. 118, the first and second medicants 842, 844 can release from the adjuncts 841, 843 coated over the staple 840 and can be delivered to the tissue 846. In this exemplary implementation, as shown in FIG. 117, the first medicant 842 can be configured to be released from the adjunct 841 on the leg 840a before the second medicant 844 is released from the adjunct 843 on the leg 840b. As mentioned above, degradation of at least one bioabsorbable polymer forming the adjunct 841 can cause the first medicant 842 to escape the adjunct. Additionally or alternatively, as mentioned above, the first medicant 842 can be released from the adjunct 841 due to deformation of the leg 840a and resulting strain applied to the adjunct 841. The second medicant 844 can subsequently be released from the adjunct 843 in the same or other manners. In some implementations, the first and second medicants 842, 844 can be configured to release from the staple 840 substantially simultaneously.

Regardless of the specific way in which the first and second medicants 842, 844, which can be the same medicant(s), are associated with the staple 840 and are releasable therefrom, these medicants can release therefrom when the staple 840 is delivered to the tissue 846. Furthermore, although not shown in FIG. 118, in addition to carrying the medicants 842, 844, the staple 840 can be used to deliver an adjunct to the tissue 846 which can be disposed over a cartridge body. Such adjunct can releasably retain at least one third medicant therein. Release of one or both of the medicants 842, 844 can affect release of the at least one third medicant in accordance with the described techniques.

As discussed above, wounded tissue can heal over four wound healing stages of hemostasis, inflammation, proliferation, and remodeling. As also discussed above, in the inflammation stage, MMPs can be released to facilitate destruction of the ECM in the proliferation stage. As also discussed above, during the proliferation stage, an epithelialization process occurs in which parts of the ECM are destroyed to facilitate the migration of epithelial cells over the wound, and fibroblasts differentiate into myofibroblasts to form a protective outer layer over the wound. In the case of a patient's tissue being wounded by having staples applied thereto, the epithelialization process generally occurs at the tissue along the one or more lines of staples applied to the tissue. The more of the ECM that is destroyed and the longer the epithelialization process lasts, the more likely the patient will experience one or adverse effects of wound healing, e.g., infection, scarring, pain, etc. In other words, the more tissue that is torn down by destruction of the ECM, the more time it takes the parts of the ECM to be destroyed, and the more time it takes the fibroblasts to differentiate into myofibroblasts to form the protective outer layer, the greater the risk that the patient will develop and/or have prolonged one or more adverse effects of wound healing. It may therefore be advantageous to reduce an amount of the ECM that is destroyed and/or to a length of the epithelialization process. In other words, it may be advantageous to accelerate the start of the proliferation stage and to reduce its duration and, consequently, reduce an amount of time before the remodeling stage begins. The patient can thus be less likely to experience complications resulting from the wound.

Various exemplary MMP inhibiting adjuncts for surgical devices are described herein. In general, an implantable adjunct can be configured to be applied to tissue by a surgical stapler in conjunction with staples. The adjunct can have at least one medicant releasably retained therein that is configured to reduce a length of the epithelialization process. In other words, the at least one medicant releasably retained in the adjunct can be configured to speed up the inflammation stage and/or the proliferation stage and, accordingly, reduce an amount of time before the remodeling stage begins. The at least one medicant can be configured to be released along the staple line defined by the staples, which may help target the at least one medicant's desired functionality to where MMPs are released and where the epithelialization process generally occurs at the wounded tissue. The adjunct and the at least one medicant releasable therefrom may thus help prevent the tissue along the staple line from becoming too weak during the wound healing process.

In at least some exemplary implementations, the at least one medicant releasably retained in the adjunct and configured to reduce a length of the epithelialization process can include a tissue matrix degradation inhibitor. In general, the tissue matrix degradation inhibitor can be configured to inhibit MMP and, hence, be configured to allow less of the ECM to be destroyed. The MMP inhibitor can be introduced to the tissue via the adjunct and thereby limit the enzymatic destruction of the underlying collagen matrix, which as discussed above can be overly accelerated by an overactive inflammation response and by macrophages. The MMP inhibitor can thus delay the destruction and therefore delay strength loss at the wound along the staple line long enough for the new collagen being laid down to reinforce the staple line and thereby help prevent staple failure.

In at least some implementations, the tissue matrix degradation inhibitor can be configured to interrupt, accelerate, and truncate the destructive aspect of the healing response while having one or more other healing influencing aspects. For example, the tissue matrix degradation inhibitor can have a primary effect on tissue that influences healing by reducing destruction of the underlying matrix and a secondary effect on tissue aspect that interrupts the macrophage component of the healing cascade. One example of such a tissue matrix degradation inhibitor is doxycycline.

In at least some exemplary implementations, the at least one medicant releasably retained in the adjunct and configured to reduce a length of the epithelialization process can include an agent configured to induce proliferation of fibroblasts. One example of an agent configured to induce proliferation of fibroblasts is an FGF. The fibroblast proliferation can encourage contraction of the wound since during the epithelialization process, as discussed above, fibroblasts differentiate into myofibroblasts to form the protective outer layer. Delivering to wounded tissue the agent configured to induce proliferation of fibroblasts can thus allow the protective outer layer to be formed faster and, accordingly, allow the remodeling stage to begin sooner and allow the overall process of wound healing to end sooner. The potential for the patient to experience any adverse effects of wound healing can thus be reduced.

Additionally, excessive myofibroblast activity at a wound site is traditionally associated with hypertrophic scars, with virtually all fibrotic diseases, and with stroma reaction to tumors. Manipulating myofibroblast activity at the wound site, e.g., along the staple line at the wound site, may alter healing outcomes. One or more medicants including an agent configured to induce proliferation of fibroblasts and releasable from an adjunct applied along the staple line may stimulate fibroblast-to-myofibroblast differentiation in order to speed the onset of the proliferation phase. Contraction and ECM formation traditionally occur days into the wound healing process, as discussed above, which is the same timescale on which most staple failings traditionally occur. In other words, most staple failings traditionally occur at a time of contraction and ECM formation in the wound healing process. The one or more medicants including an agent configured to induce proliferation of fibroblasts delivered along a staple line may thus have an enhanced advantageous effect on wound healing along a staple line, as the one or more medicants can help prevent staple failings at a critical time for staple failure as well as help reduce scarring of wound tissue by limiting myofibroblast activity at the wound site. Similarly, the one or more medicants including a tissue matrix degradation inhibitor may have an enhanced advantageous effect on wound healing when delivered along a staple line since the reduced destruction along the staple line may help reduce staple failings around a time in the process of wound healing when staples are traditionally most susceptible to failure, as well as help reduce scarring of wound tissue by limiting myofibroblast activity at the wound site.

In at least some exemplary implementations, the at least one medicant releasably retained in the adjunct can include a tissue matrix degradation inhibitor and can include an agent configured to induce proliferation of fibroblasts.

As discussed above, the at least one medicant releasably retained in the adjunct can be configured to be released from the adjunct in any of a variety of spatial and temporal patterns. One example of the temporal pattern for release of the at least one medicant configured to reduce a length of the epithelialization process can include a predetermined time release that corresponds to a start of the macrophages phase of the inflammation stage. An example of such timing is shown in FIG. 40 with the release of medicant D beginning around a start of the macrophages phase 214, e.g., about one to four days after the wound occurs. Such timing can be achieved in a variety of ways, as discussed herein, such as by the timing of when a coating of the adjunct dissolves, when a polymer having the at least one medicant disposed therein degrades, or when wound fibers forming at least part of the adjunct begin to unwind. The medicant D can be the sole medicant released from an adjunct to reduce a length of the epithelialization process, and the medicant D can be released as part of a combined dose with the medicant $D_1$ configured to reduce a length of the epithelialization process to form a combined dose "$DD_1$." The medicant D can, as discussed above, be released from an adjunct along with any one or more of the other medicants A, B, $B_1$, C, $C_1$, E, F of FIG. 40 to provide various desired effects at various stages of the wound healing process.

Another example of the temporal pattern for release of the at least one medicant configured to reduce a length of the epithelialization process can include a predetermined time release that corresponds to a start of the proliferation stage. An example of such timing is shown in FIG. 40 with the release of the medicant F beginning around a start of the proliferation stage 212, e.g., about four to seven days after the wound occurs. Such timing can be achieved in a variety of ways, as discussed herein, such as by the timing of when a coating of the adjunct dissolves, when a polymer having the at least one medicant disposed therein degrades, or when wound fibers forming at least part of the adjunct begin to unwind. The medicant F can be the sole medicant released from the adjunct to reduce a length of the epithelialization process or can be released as part of a combined dose similar to the combined dose "$DD_1$." The medicant F can, as discussed above, be released from an adjunct along with any one or more of the other medicants A, B, $B_1$, C, $C_1$, D, $D_1$, E of FIG. 40 to provide various desired effects at various stages of the wound healing process.

One example of the spatial pattern for release of the at least one medicant configured to reduce a length of the epithelialization process can include the adjunct being configured to release the at least one medicant in a direction toward the staple line formed by the staples delivered to the tissue in conjunction with the adjunct. One example of an adjunct that can so spatially release the at least one medicant includes the adjunct 100 of FIG. 6. The first medicant 102 can include a medicant configured to facilitate hemostasis in the hemostasis stage, and the second medicant 104 can include the at least one medicant configured to reduce a length of the epithelialization process. The first medicant 102 can, as discussed herein, include a medicant other than one configured to facilitate hemostasis, such as an anti-inflammatory agent, a medicant configured to reduce a length of the epithelialization process, etc. The coating A can be absorbed so as to allow the first medicant 102 to be released from the porous region 101 at the first side 100a of the adjunct 100, and the coating B can be absorbed (e.g., at a time after the coating A at least in the case of the first medicant 102 including a hemostatic agent) so as to allow the second medicant 104 to be released from the porous region 103 at the second side 100b of the adjunct 100. The adjunct 100 can be arranged on a cartridge body or on a jaw of an end effector such that the second side 100b faces the staple line when the adjunct 100 is delivered to tissue. In this way, the second medicant 104 released at the second side 100b of the adjunct 100 can be targeted to the staple line.

Another example of an adjunct that can so spatially release the at least one medicant includes the adjunct 108 of FIG. 9. Similar to that discussed above regarding the second medicant 104 disposed in the adjunct 100, one or more of the vessels 110, 112, 114, 110, 112 can include therein the at least one medicant configured to reduce a length of the epithelialization process, with the coating associated therewith being on the side 108a, 108b of the adjunct 108 facing the staple line.

Another example of an adjunct that can so spatially release the at least one medicant includes the adjunct 122 of FIG. 15. Similar to that discussed above regarding the second medicant 104 disposed in the adjunct 100, the medicant 124 can be configured to reduce a length of the epithelialization process, with the outer film layer 126 being on the side of the adjunct 122 facing the staple line.

Another example of an adjunct that can so spatially release the at least one medicant includes the adjunct 116 of FIG. 12. The first medicant 119 can include the at least one medicant configured to reduce a length of the epithelialization process. The adjunct 116 can be arranged on a cartridge body or on a jaw of an end effector such that the first layer 118 including the first medicant 119 faces the staple line when the adjunct 116 is delivered to tissue. In this way, the first medicant 119 released from the first layer 118 can be targeted to the staple line. The second medicant 121 can, as discussed herein, include at least one medicant configured to reduce a length of the epithelialization process or any of a variety of other types of medicants.

Another example of an adjunct that can so spatially release the at least one medicant includes the adjunct 162 of FIG. 26. The medicant 164 can include at least one medicant configured to reduce a length of the epithelialization process. The adjunct 162 can be arranged on a cartridge body or on a jaw of an end effector such that the adjunct 162 "unwinds" in a direction toward the staple line such that the medicant 164 "trapped" within the adjunct 162 is directed to release toward and/or along the staple line. In the process of unwinding, the adjunct 162 may cross the staple line so as to first unwind toward the staple line and then away from the staple line after crossing the staple line as the adjunct 162 continues to unwind.

Another example of an adjunct that can so spatially release the at least one medicant includes the adjunct 176 of FIG. 32. The adjunct 176 can be arranged on a cartridge body or on a jaw of an end effector such that the one or more of the portions 178a, 178b, 180a, 180b that include the at least one medicant configured to reduce a length of the epithelialization process face the staple line. The portion(s) of the adjuncts 184, 185, 187 of FIG. 33, FIG. 35, and FIG. 36, respectively, can be similarly configured to face the staple line when their associated adjunct is delivered to tissue in conjunction with staple delivery.

Some aspects of the present disclosure relate to a bioabsorbable adjunct that includes at least one fiber formed from at least one bioabsorbable polymer. The bioabsorbable adjunct can have at least one medicant releasably disposed therein such that the at least one medicant is effective to provide a desired effect on tissue in-growth. The at least one medicant can include multiple medicants and release of an effective amount of one or more of the medicants can be controlled by a degradation rate of the at least one bioabsorbable polymer.

The adjunct can be formed from one or more fibers that can be interconnected to form a fibrous material or fiber lattice or mesh. Each of the fibers can be formed from at least one absorbable polymer. Furthermore, in some implementations, one or more of the fibers in the adjunct can be formed from two or more different absorbable polymers having different absorption rates. Different types of fibers can be associated with different medicants. In this way, different medicants can be released from the adjunct at different rates over time. In some aspects, fibers of one or more types can coat fibers of another type in various ways to form an adjunct. Alternatively, an adjunct can be made from one or more fibers each formed from a respective different absorbable polymer.

Different portions or regions of the adjunct material can be formed from different bioabsorbable polymers at least some of which can have different degradation rates. Such regions can include effective amounts of the same or different medicants as the bioabsorbable polymers degrade. The adjunct material can provide different amounts of different medicants having elution characteristics that depend on degradation rates of respective polymers retaining these medicants. Accordingly, a structure of the adjunct material and degradation rates of the bioabsorbable polymers forming the adjunct can control a manner in which one or more medicants releasably disposed therein are delivered to a treatment site.

The manner in which a medicant associated with an adjunct material is delivered from the adjunct material can be controlled in a number of ways. For example, a dose delivery profile of the medicant can depend on a volume of the adjunct material (e.g., when degradation of one or more portions of the adjunct material causes at least one medicant retained therein to release), a surface area of the adjunct material (e.g., when degradation of one or more areas on a surface of the adjunct material causes at least one medicant retained therein to release), a degradation rate of the adjunct material in a physiologic environment surrounding the adjunct material, conditions at the physiologic environment and the changes in the conditions, a concentration and other properties of the medicant, the manner in which the medicant is associated with the adjunct material (e.g., the manner in which the medicant is embedded in the polymer chain of the polymer adjunct material, microencapsulation, a number of layers of bioabsorbable polymer coatings carrying the medicant, etc.) and other factors.

Figure 119:
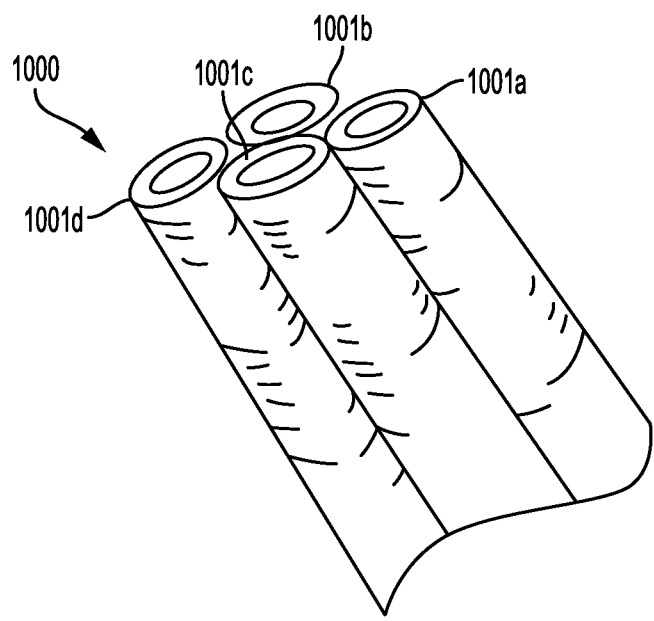

FIG. 119 illustrates an example of an adjunct 1000 including four different bundles or fibers 1001a, 1001b, 1001c, 1001d. In the example illustrated, each of the fibers 1001a, 1001b, 1001c, 1001d can be in the form of a cylindrical elongate member that are shown adjacent to each other by way of example only, as the fibers can be braided, woven, knitted, twisted or otherwise manipulated to form a desired adjunct 1000. Each of the fibers 1001a, 1001b, 1001c, 1001d can be formed from a respective different absorbable polymer having a respective different degradation rate, and each associated with at least one respective medicant. It should be appreciated, however, that each of the fibers 1001a, 1001b, 1001c, 1001d can be formed from more than one type of different absorbable polymers which can have different absorption or degradation rates. Furthermore, the fibers can form two or more concentric layers. In addition, it should be appreciated that the four fibers are shown in FIG. 119 by way of example only, as the adjunct material can include any suitable number (e.g., less than four or greater than four) of fibers as shown in FIG. 119 or other types of structures.

The fibers 1001a, 1001b, 1001c, 1001d can be associated with a respective medicant such that, when the polymers forming the fibers disintegrate, the medicants can be released at different rates. The rate of the release of the medicants can also be controlled by the way in which the fibers are wound together in the adjunct (not shown in FIG. 119). For example, the fibers can unwind in accordance with their degradation rate and a respective medicant can release from the fibers as the fibers degrade.

Figure 120:
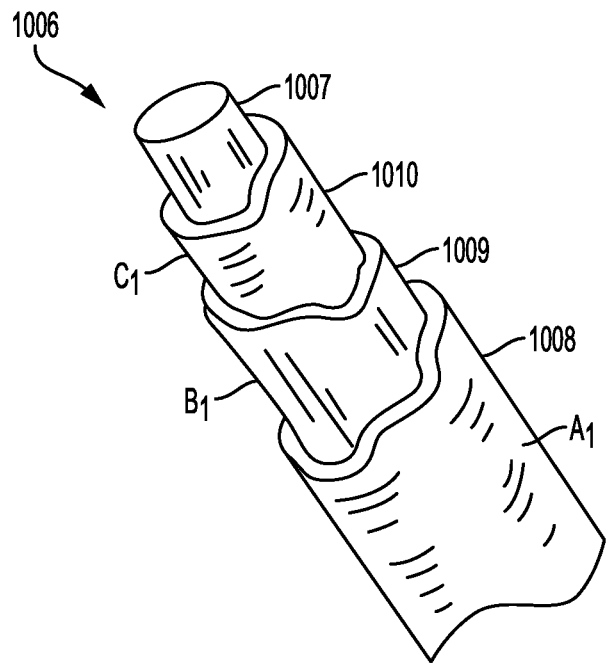

As mentioned above, in some aspects, an adjunct material can include multiple layers of absorbable polymers. FIG. 120 illustrates another example of an adjunct 1006 formed from multiple concentric layers. The adjunct 1006 includes a first outer layer 1008, a second intermediate layer 1009, and a third inner layer 1010. Each of the first, second, and third layers 1008, 1009, 1010 can be in the form of a tubular member concentrically wrapped around a respective inner layer. As shown in FIG. 120, the inner layer 1010 can be disposed over a central core component 1007. The central core 1007 having a cylindrical shape can be in the form of a fiber material or a staple. Each of the first, second, and third layers 1008, 1009, 1010 can have respective different first, second, and third medicants A1, B1, C1 releasably disposed therein.

The first, second, and third layers 1008, 1009, 1010 can be formed from respective different bioabsorbable polymers having different degradation rates. For example, the first outer layer 1008 can be formed from a first bioabsorbable polymer having a faster degradation rate than a second bioabsorbable polymer forming the second intermediate layer 1009. A degradation rate of the second bioabsorbable polymer, in turn, can be faster than a degradation rate of a third bioabsorbable polymer forming the third inner layer 1010. In this way, release of the first, second, and third medicants A1, B1, C1 can be controlled by the degradation rates of the first, second, and third bioabsorbable polymers forming the first, second, and third layers 1008, 1009, 1010, respectively. Thus, the first medicant A1 can be configured to be released from the first layer 1008 prior to the second medicant B1 being released from the second layer 1009, and the second medicant B1 can be configured to be released from the second layer 1009 prior to the third medicant C1 being released from the third layer 1010. It should be appreciated that one or more of the first, second, and third layers 1008, 1009, 1010 can be formed from more than one bioabsorbable polymer.

As mentioned above, the inner layer 1010 can be disposed over the inner component 1007, such as a fiber material or a staple leg. In aspects in which the inner component 1007 is in the form of a fiber material, such material can be formed from a bioabsorbable polymer having a degradation rate that is slower that the degradation rate of the third bioabsorbable polymer forming the third layer 1010. Similar to the first, second, and third layers 1008, 1009, 1010, the fiber material of the inner component 1007 can have a fourth medicant disposed therein that can be configured to be released from the inner component 1007 after the third medicant C1 has been released from the third layer 1010.

In some aspects, the inner component 1007 can be a staple. Thus, one or more staples of a staple cartridge, such as staple cartridge 40 of end effector 30 shown in FIG. 1 and FIG. 2, can be coated with one or more layers of bioabsorbable polymer(s), such as the first, second, and third layers 1008, 1009, 1010 shown in FIG. 120. The layers can include an innermost layer (not shown) adjacent to the staple and including antimicrobial or other medicants to prevent biofilm formation of bacterial micro growth. Alternatively, the innermost layer can be formed from a biocompatible material.

An adjunct in accordance with the described subject matter can include multiple fibers that can be wound in a number of different ways, so as to form various patters. The adjunct can have fiber forming various patterns and having medicants incorporated therein in a manner that encourages tissue in-growth in a desired manner Differently positioned fibers of the adjunct can be configured to release medicants at various times and at various rates. Examples of fiber-based adjuncts that promote tissue growth in various ways are described in U.S. patent application Ser. No. 14/840,255 entitled "Adjunct Material To Promote Tissue Growth" filed on Aug. 31, 2015, which is hereby incorporated by reference in its entirety.

Figure 121:
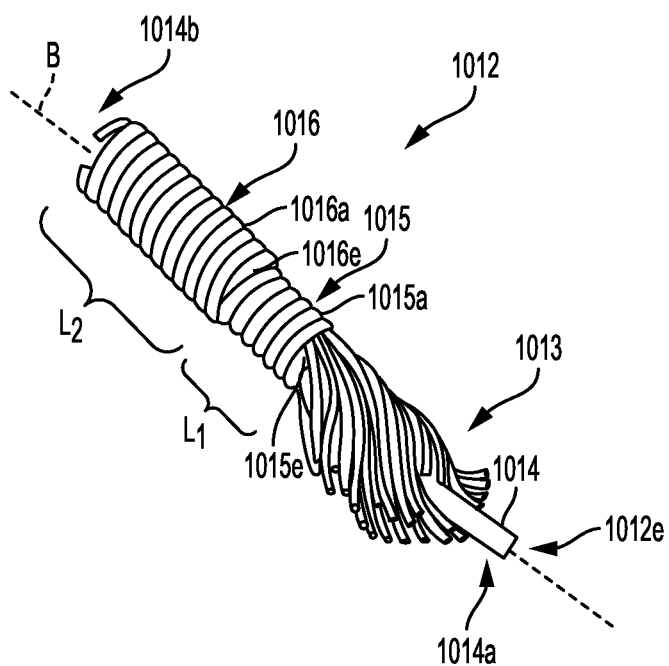

FIG. 121 illustrates an example of a fiber 1012 in the form of multiple other fibers wound or woven together. As shown, the fiber 1012 includes a plurality of first type of fibers 1013 disposed over a thicker inner or core fiber 1014 having first and second ends 1014a, 1014b. As also shown, the first type of fibers 1013 can be in the form of multiple fibers disposed near the end 1012e of the fiber 1012. The fiber 1012 also includes a second type of fiber or second fiber 1015 and a third type of fiber or third fiber 1016, with both second and third fibers 1015, 1016 being disposed at least partially over the first type of fibers 1013. The second and third fibers 1015, 1016 are wound around the first fibers 1013 so as to hold the first fibers 1013 around the core fiber 1014.

In the example illustrated, the first type of fibers 1013 can be disposed over the core fiber 1014 such that the fibers 1013 extend substantially along the length of the core fiber 1014, as shown in FIG. 121. The fibers 1013 can be in the form of multiple separate fibers surrounding the thicker core fiber 1014 that can be a reinforcement feature of the fiber 1012. It should be appreciated that the fibers 1013 can extend parallel or substantially parallel to a longitudinal axis B of the core fiber 1014, or they can be disposed at an angle with respect to the longitudinal axis B. Furthermore, different fibers of the first type of fibers 1013 can be disposed at various angles with respect to the longitudinal axis B such that the fibers 1013 are in the form of "disorganized" strands held around the core fiber 1014 by the second and third fibers 1015, 1016. The fiber 1012 can be manufactured with the first type of fibers 1013 being at least partially frayed beginning from an end 1012e of the adjunct. However, it should be appreciated that, before an adjunct including the fiber 1012 is delivered to a treatment site, the first fibers 1013 can be disposed closer to the core fiber 1014 such that they are less frayed than shown in FIG. 121 or, in some cases, substantially not frayed.

As shown in FIG. 121, the second type of fiber 1015 can be in the form of a single fiber or strand wound around the first type of fibers 1013 such that the multiple windings of the fiber 1015 extend from a point a distance away from the second end 1014b of the core fiber 1014 towards the first end 1014a of the core fiber 1014. It should be appreciated that a portion of the fiber 1012 is shown in FIG. 121 such that the second end 1014b of the core fiber 1014 can be located farther away from the first end 1014a than shown in FIG. 121. In this example, the windings of the second type of fiber 1015, collectively denoted as windings 1015a, extend along the first type of fibers 1013 for a certain first length L1 and terminate, before the first end 1014a, with an end winding 1015e. The third type of fiber 1016 can also be in the form of a single fiber or strand wound around the first type of fibers 1013 such that the multiple windings of the fiber 1016 extend from the second end 1014b of the core fiber 1014 towards the first end 1014a thereof. In this example, as shown in FIG. 121, the windings of the third type of fiber 1016, collectively denoted as windings 1016a, begin closer to the second end 1014b of the core fiber 1014, extend along the first type of fibers 1013 for a certain second length L2, and terminate with an end winding 1016e before the first winding of the windings 1015. The windings 1015a, 1016a can be formed around the first fibers 1013 such that they do not overlap. However, in some cases, one or more windings 1016a of the third type of fiber 1016 (e.g., the end winding 1016e or more than one winding) can be formed over one or more windings 1015a of the second type of fiber 1015 (e.g., the end winding 1015e or more than one winding).

As also shown in FIG. 121, the windings 1015a, 1016a of the first and second fibers 1015, 1016 can be formed around the first type of fibers 1013 such that the windings 1015a, 1016a are wound in an approximately transverse direction with respect to the longitudinal axis B of the core fiber 1014. However, a person skilled in the art will appreciate that the windings 1015a, 1016a can be formed under an angle with respect to the longitudinal axis B, including at different angles. Furthermore, in the example illustrated in FIG. 121, the windings 1015a, 1016a are formed such that adjacent windings do not overlap. However, in some aspects, depending on a particular application, one or more windings of a certain type of fibers can be formed such that they cross or otherwise overlap. In addition, it should be appreciated that one or more than two different types of fibers can be wound around the first type of fibers 1013 in various ways. For example, although the windings 1015a are shown to terminate a certain distance away from the first end 1014a of the core fiber 1014, one or more fibers can be wound around the first type of fibers 1013 substantially along the entire length of the first type of fibers 1013.

As shown in FIG. 121, the fibers forming the fiber 1012 can have a generally tubular shape and they can be various diameters. For example, the second type of fiber 1015 can be thicker than the third type of fiber 1016. The first type of fibers 1013 can be thinner (i.e., it has a smaller diameter) than the third type of fiber 1016 or the fibers 1013 can have approximately the same thickness as the third type of fiber 1016. For example, the core fiber 1014 can have a size of #11-0 (in suture size parlance) and each subsequent layer of fibers can have a size one to two sizes larger than the core fiber 1014. A maximum size of the fibers can be #4-0.

In the example illustrated in FIG. 121, the first, second, and third 1013, 1015, 1016 types of fibers can be formed from respective different first, second, and third bioabsorbable polymers having different degradation rates and including respective different medicants. For example, the first fibers 1013 can be formed from one or more polymers having a degradation rate that is faster than a degradation rate of polymer(s) forming the second fiber 1015, and the polymer(s) forming the second fiber 1015 can have the degradation rate that is faster than a degradation rate of polymer(s) forming the third fiber 1016. The fibers can be configured to unwind in accordance with their degradation rates, their position within the adjunct, and the weave pattern formed by the fibers. As each type of fiber unwinds and degrades, the medicant disposed in that fiber(s) can be released therefrom. Fibers that have a smaller diameter can unwind easier than thicker fibers. Also, fibers that form less organized structures can unwind prior to fibers forming more organized structures, such as, for example, more tightly or more regularly woven structures. Fibers that form less organized structures can provide more bonding points for tissue in-growth such that the tissue can grow into the adjunct or tissue can adhere to the adjunct.

As shown in FIG. 121, the first fibers 1013 that are thinner and more accessible to a surrounding environment that the second and third fibers 1015, 1016 can unwind first so as to cause a first medicant disposed therein to release. In the example illustrated, because the thinner first fibers 1013 are less constrained and more frayed near the end 1012e of the fiber 1012, the first fibers 1013 can begin to unwind and become more frayed at their ends, from the end 1012e of the fiber 1012 towards an opposite end thereof. The first type of fibers 1013 can be at least partially frayed before the delivery of the fiber 1012 to a treatment site to create more surface area for fibroblasts and other cells to begin growing into the adjunct.

In a certain time period after the first fibers 1013 commence to unwind and release the first medicant, the second fiber 1015, which is thicker than the first fibers 1013, can commence to unwind so as to cause a second medicant disposed therein to release (not shown). The second fiber 1015 can unwind in accordance with the degradation rate of the polymer forming it and due to the undelaying first fibers 1013 becoming looser and less constrained. These processes can occur at least partially simultaneously—e.g., as the second fiber 1015 begins to unwind and its hold onto the first fibers 1013 decreases, the first fibers 1013 become looser and release the first medicant. In this way, the first fibers 1013, particularly their frayed portion which can be disposed at an outer edge or outer surface of the adjunct, can promote tissue in-growth into this area of the adjunct.

In a certain time period after the second fiber 1015 commences to unwind and begins to release the second medicant, the third fiber 1016, which is thicker than the second fiber 1015, can commence to unwind so as to cause a third medicant disposed therein to release (not shown). The fiber 1012 can be configured such that the first, second, and third medicants release at different times or such that release of two or more of these medicants overlaps at least in part. As discussed above, the unwinding of the first, second, and third fibers 1013, 1015, 1016 and release of the respective medicants can be controlled in various ways, so as to ultimately provide desired tissue in-growth effect.

In addition, it should be appreciated that one or more than two different types of fibers can be wound around the first type of fibers 1013 in various ways. For example, although the windings 1015a are shown to terminate a certain distance away from the second end 1014b of the core fiber 1014, one or more fibers can be wound around the first type of fibers 1013 substantially along the entire length of the first type of fibers 1013. In this way, as the fibers unwind, they release a medicant disposed therein.

Figure 122:
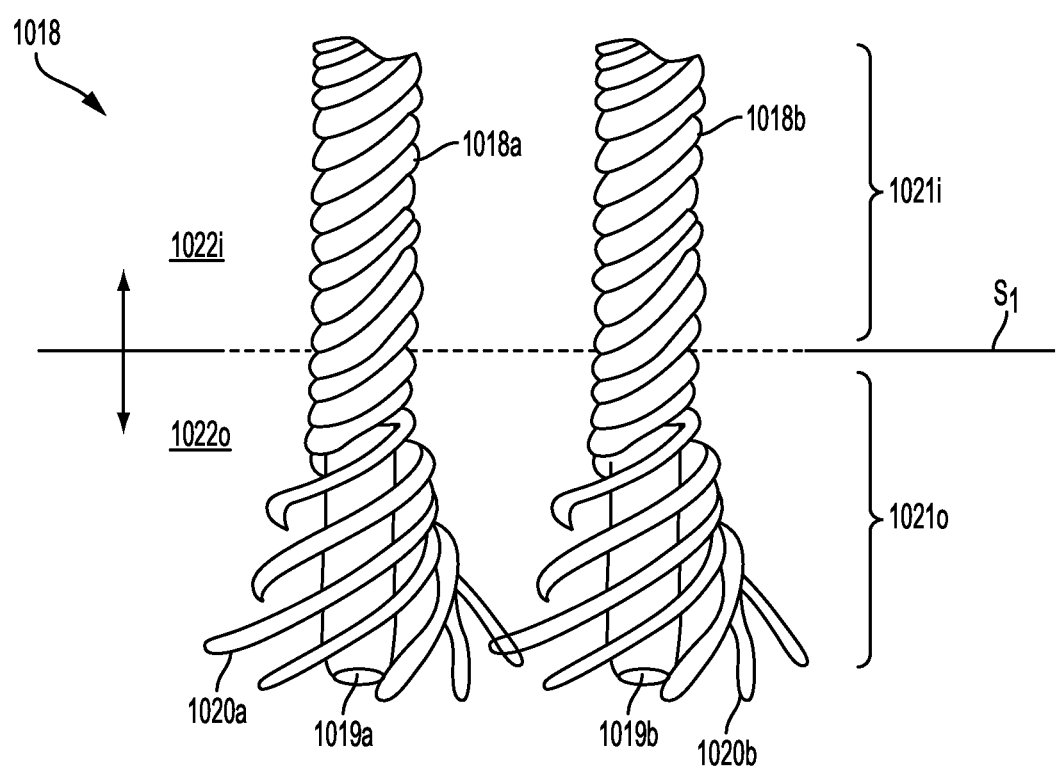

FIG. 122 illustrates an example of an adjunct 1018 that can be formed of multiple fibers, each formed from one or more fibers and associated with respective one or two medicants configured to be released therefrom. The fibers forming the adjunct 1018, two of which being shown in FIG. 122 as fibers 1018a and 1018b can be configured to unwind in accordance with the degradation rate, with the unwinding allowing release of the at least one medicant from the fibers 1018a and 1018b.

The fibers 1018a and 1018b can have a different configuration depending on their position within the adjunct, to facilitate desired pattern of tissue in-growth. Thus, in the example illustrated, portions of the fibers disposed closer to the outer edge of the adjunct can be more loose or frayed as compared to portions of the fibers disposed closer to a center or inner area thereof. Such structure of the adjunct fibers can promote tissue in-growth that will begin from the edges of the adjunct and progress toward the center thereof, to heal a wound in a desired manner. An example of wound healing states and medicants administered to promote those stages is described in FIG. 40.

The fibers 1018a and 1018b can be formed from different bioabsorbable polymers having different degradation rates. Furthermore, each of the multiple fibers forming the fibers 1018a and 1018b can be formed from different bioabsorbable polymers having different degradation rates. It should be appreciated that two fibers 1018a and 1018b disposed substantially parallel to one another are shown in FIG. 122 by way of example only, as the adjunct 1018 can include any suitable number of fibers which can be interconnected or interwoven in various ways. For example, the adjunct 1018 can be in the form of a sheet-like fiber woven mesh or in any other form. The adjunct 1018 can be configured to unwind or fray along a perimeter thereof such that the entire perimeter or a portion thereof can be unwindable or frayable. However, it should be appreciated that the adjunct 1018 can have a different structure such that only certain portions thereof can unwind or fray from edges or outer surface thereof.

In the example of FIG. 122, the fibers 1018a and 1018b can have thicker central core or inner fibers 1019a, 1019b and thinner outer fibers 1020a, 1020b wound around the respective inner fibers 1019a, 1019b. Portions of the fibers 1018a, 1018b disposed closer to the inside of the adjunct 1018 are tightly wound together such that the inner fibers 1019a, 1019b are completely covered by the wound outer fibers 1020a, 1020b prior to unwinding, as shown in a portion of the fibers 1018a, 1018b inside an edge S1 that can be taken as dividing the adjunct 1018 into an inner region 1021i and an outer region 1021o. At the same time, portions of the fibers 1018a, 1018b disposed closer to the outer edge of the adjunct 1018 are shown as frayed or unwound about the inner fibers 1019a, 1019b. The degree of tightness of the windings formed by the outer fibers 1020a, 1020b wound abound the inner fibers 1019a, 1019b increases towards the inner region 1021i and therefore towards center of the adjunct 1018, in a direction shown by an arrow 1022i in FIG. 122. On the other hand, the degree of tightness of the windings of the outer fiber decreases towards the outer edge of the adjunct 1018, in a direction shown in FIG. 122 by an arrow 1022o. The tightness of the winding along a length of a fiber can vary in the same degree for all of the fibers forming the adjunct. Alternatively, different fibers can have different winding patterns such that, for example, one type of fibers can be more frayed towards the edge of the adjunct, whereas another type of fibers can also be frayed towards the edge of the adjunct but to a lesser degree. In this way, different tissue in-growth patterns can be created for different areas of a wound.

When the adjunct 1018 is delivered to a treatment site, the outer fibers 1020a, 1020b wound around respective inner fibers 1019a, 1019b can begin to unwind or fray at the outer edge of the adjunct 1018 at the outer region 1021o prior to unwinding of the portions of the outer fibers 1020a, 1020b in the inner region 1021i, closer to the center of the adjunct. The unwinding or fraying can be caused by multiple factors, such as by the adjunct coming into contact with body fluid. As each of the outer fibers unwinds in accordance with its degradation rate, it can be release one or more respective medicants associated therewith. The inner fibers, which become more accessible to an environment external to the adjunct as the outer fiber unwinds, can also release one or more respective medicants associated therewith, if the inner fibers carry such medicant(s). The same or different medicants can be associated with a fiber forming the adjunct. For example, in some aspects, portions of the fibers located closer to the edges or external surface of the adjunct can have different medicant(s) associated therewith than portions of the fibers located closer to the center of the adjunct.

Figure 123:
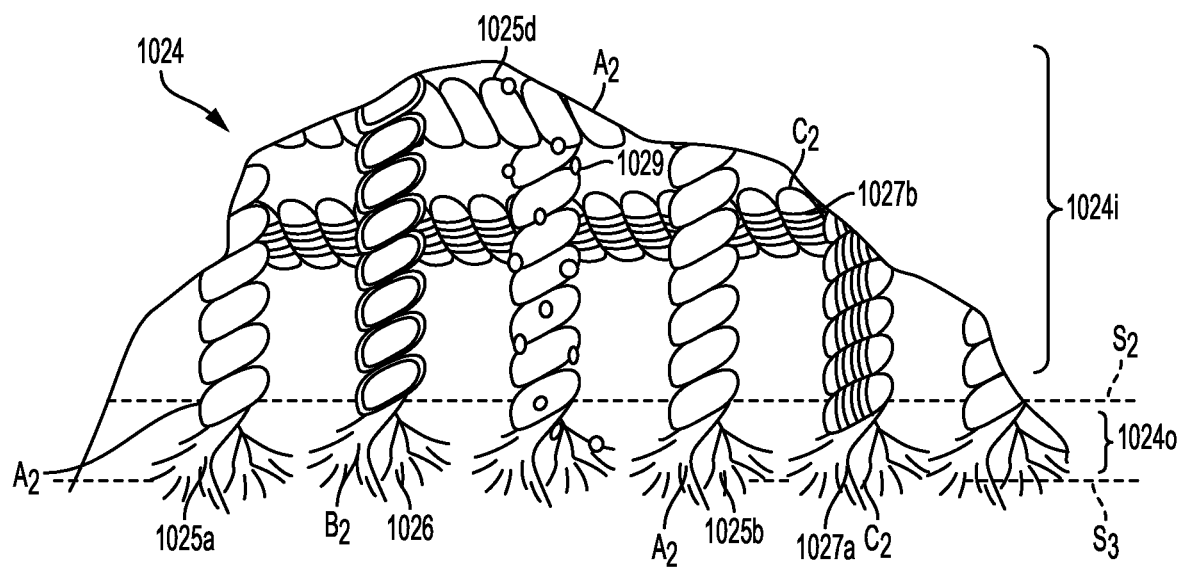

An adjunct in accordance with the described subject matter can include multiple strands or fibers of absorbable polymer, each of the strands having different absorption properties. FIG. 123 illustrates an example of a portion of an adjunct 1024 formed from multiple fibers of at least three different types that are interconnected or interwoven together in various ways to form regular and/or irregular patterns. The adjunct 1024 can be in the form of a sheet-like fiber woven mesh or in any other form.

As shown in FIG. 123, the adjunct 1024 can include different types of fibers, such as first type of fibers or first fibers 1025 (four of which are shown as fibers 1025a, 1025b, 1025c, and 1025d), second type of fibers or second fibers 1026 (one of which is shown in FIG. 123), and third type of fibers or third fibers 1027 (two of which are shown as fibers 1027a, 1027b). The different types of fibers can be formed from different bioabsorbable polymers having different degradation rates. Furthermore, the fibers of different types can differ from one another in other ways. For example, the fibers can have different thicknesses and different ways in which medicant(s) are associated therewith and are configured to be released therefrom. Thus, as shown in FIG. 123, the second fibers 1026 can be thicker than the first and third fibers 1025, 1027. Also, one or more of the multiple fibers forming the adjunct 1024 can be composed from two or more thinner constituent fibers that can be wound or woven in various ways. For example, as shown in FIG. 123, each of the first, second, and third fibers 1025, 1026, 1027 are composed of two underlying fibers wound together in the same direction into a spiral. It should be appreciated, however, that the thinner fibers forming each of the thicker fibers can be wound in other various ways. Moreover, in some implementations, the thinner fibers can, in turn, be composed or yet even thinner fibers which can have different properties.

The multiple fibers forming the adjunct 1024 can be interconnected in various ways. For example, as shown in FIG. 123, the first, second, and third fibers 1025, 1026, 1027 are interconnected in an alternating manner. Similar to adjunct 1018 (FIG. 122), the adjunct 1024 can be structured such that its inner portions that are closer to a center or middle of the adjunct can be composed of more organized and more interconnected patterns of fibers than portions of the adjunct 1024 that are closer to an outer edge or outer surface thereof. Thus, as shown in FIG. 123, a portion 1024i of the adjunct 1024 disposed above a line S2 in FIG. 123 can encompass more tightly interconnection fibers. However, a portion 1024o of the adjunct 1024 disposed between the lines S2 and S3 (which denote inner and outer boundaries of the outer edge or outer surface of the adjunct 1024, respectively) includes more disorganized fibers—in this example, frayed ends of the first, second, and third fibers 1025, 1026, 1027. In this way, tissue in-growth can begin form these ends of the fibers 1025, 1026, 1027 and can continue to progress towards the inner portions of the adjunct.

Each of the first, second, and third fibers 1025, 1026, 1027 can be releasably associated with one or more different or the same medicants that can be configured to be released from the fibers in different patterns. For example, the first fibers 1025a, 1025b, 1025c, and 1025d can be associated with a first medicant A2, the second fiber 1026 can be associated with a second medicant B2, and the third fibers 1027a, 1027b can be associated with a third medicant C2. The first, second, and third medicants A2, B2, and C2 can be coated over the fibers, encapsulated by the fibers, incorporated into the fibers, adhered to the fibers, or otherwise associated with the fibers. One or more of the medicants can be carried within vessels encapsulating the medicant(s). The patterns of associating at least one medicant with the fibers can be homogenous along a length of the fibers and throughout the volume of the adjunct. However, the medicant(s) can additionally or alternatively be associated with the fibers in non-homogenous ways, either or both along the length of the fibers and throughout the volume of the adjunct.

In the example of FIG. 123, the second fiber 1026b can have multiple vessels 1029 in the form of beads of the same or different sizes and shapes retaining the medicant B2 therein. The vessels 1029 can be applied to the second fiber 1026b as a powder or they can be bonded, anchored to, or otherwise associated with the fiber strands. The vessels 1029 can be configured to be released from the second fiber 1026b as the second fiber 1026b absorbs. The vessels 1029 can additionally or alternatively releasably retain the second medicant B2 due to a certain changeable conformation of the second fiber 1026b that allows the second medicant B2 to be released as the conformation of the second fiber 1026b changes. For example, the second fiber 1026b can release the vessels 1029 which, in turn, causes the second medicant B2 encapsulated within the vessels 1029 to release, as the fibers, forming the second fiber 1026b by being wound into the spiral, unwind and the second fiber 1026b is being absorbed. In some aspects, the second fiber 1026b can releasably retain the vessels 1029 similar to adjunct 162 shown in FIG. 26 and FIG. 27.

Regardless of the specific way in which the first, second, and third medicants A2, B2, and C2 are associated with the respective fibers of the adjunct 1024, the medicants can be released from the fibers in a desired manner, depending on a degradation rate of the fibers. For example, in some aspects, the first fibers 1025 can have a fast degradation rate such that they release the first medicant A2 substantially immediately upon delivery of the adjunct 1024 to a treatment site. In this way, acute treatment by the first medicant2 A is delivered in a bolus dose. The second fibers 1026 can also have a fast degradation rate that is, however, slower than the degradation rate of the first fibers 1025. The third fibers 1027 can have a slow degradation rate. In this way, the second fibers 1026 can absorb quickly after the first fibers 1025 have been at least partially absorbed, thus releasing a short term high dosage level of the second medicant B2 over a relatively short time period. The third fibers 1027 can commence to absorb after the second fibers 1026 have been at least partially absorbed such that a low constant dose of the third medicant C2 is released as the third fibers 1027 are absorbing slowly over time. In some aspects, the second and third medicants B2, C2 can be the same (and the same or different than the first medicant A2) and they can reinforce one another's dose in a short term with a low gradual dose also continuing for a longer term to thereby continue providing the treatment effect. Alternatively, the second and third medicants B2, C2 can be different medicants.

In some aspects of the described techniques, an adjunct can include fibers that are associated with at least one medicant that is thinly coated over the fibers, applied as a powder (by "dusting") on the fibers, or in otherwise associated with a surface of the fibers. In this way, the medicant(s) can be configured to release from the fibers to provide a bolus-like effect. Furthermore, the adjunct can be configured such that some of the fibers can release a bolus dose of medicants whereas other fibers can release medicants over longer time periods.

Figure 124:
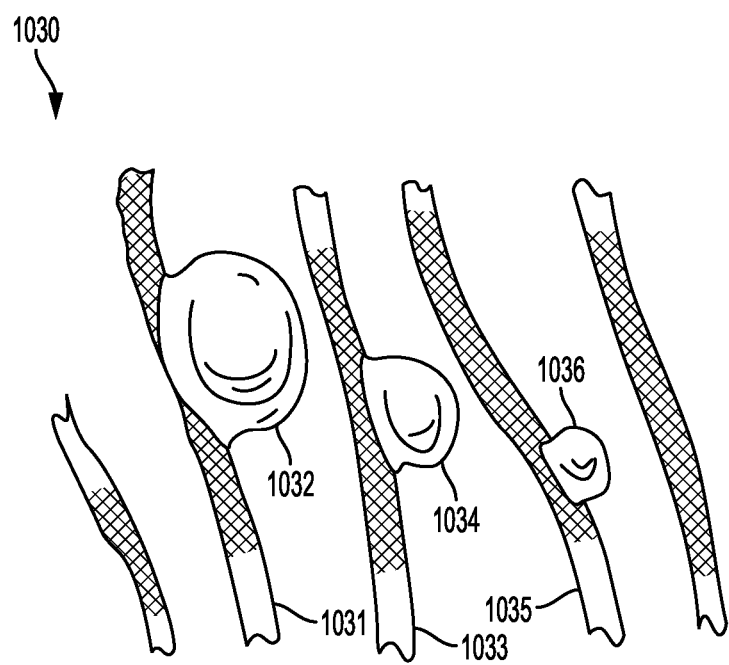
Figure 125:
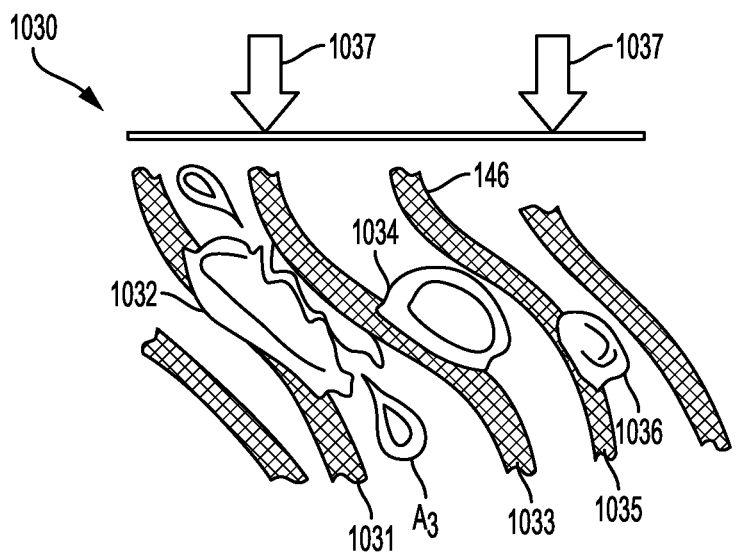

FIG. 124 and FIG. 125 illustrate an adjunct 1030 in the form of multiple fibers, three of which are denoted by way of example as fibers 1031, 1033, 1035. The fibers 1031, 1033, 1035 can have approximately the same thickness of they have different thicknesses. As shown, each of the fibers 1031, 1033, 1035 is associated with a respective one of vessels 1032, 1034, 1036 retaining a medicant. The vessels 1032, 1034, 1036 can retain the same or different medicants. In the illustrated example, the vessels 1032, 1034, 1036 are in the form of irregularly shaped rounded beads having different sizes that can be positioned at any desired location along the fibers 1031, 1033, 1035. For example, the vessel 1032 has the largest size, the vessel 1034 is smaller than the vessel 1032 but larger than the vessel 1036 that is, in turn, the smallest among the three vessels illustrated. However, the vessels can have others various shapes and sizes. The vessels 1032, 1034, 1036 can be formed from bioabsorbable polymers having different absorption rates. Each of the 1032, 1034, 1036 can be formed from one or multiple layers of the same or different polymers.

The multiple vessels can be applied to the fibers as a powder or they can be bonded, anchored to, or otherwise associated with the fiber strands. As the vessels are degraded in accordance with their absorption rates and based on other factors, the medicants incorporated therein can be released to deliver a desired treatment effect. For example, as shown in FIG. 125, the vessel 1032 associated with the fiber 1031 can degrade to deliver an effective dose medicant A3 incorporated therein. In the example illustrated, a large amount of the medicant A3 can be released from the vessel 1032 as a bolus dose. The vessel 1032 can degrade based on its absorption rate and under strain applied to the adjunct 1030 and schematically shown by arrows 1037. However, it should be appreciated that, in some aspects, the vessel 1032 can release the medicant incorporated therein as the vessel 1032 undergoes degradation, without additional influence of strain.

Although not shown in FIG. 125, the vessels 1034, 1036 can have slower absorption rates than the absorption rate of the vessel 1032, and they can release respective medicants incorporated therein at different times as a time release dosage, after the medicant incorporated into the vessel 1032 has been completely or partially released. Furthermore, the medicants incorporated into the vessels 1034, 1036 can be released over longer time periods and the amounts of the medicants can depend on a size of the vessel carrying that medicant. In addition, in some aspects, release of the medicants incorporated into the vessels 1032, 1034, 1036 can be controlled by absorption rates of the fibers 1031, 1033, 1035 that can degrade and release the vessels, which, in turn, causes the vessels to release the medicants releasably retained therein. A position of the vessel along respective fibers and within the adjunct 1030 can also affect the release of a medicant retained within the vessel.

In some aspects, an adjunct can be formed from two or more bioabsorbable polymers having different degradation rates. The polymers can be different polymers or different versions of the same bioabsorbable polymer. For example, an adjunct can include both lower and higher molecular weight versions of the same bioabsorbable polymer. Thus, the adjunct can have regions (e.g., in the form of fibers or fiber lattices) formed from lower and higher molecular weight versions of an absorbable polymer and therefore having different absorption characteristics. The regions formed from a low molecular weight version of the polymer can disintegrate faster thereby releasing medicant(s) retained therein faster, whereas the regions formed from a higher molecular weight version of the polymer can disintegrate more slowly to thus release respective medicant(s) associated therewith more slowly. The high and low molecular weight copolymers can be a blend within a fiber strand material. Alternatively, the high and low molecular weight copolymers can be different fibers disposed along a length of an adjunct in a manner so as to control degradation.

Because of the heterogeneous degradation of absorbable polymers forming the adjunct having regions with different degradation rates, such as lower and higher molecular weight versions of the same bioabsorbable polymer, one or more medicants associated with the adjunct can release in various spatial and temporal patterns. The one or more medicants can be incorporated into vessels having a dissolvable coating (e.g., like a gobstopper) such that, as the vessel is released from the adjunct and the coating is disintegrated, the medicant can be distributed as a bolus dose or as a time release dosage. Non-limiting examples of adjunct formed from layers of high and low molecular weight absorbable polymers having different degradation rates include adjunct 116 shown in FIG. 12.

Figure 126:
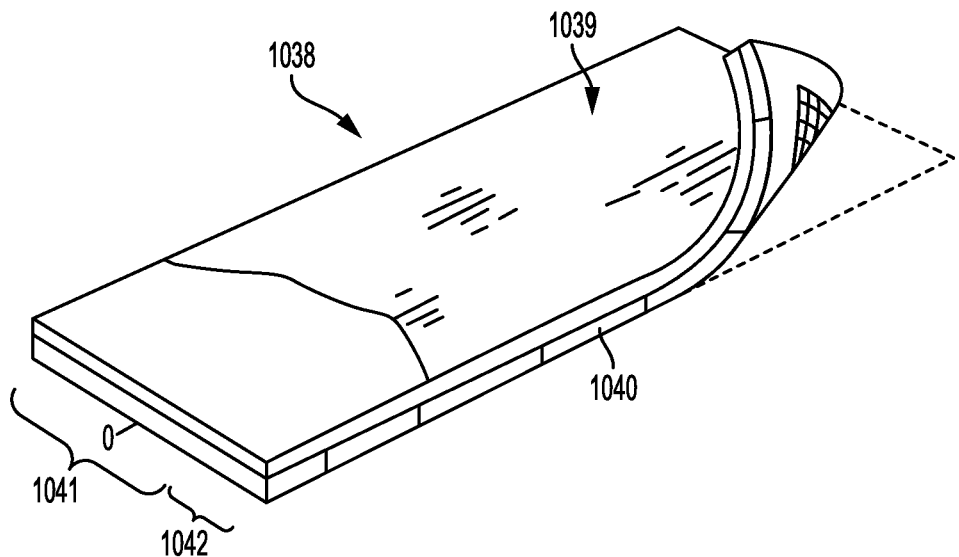

In some aspects, an adjunct can have multiple regions formed from more than one phase of the same bioabsorbable polymer. The regions can be discrete, continuous, or combinations of discrete and continuous regions. FIG. 126 illustrates an example of an adjunct 1038 formed of fibers in the form of layers that are formed from a plurality of bioabsorbable polymers. The layers can have distinct layers stacked in various ways. The layers can be formed from different polymers or from more than one phase of the same bioabsorbable polymer, such that the adjunct 1038 is configured to release one or more medicants incorporated therein in a heterogeneous manner to provide a desired effect on tissue in-growth in a predetermined manner. In this example, the adjunct 1038 can be a sheet-like fiber woven lattice or mesh, and it can have a generally rectangular shape. However, a person skilled in the art will appreciate that the adjunct 1038 can have any other shape, including an irregular shape. Similarly, a thickness of the adjunct and of its constituent portions or layers, as well as a number and patterns of the layers can vary in a number of different ways.

As shown in FIG. 126, the adjunct 1038 can include top and bottom portions or layers 1039, 1040 that can be formed from different phases of the same bioabsorbable polymer. For example, the adjunct 1038 can include an amorphous phase of the polymer configured to degrade faster and a crystalline phase of the polymer that can degrade slower than the amorphous phase. Different portions of the adjunct 1038 can be formed from different variations of the amorphous and crystalline phases of the polymer. The different phases can be combined into the adjunct 1038 in a suitable manner.

Degradation rates of the adjunct 1038 can vary in different patterns among the top and bottom layers 1039, 1040 and across each of the top and bottom layers 1039, 1040. For example, the absorption characteristics of the adjunct 1038 can vary from left (L) to the right (R) ends thereof (as measured, in this example, along a shorter side of the adjunct) such that different portions of the adjunct 1038 are configured to degrade over time at different degradation rates to release at least one medicant at different rates. In this way, left and right portions 1041, 1042 of the adjunct 1038 can be configured to release medicants incorporated therein in different manners.

Figure 127:
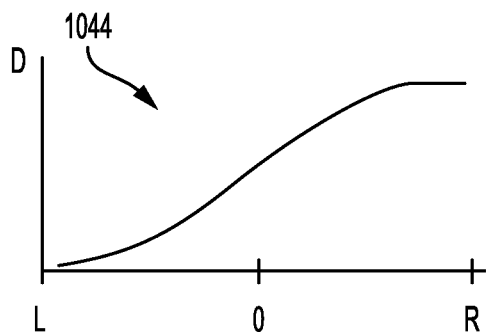
Figure 128:
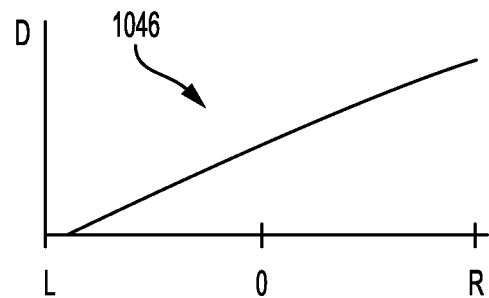
Figure 129:
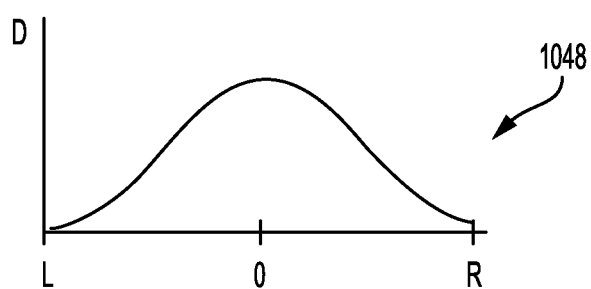

FIG. 127, FIG. 128 and FIG. 129 illustrate examples of graphs 1044, 1046, 1048 showing elution profiles of the adjunct 1038 demonstrating how the medicant(s) incorporated into the adjunct 1038 can be released in different doses (D) measured across the left L to the right R ends of the adjunct 1038, as controlled by different absorption rates of different phases of the same polymer that form the adjunct. As shown, a dosage of the medicant(s) can vary in different manners from the left L to the right R ends of the adjunct 1038 relative to a mid-portion (O) of the adjunct 1038 extending along a longer side thereof (also shown in FIG. 126). Thus, the graph 1044 in FIG. 127 illustrates that the medicant(s) can release at lower dosages at the left portion 1041 of the adjunct and at higher dosages at the right portion 1042 such that the dosage of the medicant(s) being released increases from the left L end towards the right R end of the adjunct, to ultimately reach a plateau at the right-most end R of the adjunct.

The graph 1046 in FIG. 128 illustrates that a dosage the medicant(s) released from the adjunct 1038 can gradually increase from the left L to the right R ends thereof such that the graph 1046 can follow a linear function.

The graph 1048 in FIG. 129 illustrates that a dosage of the medicant(s) released from the adjunct 1038 can gradually increase from the left L end to the mid-portion O thereof and it can then gradually decrease from the mid-portion O to the right R end of the adjunct. Thus, in FIG. 129, the release of the medicant can be substantially symmetrical with respect to the mid-portion O of the adjunct 1038 and the graph 1048 resembles a Gaussian bell curve. A person skilled in the art will appreciate that the graphs 1044, 1046, 1048 in FIG. 127, FIG. 128 and FIG. 129 are shown by way of example only, as the adjunct 1038 can be configured such that one or more medicants can be released therefrom in various patterns to provide a desired effect on tissue in-growth at a site of delivery of the adjunct.

In some aspects, an adjunct can be formed from multiple layers or other structures of the same polymer type, each of the layers having different absorption rates and therefore providing different medicant delivery profiles. Different delivery profiles can be created by having the same polymer(s) that underwent differing handling processes or treatments, or similar treatments using different process parameters. For example, the adjunct can be a woven construct or another structure made of fibers of the same type but with different pretreatments. Non-limiting examples of pretreatments that would alter a degradation rate of a polymer include irradiation (e.g., gamma sterilization, etc.), exposure to light, exposure to air, exposure to liquids that initiate hydrolysis, etc. In some cases, the process of hydrolysis is stopped before a final assembly of the fibers or other structures into the adjunct (e.g., by drying them in an oven or using a different approach).

The adjunct including multiple layers or other structures formed from the same absorbable polymer but having different absorption rates can be, for example, adjunct 116 shown in FIG. 12 or adjunct 1038 in FIG. 126.

As mentioned above, an adjunct can be formed from the same absorbable polymer treated so as to create layers or portions of the adjunct having different absorption rates. In addition to having different absorption rates, other properties of the adjunct's layers or portions, such as, for example, their thickness, amount of medicant(s) retained therein, types of the medicants and a manner in which the medicants are associated with the portions, can differ. Examples of such adjuncts are shown in FIG. 38.

In some aspects, an adjunct formed from at least one bioabsorbable polymer can be in the form of one or more layers that can have multiple reservoirs or pores releasably retaining therein effective amounts of at least two different medicants. The pores can be covered by one or more absorbable coatings having different degradation rates. In this way, the adjunct can be configured to release one or more medicants in a non-homogenous manner.

Opposing sides of the adjunct can have different absorbable coatings encapsulating pores carrying at least one medicant. For example, a first side of the adjunct can have at least first and second absorbable coatings with different first and second degradation rates. On the first side, pores of the adjunct carrying a first medicant can be coated with the first coating and pores carrying a second medicant can be coated with the second coating. A second, opposite side of the adjunct can also have the same first and second absorbable coatings that also encapsulate pores with the first and second medicant, respectively. Alternatively, the second side can have the first and second coatings forming different patterns as compared to the first side of the adjunct. As another variation, the second side can be coated with a third absorbable material having a third degradation rate that is different from the first and second degradation rates. Furthermore, one or both of the first and second sides of the adjunct can have more than more different coatings that can coat pores with at least one medicant in a number of different ways. Regardless of the specific configuration of the adjunct and materials forming it, release of the medicants contained within the pores of the adjunct is controlled by a degradation rate of the bioabsorbable polymer coatings used to releasably retain the medicants in the pores. Examples of applications that can benefit from the described techniques of delivering medicants from reservoirs is described in U.S. patent application Ser. No. 11/516,054 entitled "System And Method For Local Delivery Of Antithrombotics" filed on Sep. 5, 2006, which is hereby incorporated by reference in its entirety.

One example of an adjunct in the form of a layer having multiple pores filled with at least one medicant and covered with one or more bioabsorbable coatings can be adjunct 100 shown in FIG. 6. The adjunct 100 has multiple pores disposed at different locations and carrying different medicants that are encapsulated within the pores using absorbable coatings having different degradation rates. Another example of such an adjunct can be adjunct 108 shown in FIG. 9 that also includes multiple pores and have a more complicated pattern of bioabsorbable coatings than adjunct 100 in FIG. 6. In the example of FIG. 9, the adjunct 108 releasably retains multiple medicants that are carried by multiple vessels of different types and sizes. An adjunct can also be in the form of a laminate or film including heterogeneous portions or layers having different degradation rates and incorporating different medicants, as shown, for example, in FIG. 32.

Various exemplary surgical adjuncts with medicants affected by activator materials are described herein. In general, an adjunct is provided with at least one medicant that is configured to be activated by an activator material. The adjunct can be delivered to a tissue of a patient, where the adjunct can be implanted, as discussed herein. Various activator materials can be configured to activate the at least one medicant retained by the adjunct, the activation causing any one or more of a variety of actions. For example, the at least one medicant can be activated so as to yield at least one of a signal and/or an effect on the adjunct. The signal and/or the effect may facilitate the healing of tissue to which the adjunct is applied in conjunction with surgical staples. When surgical staples are used within a patient, a danger exists that the staples will not effectively seal the tissue of the patient, such as due to unexpected tissue tearing caused by the stapling, patient movement post-surgery, unhealthy tissue, staple failure, and/or other factors. If the seal is not fully effective and a leak occurs, e.g., fluid and/or other matter is able to leak out from within the tissue and/or from within a lumen defined by the tissue, the patient may experience discomfort and/or other adverse effects, and/or healing of the tissue may be delayed, if not prevented entirely, without further surgical intervention. The signal and/or the effect may allow for detection of the ineffective seal, e.g., for detection of the leak, thereby allowing the leak to be addressed as needed by a medical professional. The signal and/or the effect can be provided without surgical intervention to detect and/or inspect the leak, which is traditionally a way that leaks are detected and/or confirmed post-surgery. Not requiring surgical intervention may be less expensive than surgery and/or may cause the patient less emotional and/or physical stress than surgical intervention to detect and/or confirm the leak.

If a leak occurs, the leak will typically occur at least one day after the staples and the adjunct are applied to the tissue (e.g., during an inflammation stage of wound healing), such as on day 2 or day 3 after implantation of the staples and the adjunct, e.g., two or three days after the tissue is wounded. The tissue can be at its weakest during this phase of wound healing, as discussed above, thereby making the tissue generally more susceptible to developing and/or exacerbating a leak at this time. The activator material can be introduced into the patient, for example through a natural orifice thereof, at least one day after the staples and the adjunct are applied to the tissue, such as during day 2 or day 3 post-surgery (and post-tissue wounding). The exact timing of the activator material's delivery to the patient can vary based on any number of factors, e.g., based on the patient's overall healing process, on medical conditions of the patient unrelated to the condition necessitating delivery of the adjunct, etc.). The activator material's delivery can thus be advantageously timed for each particular patient and/or according to different preferences of different medical professionals.

The at least one medicant being activated by the activator material so as to provide one or both of a signal and an effect on the adjunct indicates that the activator material and the at least one medicant have been exposed to one another (e.g., come into contact with one another), thereby indicating an ineffective seal and a leak. Correspondingly, no signal or effect being provided after introduction of the activator material to the patient indicates that the seal is effective and that a leak does not exist. The activated medicant may thus serve as a warning of a leak and hence allow the leak to be addressed in any of a number of ways, as deemed appropriate for the patient by a medical professional. The activator material can be introduced into the patient so as to be located on one side of a stapled tissue while the at least one medicant is located on another, opposite side of the stapled tissue, e.g., the adjunct including the at least one medicant can be located within a tissue lumen (such as being applied thereto in an anastomosis procedure) and the activator material can be located outside of the tissue lumen. In this way, the activator material and the at least one medicant will not be exposed to one another so as to activate the at least one medicant unless the at least one medicant has been able to escape from the tissue through a leak.

As mentioned above, the activator material can be configured to be introduced into a patient through a natural orifice thereof, such as via a swallowable pill, via a drink, or via a suppository. The activator material may thus be deliverable to the patient in a familiar way, be deliverable non-surgically and hence without the cost and numerous potential complications of surgery, and/or be administered to the patient in any of a variety of settings (e.g., at a hospital, at a skilled nursing facility, at the patient's home, etc.). The activator material can instead be configured to be introduced into a patient in another way, such as by being injectable into the patient, being topically applied to the patient such as by a cream or gel, or being surgically introduced into the patient.

In addition or in alternative to the activator material being configured to facilitate identification of a leak at a tissue site (e.g., at a site of surgical stapling of the tissue), the activator material can be configured to seal the tissue site by activating the at least one medicant. In other words, the activator material can be configured to facilitate sealing of the leak through activation of the at least one medicant. An ineffective seal at the tissue site may therefore be addressed without any surgical intervention being required to address the leak and/or without the leak even being previously identified as existing at the tissue site. The activation of the at least one medicant by the activator material can cause the sealing by inducing a change in a conformation of the at least one medicant, such as by the activator material bonding to the adjunct and thereby changing the conformation of the at least one medicant to encourage bonding thereof to additional agent(s) and thereby seal or "fill" the leak.

The medicant(s) can be configured to provide at least one specific response when exposed to a specific environment that differs from an implanted state. For example, the medicant can include a reactive polymer that, in the presence of the activator material, reacts to change a radiodensity of the activator material that is passed by the patient. A user can then x-ray waste or fluids that are passed by the patient to determine the presence of a leak without having to investigate the passed waste or fluids for visual color changes. The approach may be beneficial because visual changes in waste and fluid color are not always readily determinable. Through the use of a reactive polymer, a user may be able to rapidly determine the existence of a leak.

The adjunct can be infused with the medicant configured to bond with and change its conformation in the presence of the activator material. The activator material can be delivered to the patient, and in the presence of a leak that is forming, the activator material can be configured to bond to any exposed pieces of the adjunct with the medicant infused thereon. Bonding will change the conformation of the activator material to encourage bonding to additional activator materials.

The medicant(s) are not limited to starting a reaction upon interaction with the activator material. The medicant(s) can be configured to react until there is contact between the medicant(s) and the activator material. For example, if the adjunct is delivered to tissue of a patient and fails to detect oxygen ($O_2$), the adjunct can be configured to release medicant(s) therefrom in the form of vascular endothelial growth (VEGF) and/or angiogenic (ANG) factors or matrix metalloproteinase-9 (MMP9) inhibitors to stimulate growth either until the $O_2$ is detected or until the medicant(s) are exhausted, whichever comes first. Thus, the adjunct can be configured to immediately provide a stimulating effect by releasing medicant(s) until a signal in the form of the activator material is observed. Furthermore, the medicant(s) can be contained intraluminally in such situations rather than being contained external to tissue.

The medicant(s) are not limited to reacting upon interaction with the activator material delivered through a natural orifice. The medicant(s) can be configured to react with and/or until the medicant(s) interact with the activator material, such as another medicant(s), introduced in any of a variety of ways, such as a port to a wound site of a patient (e.g., a port such as a trocar positioned in an incision formed in an abdomen the patient, a port such as a chest tube, etc.). For example, a medicant retained by an adjunct can interact with a medicant delivered through a chest tube during chest tube applications. The medicant can be configured to react until the medicant interacts with an activator material introduced to the airway of the patient in any of variety of ways, such as globally through an inhaler or locally through a bronchoscope. For example, a nebulized medicant serving as the activator material can be delivered into at least a part of an airway of the patient. If the nebulized medicant reaches the medicant configured to react until the medicant interacts with an activator material, the encounter can cause a variety of reactions, such as identify the location of a leak and/or initiate steps to aid in the sealing of the leak. For example, a medicant such as hydrogen sulfide entrapped by a polymeric matrix can provide localized protection against ventilator-induced lung injury.

The adjunct can be configured to be delivered to tissue by staples carrying the adjunct thereon, as discussed herein. The staples can be configured to attach the adjunct to an external surface of tissue, which can be especially beneficial when attaching the adjunct to lung or liver tissue. When stapling lung or liver tissue, for example, leakage is traditionally greatest along an outside edge of the tissue at a site of the staples. The one or more medicants eluting from the adjunct can be configured to have a highest dose along the outside edge and thereby help address the particular problem of leakage therealong.

FIG. 130 illustrates one implementation of an adjunct 1110 releasably retaining at least one medicant 1112, 1114 that is configured to be activated by an activator material. The adjunct 1110 is retaining two different medicants 1112, 1114 in this illustrated example. The adjunct 1110 and the medicant(s) 1112, 1114 can have any of a variety of configurations, as described herein. As shown, the adjunct 1110 is configured to change conformation. As mentioned above, at least one activator material can be introduced to the patient in a variety of ways, such as orally or through a suppository, and one or both of the first medicant 1112 and the second medicant 1114 can be configured to react with the activator material within the patient's body. In at least some implementations, at least two activator materials can be introduced into the patient, one of the activator materials being configured to react with the first medicant 1112 and another of the activator materials being configured to react with the second medicant 1114.

As in this illustrated implementation, the first medicant 1112 can be configured to react to an activator material such that the first medicant 1112 expands upon contact with the activator material. Consequently, the first medicant 1112 can be configured to form a plug at a site of any leak through tissue 1118 to which the adjunct 1110 has been applied because the first medicant 1112 can include a foaming agent that expands or fully foams in the presence of the activator material. FIG. 130 shows the adjunct 1110 delivered to an edge of tissue 1118 of a patient by deployment of staples 1116 deployed into the tissue 1118, such as a bowel or a lung lumen. If the activator material is administered and there is no leak and therefore no contact between the activator material and the first medicant 1112, there will be no reaction by the first medicant 1112. However if a leak has formed through the tissue 1118, the first medicant 1112 interacts with the activator material, which causes the foaming agent to expand to seal or plug the leak that is forming, as shown in FIG. 130.

As in this illustrated implementation, the second medicant 1114 can be configured to react to an activator material such that the second medicant 1114 becomes radiodense upon contact with the activator material. After introduction of the activator material to the patient, the patient can be imaged using an imaging system, such as an x-ray system, as will be appreciated by a person skilled in the art, configured to provide an image showing radiodense material. FIG. 131 illustrates an example of an imaging system 1136 configured to image the patient from outside the patient's body, with an external surface of the patient being schematically represented by a dotted line. If the activator material is administered and there is no leak and therefore no contact between the activator material and the second medicant 1114, there will be no radiodense portion on the image due to the second medicant 1114. However if a leak has formed through the tissue 1118, the second medicant 1114 can interact with the activator material, which can cause the medicant 1114 to become radiodense and hence be visible in the image so as to indicate a leak.

In another implementation, one or both of the first and second medicants 1112, 1114 can include a reactive dye and/or reactive polymer infused within the adjunct 1110. In the presence of the activator material, interaction between the reactive dye and/or reactive polymer and the activator material can cause the reactive dye and/or reactive polymer to change color. If the activator material is administered and there is no leak and therefore no contact between the activator material and the reactive dye and/or reactive polymer, there will be no color-changing reaction by the reactive dye and/or reactive polymer. However if a leak has formed in the tissue 1118 to which the adjunct 1110 has been applied, the reactive dye and/or reactive polymer can interact with the activator material, which can cause the reactive dye and/or reactive polymer to change color. The leak can allow the reactive dye and/or reactive polymer with the changed color to be expelled from the body and signal the existence of the leak via visual inspection thereof.

In another implementation, one or both of the first and second medicants 1112, 1114 can be configured to bond with and change its conformation in response to contact with the activator material. If the activator material is administered and there is no leak and therefore no contact between the activator material and the bondable medicant(s), there will be no bonding or change in conformation. However if a leak has formed in the tissue 1118 to which the adjunct 1110 has been applied, the bondable medicant(s) can interact with the activator material, which can cause the bonding and conformation change. The bonding will change the conformation of the medicant(s) to encourage bonding to additional agents. This is similar to how platelets act but in a polymeric form for compromised stapled tissue.

As mentioned above, although the first medicant 1112 in this illustrated embodiment is configured to expand in response to contact with an activator material and the second medicant 1114 in this illustrated embodiment is configured to become radiodense in response to contact with an activator material, the adjunct 1110 and/or another adjunct can include any combination of reactionary medicants, e.g., one or more medicants configured to expand in response to contact with an activator material, one or more medicants configured to become radiodense in response to contact with an activator material, one or more medicants configured to change color in response to contact with an activator material, and/or one or more medicants configured to bond and change in conformation in response to contact with an activator material.

FIG. 132 illustrates another implementation of an adjunct 1120 releasably retaining at least one medicant 1122, 1124 that is configured to be activated by an activator material. The adjunct 1120 is retaining two different medicants 1122, 1124 in this illustrated example. The medicants 1122, 1124 can be any combination of one or more medicants configured to expand in response to contact with an activator material, one or more medicants configured to become radiodense in response to contact with an activator material, one or more medicants configured to change color in response to contact with an activator material, and/or one or more medicants configured to bond and change in conformation in response to contact with an activator material. As shown, a surgical staple 1126 can include the adjunct 1120 disposed over both legs of the staple 1126 configured to be used in delivering the adjunct 1120 to tissue. In other implementations, only one staple leg can have an adjunct thereon, or one or both legs can have more than one adjunct thereon.

The medicants 1122, 1124 can be configured to be released from the adjunct 1120 when the staple 1126 is deformed upon deployment of the staple 1126 into tissue 1128 of a patient, e.g., a bowel, a lung, etc., as shown in FIG. 133. FIG. 134 shows the staple 1126 and a plurality of additional staples each also having an adjunct disposed thereon similar to the disposal of the adjunct 1120 on the staple 1126. FIG. 134, illustrates a side-to-side anastomosis, but the staple 1126 can be used in other surgical procedures. If an activator material is administered to the patient and there is no leak and therefore no contact between the activator material and either of the medicants 1122, 1124, there will be no reaction by the medicants 1122, 1124. However if a leak has formed through the tissue 1128, as shown on a right side of the staple 1126, in FIG. 133, the right-side medicant 1122 can interact with the activator material and thereby signal the existence of the leak. For example, a leak can allow fluid to flow within a passageway 1129 extending through the tissue 1128 and to flow outside of the passageway so that the medicant(s) 1122, 1124 can signal the existence of the leak as discussed herein.

The medicants of the adjuncts discussed above as being configured to be affected by delivery of an activator material are configured to be affected by contact with the activator material within a body of the patient within which the adjunct has been implanted. In other words, the interaction of an activator material and one or more medicants of an adjunct can be configured to activate the one or more medicants and thereby allow monitoring of the adjunct after delivery of the adjunct to tissue. The activator material in these implementations is an independent element from the adjunct and the medicant(s) retained by the adjunct, as well as from device(s) that facilitate the delivery of the adjunct and medicant(s) to tissue, such as a surgical stapler that applies the staples and the adjunct. In other implementations, one or more medicants retained by an adjunct can include at least one actuatable material configured to be activated by an external activator. In other words, the interaction of the actuatable material and the activator can be configured to allow monitoring of the adjunct after delivery of the adjunct to tissue. The actuatable material in these implementations is not an independent element from the adjunct or the medicant(s) retained by the adjunct but is instead delivered therewith to tissue, e.g., using a surgical stapler. The at least one medicant retained by the adjunct is not activated until exposure thereto to the activator located outside the patient's body. Various activators, actuatable materials, and medicants can be employed, causing a variety of actions.

The activator being located outside the patient's body may limit an amount of foreign material introduced into the patient's body, which may reduce risk of infection and/or reduce other risks caused by foreign matter in a body. The actuatable material being delivered in conjunction with the adjunct and staples may be convenient for the patient and for the patient's care provider since only one procedure need be performed to deliver all of the actuatable material, the adjunct, and the staples to the patient. Similar to that discussed above regarding the activator material being delivered to the patient after the adjunct has been delivered to the patient, the activator can be applied to the patient at any of a variety of times based on any number of factors, thereby allowing delivery of the activator to be advantageously timed for each particular patient and/or according to different preferences of different medical professionals.

The actuatable material can be delivered to the medicant(s) through various mechanisms, such as systemically, or can be present at a site of the adjunct upon delivery of the staple(s). An adjunct can thus be configured to be delivered to tissue and can be configured to retain at least one medicant. The medicant(s) can be configured to be radiodense for imaging purposes. The actuatable material can be configured to be systemically administered to the patient and can be configured to be directed toward the desired tissue post-operatively using an activator, such as present imaging modalities like a computed tomography (CT) imaging system and/or a magnetic resonance imaging (MRI) imaging system. Through targeted CT or MRI, a magnetic field is induced in which the actuatable material is attracted to the adjunct through iron nanoparticles in the actuatable material. However, any other substance that can be attracted to a magnetic charge can be used. The actuatable material can thus be directed to the site of the adjunct through use of a magnet and interact with the medicant(s), allowing the adjunct to modulate the inflammation response, attract cells to the adjunct, etc. Additionally, the actuatable material can be spread out at the site itself through the use of the magnet, allowing, for instance, a user to create vasculature in the colon at a surgery site. The actuatable material may increase blood flow and/or vascular development on the outside of the colon by being spread out and/or may affect a greater area of tissue by spreading out and thus overall improve wound healing.

Furthermore, any activity of the actuatable material with the medicant(s) can be monitored during post-operation interactions with the activator, for instance release rates, drug utilization, and/or distribution of the medicant(s). For example, the medicant can be tagged with a radio opaque or radioactive agent that allows any unreleased amount of the medicant to be monitored as well as a distribution envelope of the medicant upon release. Various medicants can be used. For example, a dye or ion salt can be used that can be monitored by fluid output of the patient or with the MRI. Alternatively, metabolized byproducts can be used. A medicant with a non-resorbable/digestible can be embedded in an absorbable polymer to enable an exit of the non-resorbable medicant from the location and subsequently the patient. Depending on a location in the patient of the adjunct, various approaches can be used to monitor the activity of the actuatable material with the medicant(s). For instance, in the gastric system the contents in chyme can be used that are inert in low pH environment; in the vascular system the user can monitor radioisotopes; and in the colorectal pathways the user can monitor what the patient passes.

Any activator capable of affecting any actuatable material can be used. For example, targeted radiation can be applied to influence the degradation profile of absorbable polymers withholding the medicant from the patient. The use of targeted radiation both can speed up release of the actuatable material with the medicant(s) by damaging chemistry holding the medicant(s) to the adjunct and can delay release by increased cross-linking or crystallization to further bind the medicant(s) to the adjunct. In such an example, various forms of imaging can be used to determine the location of the actuatable material with the medicant(s), and targeted radiation can then be applied to the location to increase or decrease the release of medicant, which could be in the form of a polymer capsule to allow for degradation or crystallization. As another example, the actuatable material can again be directed toward the site of the adjunct post-operatively using existing imaging modalities. However, a magnetic field can be induced in which the actuatable material, medicant(s), and/or adjunct becomes heated by the magnetic field passing through metallic particles. The actuatable material, medicant(s), and/or adjunct can be a thermally sensitive material where the properties of the material can be degraded, enhanced, or otherwise varied (such as a bioabsorbability rate) through the production of heat. Thus the reactions of the actuatable material and/or medicant(s) may be varied post-operatively and, if needed, multiple applications of the process can be applied over time to ensure an expected result.

For example, the adjunct 1110 of FIG. 130 can include an actuatable material that is an independent element from the adjunct 1110 and the medicant(s) 1112, 1114 retained by the adjunct 1110, or the medicant(s) 1112, 1114 retained by the adjunct 1110 can include at least one actuatable material configured to be activated by an external activator. For another example, the adjunct 1120 of FIG. 132 can include an actuatable material that is an independent element from the adjunct 1120 and the medicant(s) 1122, 1124 retained by the adjunct 1120, or the medicant(s) 1122, 1124 retained by the adjunct 1120 can include at least one actuatable material configured to be activated by an external activator.

Various exemplary adjuncts for surgical devices including agonists and antagonists are described herein. In general, an implantable adjunct can have two or more medicants releasably disposed therein that are each releasable from the adjunct. At least one of the medicants can include an agonist configured to encourage a physiological response, and at least one of the medicants can include an antagonist configured to discourage the physiological response encouraged by the agonist. In other words, the antagonist can be configured to counter the effect of the agonist. The physiological response can include an aspect related to wound healing such that the aspect related to wound healing may be both encouraged by and discouraged by the adjunct (e.g., encouraged by the agonist disposed in the adjunct and discouraged by the antagonist disposed in the adjunct), which may help accelerate wound healing through control of the physiological response and, accordingly, help reduce the adverse effects of wound healing.

For example, the physiological response can include inflammation such that the agonist is configured to encourage tissue inflammation and the antagonist is configured to discourage tissue inflammation. In this way, the agonist can encourage the inflammation that occurs in wound healing, e.g., the start of inflammation can be triggered by the agonist (e.g., the agonist can trigger the start of wound healing's inflammation stage) and/or the agonist can accelerate inflammation during wound healing's inflammation stage (e.g., cause the inflammation stage to proceed more quickly and hence be able to end sooner), and the antagonist can discourage the inflammation that occurs in wound healing, e.g., the inflammation stage can be encouraged to end by the antagonist and/or the start of wound healing's proliferation stage can be triggered by the antagonist. In other words, the agonist can be configured to encourage an acute inflammatory response, and the antagonist can be configured to prevent a chronic inflammatory response. By affecting inflammation in countering ways, the agonist and the antagonist may cooperate to limit a length of time that the wound experiences its lowest strength by limiting a duration of the inflammation stage of wound healing, and/or may cooperate to produce a higher minimum strength of the wound during healing. Thus, since a wounded tissue's strength is typically lowest during the inflammation stage, as discussed above, the agonist and the antagonist may cooperate to limit an amount of time that the tissue is at its most vulnerable to succumb to any number of inflammation's adverse effects. By way of example, with reference to FIG. 40, the agonist can include at least one of the medicant B, the medicant $B_1$, the medicant C, and the medicant $C_1$ each configured to facilitate inflammation in the inflammation stage 210, and the antagonist can include the medicant E configured to prevent inflammation in the proliferation stage 212 during the fibroblasts phase 216 thereof.

For another example, the physiological response can include a vascular response, e.g., vessel constriction and dilation. The agonist can be configured to encourage one of vessel constriction and dilation, and the antagonist can be configured to encourage the other of vessel constriction and dilation so as to counter the effect of the agonist.

For yet another example, the physiological response can include blood flow. The agonist can be configured to either encourage clotting (e.g., slow bleeding) or to discourage clotting (e.g., accelerate bleeding), and the antagonist can be configured to affect blood flow opposite to that of the agonist. The agonist can thus be configured to encourage the stoppage of acute bleeding, such as in the hemostasis stage of wound healing, and the antagonist can be configured to help prevent excessive clotting. Excessive clotting is typically not needed during the process of wound healing since a general goal of wound healing is to return the wounded tissue to a normal, pre-wounded condition.

For still another example, the physiological response can include probiotic effect or bacteria growth. The agonist can be configured to encourage proliferation of probiotics, e.g., to encourage bacterial growth, and the antagonist can be configured to discourage proliferation of probiotics, e.g., to discourage bacterial growth. Agonists and antagonists affecting probiotic effect or bacteria growth may be particularly useful for wound healing in a gastrointestinal (GI) context, such as when an adjunct having an agonist and an antagonist disposed therein is delivered to a colon, and in particular for helping to minimize loss of GI tissue wall strength during the process of wound healing.

The agonist and the antagonist can be configured to be non-homogenously released from the adjunct. To facilitate wound healing, the agonist can be configured to begin releasing from the adjunct before the antagonist begins releasing from the adjunct. In other words, each of the agonist and the antagonist can be configured to be released from the adjunct according to a different predetermined release profile, with the predetermined release profile of the agonist allowing the agonist to be releasable from the adjunct prior to the antagonist's release from the adjunct. In this way, the physiological response may be encouraged by the agonist and then subsequently discouraged by the antagonist. The physiological response may thus be temporally controlled by the adjunct including the two or more medicants. Thus, wound healing may be accelerated through temporal control of the physiological response that includes an aspect of wound healing.

Time release of the agonist and the antagonist from the adjunct can be controlled in any of a variety of ways. The time release of the agonist and the antagonist can be independently controlled, such as by timing of coating disintegration, timing of polymer dissolution (e.g., timing of the dissolution of different polymers forming the adjunct, timing of the dissolution of the same polymer forming the adjunct where the polymer is present in different molecular weights, timing of the same polymer forming the adjunct where the polymer is present in different phases such as an amorphous phase and a crystalline phase that degrades slower than the amorphous phase, timing of the same polymer forming the adjunct where the polymer is present with different pretreatments (e.g., irradiation such as gamma sterilization, exposure to light, exposure to a liquid that initiates hydrolysis that is stopped before packaging of the adjunct such as by oven drying, exposure to air, etc.) altering how the polymer degrades), or via application of pressure thereto, as discussed above. The agonist and the antagonist can thus each be configured to begin release from the adjunct at a predetermined time, with the predetermined times not being affected by one another.

Alternatively, the time release of the antagonist can be dependent on the time release of the agonist. In other words, the timing of the agonist's release from the adjunct can influence the timing of the antagonist's release from the adjunct. The antagonist's release can thus be self-regulated. For example, the agonist's release can be configured to start encouraging the physiological response, e.g., begin encouraging tissue inflammation, and the antagonist can be configured to be released proportionately to a magnitude of the physiologic response encouraged by the agonist, e.g., by a magnitude of the tissue inflammation. The antagonist may thus be able to more effectively counter the effects of the agonist by being configured to begin releasing from the adjunct before the physiological response becomes too intense, before the physiological response lasts beyond a maximum amount of tolerable time post-wound occurrence, and/or after the agonist has had sufficient time to effectively encourage the physiological response. Medicants configured to regulate the release of another medicant are further described in U.S. patent application Ser. No. 14/840,716 entitled "Adjunct Material To Provide Controlled Drug Release" filed on Aug. 31, 2015, which is hereby incorporated by reference in its entirety.

Each of the agonist and the antagonist releasably retained in the adjunct can include one or more different medicants, with each of the individual medicants being present at a single intensity or concentration or being present in two or more different intensities or concentrations.

As discussed above, release of the agonist can begin either substantially immediately upon delivery of the adjunct to tissue, or the agonist's release can be delayed until a predetermined time after the adjunct's delivery to tissue. The antagonist, being configured to begin release from the adjunct after the start of the agonist's release from the adjunct, can have its release from the adjunct delayed until a predetermined time, which can be a predetermined time after the adjunct's delivery to tissue or after the start of the agonist's release. The antagonist can be configured to start releasing from the adjunct before or after all of the agonist has been released from the adjunct. In other words, release of the agonist and the antagonist can overlap in time, or the releases can be non-overlapping in time. By way of example, with reference to FIG. 40, the agonist as including at least one of the medicants B, $B_1$, C, $C_1$ each configured to facilitate inflammation in the inflammation stage 210 and the antagonist including the medicant E configured to prevent inflammation in the proliferation stage 212 are released from an adjunct at non-overlapping times during wound healing.

The two or more medicants releasably retained in the adjunct can include only the agonist and the antagonist, e.g., include only one or more agonists and one or more antagonists. The adjunct and the medicants disposed therein may thus be targeted to affect the physiological response, which may allow the adjunct to be selected by a surgeon or other medical professional for delivery to tissue when the physiological response is of particular concern for a particular patient and/or for a particular wound type, and/or which may allow the adjunct to be delivered to a location on tissue where the physiological response may most need controlling (e.g., where the tissue is most at risk of inflammation, etc.) and one or more other adjuncts having one or more other types of medicants releasably retained therein to be delivered to another location on the tissue to target one or more other aspects of wound healing. By way of example, with reference to FIG. 40, the agonist can include at least one of the medicant B, the medicant $B_1$, the medicant C, and the medicant $C_1$, and the antagonist can include the medicant E such that the only medicants retained by the adjunct include the medicant E and one or more of the medicants B, $B_1$, C, $C_1$.

Alternatively, the two or more medicants releasably retained in the adjunct can include the agonist, the antagonist, and at least one other type of medicant, e.g., include one or more agonists, one or more antagonists, and one or more medicants configured to encourage a response other than the physiological response targeted by the agonist and the antagonist. The adjunct and the medicants disposed therein may thus be configured to affect the physiological response and to affect one or more other aspects of wound healing, which may allow the adjunct to more comprehensively improve the process of wound healing than when the adjunct only includes the agonist and the antagonist and/or may allow the adjunct to improve more stages in the process of wound healing than when the adjunct only includes the agonist and the antagonist. For example, the agonist (which can include one or more medicants) can be configured to encourage inflammation in the inflammation stage of wound healing, the antagonist (which can include one or more medicants) can be configured to discourage inflammation in the proliferation stage of wound healing, and the one or more medicants configured to encourage a response other than the physiological response can include at least one of a medicant (which can include one or more medicants) configured to facilitate hemostasis, a medicant (which can include one or more medicants) configured to inhibit MMPs during the macrophages phase of the inflammation stage, and a medicant (which can include one or more medicants) configured to facilitate tissue growth in the proliferation stage of wound healing. By way of example, with reference to FIG. 40, the agonist can include at least one of the medicant B, the medicant $B_1$, the medicant C, and the medicant $C_1$, the antagonist can include the medicant E, and the other medicant can include any one or more of the medicants A, D, $D_1$, F.

For another example, with reference to FIG. 135, the agonist can include a first medicant 1300, and the antagonist can include a second medicant 1302. The time scale in FIG. 135 is an example only. As shown, the agonist 1300 can be configured to begin release from an adjunct at a time zero (e.g., a time of wound healing), peak in dosage at a start of Day 1, and cease release from the adjunct at a start of Day 2, and the antagonist 1302 can be configured to begin release from the adjunct at a start of Day 2, peak in dosage at a start of Day 3, and cease release from the adjunct at a start of Day 4. The antagonist 1302 can thus be configured to start releasing from the adjunct when the agonist 1300 stops being released from the adjunct. The agonist 1300 can thus be allowed to induce its full effects on the targeted physiological response before the antagonist 1302 begins to cancel the effects of the agonist 1300 by discouraging the physiological response.

As discussed above, the agonist 1300 and the antagonist 1302 can be the only medicants releasably retained in the adjunct, or at least one additional medicant can be releasably retained in the adjunct. For example, as shown in FIG. 135, the adjunct can have a third medicant 1304 releasable therefrom. The third medicant 1304 can have a variety of different release timings from the adjunct. In this illustrated implementation, the third medicant 1304 is configured to begin release from the adjunct at a start of Day 1, peak in dosage at a start of Day 2, and cease release from the adjunct at a start of Day 3. The third medicant 1304 can thus be configured to be released over time to overlap with the release of both the agonist 1300 and the antagonist 1302.

In at least some implementations, instead of being a medicant other than an agonist or antagonist, the third medicant 1304 can be an agonist or an antagonist. In this way, the third medicant 1304 as an agonist can cooperate with the first agonist 1300 to encourage the same physiological response, or the third medicant 1304 as an antagonist can cooperate with the second antagonist 1302 to discourage the same physiological response.

The agonist 1300, the antagonist 1302, and (if present) the third medicant 1304 can each be released from the adjunct as a single dose, as shown by the solid lines for the agonist 1300, the antagonist 1302, and the third medicant 1304 in FIG. 135. Alternatively, any one or more of the agonist 1300, the antagonist 1302, and third medicant 1304 can be released as cumulative doses. Each additional cumulative dose released at substantially the same time as its associated single dose is shown in FIG. 135 by a dotted line, e.g., two doses of the agonist 1300 shown as dotted line 1300A, three doses of the agonist 1300 shown as dotted line 1300B, four doses of the agonist 1300 shown as dotted line 1300C, two doses of the antagonist 1302 shown as dotted line 1302A, three doses of the antagonist 1302 shown as dotted line 1302B, four doses of the antagonist 1302 shown as dotted line 1302C, two doses of the third medicant 1304 shown as dotted line 1304A, three doses of the third medicant 1304 shown as dotted line 1304B, and four doses of the third medicant 1304 shown as dotted line 1304C. A person skilled in the art will appreciate that medicants/doses may not be released at precisely the same time due to any one or more factors, such as accuracy of time measurement devices and/or small temporal differences in when medicants released from the adjunct directly contact tissue, but nevertheless be considered to be effectively released at substantially the same time.

For another example, with reference to FIG. 136, the agonist can include a first medicant including three doses 1306A, 1306B, 1306C thereof, and the antagonist can include a second medicant including a single dose 1308 thereof. The time scale in FIG. 136 is an example only. The three agonist doses 1306A, 1306B, 1306C can provide a cumulative dose 1310, as shown in FIG. 137. In other implementations, as discussed herein, the agonist and the antagonist can be delivered using other numbers of doses. As shown in FIG. 136, the first agonist dose 1306A begins releasing from the adjunct at time zero of wound creation and peaks in dosage at a start of Day 1, the second agonist dose 1306B begins releasing from the adjunct at a start of Day 1 and peaks in dosage at a start of Day 2, the third agonist dose 1306C begins releasing from the adjunct at a start of Day 2 and peaks in dosage at a start of Day 3, and the antagonist dose 1308 begins releasing from the adjunct at a start of Day 5 and peaks in dosage at a start of Day 6. Additionally, as shown, the first agonist dose 1306A stops releasing from the adjunct at a start of Day 2, the second agonist dose 1306B stops releasing from the adjunct at a start of Day 3, the third agonist dose 1306C stops releasing from the adjunct at a start of Day 4, and the antagonist dose 1308 stops releasing from the adjunct at a start of Day 7.

FIG. 138 illustrates one example of a vessel 1316 including the first and second medicants of FIG. 136. The vessel 1316 can be configured to be releasably retained in an adjunct (not shown) such that the first and second medicants can release therefrom via the vessel 1316. Similar to the vessel 174 of FIG. 31, the vessel 1316 includes a plurality of distinct concentric layers. As shown, an outermost layer includes a first dose 1318A of the agonist, a layer inner of the outermost layer includes a second dose 1318B of the agonist, a layer inner of the second dose layer includes a third dose 1318C of the agonist, and an innermost layer includes a dose 1320 of the antagonist. As discussed herein, the adjunct can include a plurality of the vessels 1316. Together, the plurality of vessels 1316 can release the first and second medicants therefrom to achieve the doses 1306A, 1306B, 1306C of the agonist and the single dose of the antagonist 1308. Thus, the first dose 1318A of each of the vessels 1316 form the first agonist dose 1306A, the second dose 1318B of each of the vessels 1316 form the second agonist dose 1306B, the third dose 1318C of each of the vessels 1316 form the third agonist dose 1306C, and the dose 1320 of each of the vessels 1316 form the antagonist dose 1308.

Referring again to FIG. 136, the agonist including the three doses 1306A, 1306B, 1306C and the antagonist including the single dose 1308 can be the only medicants releasably retained in the adjunct, or at least one additional medicant can be releasably retained in the adjunct. For example, as shown, the adjunct can have a third medicant including a single dose 1312, and can have a fourth medicant including two doses 1314A, 1314B. The third and fourth medicants can each have another number of doses than those shown in this illustrated implementation. The second and fourth medicants are each shown in FIG. 136 as single doses 1308, 1312, but one or both can include multiple doses to form a cumulative dose. Similarly, the first and third medicants are each shown in FIG. 136 as including multiple doses that form a cumulative dose, but one or both can include single doses. In an exemplary implementation, the third medicant can be configured to facilitate hemostasis in the hemostasis stage of wound healing, the first medicant (agonist) can be configured to facilitate inflammation in the inflammation stage of wound healing, the fourth medicant can be configured to inhibit MMP in the inflammation stage of wound healing, and the second medicant (antagonist) can be configured to prevent inflammation in the proliferation stage of wound healing.

As mentioned above, an adjunct including an agonist and an antagonist releasably retained therein can have a variety of configurations. One example of such an adjunct is the adjunct 171 of FIG. 30 that includes first and second vessels 170, 172 that include first and second medicants D1, D2 encapsulated within the coatings A3, B3. The first medicant 170 can include an agonist, and the second medicant 172 can include an antagonist. The agonist can thus be configured to start being released from the adjunct before the antagonist since the degradation rate of the first vessel's outer coating A3 is faster than the second vessel's outer coating B3. The time release of the first and second medicants D1, D2 can therefore be controlled by the coatings A3, B3.

In at least some implementations, an adjunct including an agonist and an antagonist releasably retained therein can be a fiber-based lattice. The adjunct as a fiber-based lattice can have a variety of configurations, as discussed herein. In general, separate fibers forming the fiber-based lattice can have discrete absorption profiles such that a first subset of the fibers breaks down in the healing cascade and thereby releases an agonist and then, subsequent to the start of the breakdown of the first subset of fibers, a second subset of the fibers breaks down in the healing cascade and thereby releases an antagonist. The first and second subsets of fibers can each include fibers having a certain conformation that is changeable, such as by the action of water and/or other agents that the adjunct is subjected to at the treatment site, e.g., the fibers can each be configured to unwind or fray. The conformation change can allow for medicant release from the fibers. For example, the first subset of fibers may begin to break down to release an inflammatory agent such as prostaglandin F2-alpha (PGF 2α), and the second subset of fibers may begin to break down at a point in time after the first subset of fibers begin to break down to release an anti-inflammatory agent such as a non-steroidal anti-inflammatory agent (NSAID) or an acetic acid derivative.

The first and second subsets of fibers can form the entire lattice of the adjunct such that the adjunct's only medicants include the agonist and the antagonist. Alternatively, the adjunct can include additional fibers that form the lattice with the first and second subsets of fibers. The additional fibers can be base fibers that are configured to not break down in the healing cascade, are configured to provide structural support to the adjunct, and are not configured to facilitate release of a medicant from the adjunct such that the adjunct's only medicants include the agonist and the antagonist. Alternatively, the additional fibers can be configured to break down in the healing cascade and release one or more medicants therefrom such that the adjunct's medicants include the agonist, the antagonist, and at least one additional type of medicant.

FIG. 139 and FIG. 140 illustrate one implementation of a fiber 1322 configured to release a medicant 1324 therefrom. The medicant 1324 can, as shown, be a coating of the fiber 1322 that has a width 1324w. The coating is only shown as being along a partial longitudinal length of the fiber 1322, but the coating can extend along a partial longitudinal length of the fiber 1322 or along the entire longitudinal length of the fiber 1322. The coating, and hence the medicant 1324, can be configured to absorb, dissolve, or otherwise disintegrate as discussed herein for coatings so as to release the medicant 1324 from an adjunct including the fiber 1322 as part of its fiber-based lattice. The adjunct can be formed from a plurality of the fibers 1322, with the fibers 1322 being the only fibers that form the fiber-based lattice or with the fibers 1322 being one or at least two types of fibers forming the fiber-based lattice.

The coating (e.g., the medicant 1324) is shown as being directly on an exterior surface of the fiber 1322. In other implementations, there can be at least one intermediate layer between the coating and the exterior surface of the fiber 1322, such as at least one coating of another medicant. Additionally, although the coating itself in this illustrated implementation includes the medicant 1324, in other implementations, the fiber 1322 can have the medicant 1324 trapped thereon by a coating disposed over the medicant 1324 that is configured to disintegrate to allow release of the medicant 1324 from the fiber 1322.

FIG. 141 and FIG. 142 illustrate another implementation of a fiber 1326 configured to release a medicant 1328 therefrom. The medicant 1328 can, as shown, be a coating of the fiber 1326 that has a width 1328w. The coating is only shown as being along a partial longitudinal length of the fiber 1326, but the coating can extend along a partial longitudinal length of the fiber 1326 or along the entire longitudinal length of the fiber 1326. The coating, and hence the medicant 1328, can be configured to absorb, dissolve, or otherwise disintegrate as discussed herein for coatings so as to release the medicant 1328 from an adjunct including the fiber 1326 as part of its fiber-based lattice. Similar to that discussed above regarding the fiber 1322 and the medicant 1324, the coating (e.g., the medicant 1328) can be directly on an exterior surface of the fiber 1326, as shown, or there can be at least one intermediate layer between the coating and the exterior surface of the fiber 1326. Also similar to that discussed above regarding the fiber 1322 and the medicant 1324, the coating can include the medicant 1328, as shown, or the coating can trap the medicant 1328 on the fiber 1326.

The adjunct can be formed from a plurality of the fibers 1326, with the fibers 1326 being the only fibers that form the fiber-based lattice or with the fibers 1326 being one or at least two types of fibers forming the fiber-based lattice. For example, the fiber-based lattice can include a plurality of the fibers 1322 and a plurality of the fibers 1326. The coating on the fibers 1322 has the width 1324w that is less than the coating on the fibers 1324w. Thus, in the case of the fiber 1322 having the medicant 1324 trapped thereon by the coating disposed thereover and the fiber 1326 having the medicant 1328 trapped thereon by the coating disposed thereover, the coatings can have a substantially same rate of degradation. A person skilled in the art will appreciate that each of the coatings may not have precisely the same rate of degradation due to any one or more factors, such as accuracy of time measurement devices and/or small temporal differences in when degradation begins, but nevertheless be considered to be the same. The medicant 1324, which can include an agonist, can thus be released before the medicant 1328, which can include an antagonist, due to the width 1324w of the coating on the fiber 1322 being less than the width 1328w of the coating on the fiber 1326.

FIG. 143 illustrates additional implementations of first, second, and third types of fibers 1330, 1332, 1334 configured to release a medicant therefrom. The first, second, and third types of fibers 1330, 1332, 1334 each include fibers having a certain conformation that is changeable by each including twisted fibers configured to change in conformation by unwinding or fraying.

The first type of fibers 1330 includes a coating 1336 thereon that is configured to absorb, dissolve, or otherwise disintegrate as discussed herein for coatings. The coating 1336 can itself include a medicant, or the coating 1336 can overlay a medicant on an outer surface of the fiber that is releasable from the fiber due to the coating's disintegration.

The second type of fibers 1332 has a plurality of pellets 1338 attached thereto. As discussed herein, the pellets 1338 can each have a dissolvable coating such that, as the coating is disintegrated, the medicant can be distributed as a bolus dose or as a time release dosage. The pellets 1338 can be more densely packed on the fibers 1332 closer to a center of an adjunct 1340 including the first, second, and third fibers 1330, 1332, 1334, which may allow more of the medicant to be delivered the more the fibers interact with fluid or other matter that dissolves the coating. Additionally or alternatively, the medicant of the pellets 1338 can be on a progressive time release pattern in which medicant adjacent the adjunct's outer edge 1342 releases faster from the pellets 1338 than from pellets 1338 more toward the center of the adjunct 1340. In at least some implementations, the medicant of the pellets 1338 closer to an outer edge 1342 of the adjunct 1340 can include an agonist, and the medicant of the pellets 1338 farther from the outer edge 1342 and closer to a center of the adjunct 1340 can include an antagonist. Thus, as the fibers 1332 unwind or fray from the outer edge 1342 toward the adjunct's center, the agonist is first released from the adjunct 1340 and the antagonist is subsequently released from the adjunct 1340.

The third type of fibers 1334 includes a plurality of smaller-diameter fibers 1344 braided together to form the fiber. A medicant can be "hidden" within the braid and be released in response to the braid unwinding or fraying. In at least some implementations, the medicant "hidden" in the braid closer to the outer edge 1342 can include an agonist, and the medicant "hidden" in the braid farther from the outer edge 1342 and closer to the adjunct's center can include an antagonist. Thus, as the fibers 1334 unwind or fray from the outer edge 1342 toward the adjunct's center, the agonist is first released from the adjunct 1340 and the antagonist is subsequently released from the adjunct 1340.

As shown, the adjunct 1340 can include a fourth type of fibers 1346, which can have a certain conformation that is not changeable, e.g., the fourth types of fibers 1346 can be configured to not unwind or fray. The non-changeable fourth type of fibers 1346 form a base of the adjunct 1340 so as to provide structural stability to the adjunct 1340 and, hence, to provide structural stability to a wound to which the adjunct 1340 is delivered.

Only a portion of the adjunct 1340 is shown at the outer edge 1342 thereof. An adjunct can include any combination of the types of fibers 1330, 1332, 1334, 1346 shown in FIG. 143.

In at least some implementations of an adjunct having an agonist and an antagonist disposed therein, the agonist can include first and second medicants each configured to encourage a physiological response, and the antagonist can include a third medicant configured to discourage the physiological response. The first medicant can be configured to begin releasing from the adjunct first among the first, second, and third medicants. The first medicant can be configured to start the physiological response, e.g., to trigger a start of the inflammation stage of wound healing.

The second medicant can be configured to begin releasing from the adjunct at a time after the first medicant has started releasing from the adjunct. The time can be either before the first medicant is fully released from the adjunct or after the first medicant has been fully released from the adjunct. The second medicant can be configured to reinforce and accelerate the physiological response. The start of the release of the second medicant from the adjunct can be based on the physiological response, such as a based on an intensity of the physiological response as indicated by pH. For example, the second medicant can be configured to begin releasing from the adjunct once the pH at the wound to which the adjunct has been delivered reaches a certain value that triggers breakdown of a coating or a polymer.

The third medicant can be configured to counter the effect of the physiological response. The start of the release of the third medicant from the adjunct can be based on the physiological response, such as a based on an intensity of the physiological response. In the case of the physiological response including inflammation, the third medicant can thus help discourage inflammation in proportion to the inflammation that actually occurred.

In an exemplary implementation, the adjunct having one or more agonists and one or more antagonists releasably disposed therein can be configured to be applied to tissue by a surgical stapler in conjunction with staples.

In some aspects of the present disclosure, an adjunct can include at least one medicant encapsulated in a plurality of vessels. The vessels can be formed from a bioabsorbable polymer that can degrade in accordance with its degradation rate and thereby control release of the at least one medicant from the vessel.

The vessels can have a variety of shapes and sizes, and they can include one or more layers. For example, the vessels can be in the form of micro beads or micro capsules, "gobstoppers," "clusterbombs," or in the form of other any structures. At least one medicant can be disposed within a vessel in a number of different ways. For example, the at least one medicant can be incorporated into one or more layers of a bioabsorbable polymer or it can be freely disposed within an outer shell of the vessel.

The adjunct can be in the form of a film or a buttress, or it can be a part of a composite structure. The vessels can be included in at least one reservoir formed in the adjunct. The adjunct can include any suitable number of similar or different reservoirs that can be disposed at different locations throughout the adjunct. The reservoir can include at least one bioabsorbable polymer that regulates dispersion of the vessels from that reservoir. The bioabsorbable polymer can be in the form of a coating disposed over a reservoir or in the form of any other structure preventing content of the reservoir from being released until the release is desired. A reservoir formed in an adjunct can releasably retain therein a plurality of vessels that, once dispersed or disassociated from the reservoir, can release at least one medicant incorporated therein. Furthermore, in some aspects, the at least one medicant can be released from the vessels while the vessels continue to be at least partially associated with the reservoir.

An adjunct can include at least one biocompatible polymer that can be disrupted in a number of ways to cause vessels retained within one or more reservoirs to be released or to release medicants contained therein. For example, a reservoir can include one or more coatings formed from a biocompatible polymer that can be disrupted to expose the content of the reservoir to the environment in which the adjunct is situated. The disruption can involve disintegration or absorption of the at least one polymer in accordance with its absorption rate, dissolution in accordance with its dissolution rate, mechanical breakage of the at least one polymer (e.g., when staplers or a tissue cutting instrument passes through at least a portion of the adjunct), or disintegration of the at least one polymer due to effects of temperature, pH, light, radiation, electrical stimuli, or other environmental factors.

Regardless of the specific way in which the at least one biocompatible polymer associated with the reservoir is disrupted, the disruption causes a plurality of vessels to be released from the adjunct and/or exposed to the environment in which the adjunct is situated. The vessels can be released from the reservoir as a bolus dose (e.g., all or substantially all vessels are released at once) such that the adjunct can be in the form of a so-called "clusterbomb." Alternatively, the vessels can be configured to be released from the reservoir as a time release dose that is a slower release of the vessels over a period of time. It should be appreciated that a reservoir can include vessels of different types, some of which can release as a bolus dose whereas others release as a time release dose.

Following the disruption of a coating or other structure maintaining the integrity of the reservoir, the vessels disposed in that reservoir become exposed to an external environment and commence to disintegrate. Thus, outer shells of vessels and/or bodies of the vessels can be disrupted by disintegration or absorption of at least one bioabsorbable polymer forming them, by applying strain to the vessels, or in any other manner. In this way, at least one medicant disposed in the vessel is released therefrom, which can occur as a bolus dose or time dose release.

Accordingly, various temporal and spatial patterns of release of the medicants from the adjunct can be provided by such two-step release in which vessels are first released from one or more reservoirs, which causes medicant(s) to be released from the vessels. In some implementations, these two processes can occur substantially simultaneously.

An example of an adjunct in a form of a carrier matrix (e.g., fiber lattice or film) including vessels (e.g., micro capsules or micro beads) incorporating at least one medicant therein is shown above in FIG. 9. In this example, the adjunct 108 includes at least one medicant encapsulated in a plurality of vessels that are releasably retained by respective reservoirs or regions that regulate the dispersion of the vessels from the adjunct. The at least one medicant can include a plurality of different medicants each disposed within a different one of the vessels. As shown in FIG. 9, the reservoirs or regions 109a, 111a, 113a, 109b, 111b retaining a plurality of respective vessels 110, 112, 114, 110, 112 are encapsulated by different coatings A1, B1, C1. As the coatings A1, B1, C1 are disrupted (e.g., by being bioabsorbed or dissolved, mechanically broken or otherwise disrupted) the contents of the regions 109a, 111a, 113a, 109b, 111b are released such that the vessels 110, 112, 114, 110, 112 are released to spread from a wound being treated with the adjunct 108.

In some implementation, the medicants retained within the vessels can be, for example, nutrient elements that attract and supplement processes performed by macrophages and fibroblasts. Thus, when the vessels are released from one or more reservoirs, the vessels release the medicants retained therein, thereby leaving a trail of nutrients along their distribution path. Other medicants can be released from the adjunct 108 as well. In this way, the adjunct 108 can be used to promote rebuilding of an extracellular matrix (ECM) and facilitate overall healing of a wound.

Other of the adjuncts described above, such as adjunct 100 in FIG. 6 can have vehicles disposed therein that are, in turn, disposed in different reservoirs that can be formed in different locations throughout the adjunct. Any number of reservoirs of any suitable type and size can be formed within an adjunct. Furthermore, as mentioned above, a reservoir can include vessels of the same or different types. For example, adjunct 171 in FIG. 30 has different types of vessels disposed therein which can include different medicants. In some implementations, as the vessels are ruptured (e.g., bioabsorbed or otherwise ruptured) in accordance with the degradation rates of their one or more layers, the retained medicants are released from the layers under control of the degradation rates.

The medicant-containing vessels retaining can have a number of different configurations. FIG. 144 illustrates an example of a vessel 1400 in the form of a pellet or capsule having an outer layer or shell 1402 and an inner portion 1404. In this example, the vessel 1400 has a spherical shape and resembles a gobstopper. However, it should be appreciated that the vessel can have any other shape. For example, the vessel can be oval, rectangular, square, or it can have any other regular or irregular shape. Also, the medicant-containing vessels can include two or more layers, some or all of which can releasably carry therein at least one medicant. For example, vessel 174 in FIG. 31 above has multiple layers each having at least one medicant encapsulated therein. The medicant can be configured to be released form the different layers in a homogeneous or non-homogeneous manner.

The outer shell 1402 can be solid such that, prior being exposed to an external environment, the outer shell 1402 remains solid. The outer shell 1402 and the inner portion 1404 can each be formed from a respective degradable (e.g., bioabsorbable or dissolvable) polymer. For example, the outer shell 1402 can be formed from a first polymer having a first degradation rate, and the inner portion 1404 can be formed from a second polymer having a second degradation rate that is slower than the first absorption rate. Thus, the outer shell 1402 can include a first medicant that can be configured to release therefrom before a second medicant included in the inner portion 1404 commences release. In this way, the first medicant can be delivered as a bolus dose and the second medicant can be delivered over a certain time period.

Although the inner portion 1404 of the vessel 1400 can include at least one polymer, in some aspects, the inner portion 1404 of can be in the form of a hollow cavity carrying at least one medicant. In such aspects, the outer shell 1402 formed from at least one degradable (e.g., bioabsorbable or dissolvable) polymer may or may not include a medicant. For example, the outer shell 1402 can be disrupted so as to release its content in the form of at least one medicant that can deliver an effective amount of a treatment as a bolus dose or as a time release dosage.

The vessel 1400 can have a number of different sizes. For example, a size of the vessel can be in a range of about 0.01 mm to 0.05 mm. A person skilled in the art will appreciate that vessels of different sizes and shapes, and carrying different medicants in different manners, can be releasably retained within the same reservoir.

FIG. 145, FIG. 146, and FIG. 147 illustrate an adjunct 1420 releasably retaining one or more medicants disposed within vessels and configured to release the medicants when one or more regions of the adjunct disintegrate. As shown, the adjunct 1420 has a body 1423 retaining at least one medicant 1424, a porous layer 1426 disposed over the body 1423, and an outer film layer 1428 disposed over the porous layer 1426 and acting as a protective layer maintaining the integrity of the content of the body 1423. In some implementations, the porous layer 1426 may not be present. The medicant 1424 can be in the form of pellets (e.g., solid micro-capsules or micro-beads or other vessels) releasably carrying one or more medicants.

In the example illustrated, the adjunct 1420 includes at least one bioabsorbable polymer that can disintegrate and release the medicant 1084 from the adjunct 1420. For example, the outer film layer 1428 can be formed from the bioabsorbable polymer and the body 1423 can include the same or different at least one absorbable polymer (e.g., gelatin, cellulose, or other polymer). The adjunct 1420 can change its configuration as the at least one bioabsorbable polymer disintegrates. For example, the adjunct can swell or otherwise change its conformation. As shown in FIG. 145, in an original configuration of the adjunct 1420, the outer film layer 1428 formed from the bioabsorbable polymer retains the medicant 1084 and other contents of the adjunct within the adjunct body 1423. If the porous layer 1426 is present, as in the illustrated example, the outer film layer 1428 can also restrain the porous layer 1426 such that the layer 1426 does not allow the medicant 1084 to escape the adjunct 1420. In the original configuration, the adjunct 1420 can have a first width X1, as shown in FIG. 145.

When the adjunct 1420 is delivered to tissue and the outer film layer 1428 is disrupted, the outer film layer 1428 can begin to disintegrate, as shown by a tear or opening 1430 in the outer film layer 1428 in FIG. 146. The at least one polymer forming the outer film layer 1428 can be disrupted by being bioabsorbed or dissolved, by being exposed to the external environment (e.g., pH, temperature, various agents, and/or other environmental conditions at the treatment site), by being subjected to strain due to deployment of staples or other strain on the adjunct 1420, or in other various manners.

The at least one polymer forming the outer film layer 1428 can be configured to be mechanically broken such that the disruption of the polymer includes the mechanical breaking. The at least one polymer forming the adjunct body 1423, which becomes exposed to the external environment, can also begin to disintegrate in a suitable manner.

Regardless of the specific factors that result in disruption of the outer film layer 1428, the medicant 1084 can be released from the adjunct 1420 to provide a desired effect on tissue in-growth. As shown in FIG. 146 and FIG. 147, upon rupture of the outer film layer 1428, the adjunct 1420 can swell or otherwise alter its conformation such that its width increases from the original width X1 to a larger width X2 (FIG. 146) and then to an even larger width X3 when the outer film layer 1428 and the body 1423 of the adjunct are substantially disintegrated (FIG. 147). The adjunct 1420 can be formed from at least one absorbable polymer that regulates dispersion of the vessels with the medicant 1084. In some aspects, as the material of the adjunct 1420 is released from the body 1423, it can act as a space filler that creates a temporary seal at a treatment site and is then dissolved to be subsequently replaced with new tissue. The medicant 1084 is released from the body 1423 to deliver appropriate therapy and can facilitate new tissue formation.

As discussed above, an adjunct having an effective amount of one or more medicants releasably retained therein can be delivered to tissue to provide a desired effect on tissue in-growth in a predetermined manner.

An adjunct in the form of a compliant adjunct carrier matrix that is releasably coupled with vessels (e.g., solid micro-capsules or micro-beads) encapsulating an effective amount of at least one medicant can be used for treatment of various wounds. In some aspects, the at least one medicant can be effective to induce tissue adhesions adjacent a line of deployed staples or in other manners. For example, the adjunct can be used to treat the thoracic cavity by inducing adhesions between the lung and the chest (rather than preventing them) at a treatment site. This can prevent air leaks which can create air pockets, leading to lung collapse. The portions or reservoirs of the adjunct can be disposed in the adjunct such that deployment of the staples from a cartridge body delivers the adjunct to lung tissue and causes coatings of the reservoirs to rupture which, in turn, causes release of at least one medicant retained in the reservoirs. When at least one coating of a reservoir is ruptured, its contents, including the medicant-containing vessels, are released. The at least one medicant can provide an effect of enhancement of the treatment that promotes adhesion formation adjacent the treatment site. An adjunct that can promote adhesion formation is further described in U.S. patent application Ser. No. 14/841,147 entitled "Inducing Tissue Adhesions Using Surgical Adjuncts And Medicants" filed on Aug. 31, 2015, which is hereby incorporated by reference in its entirety.

An adjunct in accordance with some implementations of the described techniques can be used for treatment of wounds in the thoracic cavity by delivering to a treatment site material(s) that can temporary replace, at least in part, resected lung tissue. In such implementations, one or more reservoirs of the adjunct can releasably retain therein at least one medicant and/or a space filler material, such as, for example, a gelatin, cellulose, or other polymer. In some cases, some reservoirs carry a space filler material and others carry at least one medicant, or one or more reservoirs can carry both the at least one medicant and the space filler material. Additionally or alternatively, the adjunct itself (e.g., a body of the adjunct) can be in the form of a reservoir formed at least in part from at least one space filler material such that, as the adjunct disintegrates and swells, it acts as a space filler.

When a reservoir releasably retaining therein a space filler material is ruptured (e.g., during staple line deployment to deliver the adjunct to a treatment site), the space filler material can be released. The released space filler material can swell and thereby fill in a space vacated by the resected lung tissue. At least one medicant contained within vessels (e.g., microcapsules) retained in the reservoir can also release and thus deliver desired therapy and promote tissue in-growth. The space filler material can create a temporary seal and one or more sites for new tissue to attach, and the filler material can be dissolved over time as it is replaced with appropriate tissue constructs.

Various exemplary adjunct materials for delivery to stomach tissue are described herein. In general, a biocompatible adjunct material is configured to be delivered to stomach tissue of a patient by deployment of the staples from a surgical stapler. The adjunct material is releasably retained on a cartridge body of a staple cartridge assembly and/or on a tissue-facing surface of a first or second jaw of an end effector. The adjunct material is configured to be delivered to stomach tissue by deployment of the staples in the cartridge body.

The adjunct material has a structure effective to cause a variety of desired reactions in the stomach tissue. For example, the desired reaction can include movement of the adjunct material from the external surface of the stomach tissue into the patient's stomach cavity. In one aspect, the desired reaction can include faster healing of the stapled stomach tissue. At least one medicant is disposed within and releasable from the adjunct material. The medicant is effective to encourage and/or reinforce the desired reaction in the stomach tissue. Because the stomach has the ability to erode substances quickly, the adjunct material is configured to cause desired reactions and include medicant(s) that induce erosion to accelerate the healing process in the stomach.

The adjunct material can have a variety of configurations, and can be formed from various materials as described above. For example, an adjunct material can be formed from one or more of a film, a foam, a fibrous structure, and hybrids thereof. In one aspect, the adjunct material can include a fiber or other structure with a film or foam disposed thereon.

The film can be formed from any suitable material or combination thereof, as discussed above. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

Non-limiting examples of foams include a closed-cell foam, an open-cell foam, or a sponge.

Non-limiting examples of fibrous structures include a fiber-based lattice which can be a woven fabric, knitted fabric or non-woven fabric such as a melt-blown, needle-punched or thermal-constructed loose woven fabric. An adjunct material can have multiple regions that can be formed from the same type of lattice or from different types of lattices that can together form the adjunct material in a number of different ways. For example, the fibers can be woven, braided, knitted, or otherwise interconnected so as to form a regular or irregular structure. The fibers can be interconnected such that the resulting adjunct is relatively loose. Alternatively, the adjunct material can include tightly interconnected fibers. The adjunct material can be in a form of a sheet, tube, spiral, or any other structure that can include compliant portions and/or more rigid, reinforcement portions. The adjunct material can be configured such that certain regions thereof can have more dense fibers while others have less dense fibers.

The adjunct materials described herein can be used in any surgery involving stomach tissue such as, for example, bariatric surgery. As used herein, bariatric surgery generally refers to a variety of procedures performed in a subject to achieve weight loss. For example, bariatric surgery refers to a surgical procedure to alter gastrointestinal structure or function so as to affect body weight, body composition, or energy balance regulation, or otherwise alter metabolic function. Some non-limiting examples can be any form of gastric bypass such as Roux-en-Y gastric bypass (RYGB), vertical sleeve gastrectomy, adjustable gastric banding, vertical banded gastroplasty, intragastric balloon therapy, gastric plication and other forms of gastric volume reduction (see also U.S. Pat. Pub. No. 2009/0024144, entitled "Hybrid Endoscopic/Laparoscopic Device For Forming Serosa To Serosa Plications In A Gastric Cavity," filed Jul. 18, 2007, which is hereby incorporated by reference in its entirety, Magenstrasse and Mill procedures involving an anastomotic connection of the gastrointestinal tract (e.g., jejunoileostomy, etc.), and variations of the procedures above and other methods known by those skilled in the art. In one implementation, the adjunct material can be used for a gastro-jejunostomy in a RYBG procedure. Also, see U.S. Pat. Pub. No. 2012/0318842, entitled "Tissue Stapler Having A Thickness Compensator Comprising Incorporating A Hemostatic Agent," filed Jun. 25, 2012, and hereby incorporated by reference in its entirety, for an example of staplers having a tissue thickness compensator that can be used in connection with the above procedures.

FIG. 148 illustrates an example of an adjunct material 1500 disposed on the small intestine 1502 outside an external surface of a stomach wall in connection with a gastric bypass procedure, such as a gastro-jejunostomy in a RYBG procedure. In this surgical procedure, the stomach cavity is divided into a small upper pouch 1506 and a larger lower pouch 1508 using a surgical stapling device, for example, to cut and deploy staples to form staple lines 1510 on either side of the cut. The small intestine 1502 is rearranged to connect to the upper pouch 1506 and bypass the lower pouch 1508. The adjunct material 1500 is deployed by staples forming staple line 1514. The jejunum 1516 and the duodenum 1518 are connected to create a side-to-side anastomosis 1520 through which the upper pouch 1506 and lower pouch 1508 can drain. A circular stapler can be used to deploy internal staples to form a staple line 1522 to secure the small intestine 1512 to the upper pouch 1506. The adjunct material 1500 can be applied with one or more of the staple lines 1510, 1514, 1522.

The adjunct material can be configured in various ways to induce erosion of the adjunct material after deployment of staples to stomach tissue so that the adjunct material moves from outside the stomach wall through the stomach wall and into the stomach cavity. Eroding the adjunct material in this manner accelerates the healing process in the stomach.

In one implementation, the adjunct material can be configured to apply a force or pressure to the stomach tissue to form an anastomosis such as, for example, between the stomach and the small intestine. The adjunct material thus can be configured to cause pressure induced necrosis so that the stomach can quickly heal by forming an anastomosis. An adjunct material including an expandable or swellable material that is deployed with staples can apply sufficient pressure to form the anastomosis. In one aspect, the swellable material can include, for example, a hydroscopic foam or a cross-linked polymer such as a hydrogel or other material that can absorb fluid such as water and thus swell upon contact with the fluid. In some aspects, the swellable material can be a dry substance, such as a lyophilized polymer or a powder, that is swellable upon delivery to the stomach tissue. The swellable material of the adjunct material can be configured to elute one or more medicants that promote the healing response necessary to seal the tissue adjacent to the regions with pressure induced necrosis.

FIG. 149 through FIG. 152 illustrate an example of the process of an adjunct material being deployed to stomach tissue, eroded into the tissue, and moved into the stomach cavity.

FIG. 149 is a cross-sectional side view of this example of an adjunct material 1530 deployed to an external surface 1532 of a wall of stomach tissue 1534 by a plurality of staples 1536. In some aspects, the adjunct material 1530 can be deployed with staples 1536 inserted through tissue of the small intestine and stomach tissue 1534. Thus, the adjunct material 1530 can be used in connection with any staples 1536 deployed in connection with a gastric surgery. The adjunct material 1530 in FIG. 2 can be configured to apply a force or pressure to stomach tissue 1534. For example, the adjunct material 1530 can be configured to expand or swell thereby causing pressure on the stomach tissue 1534. The adjunct material 1530 can include one or more of the swellable materials described above. Also, one or more medicants can be released from the adjunct material 1530 to create pressure on the wall of the stomach tissue 1534. The medicant can be, for example, any material that swells when in contact with fluid and thus applies pressure to the wall of the stomach tissue 1534. In one aspect, the medicant is ORC.

FIG. 150 represents the adjunct material 1530 of FIG. 149 at a period of time after staple deployment. The adjunct material 1530 is starting to absorb or erode into the wall of the stomach tissue 1534 due to the swellable materials in the adjunct material 1530 expanding and/or medicant(s) eluting from the adjunct material 1530.

FIG. 151 represents the adjunct material 1530 of FIG. 150 after an additional period of time. The adjunct material 1530 has eroded into the stomach tissue 1534 and has begun to move inside the stomach cavity 1538.

FIG. 152 represents the adjunct material 1530 of FIG. 151 after an additional period of time. In this figure, the adjunct material 1530 has eroded through the stomach tissue 1534 and into the stomach cavity 1538 where the adjunct material can be digested.

One or more medicants can be released at any desired time during the above process to further induce pressure on the stomach tissue or cause other desired effects. The same or different medicants can be released at different times. One or more medicants can have different release or absorption profiles as discussed above. For example, the medicant can dissolve or absorb into tissue upon delivery or be released over time. The medicant can be formulated in a number of ways as described above. The medicant can be placed in different areas of the adjunct material.

Non-limiting medicants include, for example, any medicants set forth above. For example, the one or more medicants can include, but are not limited to, drugs or other agents included within, or associated with, the adjunct material that is deployed to the stomach tissue. The medicants include, but are not limited to, for example, antimicrobial agents such as antibacterial and antibiotic agents, antifungal agents, antiviral agents, anti-inflammatory agents, growth factors, analgesics, anti-cancer agents, and other agents that elicit a biological response. For example, the medicant can be a drug, hemostat, or any other desired substance described above that elutes from the adjunct material after deployment to tissue.

As stated above, the adjunct material can be configured to cause a desired effect or response. In some aspects, the adjunct material can be in the form of a matrix that induces a healing response. In particular, the adjunct material can be configured to induce an inflammatory response as described above. By inducing the inflammatory response, the adjunct material can erode into the stomach tissue wall and move into the stomach cavity. One or more medicants can also be released from the adjunct material in a desired manner to encourage the inflammatory response and the erosion or any other desired effects that will accelerate the wound healing process, which is described above.

In one aspect, the adjunct material can be configured to cause an inflammatory response. For example, the adjunct material can be configured to induce encapsulation of bacteria and other irritants within the adjunct material, but prevent natural healing mechanisms, e.g., white blood cells, access to the bacteria, thereby encouraging an inflammatory response. In particular, the adjunct material can be formed of a material having a plurality of pores. In some aspects, the adjunct material can be in the form of a foam, a woven construct, or a plurality of fibers, each having a plurality of small pores therein. In an aspect, the pores are sufficiently small that white blood cells cannot enter to attack any bacteria or irritants encapsulated within the adjunct material. The pores can be in one implementation less than about 100 microns. With sufficiently small pores, the bacteria or other irritants can remain in the adjunct material for an extended period of time. The bacteria inside the adjunct material is essentially an infection that causes an inflammatory response in the body because the infection cannot be treated with white blood cells. In the inflammatory response, the stomach encapsulates the adjunct material including the bacteria and irritants contained therein and the adjunct material then erodes into the stomach wall and moves into the stomach cavity which can then digest the adjunct material, as shown in FIG. 149 through FIG. 152.

The adjunct material can include at least one medicant configured to have a delayed release. The adjunct material can be configured to delay the release of a medicant, such as an antibiotic, for an extended period of time, thereby allowing an aggressive immune response to enhance the rate of encapsulation of the adjunct material and healing of the tissue adjacent to the adjunct material.

In another aspect, the adjunct material can be configured to create an irritant response to the stomach wall. In one implementation, the adjunct material can have a surface with a texture that is capable of inducing an inflammatory response. At least a portion of the tissue-facing surface of the adjunct material can include the textured surface. The textured surface can be an abrasive textured surface. In one aspect, the adjunct material can be in the form of a film or include a film with an abrasive textured surface. The stapled adjunct material can be configured to aggressively abrade the stomach tissue wall. The stomach's natural peristaltic motions can enhance this effect. As the adjunct material is abraded, it begins to erode into the stomach wall tissue and move into the stomach cavity, as described above.

The adjunct material can include one or more medicants that induces inflammation to complement the irritant response caused by the textured surface. In some aspects, the adjunct material can be configured to elute pro-inflammatory medicants to accelerate the healing process. Non-limiting examples of pro-inflammatory medicants include interleukins such as IL-1a (which may activate TNF-a, stimulate fibroblast proliferation, activate lymphocytes, increase blood neutrophil count, stimulate expression of FGF and EGF, and increase collagen production), IL-1b (which may be produced by activated macrophages and may induce inflammation), IL-2 (which may induce proliferation of responsive T cells and act on some B cells as a growth factor), IL-3 (which may stimulate proliferation of granulocytes and monocytes and stimulate the differentiation of multipotent hematopoietic stem cells; similar to GM-CSF), IL-6 (which may act as a pro-inflammatory and anti-inflammatory important in growth and differentiation of B cells, production of neutrophils, and inflamation mediation during muscle contraction), IL-8 (which may cause neutrophils and other granulocytes to migrate towards an infection and induce phagocytosis when they arrive at site, may promote angiogenesis, and may promote colorectal cancer growth), IL-10 (which may inhibit synthesis of certain cytokines including IL-2, IL-3, TNF, and GM-CSF, and can be used in Crohn's disease patients to limit the effects of the disease), and IL-11 (which may increase production of platelets, activate osteoclasts, and inhibit epithelial cell proliferation and apoptosis) and any other substance that causes inflammation.

The adjunct material with a textured surface can have a number of variations. In one implementation, the abraded surface of the adjunct material can include an uneven surface such as, for example, macro-features similar to a coarse sandpaper. These textured surfaces can be in any pattern on at least a portion of the surface of the adjunct material. The textured surface can be in a distinct pattern with repeatable geometry such as micro-needles. For examples of such patterns, see U.S. Pat. Pub. No. 2013/0146643 entitled "Adhesive Film Laminate" and filed Feb. 8, 2013, which is hereby incorporated by reference in its entirety. The uneven surface of the adjunct material can be configured to erode as it is moved against the stomach tissue, much like sandpaper as it is used.

In another aspect, a drying agent can be applied to the adjunct material to induce an irritant response or other desired reaction. The drying agent can be, for example, talc or any other material that can absorb water or other liquid. In one aspect, the drying agent can be applied as a film on the adjunct material. A drying agent can be used to induce adhesions by reducing the lubrication between the tissue and the adjunct material.

In another aspect, an adjunct material can be configured to have pores that are sufficiently small to prevent tissue ingrowth during the early phases of degradation. The adjunct material can be made from a variety of materials and have a variety of configurations to accomplish this effect. The adjunct material can include, for example, a polymeric or matrix structure in the form of a foam or fibrous material. The adjunct material can have any desired degradation profile. For example, the degradation profile can be selected such that by the time the mechanical structure of the adjunct material sufficiently breaks down to allow stomach tissue in-growth, the amount of acids created from hydrolysis in the stomach is sufficiently high to create a significant inflammatory response.

The adjunct material can elute one or more medicants to enhance or exaggerate the inflammatory response of the adjunct material having the small pores preventing tissue in-growth. The medicants can accelerate the passing of the adjunct material through the stomach wall and into the stomach cavity. For example, the medicant can include any pro-inflammatory agent or other materials that can augment the inflammatory response.

In one aspect, the adjunct material configured to have pores that are sufficiently small to prevent tissue ingrowth can include a high molecular weight (e.g., in a range of about 80,000 g/mol to 200,000 g/mol) polymer such as PGA/PCL. The polymer is sufficiently large to degrade quickly which results in a large bolus of acid that creates an inflammatory response. In other words, the sufficiently small pore size in the adjunct material prevents macrophages from entering the adjunct material and degrading the large polymer, thereby resulting in a higher concentration of acid and the bulk degradation of the polymer.

The adjunct materials described herein can have any combination of the configurations, materials.

Various exemplary surgical adjuncts and medicants for promoting lung function are described herein. In general, an implantable adjunct can have one or more medicants releasably retained therein that are configured to promote lung function. The adjunct can be configured to be applied to lung tissue in conjunction with surgical staples using a surgical stapler, as discussed herein. When a lung is stapled during a surgical procedure, the lung is typically in a deflated or collapsed state, as will be appreciated by a person skilled in the art. After the stapling, the lung is inflated to facilitate the lung's return to normal expansion/contraction function during patient breathing. However, the staples may hinder the inflation and the expansion/contraction of the lung. In particular, the staples can cause significant tissue compression. Any lung tissue that is immediately adjacent to a staple line defined by the staples can experience significant compression that limits inflation and expansion/contraction while lung tissue that is farther away from the staple line can more normally transition from compression (e.g., from the collapsed or deflated state) to normal homeostatic levels.

Lung tissue can experience a much greater area of compression due to the stapling than other types of tissue to which staples are applied because lung tissue is naturally expansive and extensible. Thus, any problems caused by compression of tissue, such as issues with proper tissue cell functions, can be exacerbated when lung tissue is compressed by stapling. For example, alveoli cells in lung tissue are responsible for oxygen transportation and oxygen/carbon dioxide exchange. The alveoli cells require the ability to expand to properly function. Compression of the lung tissue can cause the alveoli cells to at least temporarily be unable to expand properly, which can lead to a variety of problems. For instance, the alveoli cells have natural mechanisms to treat and effectively eradicate contaminants in the lungs. However, when the functionality of the alveoli cells is damaged by compression of the lung tissue, infections can occur in the lungs. Infection can cause a fluid build-up in the lung tissue, which in turn can further reduce lung function. Thus a cycle can occur of decreased lung function and infection, which can prolong or even prevent the lung tissue from healing after stapling of the lung tissue and/or can cause other problems, including complete lung failure and death.

The at least one medicant disposed within and releasable from the adjunct can be configured to promote lung function, which may help reduce, if not eliminate, any one or more of the adverse effects of compressed lung tissue to which the adjunct is applied. The adjunct including the one or more medicants may thus help encourage proper lung function after surgical stapling of the lung. The one or more medicants can be configured to promote lung function in a variety of ways. For example, the one or more medicants can be effective to increase oxygen concentration. The one or more medicants may thus encourage oxygen flow in the lung, e.g., in the lung's alveoli, which are responsible for oxygen transport and require expansion for proper functionality. The lung's compression and reduced oxygen flow caused by stapling may thus be counteracted with an increase in oxygen concentration caused by the one or more medicants. The increase in oxygen concentration may be directed along the staple line because, as discussed herein, the adjunct can be applied to the lung tissue with the staples such that the one or more medicants can be released from the adjunct along the staple line. The one or more medicants can be effective to increase oxygen concentration of any blood in any one or more ways, such as by being effective to promote elastic deposition, by being effective to promote elastin release, and/or by being effective to promote separation of alveoli by promoting presence of surfactant at the alveoli that is adjacent to the staple(s). Examples of medicants configured to be effective to increase oxygen concentration includes expectorants, euritics, bronchodilators (e.g., medicants configured to dilate a lung's bronchi and bronchiole), immunosuppressants, antihistamines, and corticosteroids.

For another example of the one or more medicants being configured to promote lung function, the at least one medicant can be configured to treat contaminants in lung tissue, which may help to alleviate compromised functionality of alveoli cells in the lung tissue and thereby allow the lung tissue to return to normal homeostatic levels more rapidly after stapling of the lung tissue. The one or more medicants can thus be configured to target alveoli function by treating contamination of the alveoli, which contain non-sterile air. Examples of such medicants include antimicrobial agents and immunosuppressants.

In addition to being configured to promote lung function, the one or more medicants can be configured to facilitate one or more aspects of wound healing, e.g., encourage hemostasis, encourage tissue growth, etc., and/or to induce tissue adhesions. The one or more medicants can thus be configured to facilitate healing of the wounded lung, e.g., the healing of the stapled lung tissue, and/or to induce tissue adhesions. Adjuncts and medicants configured to induce tissue adhesions are described further in U.S. patent application Ser. No. 14/841,147 entitled "Inducing Tissue Adhesions Using Surgical Adjuncts And Medicants" filed on Aug. 31, 2015, which is incorporated by reference in its entirety.

The adjunct including the at least one medicant configured to promote lung function can be configured in a variety of ways, as discussed herein, such as by including a fiber-based lattice, a foam, and/or a film. As discussed above, the at least one medicant releasably retained by the adjunct can be configured to be release according to any of a variety of temporal patterns, such as by being a bolus dose or a time release dose, and to any of a variety of spatial patterns. The one or more medicants can be releasably retained by the adjunct in a variety of ways, as discussed above, such as by being coated thereon, included in one or more vessels coupled thereto, etc.

Although a variety of temporal patterns can be used for the one or more medicants configured to promote lung function, the one or more medicants including bronchodilators and/or corticosteroids can be configured to be released as a time release dosage, which may facilitate a more long term treatment of the lung. In other words, the time release dosage may help improve lung function over the long term since the bronchodilators and/or corticosteroids can be released over time to improve lung function over the long term as opposed to being released all at once in a bolus dose, which may provide a burst of improved lung function instead of the more long term treatment of a time release dosage.

A patient having implanted therein an adjunct including one or more medicants configured to promote lung function can be prescribed one or more medications, e.g., orally taken pills, that are configured to promote lung function. These medications can further help improve the patient's lung function after the surgical procedure involving the surgical stapling and delivery of the adjunct to the lung.

FIG. 153 illustrates one implementation of an adjunct 1600 having at least one medicant 1608 releasably retained therein and configured to promote lung function. In general, the adjunct 1600 has multiple layers including a barrier layer 1604 disposed between a conformable layer 1606 and a reinforcing layer 1602. The conformable layer 1606 can be formed of a material configured to conform to an irregular surface and to be viscous and flowable. As shown, the at least one medicant 1608 can be disposed in the conformable layer 1606. The adjunct 1600 including the conformable layer 1606 may thus be particularly well suited for delivery to lung tissue, which as mentioned above is naturally expansive and extensible. Implementations of adjuncts including multiple layers are further described in U.S. patent application Ser. No. 14/840,527 entitled "Composite Adjunct Materials For Delivering Medicants" filed on Aug. 31, 2015, which is hereby incorporated by reference in its entirety.

FIG. 154 shows the adjunct material 1600 secured to an exterior surface of lung tissue 1610 with a staple 1620. The conformable layer 1606 is compressed by pressure from the staple 1620. Only one staple 1620 is shown for ease of illustration. A plurality of the staples 1620 would typically be used to secure the adjunct 1600 to the tissue 1610. As shown, the at least one medicant 1608 is not eluting out of the conformable layer 1606 and into the reinforcing layer 1602 due to the barrier layer 1604. The medicant 1608 is, however, eluting laterally away from a crown 1622 of the staple 1620. The lateral elution of the at least one medicant 1608 may help the at least one medicant 1608 promote lung function near the area of wounding, e.g., near the staple 1620, and, similarly, near the plurality of staples attaching the adjunct 1600 to the tissue 1620. When stapling a lung, leakage is traditionally greatest along an outside edge of the lung. The lateral elution of the at least one medicant 1608 may help the at least one medicant 1608 approach and/or seep over the outside edge of the lung that includes the lung tissue 1610 and thereby help address leakage at the lung's edge, e.g., by the one or more medicants 1608 including one or more hemostatic agents configured to facilitate sealing.

As mentioned above, the time release rate of the at least medicant 1608 from the adjunct 1600 can be different in different implementations. For example, the conformable layer 1606 can be varied (e.g., varied between implementations to be formed of different materials, to have different rates of disintegration, etc.) to allow for a selectable rate of release of the at least one medicant 1608. For example, the conformable layer 1606 can vary from rapid dissolving, allowing the at least one medicant 1608 to be rapidly released from the adjunct 1600, to slow dissolving, allowing the at least one medicant 1608 to be slowly released from the adjunct 1600. As also mentioned above, a slow time release rate may be particularly useful for medicants configured to promote lung function in order to promote the lung function over a longer period of time than may be achieved with a bolus dose or if released at a faster release rate.

FIG. 155 and FIG. 156 illustrate another implementation of an adjunct 1660 with one or more medicants (not labeled in FIG. 155 or FIG. 156) releasably retained therein and configured to promote lung function. FIG. 155 shows the adjunct 1660 applied to a lung 1640 in a deflated or collapsed state, and FIG. 156 shows the adjunct 1660 applied to the lung 1640 in an inflated or expanded state. For comparison purposes, FIG. 155 shows a traditional adjunct 1650 not including any medicants configured to promote lung function applied to a lung 1642 in a deflated or collapsed state, and FIG. 156 shows the traditional adjunct 1650 applied to the lung 1642 in an inflated or expanded state. With the lungs 1640, 1642 in the deflated state, as shown in FIG. 155, the lungs 1640, 1642 where the adjuncts 1650, 1660 are applied each have a width x. With the lungs 1640, 1642 in the inflated state, as shown in FIG. 156, the lung 1640 having the adjunct 1660 applied thereto has a width at a location of the adjunct 1660, e.g., at the staple line on the lung 1640, that is greater than the width x. The adjunct 1660 also expands to this greater width. Conversely, the lung 1642 having the traditional adjunct 1650 applied thereto is constricted at the staple line on the lung 1642 and the traditional adjunct 1650 remains at the width x at the staple line on the lung 1642. The lung 1640 having the adjunct 1660 applied thereto can thus expand better than the lung 1642 having the traditional adjunct 1650 applied thereto and may thus have improved lung function. This increased expansion of the lung 1640 at the staple line may be facilitated by the medicant(s) configured to promote lung function. The adjunct 1660 can be configured to facilitate formation of a flexible staple line that helps the lung 1642 expand by the adjunct 1660 also expanding, such as by the adjunct 1660 being formed from a flexible material. Adjuncts configured to facilitate formation of a flexible staple line are further described in U.S. patent application Ser. No. 14/498,145 entitled "Method For Creating A Staple Line" filed on Sep. 26, 2014, which is hereby incorporated by reference in its entirety.

Various exemplary adjunct materials for delivery to colon tissue are described herein. In general, a biocompatible adjunct material can be configured to be applied to colon tissue by deployment of staples from a surgical stapler.

During a surgical procedure on the colon, a surgical stapling device can be used to transect the colon and deploy a line of staples. During this procedure, the surgeon must cut the mesentery to access the colon. FIG. 157 is a schematic representation of a portion of the mesentery 1700 attached to a portion of the colon tissue 1702. FIG. 158 is a representation of the mesentery 1700. The mesentery is tissue that is outside the colon, as shown in FIG. 157, and contains the primary blood supply to the colon. This blood supply is necessary to heal the colon tissue along a staple line and the adjacent area. Cutting the mesentery prevents blood flow to the colon (i.e., ischemia). Ischemia may cause leaks in the intestinal anastomosis which can be potentially life-threatening. Thus, quickly regrowing blood vessels to restore blood supply in the treatment area of the colon and the region adjacent thereto (i.e., within inches) is necessary.

The adjunct material described herein is particularly well suited to be applied to colon tissue to encourage a variety of desired effects on blood vessels including, for example, preventing ischemia and leaks, promoting angiogenesis, healing in the vicinity of the anastomosis, and vasodilation, or any combination of these effects. An adjunct material having one or more medicants releasably retained therein for delivery to the colon tissue at the anastomosis wound site can be configured to have one or more of these effects.

The adjunct material can be delivered to the colon tissue using a surgical instrument such as a surgical stapling device, including those devices discussed above. In one aspect, the surgical stapler includes a staple cartridge assembly that includes a cartridge body having a plurality of staple cavities, each containing a staple. In another aspect, the surgical instrument includes an end effector having a first jaw and a second jaw, where at least one of the first and second jaws is movable relative to the other. A cartridge body can be removably attached to the first jaw and has a tissue-facing surface with a plurality of staple cavities configured to seat staples therein. The second jaw can have an anvil with a plurality of staple forming cavities formed on a tissue-facing surface thereof.

The adjunct material can be releasably retained on the cartridge body of a staple cartridge assembly and/or on a tissue-facing surface of a first or second jaw of an end effector. The adjunct material is configured to be delivered to colon tissue by deployment of the staples in the cartridge body to form at least one line of deployed staples. The medicant is disposed within and releasable from the adjunct material, and is effective to encourage a desired effect on blood vessels along the at least one line of deployed staples.

The adjunct material can be configured in various ways. In some aspects, the adjunct material includes a first portion and a second portion. These portions can have the same or different configurations. The first portion and the second portion of the adjunct material can have any number of configurations such as, for example, at least one of a fiber and a film or any other material or structure described above. In one aspect, the first portion includes at least one of a buttress and a film, and the second portion includes a plurality of fibers releasably attached to one another. In another aspect, the second portion can be configured to detach from the first portion following deployment of the staples.

The first portion and the second portion can be made from any materials. The materials of the first portion and the second portion can include, for example, bioabsorbable and biocompatible polymers, such as homopolymers and copolymers. Non-limiting examples of homopolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA). Non-limiting examples of copolymers include poly(glycolic acid-co-lactic acid) (PLA/PGA) (e.g., PLA/PGA materials used in Vicryl, Vicryl Rapide, PolySorb, and Biofix), polyurethanes such as Elastane, Biospan, Tecoflex, Bionate, and Pellethane fibers, polyorthoesters, polyanhydrides (e.g., Gliadel and Biodel polymers), polyoxaesters, polyesteramides, tyrosine-based polyesteramides. The copolymers can also include poly(lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima). In one aspect, the first portion can be formed of a material having a higher molecular weight than a material that forms the second portion. For example, the first portion can have a molecular weight in a range of about 80,000 g/mol to 100,000 g/mol, and the second portion can have a molecular weight in a range of about 10,000 g/mol to 20,000 g/mol. The second portion can have a size of #4-0 (in suture size parlance) or smaller, such as in a range of #8-0 to #6-0.

In one aspect, the first portion and the second portion of the adjunct material includes fibers. The fibers can be configured in a number of ways.

In one implementation, the first portion and the second portion can include a plurality of longitudinal fibers. At least some of the longitudinal fibers can be configured to detach from the other fibers that remain stapled to colon tissue. In this way, the detached fibers can migrate relative to the colon tissue or extend to nearby tissue of the mesentery while other fibers remain stapled to the colon tissue.

FIG. 159 is a plan view of an example of an adjunct material 1710 secured to colon tissue 1702 by deployment of a plurality of staples 1712 and having a first portion and a second portion. The first portion includes a first plurality of longitudinal fibers 1714. The second portion includes a second plurality of longitudinal fibers 1716 extending transversely to the first plurality of longitudinal fibers 1714. As shown, the staples 1712 extend substantially parallel to the first plurality of longitudinal fibers 1714. In some aspects, the second plurality of longitudinal fibers 1716 can be configured to detach from the first plurality of longitudinal fibers 1714 following the deployment of the staples 1712. The detached longitudinal fibers 1718 of the second plurality of longitudinal fibers 1716 can migrate relative to the colon tissue 1702 while the first plurality of longitudinal fibers 1714 remain stapled to the colon tissue 1702. As shown in FIG. 159, the portions of the second plurality of longitudinal fibers 1716 that have detached are generally short detached longitudinal fibers 1718. These detached longitudinal fibers 1718 can migrate to target tissue such as nearby colon tissue or mesentery tissue. At least some of the ends of the longitudinal fibers 1720 that remain stapled to the colon tissue can fan out due to movement in the tissue such as by peristalsis. In this manner, these fibers 1720 also can extend to nearby tissue.

Fibers may be transported due to the movement of the intestines resulting from peristalsis. Thus, the mobility of the fibers can allow medicants to be delivered to adjacent structures.

In one aspect, the adjunct material includes fibers configured to form a quick absorbing material. This material can include any material that absorbs into tissue upon deployment of the staples such as, for example, any bioabsorbable material set forth above. The fibers can include a first plurality of longitudinal fibers 1714 shown in FIG. 159 that are anchored by the deployed staples 1712. The fibers can also include a second plurality of longitudinal fibers 1716 that includes an absorbable material. The second plurality of longitudinal fibers 1716 thus quickly absorb after deployment of the staples, thereby allowing the anchored first plurality of longitudinal fibers 1714 to unravel. The fibers 1720 fan out to the adjacent tissue and the mesentery and can deliver one or more medicants to the tissue. For example, the fibers 1720 can deliver medicant(s) that promote angiogenesis and/or healing and/or medicant(s) that prevent adhesion and stricture formation.

In another aspect, the adjunct material can include fibers configured to form a rapidly degradable material. The adjunct material can include a polymeric matrix that becomes fluidic and/or breaks into small particles. For example, the fibers can be in the form of a woven construct that is able to unravel and/or break away. FIG. 159 shows an example of such fibers. In particular, as explained above, unattached ends of anchored fibers 1720 can fan out to nearby tissue. Also, detached longitudinal fibers 1718 can migrate to nearby tissue because these fibers are not anchored to the staple line and therefore mobile. The fibers in this aspect can contain medicants to promote angiogenesis and/or healing or prevents adhesion or stricture formation. The detached or unraveled fibers can deliver medicants to adjacent or nearby tissue. Medicants can include any medicant described above including, for example, an anti-adhesion agent that prevent adhesions and/or an agent that prevents stricture formation.

The adjunct materials described herein can releasably retain therein at least one medicant, or drug, that can be selected from a large number of different medicants. Medicants include, but are not limited to, drugs or other agents included within, or associated with, the adjunct material that has a desired functionality. The medicants include, but are not limited to, for example, antimicrobial agents such as antibacterial and antibiotic agents, antifungal agents, antiviral agents, anti-inflammatory agents, growth factors, analgesics, anti-cancer agents (inhibitors of the angiogenic agents have been used as anti-cancer agents, for example inhibiting VEGF in cancer cases can be beneficial), and other agents that elicit a biological response. Examples of these medicants are set forth above. In some aspects, the adjunct material can include one or more medicants to promote blood flow and tissue growth such as, for example, vasodilators such as epinephrine, histamine, prostacyclin, sodium nitroprusside, and glyceryl trinitrate, or agents to promote angiogenesis and/or vasculogenesis such as angiopoietin-1, vascular endothelial growth factor, relaxin, and fibroblast growth factor. Some agents can work in conjunction with one another. For example, angiopoietin-2 alone does not encourage angiogenesis, but along with VEGF will promote angiogenesis. In other aspects, the adjunct material can include one or more medicants that prevent adhesion and stricture formation. Exemplary anti-adhesion agents include Hyaluronic acid/Carboxymethyl cellulose (Seprafilm), Oxidized Regenerated Cellulose (Interceed), and Icodextrin 4% (Extraneal, Adept).

One or more medicants can be delivered via the fibers or microcapsules described above to treat certain patient populations or to treat other conditions.

In one implementation, the medicant is selected to treat diabetic patients. In diabetic patients, surgical procedures involving the colon can result in reduced erythrocyte flexibility, hardened arteries (atherosclerosis), thickened capillary walls, and nerve damage. A suitable medicant includes substances that increase flexibility of red blood cells, which promotes healing and improves perfusion. For example, the medicant can include pentoxifylline (Trental) or any other medicant that can improve the flow of blood through blood vessels, such as sildenafil and glyceryl trinitrate. Alternatively or in addition, a medicant such as NGF (nerve growth factor) can be released within the adjunct material to protect nerves and promote repair/regeneration of new nerves in areas with poor perfusion.

In another implementation, the medicant can be selected to treat or prevent a number of conditions. For example, the medicant can be selected to prevent hypoxia. Non-limiting examples of such medicants include nitrates such as glyceryl trinitrate, isosorbide dinitrate, and isosorbide mononitrate, or any other medicant that can increase the amount of oxygen reaching the colon tissue. In one aspect, to prevent hypoxia, one or more nitrates can be embedded in microcapsules or within a hydrogel. Degradation releases the nitrates which are converted to nitric oxide in vivo, thereby resulting in vasodilation. The medicant can be a bolus release dose or a time-release dosage form. Alternatively or in addition, medicants such as angiopoietin-1 (ANG-1) and vascular endothelial growth factor (VEGF) can be embedded in a degradable polymeric matrix or in microcapsules to increase vascularization.

The adjunct material can include one or more medicants in a variety of forms. In one aspect, the adjunct material includes pellets or microcapsules containing a medicant such as an angiogenic compound. As the adjunct material degrades, the microcapsules can be released to nearby tissue due to the mobility of the intestines and peristalsis.

FIG. 6 through FIG. 17 show various examples of ways to deliver such microcapsules to colon tissue. Any of the mechanisms described above can be used to deliver one or more medicants, such as angiogenic compounds, to colon tissue by deployment of staples.

As explained above, FIG. 6 through FIG. 8 illustrate a biocompatible adjunct material having multiple pores carrying different medicants that are encapsulated within the pores disposed at different locations and using different absorbable coatings.

In some aspects, an adjunct can include regions (e.g., pores or other reservoirs) releasably retaining a plurality of vessels, such as micro beads or other vessels, that have one or more medicants encapsulated therein. FIG. 9 through FIG. 11 illustrate an adjunct material including at least one medicant encapsulated in a plurality of vessels that are releasably retained by respective regions that regulate the dispersion of the vessels from the adjunct material. The vessels can be micro capsules, micro beads, or any other types of vessels of a suitable size and shape.

In one aspect, an adjunct material has a first (top) and second (bottom) layers formed from absorbable polymers having different degradation rates, as shown in FIG. 7 through FIG. 9 [of the drug release section].

In some aspects, an adjunct material releasably retaining one or more medicants can be configured such that one or more regions of the adjunct material disintegrate due to effects of temperature, pH, light, or other environmental factors so as to release the medicant(s), as shown in FIG. 15 through FIG. 17.

In one implementation, the adjunct material can have a plurality of reservoirs formed therein. Each of the reservoirs can be sealed with at least one coating on the adjunct material. Each of the reservoirs can have at least some of the at least one medicant disposed therein. The at least one coating can be configured to disintegrate to allow release of the at least one medicant from the reservoirs.

In one aspect, a method of using a staple cartridge assembly or an end effector as described above to apply the adjunct materials described herein to colon tissue is provided. The method includes in one implementation removably attaching the cartridge body to a surgical stapler. The method further can include positioning the stapler at a target location adjacent colon tissue. With the stapler positioned at the target location, the stapler can be actuated to deploy the staples from the cartridge body and deliver the adjunct material to the colon tissue.

Various exemplary adjunct materials for delivery to liver tissue are described herein. In general, a biocompatible adjunct material can be configured to be applied to liver tissue by a surgical stapler in conjunction with staples.

As a result of the pressure applied to the liver during the use of a surgical stapler during a surgical procedure affecting the liver, the wall of the liver can shear or tear away and crack or fracture. Such results can cause excessive bleeding along the staple line and even at locations remote from the staple line. Hemostasis is thus necessary in the regions sheared or cracked surfaces. If a scab is formed on the liver, then the liver can regrow. However, the liver has a high level of vascularity and it is not pressurized. As a result, clot formation in liver tissue can be a challenge and it is thus difficult to seal the cracks and fractures within the liver.

The adjunct material described herein is particularly well suited to be applied to liver tissue as it can seal and fill cracks in the damaged tissue and/or apply pressure to stop bleeding. In one aspect, the adjunct material is configured to include an effective amount of one or more medicants, such as a hemostatic agent or a tissue healing agent, disposed within and releasable from the adjunct material for delivery to the liver tissue. Alternatively or additionally, the adjunct material is configured to expand upon delivery to apply pressure to liver tissue to facilitate sealing of one or more fractures in the liver tissue. In one aspect, the adjunct material is in the form of a matrix with zones for reinforcement that create edge conditions capable of preventing viscous motions of constituents within the liver, cracking or fractures of the liver wall, and bleeding.

The adjunct material can be delivered to the liver tissue using a surgical instrument such as a surgical stapling devices including those discussed above. In one aspect, the surgical stapler includes a staple cartridge assembly that includes a cartridge body having a plurality of staple cavities, each containing a staple. In another aspect, the surgical instrument includes an end effector having a first jaw and a second jaw, where at least one of the first and second jaws is movable relative to the other. A cartridge body is removably attached to the first jaw and has a tissue-facing surface with a plurality of staple cavities configured to seat staples therein. The second jaw can have an anvil with a plurality of staple forming cavities formed on a tissue-facing surface thereof.

The adjunct material can be releasably retained in an unexpanded configuration on the cartridge body of a staple cartridge assembly or on a tissue-facing surface of a first or second jaw of an end effector. The adjunct material is configured to be delivered to liver tissue by deployment of the staples in the cartridge body.

The adjunct material can have various configurations. In one aspect, the adjunct material is expandable after staple deployment to extend beyond a staple line and deliver one or more medicants to damaged liver tissue.

In one aspect, the adjunct material is configured for delivery to liver tissue in an unexpanded or collapsed configuration and transitions to an expanded configuration after deployment of the staples to the liver tissue.

The adjunct material can be configured in any number of ways to have an unexpanded configuration and expanded configuration that will extend the adjunct material in a direction away from the staple line. For example, the adjunct material can be folded or rolled in the unexpanded configuration and can be correspondingly unfolded or unrolled in the expanded configuration after delivery to liver tissue. The adjunct material can be folded or rolled one or more times when in the unexpanded configuration.

During staple deployment, the adjunct material can be placed in any desired position on the liver tissue wall. When first applied to the liver tissue, the adjunct material wall can be positioned along a staple line in the liver tissue. In one aspect, the adjunct material can also have a portion positioned adjacent to the deployed staples that define a staple line. The adjunct material, in another aspect, may not extend appreciably beyond the length of the staple line when first deployed to the liver tissue.

When transitioning to an expanded configuration, the adjunct material will unfold or unroll so that a portion of the adjunct material can be deployed at a position remote from the staple line, such as in the form of a wing-like structure. In some aspects, the adjunct material can be applied along the staple line and beyond the staple line in the folded or rolled state and then expand further beyond the staple line when unfolded or unrolled. The adjunct material thus can expand a distance from the staple line to cover portions of liver tissue that have been sheared away, cracked, or fractured and that give rise to bleeding.

The adjunct material can be made of any number of materials including those described above. For example, the adjunct material can be made of a woven material. In one implementation, the adjunct material can include a plurality of reinforcement fibers that define zones therebetween in which a swellable absorbable material can be disposed. The plurality of fibers can be compressed in the unexpanded configuration and can be lengthened in the expanded configuration.

In one example, the expandable adjunct material can include a swellable absorbable material for delivery of one or more medicants. The swellable absorbable material can be configured to facilitate transitioning of the adjunct material from the unexpanded configuration to the expanded configuration. For example, the swellable absorbable material can swell when in contact with fluids in the tissue and thus transition to the expanded configuration. For another example, the swellable absorbable material can include one or more shape memory biomaterial, such as sulfated glycose based polyurethane/ureas. A number of swellable absorbable materials can be included in the adjunct materials described herein. Non-limiting examples of swellable absorbable materials include a cross-linked polymeric material such as a hydrogel or other material that can absorb fluid such as water and thus swell upon contact with the fluid. Other non-limiting examples include network alginate biomaterials and galactose based polyacrylates (and other hydrophilic co-polymer hydrogels).

As stated above, one or more medicants can be disposed within and releasable from the adjunct material. The medicants can vary in any number of ways including those described above. For example, the medicants can have any desired release profile, concentration, or absorption rate. The medicants can have different properties at different locations in the adjunct material. The same or different medicants can be placed at different locations with different properties. For example, the wings (i.e., expanded or unfolded regions) of the adjunct material can have a different medicant or the same medicant with different properties than a medicant in the portion of the adjunct material that is placed along the staple line. The adjunct material can be configured to release the same or different medicants at various times during or after delivery of the adjunct material to the liver tissue.

The medicant can be selected from a large number of different medicants. Medicants can include, but are not limited to, drugs or other agents included within, or associated with, the adjunct material that have a desired functionality. The medicants include, but are not limited to, for example, antimicrobial agents such as antibacterial and antibiotic agents, antifungal agents, antiviral agents, anti-inflammatory agents, growth factors, analgesics, anti-cancer agents, and other agents that elicit a biological response. In one aspect, the medicant can include at least one of a hemostatic agent and a tissue healing agent.

The hemostatic agent can be any medicant that facilitates hemostasis. The administration of the hemostatic agent may thus help stop bleeding and help shorten a length of the hemostasis stage and, accordingly, help the inflammation stage begin sooner than in a typical wound healing process, as described above. Non-limiting examples of hemostatic agents include cellulose such as Oxidized Regenerated Cellulose (ORC) (e.g., Surgicel and Interceed), fibrin and thrombin (e.g., Thrombin-JMI, TachoSil, Tiseel, Floseal, Evicel, TachoComb, Vivostat, and Everrast), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutaraldehyde, human serum albumin and polyethylene having a cross-linking component, and ethylene glycol and trimethylene carbonate. In one aspect, the polymeric sealant is FocalSeal surgical sealant developed by Focal Inc. The hemostatic agent can include a collagen scaffold or matrix. An example of how such a scaffold or matrix can be fabricated is from animal derived collagen, such as porcine tendon, that can then be processed and lyophilized into a foam structure. Examples of hemostatic agents configured to promote hemostasis and delivery thereof are also described in previously mentioned U.S. Pat. Pub. No. 2013/0149343, entitled "Hemostatic Bioabsorbable Device with Polyethylene Glycol Binder" filed Dec. 13, 2011, U.S. Pat. No. 8,383,147 entitled "Reinforced Absorbable Synthetic Matrix For Hemostatic Applications" filed Aug. 22, 2012, and U.S. Pat. No. 8,329,211 entitled "Reinforced Absorbable Multi-Layered Fabric For Hemostatic Applications" filed May 17, 2010.

The tissue healing agent can be any material that can act to promote healing of the liver tissue damaged by the surgical procedure and/or the stapling process. Non-limiting examples of tissue healing agents include, for example, antimicrobial agents (such as antibacterial and antibiotic agents), antifungal agents, antiviral agents, anti-inflammatory agents, growth factors, analgesics, anti-cancer agents, and other agents that elicit a biological response, including those set forth above.

FIG. 160 and FIG. 161 show an example of an expandable adjunct material 1800a,1800b applied to liver tissue for delivering one or more medicants. The adjunct material can have a porous structure containing a swellable medium therein.

FIG. 160 is a cross-sectional side view of an adjunct material 1800a, 1800b applied to liver tissue 1802 by deployment of staples 1804 that form a staple line 1806. The staples 1804 hold a portion of the adjunct material 1800a, 1800b in contact with the surface of the liver tissue 1802 while another portion of the adjunct material 1800a, 1800b in the form of wings extends beyond the staple line 1806. As explained above, application of the adjunct material 1800a, 1800b by deployment of the staples 1804 to the liver tissue 1802 can cause fractures or cracks 1808 in the liver tissue 1802 and loss of fluid 1810, such as blood. The extended portion of the adjunct material 1800a, 1800b is configured to have desired healing effects on the damaged liver tissue, and the associated bleeding that occurs beyond the staple line 1806.

The top portion of FIG. 160 shows the adjunct material 1800a in an unexpanded configuration when it is first delivered to liver tissue 1802. The adjunct material 1800a has an extended portion or wing in the form of a folded portion 1812 adjacent to and extending beyond the staple line 1806.

The bottom portion of FIG. 160 shows the adjunct material 1800b in an expanded configuration at a period of time after it is delivered to liver tissue 1802. As shown, adjunct material 1800b has an extended portion or wings in the form of an expanded or unfolded portion 1814 that is adjacent to and extending beyond the staple line 1806. As shown in FIG. 160, the direction of unfolding 1816 is away from the staple line 1806. Also, relative size and position of the adjunct 1800b along the staple line and the expanded portion 1814 results in a force 1818 being exerted by portion 1814 in a direction towards liver tissue 1802 to control or prevent bleeding. In particular, expanded region 1800b overlies and applies pressure to cracks 1808 formed in liver tissue 1802.

FIG. 161 is a detailed view of adjunct material 1800b of FIG. 160 in the expanded and unfolded portion 1814. As shown, fluids 1810 such as blood from liver tissue 1802 contact adjunct material 1800b and cause the adjunct material 1800b to expand. In one implementation, the adjunct material 1800b includes a swellable absorbable material 1820 such as a hydrogel, as discussed above. As shown, fluids 1810 from the damaged liver tissue 1802 have a direction of flow 1824 into the adjunct material 1800b to be absorbed by the swellable absorbable material 1820. The swellable absorbable material 1820 then expands in a direction 1826 towards other swellable absorbable material and in an outward direction 1828 to cause the adjunct material 1800b to expand. Thus, contact with fluids 1810, such as from liver tissue 1802, causes the swellable absorbable material 1820 to swell thereby expanding the adjunct material 1800b. This swelling can cause one or more medicants 1822 to be released from the adjunct material 1800b in a direction 1830 out of the adjunct material 1800b. The adjunct material 1800b can be configured to release the medicant(s) 1822 both along the staple line 1806 and from the adjacent unexpanded portion 1814.

In some implementations, the adjunct material can have a porous structure. FIG. 161 shows an example of an adjunct material 1800b that has a plurality of pores 1832. The pores 1832 can be of any desired size, concentration, or density. For example, the pores 1832 can have a size in a film in a range of about 0.05 mm to 1 mm Pore patterns in an adjunct material can be homogenous or heterogeneous with grouping around targeted areas for targeted release from the adjunct material. The pores 1832 can be formed in any number of ways. As shown in FIG. 161, in one implementation, pores 1832 can be formed from a woven material, such as those described above. The adjunct material 1800b can be configured to have pores 1832 sized for passage of particular components from within the adjunct material 1800b to liver tissue 1802. For example, the adjunct material 1800b can include a swellable absorbable material 1820 that is configured to pass through the pores 1832 when the adjunct material 1800b transitions from the unexpanded configuration to the expanded configuration. In some aspects, a medicant 1822 can be configured to be released through the pores 1832 from the adjunct material 1800b in the expanded configuration.

As the adjunct material swells and transitions to the expanded configuration (e.g, the unfolded or unrolled position), the porous structure of the adjunct material permits swellable absorbable material and hemostatic medicants to pass through the barrier and onto the sheared surface of liver tissue. Passage of these substances through the pores also prevents the adjunct material from rupturing due to the internal pressures from swelling.

In another implementation, the adjunct material can be applied to stapled liver tissue to provide pressure to the stapled liver tissue to cause hemostasis and induce sealing. For example, the adjunct material can be in the form of a sheet with swellable absorbable material disposed on at least a tissue-facing surface. When the adjunct material swells or expands, the adjunct material applies a force or pressure to the liver tissue and can fill in and/or seal fractures in the liver tissue. In one aspect, the adjunct material can be configured to adhere to the liver tissue when applying the pressure to the liver tissue.

In some aspects, the adjunct material can elute a plurality of medicants. In one implementation, the adjunct material can also be configured to elute a first medicant to the liver tissue to cause hemostasis. The first medicant can be any substance that can cause hemostasis such as those set forth above. The adjunct material can elute a second medicant that can apply pressure to seal the fractures in the liver tissue. The second medicant can be, for example, a material that swells when in contact with fluid and thus applies pressure to the surface of the liver tissue. The second medicant can be, for example, ORC. The medicants can be released at any desired times. For example, a first medicant can be released when the adjunct material is first applied to the liver tissue, and the second medicant can be applied at any time thereafter.

FIG. 162 is a cross-sectional side view of an adjunct material 1850a, 1850b that is applied to liver tissue 1802 along a staple line 1806, with the ability to expand to apply pressure and one or more medicants 1822 to the stapled liver tissue. The top portion of FIG. 162 shows the adjunct material 1850a when first deployed to the liver tissue 1802 and in a relatively unexpanded configuration 1852. The portion of the adjunct material 1850a adjacent to the staple line 1806 may partially but not fully cover the sheared zone of the liver tissue 1802. A medicant 1822 can be released immediately upon deployment of the adjunct material 1850a to the liver tissue 1802 or a medicant 1822 can be released after a period of time in contact with the liver tissue 1802.

The bottom portion of FIG. 162 shows the adjunct material 1850b in an expanded configuration 1854 at a period of time after deployment of staples 1804. The adjunct material 1850b tends to expand beyond the staple line 1806 when transitioning from the unexpanded configuration to the expanded configuration. The deployed staples 1804 can secure the adjunct material 1850a to an external surface of the liver tissue 1802 to cover a first surface area thereof. The adjunct material 1850b can transition to the expanded configuration 1854 to cover a second surface area of the external surface of the liver tissue 1802 that is greater than the first surface area. In some aspects, the first surface area can be the same or greater than the second surface area. The adjunct material 1850b can have any other desired features. In one implementation, the adjunct material 1850b can be configured to adhere to the liver tissue 1802. In some aspects, the adjunct material can elute a plurality of medicants. For example, as discussed above, a first medicant can be released to cause hemostasis and then a second medicant can be released to apply pressure to seal the fractures in the liver tissue.

In another implementation, adjunct materials for deployment by a surgical stapler can be in the form of a sheet that can extend beyond the sheared liver tissue to undamaged liver tissue surfaces. In one aspect, the adjunct material can have a portion covering damaged portions of liver tissue and another portion such as in the form of flaps covering the undamaged portions.

Anchors or other devices can be applied to secure the flaps of the adjunct material to the liver tissue. A person skilled in the art will appreciate that a number of devices can be used to secure the adjunct material to the liver tissue. Non-limiting examples of suitable anchors include, for example, a hernia tacker, an adhesive, or similar fixation device. The anchor can be any desired absorbable fastener such as, for example, Secure Strap sold by Ethicon, Inc.

When the adjunct material is deployed to the liver tissue, a first medicant can be released to stop bleeding, heal tissue, apply pressure, or to perform a combination of these functions. After the adjunct material is secured to the sheared liver tissue by an anchor, a second medicant can be delivered to the tissue. The second medicant can be eluted at any desired time and rate after the deployment of the adjunct material to the liver tissue. The medicant can be any material that has a desired effect on the liver tissue. For example, the second medicant can be a material that expands so as to apply pressure to the liver tissue such as those set forth above. In one aspect, the second medicant can apply local pressure in the fractures of the sheared liver tissue leading to pressure induced hemostasis. FIG. 3 shows a medicant released from the adjunct material 1850b and delivered to the liver tissue that is in an expanded configuration to apply pressure to the liver tissue.

In one aspect, a method of using a staple cartridge assembly or an end effector described above to apply the adjunct materials described above is provided. The method includes in one implementation removably attaching the cartridge body to a surgical stapler. The method further can include positioning the stapler at a target location adjacent liver tissue. With the stapler positioned at the target location, the stapler can be actuated to deploy the staples from the cartridge body and deliver the adjunct material in the unexpanded configuration to the liver tissue. In one implementation, the adjunct material can release one or more medicants when in the expanded configuration. In some aspects, the adjunct material in the expanded configuration applies pressure to the liver tissue to facilitate sealing of one or more fractures in the liver tissue.

Various exemplary tubular surgical constructs including adjunct material are described herein. In general, a tubular construct can be configured to be applied to tissue of a patient. The tubular construct can be configured to be implantable and to be implanted within a tissue lumen, such as within a lumen of an esophagus or within a gastrointestinal (GI) lumen (e.g., within an intestine, such as a colon). The tubular nature of the construct may allow the construct to be implanted within a tissue lumen without obstructing passage of fluid and/or other matter that passes through the tissue lumen. In other words, the tubular construct can have a lumen extending therethrough, and the construct's lumen can be in communication with the tissue's lumen when the construct is implanted therein such that fluid and/or other matter that would typically flow through the tissue lumen can flow through the implanted tubular construct so as to not obstruct the typical flow of fluid/matter through the tissue lumen. The tubular construct being implanted within a tissue lumen may allow the tissue lumen to be reinforced by the tubular construct. In other words, the construct may provide structural stability to the tissue lumen. The construct may thus help stabilize the lumen when it is weaker than normal, such as when the tissue lumen is wounded and experiencing the process of wound healing.

The tubular construct can be configured to radially expand and radially constrict. In other words, the tubular construct can have a changeable diameter. An outer diameter of the construct can be configured to change due to the radial expansion/constriction, and, similarly, a diameter of an inner passageway extending through the construct can be configured to change due to the radial expansion/constriction. The radial movement of the construct may allow dynamic movement of the construct with a tissue to which the construct is applied. The construct may thus be able to mimic the natural movement of the tissue (e.g., the natural radial expansion/constriction of a tissue lumen) and thereby limit the construct's interference with natural function of the tissue.

The tubular construct can have an adjunct (also referred to herein as an "adjunct material") disposed thereon. The adjunct can thus be configured to be implanted with the construct. The adjunct can be disposed on the construct so as to be a covering thereon. The adjunct may help thus protect the structural elements forming the construct from an outside environment. The structural elements may thus be less likely to reduce in strength after being implanted, which may in turn help maximize an amount of reinforcement the construct provides to the tissue lumen. The adjunct can have any of a variety of configurations, as described herein, such as by including a fiber-based lattice, a foam, and/or a film. Adjuncts in the form of a fiber-based lattice are further described in U.S. patent application Ser. No. 14/840,255 entitled "Adjunct Material To Promote Tissue Growth" filed on Aug. 31, 2015, which is hereby incorporated by reference in its entirety. The fiber-based lattice can be configured to encourage tissue growth to be in a certain direction and/or discourage tissue growth in a certain area and/or on a certain structure, as also further described in U.S. patent application Ser. No. 14/840,255 entitled "Adjunct Material To Promote Tissue Growth" filed on Aug. 31, 2015.

Similar to the construct being configured to radially expand and radially constrict, the adjunct disposed thereon the construct can be configured to radially expand and radially constrict therewith, such as by including a fiber-based lattice, a foam, and/or a film The adjunct can have one or more medicants releasably retained therein, as discussed herein. The at least one medicant can be configured to be release according to any of a variety of temporal patterns, as discussed above, such as by being a bolus dose or a time release dose, and to any of a variety of spatial patterns, as also discussed above. Each of the one or more medicants can be effective to provide a desired effect on tissue in a predetermined manner, which may facilitate wound healing, as also discussed herein, and/or may affect other aspects of healing as discussed herein. The tubular construct can thus be configured as a drug delivery mechanism. In other words, the construct can be a mechanical structure configured to deliver at least one medicant to wounded tissue, which as discussed herein can facilitate wound healing. The one or more medicants can be releasably retained by the adjunct in a variety of ways, as discussed above, such as by being coated thereon, included in one or more vessels coupled thereto, etc.

In at least some implementations, the at least one medicant releasably retained in the adjunct and coupled to the tubular construct can be configured to facilitate tissue growth and remodeling, such as by including at least one of a growth factor (e.g., TGF-B, IGF-1, etc.), an agent that passively contributes to wound healing such as Dextran, and an active agent (e.g., diced autologous tissue, agents used for stem cell therapy, etc.). In the case of a tubular construct being applied to a tissue lumen, such as by being stapled thereto in an anastomosis procedure, the at least one medicant being configured to facilitate tissue growth and remodeling may help the tissue lumen regain structural integrity as quickly as possible. Such strength may be particularly important in such procedures because failure of the tissue lumen due to a leak at the staple line, due to tissue weakness limiting passage of material through the lumen, and/or due to another factor can slow healing, if not prevent healing entirely without further surgical intervention.

In at least some implementations, the at least one medicant releasably retained in the adjunct and coupled to the tubular construct can be configured to perform a function of any one or more of slowing down macrophage function and/or production, increasing fibroblast activity and attraction, and reducing inflammation. The at least one medicant can thus be configured to improve healing during the inflammation stage and/or the proliferation stage of wound healing, which as discussed herein, can allow the remodeling stage to begin sooner and thereby facilitate the tissue regaining strength as quickly as possible. In the case of a tubular construct being applied to a tissue lumen, such as by being stapled thereto in an anastomosis procedure, the at least one medicant being configured to slow down macrophage function and/or production, increase fibroblast activity and attraction, and/or reduce inflammation may facilitate the tissue lumen regaining structural integrity as quickly as possible, which as mentioned above may be particularly important in such procedures.

The at least one medicant releasably retained in the adjunct and coupled to the tubular construct can be targeted to treat a specific tissue and/or targeted to treat a specific disease. The at least one medicant can thus be selected for a particular use to maximize its positive impact on healing.

For example, colectomies are a common treatment for certain types of cancer such as colon cancer and colorectal cancer. In resecting the colon in the colectomy using surgical staples, a tubular construct, having an adjunct and medicant(s) coupled thereto, can be applied to the colon in conjunction with the staples. The at least one medicant can include an anti-cancer agent (e.g., a monoclonal antibody, a chemotherapy agent such as an alkylating agent, etc.) so as to be targeted to treat a specific disease, in this case cancer. The adjunct can releasably retain the one or more medicants targeted to treat cancer in any of a variety of ways, as discussed herein. For example, the adjunct can be formed from one or more bioabsorbable and biocompatible polymers having known degradation rates, as discussed above for example regarding the adjunct 116 of FIG. 12, and having the one or more medicants releasably trapped therein. For another example, the adjunct can be formed from one or more bioabsorbable and biocompatible polymers configured to disintegrate due to effects of temperature, pH, light, or other environmental factors so as to release the medicant(s) retained therein, as discussed above for example regarding the adjunct 122 of FIG. 15.

For another example, a tubular construct, having an adjunct and medicant(s) coupled thereto, can be applied to a tissue in conjunction with staples in an anastomosis being performed as part of a cancer treatment of a tissue lumen such as the colon or the esophagus. Irradiation of the tissue following the performance of the anastomosis may also be part of the cancer treatment. The adjunct releasably retaining the at least one medicant can be formed from one or more polymers configured to degrade in the presence of radiation. In this way, the post-anastomosis radiation can cause the degradation of the polymer and thereby allow release of the one or more medicants from the adjunct. The at least one medicant can include an agent configured to address adverse effect(s) of radiation, such as an agent configured to improve renal function (e.g., bardoxolone, etc.), since radiation nephropathy is an injury that may occur due to radiation therapy. The at least one medicant may thus help maintain and/or improve kidney function. In addition to or instead of the at least one medicant being including an agent configured to address adverse effect(s) of radiation, the at least one medicant can include an anti-cancer agent such as cytosine arabinoside, Cyclophosphamide, methotrexate, or other agent configured to protect healthy tissue during the radiation therapy.

In at least some implementations, when irradiation of the tissue following performance of the anastomosis in which the tubular construct is applied is also part of the cancer treatment, the at least one medicant can be configured to deliver at least some of the radiation. The at least one medicant can in the form of one or more radiation seeds configured to deliver radiation within a patient's body, as will be appreciated by a person skilled in the art. For example, the adjunct coupled to the tubular construct can have a plurality of vessels disposed therein, such as by being a fiber-based lattice defining one or more cavities therein. Each of the plurality of vessels can include one or more radiation seeds, and the vessels can be contained within the cavities.

For yet another example, a tubular construct, having an adjunct and medicant(s) coupled thereto, can be applied to a colon as part of a treatment for irritable bowel syndrome or Crohn's disease. The at least one medicant can include an anti-inflammatory agent, e.g., a monoclonal antibody, tumor necrosis factor alpha (TNF-A), an interleukin-2 (IL-2) inhibitor, etc. The at least one medicant can thus be configured to help reduce inflammation at the wound site and, accordingly, help treat the underlying disease and/or help end the inflammation stage of wound healing when the colon would typically be at its weakest during the wound healing. For example, the adjunct can be formed from one or more bioabsorbable and biocompatible polymers having known degradation rates and/or one or more bioabsorbable and biocompatible polymers configured to disintegrate due to effects of temperature, pH, light, or other environmental factors.

The tubular construct can include a single tubular member or multiple independent tubular members that together define the construct. In general, a tubular member generally has the structure of a tube with an inner passageway extending between opposed openings of the tube. The tube's diameter can be constant along its longitudinal length or can vary therealong. The openings can each have a same diameter or a different diameter. Additionally, as mentioned above, a tubular construct can be radially expandable/constrictable such that the tube's diameter can dynamically vary and the size of the openings can dynamically vary.

In an exemplary implementation of the tubular construct including multiple independent tubular members, the tubular construct can include two tubular members (i.e., first and second tubular members). The first and second tubular members can thus together define a tubular construct configured to be secured to tissue. The first and second tubular members can each have a variety of sizes, shapes, and configurations.

In at least some implementations, the first and second tubular members that collectively define the tubular construct can be the same as one another. The first and second tubular members being the same as one another may facilitate assembly (whether the first and second tubular members are releasably coupled to a surgical stapler during manufacturing or during preparation for a surgical procedure when a surgeon or other user releasably couples the first and second tubular members to a surgical stapler) since it does not matter which of the first and second tubular members is attached to an anvil of the stapler and which is attached to a cartridge assembly of the stapler. The first and second tubular members being the same as one another may facilitate performance of a surgical procedure in which the first and second tubular members are secured to tissue using a surgical stapler because the stapler can be positioned relative to the tissue according to surgeon preference without regard to which side of the tissue the first and second tubular members will be respectively deployed because the sides of tissue will each have a same tubular member applied thereto.

Regardless of whether the first and second tubular members releasably coupled to a surgical stapler are identical to one another or not, each of the first and second tubular members can have an adjunct coupled thereto, e.g., the first tubular member having a first adjunct coupled thereto and the second tubular member having a second adjunct coupled thereto. The first and second adjuncts can be the same as one another or can be different from one another. The first and second adjuncts being the same as one another may facilitate assembly, similar to that discussed above regarding same tubular members. The one or more medicants releasably retained by each of the first and second adjuncts can be the same for each of the first and second adjuncts or can be different from one another. The medicants of the first and second adjuncts being the same as one another may facilitate assembly, similar to that discussed above regarding same tubular members. The medicants of the first and second adjuncts being different from one another may allow the tubular construct to provide more varied treatments, e.g., include at least one medicant directed to wound healing and at least one medicant directed to cancer treatment.

FIG. 163 illustrates one implementation of a tubular member 900. The tubular member 900 can alone define a tubular construct deliverable to tissue or can define a tubular construct together with at least one other tubular member, such as with a second tubular member 902 illustrated in FIG. 164. The tubular member 900 can have a variety of sizes, shapes, and configurations. The tubular member 900 can have an inner passageway 912 extending longitudinally therethrough between opposed openings 914a, 914b of the tubular member 900 (see also FIG. 165). The opposed openings 914a, 914b can be at opposite vertical ends 916a, 916b, e.g., proximal and distal ends, of the tubular member 900, with the vertical direction being defined for the tubular member 900 by a longitudinal axis 900A of the tubular member 900.

The tubular member 900 can have a tapered funnel shape with one of the vertical ends 916a, 916b having a diameter that is less than a diameter at the other of the vertical ends 916a, 916b at least when the tubular member 900 is in its default, natural shape. Here, the bottom or distal end 916b of the tubular member 900 has a diameter that is less than a diameter of the top or proximal end 916a of the tubular member 900 at least when the tubular member 900 is in its default, natural shape. The tubular member 900 is shown in its default, natural shape in FIG. 163. As mentioned above, the tubular member 900 can be configured to radially expand and radially constrict. The diameters at the vertical ends 916a, 916b can thus change while the tubular member 900 is deployed within a tissue lumen and/or during the process of deploying the tubular member 900 within the tissue lumen such that the diameters at the vertical ends 916a, 916b are equal to one another or so that the diameter of the top end 916*b* becomes greater than the diameter of the bottom end 916*a*. The tubular member 900 can be deployed within a tissue lumen such that a direction of fluid flow within the tissue lumen is from the larger vertical end 916*a* to the smaller vertical end 916*b*. The tapered funnel shape of the tubular member 900 may thus facilitate the passage of fluid and/or other matter through a tissue lumen within which the tubular member 900 is deployed.

The tubular member 900 can include a scaffold configured to support an adjunct material 904 thereon, and hence also support one or more medicants 906 releasably retained by the adjunct material 904. The tubular member 900 can thus function as a buttress by supporting the adjunct material 904 and the medicant(s) 906 and, when applied to tissue, by providing structural support to the tissue. The adjunct material 904 is shown partially cutaway from the scaffold in FIG. 163 for clarity of illustration. The adjunct material 904 fully covers an exterior surface of the illustrated scaffold (see also FIG. 165 and FIG. 167). The adjunct 904 fully covering the scaffold's exterior surface may help the medicant(s) 906 release over more area of tissue against which the adjunct 904 abuts, may help the tubular member 900 grip tissue to which it is delivered and thereby help the tubular member 900 stay in place relative to the tissue, and/or may help more evenly distribute pressure exerted outwardly by the tubular member 900 on tissue so as to help irritate the tissue less as foreign matter implanted within the body.

The scaffold can have a variety of sizes, shapes, and configurations. As illustrated, the scaffold can include a plurality of circumferential rings 908*a*, 908*b*, 908*c* and a support member 910 that couples the rings 908*a*, 908*b*, 908*c* together. The tubular member 900 in this illustrated implementation includes three rings 908*a*, 908*b*, 908*c*, but a tubular member can have another plural number of rings, e.g., two, four, five, etc. In general, the more rings that a tubular member has, the more structural stability that the tubular member can provide to the adjunct material thereon and to the tissue to which the tubular member is delivered, the more pressure can be distributed along the longitudinal length of the tubular member so as to help reduce an amount of pressure that the tubular member exerts at any one axial position along a tissue lumen within which the tubular member is deployed, and/or the less pressure may be exerted along a staple line near which the tubular member is deployed. In general, the less pressure exerted on a wounded tissue, the better the tissue can heal.

The rings 908*a*, 908*b*, 908*c* can extend horizontally, with reference to the vertically-extending longitudinal axis 900A of the tubular member 900. The horizontal positioning of the rings 908*a*, 908*b*, 908*c* may facilitate a more even distribution of pressure along the longitudinal length of the tubular member 900 and hence may facilitate tissue healing and/or may help relieve pressure along a staple line near which the tubular member 900 is deployed.

In an exemplary implementation, each of the rings 908*a*, 908*b*, 908*c* has a same shape as one another. As shown, the rings 908*a*, 908*b*, 908*c* each have a circular shape. Tissue lumens typically have a circular inner diameter. Thus, the rings' circular shape may allow the rings 908*a*, 908*b*, 908*c* to mimic the shape of a tissue lumen's inner diameter within which the tubular member 900 may be deployed. The rings 908*a*, 908*b*, 908*c* may thus help the tubular member 900 conform to the shape of the tissue lumen and, hence and/or may help allow the tubular member 900 to be less obstructive to the tissue lumen's natural passageway. In other words, the rings' circular shape may help maximize a size of the passageway through which fluid and/or other matter can flow through the tissue lumen at the location thereof having the tubular member 900 deployed therein. In other implementations, a tubular member's rings can have another shape, such as ovular.

Each of the rings 908*a*, 908*b*, 908*c* can have a same diameter as one another, or any one or more of the rings 908*a*, 908*b*, 908*c* can have a different diameter than any of the other rings 908*a*, 908*b*, 908*c*. All of the rings 908*a*, 908*b*, 908*c* having a same diameter results in the tubular member 900 having a substantially constant diameter along its longitudinal length. A person skilled in the art will appreciate that the tubular member's diameter may not be precisely constant along its longitudinal length due to any one or more factors, such as sensitivity of measurement devices and flexibility of the support member 910 extending between the rings 908*a*, 908*b*, 908*c*. Alternatively, one or more of the rings 908*a*, 908*b*, 908*c* having different diameters results in the tubular member 900 having a non-constant diameter along its longitudinal length. As shown in FIG. 163 and FIG. 165, the tubular member 900 has a non-constant diameter along its longitudinal length, with a diameter 918*a* of the top-most ring 908*a* being greater than a diameter 918*c* of the bottom-most ring 908*c*. The tubular member 900 thus has a tapered funnel shape from top to bottom due to the differing ring diameters. The middle ring 908*b* has a same diameter 918*b* as the top-most ring 908*b* in this illustrated implementation.

The rings 908*a*, 908*b*, 908*c* can be configured to be crush-resistant. This resistance may facilitate the radial expansion/contraction of the tubular member 900 without the tubular member 900 breaking or otherwise reducing in structural integrity. The rings 908*a*, 908*b*, 908*c* can be made from a variety of materials to facilitate the crush resistance, as will be appreciated by a person skilled in the art, such as one or more biocompatible polymers.

The support member 910 can have a variety of sizes, shapes, and configurations. In general, the support member 910 can be configured to attach the rings 908*a*, 908*b*, 908*c* together and hold the rings 908*a*, 908*b*, 908*c* in substantially constant axial positions along the tubular member's longitudinal axis 900A. A person skilled in the art will appreciate that the rings' axial positions may not be precisely constant along the longitudinal axis 900A due to any one or more factors, such as sensitivity of measurement devices, flexibility of the support member 910, and movement of the rings 908*a*, 908*b*, 908*c* during radial expansion/constriction of the tubular member 900.

In general, the support member 910 can be configured to provide axial strength to the tubular member 900. The support member 910 can extend transversely to the rings 908*a*, 908*b*, 908*c*, which may help provide further structural stability to the tubular member 900. The support member 910 can extend vertically so as to be parallel to the tubular member's longitudinal axis 900A and/or can extend at a non-perpendicular angle to longitudinal axis 900A. In other words, the support member 910 can extend transversely to first, second, and third substantially parallel planes defined by the first, second, and third rings 908*a*, 908*b*, 908*c*, respectively. In this illustrated implementation, the support member 910 has a cross-hatched pattern. Although the support member 910 does not extend horizontally at all in this illustrated embodiment, a support member in another implementation may include some horizontally-extending portions, which may help provide additional horizontal stability to the tubular member at axial positions between the tubular member's rings.

As shown, the support member 910 can include a plurality of fibers that together define the support member 910 and that are woven together to define the cross-hatched pattern. The fibers can be woven, braided, knitted, or otherwise interconnected, similar to that discussed above regarding an adjunct's fiber-based lattice. The fibers can have at least some space therebetween, thereby allowing the one or more medicant(s) 906 to leak or otherwise pass therethrough. Instead of including a plurality of fibers woven together, a support member can include a single fiber wound in a pattern.

The support member 910 can be exposed on an interior surface of the tubular member 900, as shown in FIG. 165. In other words, the adjunct material 904 can cover only an exterior surface of the scaffold, thereby leaving the interior surface of the scaffold adjunct-free. In at least some implementations, the adjunct material 904 may cover some portion of the scaffold's interior surface while leaving another portion of the scaffold's interior surface adjunct-free. The exposed fibers of the support member 910 on the scaffold's interior surface can be configured to facilitate tissue growth. Cells may attach to the fibers of the support member 910 on the exposed interior surface, which may facilitate tissue healing as discussed herein, e.g., by facilitating ECM formation. The fibers can be configured to encourage tissue growth to be in a certain direction and/or discourage tissue growth in a certain area and/or on a certain structure, similar to the fiber-based lattice adjunct mentioned above and as further described in U.S. patent application Ser. No. 14/840, 255 entitled "Adjunct Material To Promote Tissue Growth" filed on Aug. 31, 2015. Additionally, since the adjunct 904 covering the scaffold can be configured to disintegrate, as discussed herein, an exterior surface of the support member 910 that was previously covered by the adjunct 904 can become exposed to an external environment over time due to the adjunct's disintegration. Once exposed, cells may attach to the fibers of the support member 910 from an exterior side of the tubular member 900 and thereby encourage tissue growth to be in a certain direction and/or discourage tissue growth in a certain area and/or on a certain structure.

The tubular member 900 can include one or more bioabsorbable ties (not shown), e.g., one or more bioabsorbable fibers, configured to reduce a size of the tubular member 900 to facilitate insertion of the tubular member 900 into a patient's body and/or into a tissue lumen. The one or more ties can be configured to collapse the tubular member 900 to a reduced diameter by causing the rings 908a, 908b, 908c to fold, bend, or otherwise compress in size and/or by causing the support member 910 to fold, bend, or otherwise compress in size. It may therefore be easier for the tubular member 900 to be inserted into a tissue lumen and/or into a body of a patient through an incision formed therein or through a natural orifice thereof. The one or more ties can be configured to bioabsorb very quickly within the tissue lumen, thereby allowing the tubular member 900 to assume its "normal" size and shape and conform to the size of the tissue lumen to which the tubular member 900 is applied. Whether or not the tubular member 900 includes one or more bioabsorbable ties, the tubular member 900 can be manually compressed to help the tubular member 900 be inserted into a tissue lumen and/or into a patient's body. The rings 908a, 908b, 908c and the support member 910 can thus be flexible (e.g., be able to bend without breaking or permanently deforming in form) to facilitate insertion of the tubular member 900.

The second tubular member 902 of FIG. 164 and FIG. 165 can have a variety of sizes, shapes, and configurations. As shown, the second tubular member 902 is the same as the first tubular member 900 and includes a scaffold or buttress including a plurality of rings 922a, 922b, 922c, including a support member 924, and configured to support an adjunct material 926 thereon, and hence also support one or more medicants 928 releasably retained by the adjunct material 926. The adjunct material 926 is shown partially cutaway from the scaffold in FIG. 164 for clarity of illustration. The adjunct material 926 fully covers an exterior surface of the illustrated scaffold (see also FIG. 165 and FIG. 167).

FIG. 166 illustrates another implementation of a tubular member 930. The tubular member 930 can alone define a tubular construct or can be used with at least one additional tubular member to together define a tubular construct similar to the first and second tubular members 900, 902 together defining a tubular construct. The tubular member 930 can generally be configured and used similar to the first tubular member 900 and can include a scaffold or buttress including a plurality of rings 932a, 932b, 932c, including a support member 934, and configured to support an adjunct material 936 thereon, and hence also support one or more medicants 938 releasably retained by the adjunct material 936. The adjunct material 936 is shown partially cutaway from the scaffold in FIG. 166 for clarity of illustration. The adjunct material 936 fully covers exterior and interior surfaces of the illustrated scaffold.

Like the first tubular member 900, the tubular member 930 includes three horizontally-extending rings 932a, 932b, 932c, with the upper two rings 932a, 932b having a same diameter and the lower ring 932c having a smaller diameter such that the tubular member 930 has a tapered funnel shape. Also like the first tubular member 900, the support member 934 of the tubular member 930 includes a plurality of fibers. The fibers in this illustrated implementation extend transversely to the rings 932a, 932b, 932c, with some of the fibers extending substantially parallel to the tubular member's longitudinal axis 930A and substantially perpendicular to planes defined by each of the rings 932a, 932b 932c between the upper two rings 932a, 932b and with some of the fibers extending transversely to the to the member's longitudinal axis 930A between the bottom two rings 932b, 932c. At least some of the fibers thus extend vertically. A person skilled in the art will appreciate that the fibers extending between the upper two rings 932a, 932b may not be precisely parallel to the member's longitudinal axis 930A or precisely perpendicular to planes defined by each of the rings 932a, 932b 932c due to any one or more factors, such as sensitivity of measurement devices, flexibility of the fibers, and movement of the rings 932a, 932b 932c during radial expansion/ constriction of the tubular member 930.

In general, a tubular construct having an adjunct disposed thereon, the adjunct releasably retaining at least one medicant, can be configured to be applied to tissue by a surgical stapler in conjunction with staples. The at least one medicant can be configured to be released along the staple line defined by the staples, which can help target the at least one medicant's desired functionality to where the wounded tissue is typically weakest. The at least one medicant may thus help prevent the tissue along the staple line from becoming too weak during the wound healing process. The construct can be configured to be positioned on both sides of the staple line, which may help provide structural stability to the tissue around the staple line during the process of wound healing. For example, a first tubular member of the construct can be positioned on one side of the staple line, and a second tubular member of the construct can be positioned on the other side of the staple line.

A tubular construct having an adjunct disposed thereon that is releasably retaining at least one medicant may be applied to a tissue lumen, as mentioned above. Tissue structure of a tissue lumen is generally organized to facilitate radial expansion or stretching (distension) and to limit longitudinal expansion or stretching (e.g., expansion or stretching along a longitudinal axis of the colon). Additionally, an anastomosis performed in a surgical procedure, such as in a colectomy, a Roux en-Y gastric bypass (RYGB), or an esophagectomy, using a stapler leaves a staple line within the tissue lumen. The tubular construct being radially conformable may facilitate radial expansion or stretching of the tissue lumen and may limit longitudinal expansion or stretching and, thus, be well suited for delivery to a tissue lumen. The adjunct can be configured to focus encouraged tissue growth in a direction in accordance with the lumen's natural radial expansion and contraction. This encouragement can be caused in any number of ways, as further discussed in previously mentioned U.S. patent application Ser. No. 14/840,255 entitled "Adjunct Material To Promote Tissue Growth" filed on Aug. 31, 2015. The construct, and hence the adjunct and medicant(s) coupled thereto, may be applied to the tissue lumen adjacent the staple line to reflect the endolumenal nature of the staple line, to provide strength along the staple line where anastomosis tissues are attached together, and/or to help focus the wound healing benefits of the adjunct and/or its associated medicant(s) along the area where leaks are most common. For colorectal procedures in particular, leaks at an anastomosis wound site are a common and potentially life-threatening event. Adjuncts and medicants configured to facilitate leak identification and/or leak sealing, such as via color change, foaming, or a change in adjunct conformation, are further described in U.S. patent application Ser. No. 14/840,431 entitled "Surgical Adjuncts With Medicants Affected By Activator Materials" filed on Aug. 31, 2015, which is hereby incorporated by reference in its entirety.

FIG. 165 illustrates the first and second tubular members 900, 902 loaded on an implementation of a circular surgical stapler for delivery to a tissue. For clarity of illustration, only a distal portion of the stapler is shown in FIG. 165. The first tubular member 900 is loaded on an anvil 940 of the stapler, and the second tubular member 902 is loaded on a cartridge assembly 942 of the stapler. As discussed above, the cartridge assembly 942 can have a plurality of staples 944 loaded therein that are configured to be driven therefrom toward staple-forming cavities 946 formed in the anvil 940. Thus, tissue positioned in a space 952 between opposed tissue-facing surfaces 948, 950 of the anvil 940 and the cartridge assembly 942 can have the staples 944 driven therethrough.

The first tubular member 900 can be loaded on the anvil 940 with its lower diameter end, e.g., the bottom end 916b, facing proximally toward the cartridge assembly 942 and hence toward the second tubular member 902 loaded on the cartridge assembly 942. The second tubular member 902 can be loaded on the cartridge assembly 942 with its lower diameter end facing distally toward the anvil 940 and hence toward the first tubular member 900 loaded on the anvil 940. In this way, when the tubular construct is applied to tissue, the lower diameter bottom ends will face one another such that the tubular construct has an hourglass shape, as shown for example in FIG. 167, which is discussed further below. The hourglass shape can facilitate passage of fluid and/or other matter through the construct, similar to that discussed above. The radially conformable nature of the first and second tubular members 900, 902 may facilitate their loading onto the stapler, as may one or more bioabsorbable ties (not shown) coupled to one or both of the first and second tubular members 900, 902.

At least one of the anvil 940 and the cartridge assembly 942 can be movable relative to the other to facilitate the deployment of the staples 944, as discussed herein. Accordingly, at least one of the first and second tubular members 900, 902 can be movable relative to the other to facilitate the deployment of the tubular construct.

FIG. 167 illustrates one implementation of the tubular construct including the first and second tubular members 900, 902 delivered to a tissue lumen 954 with the plurality of staples 944 in an end-to-end anastomosis procedure using the circular surgical stapler of FIG. 165 attaching together two tissues 954, 954b defining the lumen 954. The implementation of FIG. 167 is described with respect to the tubular members 900, 902 of FIG. 163 and FIG. 164, but other tubular constructs can be similarly applied. Also, the implementation of FIG. 167 is described with respect to the tubular members 900, 902 being applied to the tissue lumen 954 using the stapler of FIG. 165, but this or other tubular constructs can be delivered to this or to another tissue using a different surgical stapler.

The staples 944 can secure both of the first and second tubular members 900, 902 to the tissue 954, as shown. The positioning of the first and second tubular members 900, 902 on the stapler shown in FIG. 165 facilitates this stapling since both of the first and second tubular members 900, 902 are positioned between the staples 944 and the staple cavities 946 prior to the deployment of the staples 944. The staples 944 may help hold the tubular construct in place relative to the staple line, which may facilitate delivery of the one or more medicants 906, 928 along the staple line where they may best facilitate wound healing.

As shown, the tubular construct, e.g., the first and second tubular members 900, 902, is intralumenally placed, e.g., is located within an inner passageway 956 of the tissue lumen 954, with the adjunct material 904, 926 facing an interior surface of the lumen 954 and abutting thereagainst. The radial conformability of the tubular construct may allow the construct to conform to the lumen's natural size and shape, as shown. The staple line formed by the staples 944 may extend generally transverse to the tissue lumen's natural direction of distension, as shown. The horizontal extension of the rings 908a, 908b, 908c, 922a, 922b 922c relative to the longitudinal axes 900A, 902A of the tubular members 900, 902, and hence to a longitudinal axis 958 of the tissue lumen 954, may help relieve pressure on the tissue and/or may help urge the inner passageway 956 wider to help fluid and/or other matter flow therethrough.

The tubular construct deployed within the tissue lumen 954 is configured to reinforce the wounded tissue during its process of healing starting at a time the staples 944 are applied since the construct is delivered in conjunction with the staples 944. The construct can be configured to reinforce the wounded tissue throughout the entire process of wound healing (e.g., through all of the hemostasis, inflammation, proliferation, and remodeling stages) or through a partial portion thereof (e.g., from the time of stapling to a time at some point in one of the four stages before the remodeling stage ends). The construct can be configured to disintegrate, in any of the ways discussed herein (e.g., by being formed of bioabsorbable material, etc.), so as to stop providing structural support to the lumen 954 after its disintegration or at some point when the construct has partially disintegrated to a point of lost structural integrity.

Various exemplary surgical adjuncts and medicants for inducing tissue adhesions are described herein. In general, an implantable adjunct can have one or more medicants releasably retained therein that are configured to induce tissue adhesions. The adjunct can be configured to be applied to lung tissue in conjunction with surgical staples using a surgical stapler, as discussed herein.

Surgical procedures involving lung tissue can result in air leaks at the lung, such as along any staple lines applied to the lung tissue in the surgical procedure. Air leaks are especially problematic when attempting to close lung tissue using staples in surgical procedures such as a lung resection given the need for the lungs to inflate and deflate post-surgery without leaking or causing patient pain. Surgeons typically prefer to allow air leaks in patient lung tissue to close on their own. However, if an air leak fails to correct itself, or if a surgeon chooses to intervene without waiting for the air leak to heal itself, a surgeon will typically inject a blood sample into a chest cavity of the patient in a process called pleurodesis. Pleurodesis generally involves inducing adhesions by causing pleural surfaces (e.g., pleural membranes) around the lungs to stick together and thereby prevent fluid from building up in a space (e.g., pleural space) between the pleural surfaces. The presence of the blood sample in the chest cavity upsets the patient's tissue and causes adhesions to form between the lung tissue and the chest cavity of the patient. The adhesions are intended to stop and/or prevent air leaks. However, air leaks can be very difficult to detect such that they may not be detected even if they exist and, accordingly, it may not be known that pleurodesis is necessary. To address this uncertainty, surgeons traditionally apply adhesion-inducing substances to a surface of the lung intra-operatively during the performance of the surgical procedure that may cause air leaks or apply the adhesion-inducing substances through a chest tube post-operatively. However, these intra-operative and post-operative approaches are time-consuming since they add to the procedure's length (in the case of intraoperative intervention) or require additional patient trauma (in the case of post-operative intervention). The intraoperative and postoperative approaches can also be challenging to perform, particularly for less experienced surgeons.

The at least one medicant disposed within and releasable from the adjunct can be configured to induce tissue adhesions and thus help prevent air leaks and/or render the pleurodesis procedure of introducing a blood sample into the patient's chest cavity unnecessary, either intra-operatively or post-operatively. In other words, pleurodesis can be encouraged through delivery of the adjunct to lung tissue. The adjunct being deliverable in conjunction with surgical staples may be much less challenging than traditional pleurodesis of manually applying adhesion-inducing substances during a surgical procedure in which lung tissue is stapled and/or applying substances through a chest tube after a surgical procedure in which lung tissue is stapled at least because the stapling is part of the procedure itself and is not a step performed thereafter.

In addition to being configured to induce tissue adhesions, the one or more medicants can be configured to facilitate one or more aspects of wound healing, e.g., encourage hemostasis, encourage tissue growth, etc., and/or to promote lung function. The one or more medicants can thus be configured to induce tissue adhesions as well as be configured to facilitate healing of the wounded lung, e.g., the healing of the stapled lung tissue, and/or to promote lung function. Adjuncts and medicants configured to promote lung function are described further in U.S. patent application Ser. No. 14/840,878 entitled "Surgical Adjuncts And Medicants For Promoting Lung Function" filed on Aug. 31, 2015, which is incorporated by reference in its entirety.

The adjunct including the at least one medicant configured to induce tissue adhesions can be configured in a variety of ways, as discussed herein, such as by including a fiber-based lattice, a foam, and/or a film.

In at least some implementations, the adjunct can include a carrier configured to facilitate release of the at least one medicant from the adjunct. The carrier can itself form the adjunct or can be disposed therein, e.g., disposed in a polymer forming the adjunct. The carrier can be configured to undergo a phase change from a solid state to a liquid state, such as by being configured to change state due to effects of temperature, pH, light, and/or other environmental factors. One example of a carrier configured to undergo a phase change from a solid state to a liquid state is polyethylene glycol (PEG), which is configured to change state in response to temperature (e.g., room temperature to body temperature). When the carrier is in the solid state, the at least one medicant can be held by the adjunct so as to not be releasing therefrom. When the carrier is in the liquid state, the at least one medicant can be released from the adjunct, e.g., by the carrier flowing out of the adjunct or by the adjunct itself turning into the liquid state. The at least one medicant can be dispersed within the carrier in the solid state such that the at least one medicant can be carried by the carrier in its liquid state. For example, the at least one medicant can be encapsulated in microcapsules, microbeads, or any other vessel, as discussed above, that are dispersed in the carrier. The microcapsules, microbeads, or other vessel can be configured to adhere to soft tissue, e.g., to pleural surfaces, such as by having a coating thereon of an adhesive or other tissue adherent agent. The medicant(s) contained in the microcapsules, microbeads, or other vessel can thus be configured to induce tissue adhesion where the microcapsules, microbeads, or other vessels adhere to the soft tissue. Elution of the one or more medicants can occur throughout initial release via the carrier and/or through absorption of coatings of the microcapsules, microcapsules, microbeads, or other vessels. The at least one medicant being carried by the carrier in the liquid state may allow the at least one medicant to be broadly dispersed through normal lung function (e.g., expansion and contraction of lungs) since the normal lung function can facilitate motion of the carrier in the liquid state between lung lobes, chest wall, diaphragm, etc.

As discussed above, the at least one medicant releasably retained by the adjunct can be configured to be release according to any of a variety of temporal patterns, such as by being a bolus dose or a time release dose, and to any of a variety of spatial patterns. The at least one medicant being configured to be released from the adjunct as a single dose, e.g., as a bolus dose, may allow for faster inducement of tissue adhesions. The faster creation of the adhesions may help prevent any leaks and thus the problems associated therewith. The at least one medicant being configured to be released from the adjunct as a time release dose over time may allow for adhesions to be formed over a greater area because the medicant can flow, seep, or otherwise travel over or past areas where tissue adhesions have previously formed so as to induce adhesions in a new area. Leaks may thus be preventable over a larger area. The one or more medicants can be releasably retained by the adjunct in a variety of ways, as discussed above, such as by being coated thereon, included in one or more vessels coupled thereto, etc. A variety of different medicants can be configured to induce tissue adhesions. Non-limiting examples of medicants configured to induce tissue adhesions include growth factors (e.g., IL beta, TGF-B, etc.) and platelet rich plasma.

Broad dispersal of the one or more medicants configured to induce tissue adhesions can lead to a broad distribution of tissue adhesions in a patient. If another surgical procedure is performed in the patient's chest after the adhesions have formed, the broad distribution of adhesions may make the subsequent surgical procedure more difficult to perform. In at least some implementations, a marker such as a fiducial marker (e.g., a radiopaque marker) can be attached to an adjunct that retains one or more medicants configured to induce tissue adhesions. The marker can be configured to remain in place permanently. The marker may help surgeon(s) performing subsequent surgical procedure(s) on the patient in the chest area to return to a same anatomical location, e.g., to the location where the adjunct was applied and hence at or near an area where the tissue adhesions were formed, in the subsequent procedure(s). The marker may therefore aid in surgical planning and guidance. One or more markers can be attached to the adjunct and delivered therewith.

FIG. 168 illustrates one implementation of an adjunct 2000 having at least one medicant 2008 releasably retained therein and configured to induce tissue adhesions. In general, the adjunct 2000 has multiple layers including a barrier layer 2004 disposed between a conformable layer 2006 and a reinforcing layer 2002. The conformable layer 2006 can be formed of a material configured to conform to an irregular surface and to be viscous and flowable. As shown, the at least one medicant 2008 can be disposed in the conformable layer 2006. The adjunct 2000 including the conformable layer 2006 may thus be particularly well suited for delivery to lung tissue, which is naturally expansive and extensible. Implementations of adjuncts including multiple layers are further described in U.S. patent application Ser. No. 14/840, 527 entitled "Composite Adjunct Materials For Delivering Medicants" filed on Aug. 31, 2015, which is hereby incorporated by reference in its entirety.

FIG. 169 shows the adjunct material 2000 secured to an exterior surface of lung tissue 2010 with a staple 2020. The conformable layer 2006 is compressed by the pressure from the staple 2020. Only one staple 2020 is shown for ease of illustration. A plurality of the staples 2020 would typically be used to secure the adjunct 2000 to the tissue 2010. As shown, the at least one medicant 2008 is not eluting out of the conformable layer 2006 and into the reinforcing layer 2002 due to the barrier layer 2004. The medicant 2008 is, however, eluting laterally away from a staple crown 2022. The lateral elution of the at least one medicant 2008 may help the at least one medicant 2008 induce tissue adhesions near the area of wounding, e.g., near the staple 2020, and, similarly, near the plurality of staples attaching the adjunct 2000 to the tissue 2020. When stapling a lung, leakage is traditionally greatest along an outside edge of the lung. The lateral elution of the at least one medicant 2008 may help the at least one medicant 2008 approach and/or seep over the outside edge of the lung that includes the lung tissue 2010 and thereby help address leakage at the lung's edge, e.g., by the one or more medicants 2008 including one or more hemostatic agents configured to facilitate sealing.

As mentioned above, the time release rate of the at least medicant 2008 from the adjunct 2000 can be different in different implementations. For example, the conformable layer 2006 can be varied (e.g., varied between implementations to be formed of different materials, to have different rates of disintegration, etc.) to allow for a selectable rate of release of the at least one medicant 2008. For example, the conformable layer 2006 can vary from rapid dissolving, allowing the at least one medicant 2008 to be rapidly released from the adjunct 2000, to slow dissolving, allowing the at least one medicant 2008 to be slowly released from the adjunct 2000. As also mentioned above, a slow time release rate may be particularly useful for medicants configured to induce tissue adhesions in order to induce more tissue adhesions and/or stronger tissue adhesions over a longer period of time than may be achieved with a bolus dose or if released at a faster release rate.

FIG. 170 and FIG. 171 illustrate another implementation of an adjunct 2030 having at least one medicant 2032 releasably retained therein and configured to induce tissue adhesions. FIG. 170 and FIG. 171 show the adjunct 2030 attached to a lung 2040 with a plurality of staples 2042 with part of the lung 2040 removed, such as by a resection procedure. FIG. 170 shows the lung 2040 in a relaxed state (e.g., with the lung 2040 in a deflated state during normal lung function). FIG. 171 shows the lung 2040 in an expanded state (e.g., with the lung 2040 in an inflated state during normal lung function). As illustrated in FIG. 171, the at least one medicant 2032 can be released from the adjunct 2030 into and/or near a pleural space 2052, where, as discussed herein, the at least one medicant 2032 can be configured to induce tissue adhesions.

The adjunct 2030 can be configured to have a structure that facilitates distribution of effective amounts of the one or more medicants 2032 to provide a desired effect, as discussed above. The desired effect can include, as in this illustrated implementation, directing the one or medicants 2032 into the pleural space 2052. For example, the targeted delivery of the one or more medicants 2032 can be accomplished by incorporating the one or more medicants 2032 into regions within the adjunct 2030 formed in a pattern that allows a spatial distribution of the one or more medicants 2032 into the pleural cavity 2052 upon their release from the adjunct 2030.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:

positioning an end effector of a surgical stapler adjacent tissue of a patient, the end effector having disposed therein a cartridge body including a plurality of staples, and the end effector having releasably disposed thereon a biocompatible adjunct material, the adjunct material having an effective amount of at least one medicant disposed within and releasable from the adjunct material, the adjunct material having at least a first layer and a second layer, the first layer including at least first and second distinct portions disposed along at least an outer surface of the first layer, each of the first and second distinct portions of the first layer having a distinct degradation rate from each of the other first and second distinct portion of the first layer, each of the first and second distinct portions being arranged on the outer surface such that a degradation rate of the first layer varies along at least one of a total length and a total width of the outer surface, the first distinct portion being disposed along only a first side of the outer surface of the first layer, the second distinct portion being disposed along only a second side of the outer surface of the first layer, the second layer being disposed entirely within the first layer; and actuating the stapler to eject the staples out of openings in the cartridge body, thereby stapling the adjunct material to the tissue and releasing the adjunct material from the cartridge body, the at least one medicant being releasable from the adjunct material to the tissue according to at least a predetermined temporal pattern that is defined by the degradation rates of the at least first and second distinct portions of the first layer and a different degradation rate of the second layer;

wherein the first distinct portion has thin fibers configured to encourage regrowth, and the second distinct portion has thicker fibers relative to the thin fibers of the first distinct portion configured to discourage regrowth.

2. The method of claim 1, wherein the at least one medicant is releasable from the adjunct material to the tissue according to at least the predetermined temporal pattern, and the predetermined temporal pattern includes a substantially immediate release of the at least one medicant upon the stapling of the adjunct material.

3. The method of claim 1, wherein the at least one medicant is releasable from the adjunct material to the tissue according to at least the predetermined temporal pattern, and the predetermined temporal pattern includes the at least one medicant not being released from the adjunct material until a predetermined amount of time after the stapling of the adjunct material.

4. The method of claim 1, wherein the at least one medicant is releasable from the adjunct material to the tissue according to at least the predetermined temporal pattern, and the predetermined temporal pattern is defined by at least one of a degradation rate of a region within the adjunct material from which the at least one medicant is being released, a degradation rate of one or more coatings retaining the at least one medicant within the adjunct material, and an environmental condition at the tissue.

5. The method of claim 1, wherein the at least one medicant is releasable from the adjunct material to the tissue according to at least a predetermined spatial pattern, the adjunct material including a plurality of distinct regions each releasably retaining therein the at least one medicant, the at least one medicant being releasable from each of the regions in a different spatial pattern.

6. The method of claim 1, further comprising, prior to positioning the end effector adjacent the tissue of the patient, removably disposing the cartridge body into the end effector.

7. The method of claim 1, further comprising removing the surgical stapler from the patient, the staples and the adjunct material remaining within the patient.

8. The method of claim 1, wherein the at least one medicant includes at least one of an antimicrobial agent, an antifungal agent, an antiviral agent, an anti-inflammatory agent, a growth factor, an analgesic, an anesthetic, a tissue matrix degradation inhibitor, an anti-cancer agent, and a hemostatic agent.

9. The method of claim 1, wherein the at least one medicant includes a first medicant and a second medicant that is different than the first medicant, the first layer has only the first medicant disposed therein, and the second layer has only the second medicant disposed therein.

10. The method of claim 1, wherein the at least one medicant includes only a first medicant, and the first and second layer each have the first medicant disposed therein.

11. The method of claim 1, wherein the first and second sides of the outer surface of the first layer are disposed opposite to each other relative to only one of the total length and the total width of the outer surface such that the degradation rate of the first layer is configured to release the at least one medicant in a first elution profile along the total length and a second elution profile along the total width, the first and second elution profiles being different from each other.

12. The method of claim 1, wherein each of the first and second distinct portions are arranged such that the degradation rate of the first layer varies continuously across one of the total length or the total width of the outer surface.

13. A surgical method, comprising:

positioning an end effector of a surgical stapler adjacent an organ of a patient, the end effector having disposed therein a cartridge body including a plurality of staples, and the end effector having a biocompatible adjunct material releasably disposed on a first external surface thereof, the adjunct material having a plurality of distinct regions each having an effective amount of at least one medicant disposed within and releasable therefrom;

actuating the stapler to deploy the staples from the cartridge body, thereby stapling the adjunct material to the organ and releasing the adjunct material from the end effector, the plurality of distinct regions releasing the medicant in a predetermined spatial pattern, the adjunct material having a predetermined spatial structure, and the spatial pattern of the plurality of distinct regions and the spatial structure of the adjunct material encouraging regrowth of tissue of the organ in at least a first location on the organ and discourage regrowth of tissue in at least a second location of the organ, the plurality of distinct regions including a first fiber lattice section having a first plurality of fibers configured to encourage the regrowth and a second fiber lattice section having a second plurality of fibers being less tightly spaced relative to the fibers of the first plurality of fibers and configured to discourage the regrowth, the first and second fiber lattice sections being disposed together along a second external surface of the adjunct material, each fiber of the first plurality of fibers extending substantially parallel to each other fiber of the first plurality of fibers along the second external surface, and each fiber of the second plurality of fibers extending substantially parallel to each other fiber of the second plurality of fibers along the second external surface; and after the actuation, removing the end effector with the cartridge body disposed therein from the patient;

wherein the first fiber lattice section has thin fibers configured to encourage regrowth, and the second fiber lattice section has thicker fibers relative to the thin fibers of the first fiber lattice section configured to discourage regrowth.

14. The method of claim 13, wherein the predetermined treatment includes at least one of an antimicrobial effect, an antifungal effect, an antiviral effect, an anti-inflammatory effect, a growth factor effect, an analgesic effect, an anesthetic effect, tissue matrix degradation inhibition, an anticancer effect, and a hemostatic effect.

15. The method of claim 13, wherein encouraging regrowth of tissue of the organ includes causing the tissue to regrow in a direction that mimics a natural direction of tissue fibers of the organ.

16. The method of claim 13, wherein the adjunct material is stapled to an exterior surface of the organ.

17. The method of claim 13, wherein the adjunct material is stapled to an interior surface of the organ.

18. The method of claim 13, wherein the organ includes one of a stomach, an intestine, a liver, and a lung.

19. The method of claim 13, further comprising removably and replaceably disposing the cartridge body with the staples therein into the end effector.

20. The method of claim 13, wherein the second external surface of the adjunct material extends parallel to the first external surface of the end effector.

21. A surgical method, comprising:
positioning an end effector of a surgical stapler adjacent an organ of a patient, the end effector having disposed therein a cartridge body including a plurality of staples, and the end effector having a biocompatible adjunct material releasably disposed on a first external surface thereof, the adjunct material having a plurality of distinct regions each having an effective amount of at least one medicant disposed within and releasable therefrom;

actuating the stapler to deploy the staples from the cartridge body, thereby stapling the adjunct material to the organ and releasing the adjunct material from the end effector, the plurality of distinct regions releasing the medicant in a predetermined spatial pattern, the adjunct material having a predetermined spatial structure, and the spatial pattern of the plurality of distinct regions and the spatial structure of the adjunct material encouraging regrowth of tissue of the organ in at least a first location on the organ and discourage regrowth of tissue in at least a second location of the organ, the plurality of distinct regions including a first fiber lattice section having a first plurality of fibers configured to encourage the regrowth and a second fiber lattice section having a second plurality of fibers being less tightly spaced relative to the fibers of the first plurality of fibers and configured to discourage the regrowth, the first and second fiber lattice sections being disposed together along a second external surface of the adjunct material, each fiber of the first plurality of fibers extending substantially parallel to each other fiber of the first plurality of fibers along the second external surface, and each fiber of the second plurality of fibers extending substantially parallel to each other fiber of the second plurality of fibers along the second external surface; and after the actuation, removing the end effector with the cartridge body disposed therein from the patient;

wherein the first fiber lattice section has positively charged fibers configured to encourage regrowth, and the second fiber lattice section has negatively charged fibers configured to discourage regrowth.

* * * * *

UNITED STATES PATENT AND TRADEMARK OFFICE
CERTIFICATE OF CORRECTION

| | | |
|---|---|---|
| PATENT NO. | : 10,569,071 B2 | Page 1 of 1 |
| APPLICATION NO. | : 14/840613 | |
| DATED | : February 25, 2020 | |
| INVENTOR(S) | : Harris et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this
Twenty-fourth Day of November, 2020

Andrei Iancu
*Director of the United States Patent and Trademark Office*